(12) United States Patent
Piedrahita et al.

(10) Patent No.: US 6,271,436 B1
(45) Date of Patent: Aug. 7, 2001

(54) CELLS AND METHODS FOR THE GENERATION OF TRANSGENIC PIGS

(75) Inventors: Jorge A. Piedrahita; Fuller W. Bazer, both of College Station, TX (US)

(73) Assignee: The Texas A & M University System, College Station, TX (US)

(*) Notice: Subject to any disclaimer, the term of this patent is extended or adjusted under 35 U.S.C. 154(b) by 0 days.

(21) Appl. No.: 08/949,155

(22) Filed: Oct. 10, 1997

Related U.S. Application Data

(60) Provisional application No. 60/046,094, filed on May 9, 1997, and provisional application No. 60/027,338, filed on Oct. 11, 1996.

(51) Int. Cl.$^7$ ........................... C12N 15/09; C12N 15/00; C12N 15/63; C12N 5/00
(52) U.S. Cl. ................................ 800/21; 800/22; 800/24; 800/25; 800/14; 800/17; 800/18; 800/15; 800/16; 435/325; 435/383; 435/384; 435/455; 435/463; 435/461; 435/459; 435/462
(58) Field of Search ..................................... 435/325, 383, 435/384, 455, 463, 461, 459, 462; 800/13, 14, 15, 16, 17, 21, 22, 24, 25, 18

(56) References Cited

U.S. PATENT DOCUMENTS

| | | | |
|---|---|---|---|
| 5,258,367 | 11/1993 | Bazer et al. | 514/6 |
| 5,453,357 | 9/1995 | Hogan | 435/7.21 |
| 5,523,226 | 6/1996 | Wheeler | 435/240.2 |
| 5,573,933 | 11/1996 | Seamark et al. | 435/172.3 |
| 5,641,676 | 6/1997 | Gough et al. | 435/325 |
| 5,670,372 | 9/1997 | Hogan | 435/240.2 |
| 5,690,926 | 11/1997 | Hogan | 424/93.1 |

FOREIGN PATENT DOCUMENTS

| | | |
|---|---|---|
| 0774510 | 5/1997 | (EP). |
| WO 94/07997 | 4/1994 | (WO). |
| WO 95/10599 | 4/1995 | (WO). |
| WO 95/34636 | 12/1995 | (WO). |
| WO 97/07668 | 3/1997 | (WO). |
| WO 97/07669 | 3/1997 | (WO). |
| WO 97/41209 | 11/1997 | (WO). |
| WO 97/47734 | 12/1997 | (WO). |
| WO 98/07841 | 2/1998 | (WO). |

OTHER PUBLICATIONS

Moreadith et al., J. Mol. Med., vol. 75, pp. 208–216, 1997.*

Hammer et al., J. Anim. Sci., vol. 63, pp. 269–278, 1986.*

Anderson, G. B., Choi, S. J. and BonDurant, R. H., "Survival of porcine inner cell masses in culture and after injection into blastocysts," Theriogenology 42:204–212, 1994.

Barnes et al., "Embryo cloning in cattle: The use of in vitro matured oocytes," J. Reprod. Fert., 97:317–323, 1993a.

Barnes et al., "Influences of recipient oocyte cell cycle stage on DNA synthesis, nuclear envelope breakdown, chromosome constitution, and development in nuclear transplant bovine embryos," Mol. Reprod. Dev., 36:33–39, 1993b.

Barnes, Robl, First, "Nuclear transplantation in mouse embryos: Assessment of nuclear function," Biol. Reprod., 36:1267–1272, 1987.

Bavister et al., "Development of preimplantation embryos of the golden hamster in a defined culture medium," Biol. Reprod., 28:237–242, 1993.

Behboodi et al., "Birth of large calves that developed from in vitro–derived bovine embryos," Theriogenology, 44:227, 1995.

Bondioli et al., "Prodution of identical bovine offspring by nuclear transfer," Theriogenology, 33:165, 1990.

Bondioli et al., "Production of transgenic cattle by pronuclear injection," In: Transgenic Animals, First and Haseltine (eds.), Butterwort–Heinnemann, MA, 265–273, 1991.

Bradley, A., Evans, M., Kaufman, M. H. and Robertson, E., "Formation of germline chimaeras from embryo–derived teratocarcinoma cell lines," Nature 309:255–256, 1984.

Brinster, Braun, Lo, Avarbock, Oran, Palmiter, Proc. Natl. Acad. Sci. USA, 86:7087–7091, 1989.

Campbell et al., "Improved development to blastocyst of bovine nuclear transfer embryos reconstructed during the presumptive S–phase of enucleated activated oocytes," Biol. Reprod., 50:1385–1390, 1994.

Campbell, McWhir, Ritchie, Wilmut, "Production of live lambs following nuclear transfer of cultured embryonic disc cells," Theriogenology 43:181 (Abstr.), 1995.

Campbell, McWhir, Ritchie, Wilmut, "Sheep cloned by nuclear transfer from a cultured cell line," Nature, 380:64, 1996.

Capel et al., "Establishment and characterization of condionally immortalized cells from the mouse urogenital ridge," J. Cell Sci., 109:899–909, 1996.

Cheong et al., "Birth of mice after transplantation of early cell–cycle stage embryonic nuclei into enucleated oocytes," Biol. Reprod., 48:958–965, 1993.

(List continued on next page.)

Primary Examiner—Jill D. Martin
(74) Attorney, Agent, or Firm—Williams, Morgan & Amerson

(57) ABSTRACT

Disclosed are methods for the isolation of primordial germ cells, culturing these cells to produce primordial germ cell–derived cell lines, methods for transforming both the primordial germ cells and the cultured cell lines, and using these transformed cells and cell lines to generate transgenic animals. The efficiency at which transgenic animals are generated by the present invention is greatly increased, thereby allowing the use of homologous recombination in producing transgenic non-rodent animal species.

69 Claims, 2 Drawing Sheets

OTHER PUBLICATIONS

Cherny and Merei, "Evidence for pluripotency of bovine primordial germ cell–derived cell lines maintained in long–term culture," *Theriogenology*, 41:175, 1994.

Cibelli et al., "Production of germline chimeric bovine fetuses from transgenic embryonic stem cells," *Theriogenology*, 46:241, 1997.

Clark, "Prospects for the genetic engineering of milk," *J. Cell. Biochem.*, 49:121, 1992.

Clark, Bessos, Bishop, Brown, Harris, Lathe, McClenaghan, Prowse, Simons, Whitelaw, Wilmut, "Expression of human antihemophilic factor IX in the milk of transgenic sheep," *Biotechnology*, 7:487–492, 1989.

Clements Wall, Narayan, Hauer, Schoborg, Sheffer, Powell, Carruth, Zink, Rexroad, "Development of transgenic sheep that express the visna virus envelope gene," *Virology*, 200:370–380, 1994.

Collas, P., Balise, J. J., Hofmann, G. A. and Robl, J. M., "Electrical activation of mouse oocytes," *Theriogenology* 32:835, 1989.

Conover, Ip, Poueymirou, Bates, Goldfarb, DeChiara, Yancopoulos, "Ciliary neurtrophic factor maintains the pluripotentiality of embryonic stem cells," *Development*, 119:559–565, 1993.

Crister et al., "Influences of cumulus cell association during in vitro maturation of bovine oocytes on embryo development," *Society for the Study of Reproduction.*, Supplement 1, vol. 34:192–198, Abstract #286, 1986.

Danoff et al., "Screening for homologous recombination in ES cells using RT–PCR," *BioTechniques*, 22(1):22–26, 1997.

Delhaise et al., "Nuclear transplantation using bovine primordial germ cells from male fetuses," *Reprod. Fertil. Dev.*, 7:1217–1219, 1995.

Doetschman, Williams, Maeda, "Establishment of hamster blastocyst–derived embryonic stem (ES) cells," *Dev. Biol.*, 127:224–227, 1988.

Doetschman et al., "Targeted correction of a mutant HPRT gene in mouse embryonic stem cells," *Nature*, 330:576–578, 1987.

Doetschman et al., "The in vitro development of blastocyst–derived embryonic stem cell lines: Formation of visceral yolk sac, blood islands and myocardium," *J. Embryol. Exp. Morph.*, 87:27–45, 1985.

Donavan, Stott, Cairns, Heasman, Wylie, "Migratory and postmigratory mouse primordial germ cells behave differently in culture," *Cell*, 44:831–838, 1986.

Evans, Notarianni, Laurie, Moor, "Derivation and preliminary characterization of pluripotent cell lines from porcine and bovine blastocysts," *Theriogenology*, 33:125–128, 1990.

Evans and Kaufman, "Pluripotential cells grow directly from normal mouse embryos," *Cancer Surveys*, 2:185–207, 1983.

Gerfen and Wheeler, "Isolation of embryonic cell–lines from porcine blastocysts," *Anim. Biotech.* 6:1–14, 1995.

Giles, Yang, Mark, Foote, "Pluripotency of cultured rabbit inner cell mass cells detected by isozyme analysis and eye pigmentation of fetuses following injections into blastocysts or morulae," *Mol. Reprod. Dev.* 36:130, 1993.

Gordon, Lee, Vitale, Smith, Westphal, Hennighausen, "Production of human tissue plasminogen activator in transgenic mouse milk," *Biotechnology*, 5:1183–1187, 1987.

Graves and Moreadith, "Derivation and characterization of putative pluripotent embryonic stem cells from preimplantation rabbit embryos," *Mol. Reprod. Dev.*, 36:424, 1993.

Handyside, Hooper, Kaufman Wilmut, "Towards the isolation of embryonal stem cell lines from the sheep," *Roux's Arch. Dev. Biol.*, 196:185–190, 1987.

Hasty et al., "The length of homology required for gene targeting in embryonic stem cells," *Mol. Cell. Biol.*, 11:4509–4517, 1991.

Hill et al., "Production of transgenic cattle by pronuclear injection," *Theriogenology*, 37:222, 1992.

Houdebine, "Production of pharmaceutical proteins from transgenic animals," *Journal of Biotechnology*, 34:269–287, 1994.

Keefer, Stice, Mathews "Bovine inner cell mass cells as donor nuclei in the production of nuclear transfer embryos and calves," *Biol. Reprod.*, 50:935–939, 1994.

Labosky, Barlow, Hogan, "Mouse embryonic germ (EG) cell lines: transmission through the germline and differences in the methylation imprint of insulin–like growth factor 2 receptor (lgf2r) gene compared with embryonic stem (ES) cell lines," *Development*, 120:3197–3204, 1994.

Lavoir et al., "Development of bovine nuclear transfer embryos made with oogonia," *Biol. Reprod.*, 56:194–199, 1997.

Lavoir et al., "Isolation and identification of germ cells from fetal bovine ovaries," *Molecular Reproduction and Development*, 37:413–424, 1994.

Leichthammer and Brem, "In vitro culture and cryopreservation of farm animals' primordial germ cells," *Theriogenology* 33:272, 1990.

Liu, Moor, Laurie, Notarianni., "Nuclear remodelling and early development in cryopreserved, porcine primordial germ cells following nuclear transfer into in vitro–matured oocytes," *Int. J. Dev. Biol.*, 39:639–644, 1995.

Lo, Pursel, Linton, Sandgren, Behringer, Rexroad, Palmitter, Brinster, "Expression of mouse IgA by transgenic mice, pigs and sheep," *Eur. J. Immunol.*, 21:1001–1006, 1991.

Macháty, Funahashi, Mayes, Day, Prather, "Effect of injecting calcium chloride into in vitro–matured porcine oocytes," *Biol. Reprod.*, 54:316–322, 1996.

Martin, "Isolation of a pluripotent cell line from early mouse embryos cultured in medium conditioned by teratocarcinoma stem cells," *Proc. Natl. Acad. Sci. USA*, 78:7634–7638, 1981.

Martin and Lock, "Pluripotent cell lines derived from early mouse embryos in medium conditioned by teratocarcinoma stem cells," In: *Teratocarcinoma Stem Cells*. Silver et al., (eds), Cold Spring Harbor Conference on Cell Proliferation, vol. 10, Cold Spring Harbor Laboratory, Cold Spring Harbor, NY. 635–646, 1983.

Matsui, Zsebo, Hogan., "Derivation of pluripotential embryonic stem cells from murine primordial germ cells in culture," *Cell*, 70:841–847, 1992.

Meade, Gates, Kacy, Lonberg, "Bovine $\alpha_{S1}$–casein gene sequences direct high level expression of active human urokinase in mouse milk," *Biotechnology*, 8:433–446, 1990.

Moens et al., "Assessment of nuclear totipotency of fetal bovine diploid germ cells by nuclear transfer," *Theriogenology*, 46:871–880, 1996.

Moore and Piedrahita, "Effects of heterologous hematopoietic cytokines on in vitro differentiation of cultured porcine inner cell masses," *Mol. Reprod. Dev.*, 45:139–144, 1996.

Moore and Piedrahita, "The effects of human leukemia inhibitory factor (HLIF) and culture medium on in vitro differentiation of cultured porcine inner cell mass (PICM)," *In vitro Cell Dev. Biol.—Animal*, 33:62–71, 1997.

Moreno and Westhusin, "A comparison of two systems for culture of bovine zygotesin vitro," *Biol. Reprod.*, 48(1):169, 1993.

Nagy et al., "Embryonic stem cells alone are able to support fetal development in the mouse," *Development*, 110:815–821, 1990.

Neimman, and Reichelt, "Manipulating early pig embryos," *J. Reprod. Fertil.*, 48:75–94, 1993.

Notarianni, Galli, Laurie, Moor, Evans, "Derivation of pluripotent, embryonic cell lines from pig and sheep," *J. Reprod. Fertil.* 43 (suppl.):255, 1991.

Notarianni, Laurie, Moor, Evans, "Maintenance and differentiation in culture of pluripotential embryonic cell lines from pig blastocysts," *J. Reprod. Fertil.* 41 (Suppl.):51–56, 1990.

Onishi et al., "Production of chimeric pigs and the analysis of chimerism using mitochondrial deoxyribonucleic acid as a cell marker," *Biol. Reprod.*, 51:1069–1075, 1994.

Pesce and de Felici, "Apoptosis in mouse primordial germ cells: a study by transmission and scanning electron microscope," *Anat. Embryol*, 189:435–440, 1994.

Pease and Williams, "Formation of Germ–line Chimeras from Embryonic Stem Cells maintained with Recombinant Leukemia Inhibitory Factor," *Experimental Cell Research*, 190:209–211, 1990.

Pease, Braghetta, Gearing, Grail, Williams, "Isolation of embryoinc stem (ES) cells in media supplemented with recombinant leukemia inhibitory factor (LIF)," *Dev. Biol.*, 141:344–52, 1990.

Pesce et al., "Stem Cell Factor and Leukemia Inhibitory Factor Promote Primordial Germ Cell Survival By Suppressing Programmed Cell Death (Apoptosis)," *Development*, 118:1089–1094, 1993.

Petters and Wells, "Culture of pig embryos," *J. Reprod. Fert. Suppl.*, 48:61–73, 1993.

Piedrahita JA, Zhang SH, Hagaman JR, Clark PM, and Maeda N., "Generation of mice carrying a mutant apolipoprotein E gene inactivated by gene targeting in mouse embryonic stem cells," *Proc. Natl. Acad. Sci. USA*, 89:4471–4475, 1992.

Piedrahita, Weaks, Petrescu, Derr, Shrode, Womack JE, "Genetic characterization of the bovine leukemia inhibitory factor: Cloning and sequencing, chromosome assignment, and microsatellite analysis," *Animal Genetics*, 28:14–20, 1997.

Piedrahita, Anderson, BonDurant, "Influence of feeder layer type on the efficiency of isolation of porcine embryo–derived cell lines," *Theriogenology*, 34(5):865–877, 1990.

Piedrahita, Anderson, BonDurant, "On the isolation of embryonic stem (ES) cells: Comparative behavior of murine, porcine, and ovine embryos," *Theriogenology*, 34:879–901, 1990.

Plump, Smith, Hayek, Aalto–Setala, Walsh, Verstuyft, Rubin, Breslow, "Severe hypercholesterolemia and atherosclerosis in apolipoprotein E–deficient mice created by homologous recombination in ES cells," *Cell*, 71:343–353, 1992.

Prather, R. S. and First, N. L., "Cloning of embryos," *J. Reprod. Fertil.*, 40 (suppl):227, 1990.

Prather, R. S., Barnes, F. L., Sims, M. M., Robl, J. M., Eyestone, W. H. and First, N. L., "Nuclear transplantation in the bovine embryo: Assessment of donor nuclei and recipient oocyte stage," *Biol. Reprod.*, 37:859–368, 1987.

Prather, R. S., Sims and First, N. L., "Nuclear transplantation in pig embryos," *Biol. Reprod.*, 41:414–418, 1989.

Pursel et al., "Genetic engineering of livestock," *Science*, 244:1281–1288, 1989.

Pursel and Rexroad Jr., "Status of research with transgenic farm animals," *J. Anim. Sci.*, 71 Suppl. 3:10–19, 1993.

Robl, Gilligan, Critser, First, "Nuclear transplantation in mouse embryos: Assessment of recipient cell stage," *Biol. Reprod.*, 43:733–738, 1986.

Robl and Stice, "Prospects for the commercial cloning of animals by nuclear transplantation," *Theriogenology*, 31:75–81, 1989.

Saito, Streichenko, Niemann, "Bovine embryonic stem cell–like cell lines cultured over several passages," *Roux's Arch. Dev. Biol.*, 201:134–141, 1992.

Shim Gutiérrez–Adán, Chen, BonDurant, Anderson, "Isolation of pluripotent stem cells from cultured porcine primordial germ cells," *Theriogenology*, 46:245, 1997.

Shim and Anderson, "Putative Porcine Embryonic Germ Cells maintained in Long–term Culture," *Society for the Study of Reproduction, Biology of Reproduction*, 28th Annual Meeting, University of California, vol. 52/Supplement 1:317–320, Abstract 320, Jul. 9–12, 1995.

Sims and First, "Production of calves by transfer of nuclei from cultured inner cell mass cells," *Proc. Natl. Acad. Sci. USA*, 91:6143–6147, 1994.

Smith and Hooper, "Buffalo rat liver cells produce a diffusible activity which inhibits the differentiation of murine embryonal carcinoma and embryonic stem cells," *Dev. Biol.*, 121:1–9, 1987.

Smith and Wilmut, "Influence of nuclear and cytoplasmic activity on the development in vivo of sheep embryos after nuclear transfer," *Biol. Reprod.*, 40:1027–1032, 1989.

Smith, Heath, Donaldson, Wong, Moreau, Stahl, Rogers, "Inhibition of pluripotential embryonic stem cell differentiation by purified polypeptides," *Nature*, 336:688–690, 1988a.

Smithies, "Altering genes in animals and humans," In: *Etiology of Human Disease at the DNA Level*, J. Lindsten and U. Pettersson, eds, Nobel Symposium 80, Raven Press, NY., 221–231, 1991.

Smithies, Gregg, Boggs, Koralewski, Kucherlapati, "Insertion of DNA sequences into the human chromosomal beta–globin locus by homologous recombination," *Nature*, 317:230–234, 1985.

Stewart, Vanek, Wagner, "Expression of foreign genes from retroviral vectors in mouse teratocarcinoma chimeras," *EMBO J.*, 4:3701–3709, 1985.

Stewart, Gadi, Blatt, "Stem cells from primordial germ cells can reenter the germline," *Dev. Biol.*, 161:626–628, 1994.

Stice and Strelchenko, "Domestic animal embryonic stem cells: Progress toward germ–line contribution," In: *Biotechnology's Role in the Genetic Improvement of Farm Animals*, Miller, Pursel, Norman, eds., Beltsville Symposia in Agricultural Research XX, Beltsville, MD., 189–201, 1995.

Stice and Robl, "Nuclear reprogramming in nuclear transplant rabbit embryos," *Biol. Reprod.*, 39:657–668, 1988.

Stice, Strelchenko, Keefer, Matthews, "Pluripotent bovine embryonic cell lines direct embryonic development following nuclear transfer," *Biol. Reprod.*, 54:100–110, 1996.

Stokes et al., "Production of chimaeric bovine embryos," *Theriogenology*, 41:303–309, 1994.

Strelchenko, "Bovine pluripotent stem cells," *Theriogenology*, 45:131–140, 1996.

Strojek, Reed, Hoover, Wagner, "A method for cultivating morphologically undifferentiated embryonic stem cells from porcine blastocysts," *Theriogenology*, 33:901, 1990.

Sukoyan, Vatolin, Golubista, Zhelezova, Seminova, Serov, "Embryonic stem cells derived from morulae, inner cell mass, and blastocyst of mink: Comparisons of their pluripotencies," *Mol. Reprod. Dev.*, 36:148, 1993.

Sukoyan, Golubista, Zhelezova, Shilov, Vatolin, Maximovsky, Andreeva, McWhir, Pack, Bayborodin, Kerkis, Kizilova, Serov, "Isolation and cultivation of blastocyst–derived stem cell lines from American mink (Mustela vision)," *Mol. Reprod. Dev.*, 33:418, 1992.

Talbot, Rexroad, Pursel, Powell et al., "Alkaline phosphatase staining of pig and sheep epiblast cells in culture," *Mol. Reprod. Dev.*, 36:139–147, 1993b.

Talbot, Rexroad, Pursel, Powell, Nel, "Culturing the epiblast cells of the pig blastocyst," *In vitro Cell. Dev. Biol.*, 29A:543–550, 1993a.

Thomson et al., "Isolation of a primate embryonic stem cell line," *Proc. Natl. Acad. Sci. USA*, 92:7844–7848, 1995.

Tilly, J. L. and Tilly, K. I., "Inhibitors of oxidative stress mimic the ability of follicle–stimulating hormone to suppress apoptosis in cultured rat ovarian follicles," *Endocrinology* 136:242–252, 1995.

Ueda, Jishage, Kamada, Uchida, Suzuki, "Production of mice entirely derived from embryonic stem (ES) cell with many passages by coculture of ES cells with cytochalasin B induced tetraploid embryos," *Experimental Animals*, 44(3):205–210, 1995.

Van Stekelenburg–Hamers, Van Achterberg, Rebel, Flechon, Campbell, Weima, Mummery, "Isolation and characterization of permanent cell lines from inner cell mass cells of bovine blastocyst," *Mol. Reprod. Dev.*, 40:444–454, 1995.

Wall, "Modification of milk composition in transgenic animals," In: *Biotechnology's Role in the Genetic Improvement of Farm Animals*, Miller et al. (eds.), Beltsville Symposia in Agricultural Research, Beltsville, MD. 165–188, 1995.

Wall, "Transgenic livestock: Progress and prospects for the future," *Theriogenology*, 45:57–68, 1996.

Watanabe, M., Shirayoshi, Y., Koshimizu, U., Hashimoto, S., Yonehara, S., Eguchi, Y., Tsujimoto, Y. and Nakatsuji, N., "Gene transfection of mouse prmordial germ cells in vitro and analysis of their survival and growth control," *Exp. Cell Res.* 230:76–83, 1997.

Weidle, Lenz, Brem, "Genes encoding a mouse monoclonal antibody are expressed in transgenic mice, rabbits and pigs," *Gene*, 98:185–191, 1991.

Wheeler, "Development and validation of swine embryonic stem cells—A review," *Reprod. Fertil. Dev.*, 6:563–570, 1994.

Wheeler et al., "Production of Chimeric Swine from Embryonic Stem (ES) Cells," *Society for the Study of Reproduction, Biology of Reproduction*, 28th Annual Meeting, University of California, vol. 52/Supplement 1:317–320, Abstract 319, Jul. 9–12, 1995.

Willadsen, "Cloning of sheep and cow embryos," *Genome*, 31:956, 1989.

Willadsen, S. M., "Nuclear transplantation in sheep embryos," *Nature* 320:63, 1986.

Willams, Hilton, Pease, Wilson, Steward, Gearing, Wagner, Metcalf, Nicola, Gough, "Myeloid leukemia inhibitory factor maintains the developmental potential of embryonic stem cells," *Nature*, 336:684–687, 1988.

Wilmut, Schuleke, McWhir, Kind, Campbell, "Viable offspring derived from fetal and adult mammalian cells," *Nature*, 385:810–813, 1997.

Wobus, Holzhausen, Jakel, Schoneich, "Characterization of a pluripotent stem cell line derived from a mouse embryo," *Exp. Cell Res.*, 152:212–219, 1984.

Yoshida, Chambers, Nichols, Smith, Mikiyoshi, Yasukawa, Shoyab, Taga, Kishimoto, "Maintenance of the pluripotential phenotype of embryonic stem cells through direct activation of gp130 signalling pathways," *Mechanisms of Development*, 45:163–171, 1994.

International Search Report dated Mar. 20, 1998 (PCT/US97/18644) (TAMK:177P).

Stice, Strelchenko, Betthauser, Scott, Jugella, Jackson, David, Keefer, Matthews, "Bovine pluripotent embryonic cells contribute to nuclear transfer and chimeric fetuses," *Theriogenology*, 41:301 (Abstr.), 1994.

van Deursen and Wieringa, "Targeting of the creatine kinase M gene in embryonic stem cells using isogenic and nonisogenic vectors," *Nucl. Acid Res.*, 20:3815–3820, 1992.

Walker et al., "The production of unusually large offspring following embryo manipulation: Concepts and challenges," *Theriogenology*, 45(1):111, 1996.

* cited by examiner

CELLS AND METHODS FOR THE GENERATION OF TRANSGENIC PIGS

The present application claims the priority of co-pending U.S. Provisional Patent Application Ser. No. 60/027,338, filed Oct. 11, 1996, and Ser. No. 60/046,094, filed May 9, 1997, the entire disclosures of which are incorporated herein by reference without disclaimer.

The U.S. government owns rights in the present invention pursuant to grant number HL 51587 from the National Institutes of Health.

BACKGROUND OF THE INVENTION

1. Field of the Invention

The present invention relates generally to the field of transgenic animals. More particularly, it concerns methods for generating primordial germ cell-derived cell lines, transforming primordial germ cells and primordial germ cell-derived cell lines, and using these transformed cells and cell lines to generate transgenic non-rodent animal species.

2. Description of Related Art

Animals having certain desired traits or characteristics, such as increased weight gain, feed efficiency, carcass composition, milk production or content and disease resistance have long been desired. Traditional breeding processes are capable of producing animals with some desired traits, but these are often accompanied by a number of undesired characteristics, and is an extremely costly and time consuming process.

The development of transgenic animal technology holds great promise for the production of animals having specific, desired traits. Transgenic animals are animals that carry a gene that has been deliberately introduced into somatic and germline cells at an early stage of development. Although transgenic animals have been produced by various methods in several different species, methods to readily and reproducibly produce transgenic large mammals at reasonable costs are still lacking.

At present the only techniques available for the generation of transgenic domestic animals are by pronuclear injection or use of viral vectors. In both cases the incoming DNA inserts at random, which can cause a variety of problems. The first of these problems is insertional inactivation, which is inactivation of an essential gene due to disruption of the coding or regulatory sequences by the incoming DNA. Another problem is that the transgene may either be not incorporated at all, or incorporated but not expressed. A further problem is the possibility of inaccurate regulation due to positional effects. This refers to the variability in the level of gene expression and the accuracy of gene regulation between different founder animals produced with the same transgenic constructs. Thus, it is not uncommon to generate 10 founder animals and identify only one that expresses the transgene in a manner that warrants the maintenance of the transgenic line.

Additionally, using the present technology, it is not possible to fully inactivate or remove genes in transgenic animals, only add new genes. As a result it is not possible to delete genes involved in undesired cellular processes, or to undertake any genetic modification that entails changes in existing genes. Moreover, the efficiency of generating transgenic domestic animals is low, with efficiencies of 1 in 100 offspring generated being transgenic not uncommon (Wall, 1996). As a result the cost associated with generation of transgenic animals can be as much as 250–500 thousand dollars per expressing animal (Wall, 1996).

These drawbacks are overcome by the utilization of homologous recombination (Koller and Smithies, 1992), which directs the insertion of the transgene to a specific location. This technique allows the precise modification of existing genes, and overcomes the problems of positional effects and insertional inactivation. Additionally, it allows the inactivation of specific genes as well as the replacement of one gene for another. Unfortunately the efficiency of the procedure is so low that it cannot be utilized directly on embryos but must make use of a carrier cell line. The availability of appropriate cell lines will allow the precise manipulation of the genomic material followed by the generation of a living animal carrying those changes.

Embryonic stem (ES) cells, isolated from the inner cell mass (ICM) of the preimplantation embryo, possess the ability to proliferate indefinitely in an undifferentiated state, and are capable of contributing to the formation of normal tissues and organs of a chimeric individual when injected into a host embryo. The ES cell line allows manipulation and selection in vitro, followed by the generation of a transgenic animal carrying those changes. The ability to colonize the germ line following culture and genetic manipulation have made ES cells a powerful tool for the modification of the genome in the mouse species. Chimeras produced between genetically modified ES cells and normal embryos have been used to study in vivo gene regulation (Stewart et al., 1985), as well as germ-line transmission of introduced genes (Smithies 1991). In addition, ES cells have been used to study targeted modification of genes by homologous recombination (Smithies 1991).

The use of chimeras has been shown to be effective in producing transgenic mice. About 70% of expanded mouse blastocysts develop into live young with about 50% of the young born being chimeric (Bradley et al., 1984). Twenty percent of these chimeric young have germ cell chimerism. Utilizing this method it is possible that chimerism in the germ line may be 20–30%. However, the ES-cell method has not been successfully applied to production of larger transgenic mammals, for example, transgenic pigs, cattle, goats or sheep. A reason for the failure to extrapolate methods from mice to larger mammals may be the difference in developmental stages of the species (Wheeler, 1996).

Recently, it has been reported that murine cell lines derived from primordial germ cells (PGC) behave similarly to ES cells and are capable of contributing to the germ line (Labosky et al., 1994). These cells, referred to as embryonic germ (EG) cells or PGC-derived cells (Labosky et al., 1994; Strelchenko, 1996), are indistinguishable from ES cells in terms of markers of the undifferentiated state as well as their ability to colonize the germ line following injection into host blastocysts (Labosky et al., 1994; Stewart et al., 1994). Thus, even though the starting tissue source or cellular phenotype differ from the ICM-derived cell lines, once established they have similar, if not identical, properties.

Although the majority of the research on ES and primordial germ cells has been done in the mouse, attempts at developing this technology in other mammalian species have been reported. Embryonic cell lines have been described from hamster (Doetschman et al. 1988), mink (Sukoyan et al., 1992, 1993), rabbit (Graves and Moreadith, 1993; Giles et al., 1993), pig (Piedrahita et al., 1990; Strojek et al., 1990; Notarianni et al., 1990; Talbot et al., 1993; Wheeler, 1994; Gerfen and Wheeler, 1995; Shim and Anderson, 1995), sheep (Handyside et al., 1987; Piedrahita et al., 1990; Notarianni et al., 1991; Campbell et al., 1995) and cattle (Saito et al., 1992; Sims and First, 1993; Stice et al., 1994; Strelchenko, 1996; Stice and Strelchenko, 1996).

Although each of these cell lines have some of the characteristics of the ES cells described from mice, germ line transmission, a prerequisite for generation of a transgenic line of animals, has not been demonstrated.

Another problem associated with the generation of transgenic animals is the difficulty with transformation of ES or EG cells with DNA carrying a desired trait or traits. These difficulties are related to the inability of the cells to remain unchanged (undifferentiated) upon repeated passage. This is in contrast with mouse ES cells, which can be passaged multiple times without major changes in the potential to generate a transgenic animal. To date there have been no reports on the generation of undifferentiated transformed transgenic cell lines of embryo-derived or PGC-derived cell lines in any non-rodent domestic animal species.

A genetically transformed ES or PGC-derived cell line capable of taking part in chimera formation, or nuclear transfer development in enucleated oocytes, would be of great value for the medical, veterinary, and agricultural community. In the medical and veterinary field it would allow the generation of biopharmaceuticals and oral immunogens in the milk, the generation of animals that can be used as human tissue donors, the development of animal models of human disease that can speed the development of alternative therapeutic methods including gene therapy, and the development of blood substitutes. In the veterinary field it would allow the generation of animals that are naturally immune to particular diseases. In the agricultural field it will allow the modification of the milk composition to increase shelf life, cheese yield, and permit lactose intolerant individuals to safely consume the modified milk. It will also allow the introduction of small genetic changes that can modify disease resistance, growth rate and carcass composition, wool composition, and nutritional efficiency, among others. Unfortunately, to date, there has been no description of transformed non-rodent ES or PGC-derived cell lines.

SUMMARY OF THE INVENTION

The present invention overcomes the problems in generating non-rodent transgenic animals described in the art by providing methods for the isolation of primordial germ cells, culturing these cells to produce primordial germ cell-derived cell lines, methods for transforming both the primordial germ cells and the cultured cell lines, and using these transformed cells and cell lines to generate transgenic animals. The efficiency at which transgenic animals are generated by the present invention is greatly increased, thereby allowing the use of homologous recombination in producing transgenic non-rodent animal species.

Accordingly, the present invention provides a method of growing primordial germ cells from a non-rodent animal species comprising plating the primordial germ cells on feeder cells, the feeder cells at a density of between about $1.5 \times 10^5$ cells/cm$^2$ and about $10^6$ cells/cm$^2$, in a culture medium comprising an effective amount of basic fibroblast growth factor. In certain aspects, the method may comprise plating the primordial germ cells on feeder cells, the feeder cells at a density of between about $1.5 \times 10^5$ cells/cm and about 10 cells/cm$^2$, in a culture medium comprising an effective amount of basic fibroblast growth factor, for an amount of time sufficient to obtain an undifferentiated primordial germ cell colony.

In an alternative aspect, the invention provides a method of growing primordial germ cells from a non-rodent animal species, comprising plating a composition comprising primordial germ cells from an embryo of said non-rodent animal species on STO feeder cells, said STO feeder cells at a density of between about $1.5 \times 10^5$ cells/cm$^2$ and about $10^6$ cells/cm$^2$, in a culture medium comprising an effective amount of basic fibroblast growth factor.

In yet another aspect, the invention provides a method of growing primordial germ cells from a non-rodent animal species, comprising plating a composition comprising primordial germ cells from an embryo of said non-rodent animal species on feeder cells, said feeder cells at a density of between about $1.5 \times 10^5$ cells/cm$^2$ and about $10^6$ cells/cm$^2$, in a culture medium comprising an effective amount of basic fibroblast growth factor, said culture medium including no exogenously added soluble stem cell factor.

In a further aspect, the invention provides a method of growing primordial germ cells from a non-rodent animal species, comprising plating a composition comprising primordial germ cells from an embryo of said non-rodent animal species on feeder cells, said feeder cells at a density of between about $1.5 \times 10^5$ cells/cm$^2$ and about $10^6$ cells/cm$^2$, in a culture medium comprising an effective amount of basic fibroblast growth factor, said culture medium including no exogenously added leukemia inhibitory factor.

In a further aspect, the invention provides a method of growing primordial germ cells from a non-rodent animal species, comprising plating a composition comprising primordial germ cells from an embryo of said non-rodent animal species on feeder cells, said feeder cells at a density of between about $1.5 \times 10^5$ cells/cm$^2$ and about $10^6$ cells/cm$^2$, in a culture medium comprising an effective amount of basic fibroblast growth factor, said culture medium including no exogenously added soluble stem cell factor or leukemia inhibitory factor.

Additionally, the invention provides a method of growing primordial germ cells from a non-rodent animal species, comprising plating a composition comprising primordial germ cells from an embryo of said non-rodent animal species on feeder cells other than S1/S1$^4$ or S1-m220, said feeder cells at a density of between about $1.5 \times 10^5$ cells/cm$^2$ and about $10^6$ cells/cm$^2$, in a culture medium comprising an effective amount of basic fibroblast growth factor.

The invention also provides a method of growing primordial germ cells from a non-rodent animal species, comprising plating a composition comprising primordial germ cells from an embryo of said non-rodent animal species on feeder cells other than S1/S14 or S1-m220, said feeder cells at a density of between about $1.5 \times 10^5$ cells/cm$^2$ and about $10^6$ cells/cm$^2$, in a culture medium comprising an effective amount of basic fibroblast growth factor, said culture medium including no exogenously added soluble stem cell factor or leukemia inhibitory factor.

In certain preferred embodiments, the composition comprising the primordial germ cells is isolated from an embryo of the non-rodent animal species by the steps of collecting an embryo of a non-rodent animal species, removing the genital ridge from the embryo, incubating the genital ridge in a biologically acceptable solution, disrupting the genital ridge thereby releasing the primordial germ cells, and collecting the primordial germ cells to provide the composition comprising the primordial germ cells. In certain embodiments, the primordial germ cells are collected by centriftigation.

In particular aspects of the present invention, the primordial germ cells comprise at least a first exogenous DNA segment. Primordial germ cells comprising exogenous DNA are referred to as genetically transformed primordial germ cells. In further embodiments, the primordial germ cells are provided with an exogenous, selected DNA segment by electroporation, particle bombardment or calcium phosphate precipitation. In certain aspects of the invention the composition comprising primordial germ cells is provided with a selected DNA segment and the primordial germ cells that contain the selected DNA segment are selected and optionally separated away from the primordial germ cells of the composition that do not contain the selected DNA segment.

The density of the feeder cells is critical to the success of a number of the methods described herein. Within the range of densities of between about $1.5 \times 10^5$ cells/cm$^2$ and about $10^6$ cells/cm$^2$, the actual density may vary, depending on the particular application. Therefore, in certain aspects of the present invention, the density of the feeder cells may be between about $1.5 \times 10^5$ cells/cm$^2$ and about $5 \times 10^5$ cells/cm$^2$, between about $1.5 \times 10^5$ cells/cm$^2$ and about $10^6$ cells/cm$^2$, between about $2 \times 10^5$ cells/cm$^2$ and about $9 \times 10^5$ cells/cm$^2$, between about $3 \times 10^5$ cells/cm$^2$ and about $8 \times 10^5$ cells/cm$^2$, between about $2 \times 10^5$ cells/cm$^2$ and about $5 \times 10^5$ cells/cm$^2$, between about $4 \times 10^5$ cells/cm$^2$ and about $7 \times 10^5$ cells/cm$^2$, between about $2.5 \times 10^5$ cells/cm$^2$ and about $7.5 \times 10^5$ cells/cm$^2$, between about $5 \times 10^5$ cells/cm$^2$ and about $8 \times 10^5$ cells/cm$^2$, between about $1.5 \times 10^5$ cells/cm$^2$ and about $3 \times 10^5$ cells/cm$^2$, between about $5 \times 10^5$ cells/cm$^2$ and about $6 \times 10^5$ cells/cm$^2$, between about $4 \times 10^5$ cells/cm$^2$ and about $6.5 \times 10^5$ cells/cm$^2$, between about $5 \times 10^5$ cells/cm$^2$ and about $1 \times 10^6$ cells/cm$^2$, between about $8 \times 10^5$ cells/cm$^2$ and about $9 \times 10^5$ cells/cm$^2$, between about $2.5 \times 10^5$ cells/cm$^2$ and about $5 \times 10^5$ cells/cm$^2$, or any combination of densities within the range.

Thus for a particular embodiment, the density of the stock of feeder cells may be about $1.5 \times 10^5$ cells/cm$^2$, $2 \times 10^5$ cells/cm$^2$, $2.5 \times 10^5$ cells/cm$^2$, $3 \times 10^5$ cells/cm$^2$, $4 \times 10^5$ cells/cm$^2$, $5 \times 10^5$ cells/cm$^2$, $6 \times 10^5$ cells/cm$^2$, $7 \times 10^5$ cells/cm$^2$, $7.5 \times 10^5$ cells/cm$^2$, $8 \times 10^5$ cells/cm$^2$ $9 \times 10^5$ cells/cm$^2$, or $1 \times 10^6$ cells/cm$^2$. Another way of expressing the density of the feeder cells is by calculating the number of feeder cells used per 35 mm well. Thus, densities of feeder cells of between about 1 million and about 9 million or so per 35 mm well are preferred for use in the present invention. Thus the density of feeder cells may be about 1 million, about 1.5 million, about 2 million, about 3 million, about 4 million, about 5 million, about 6 million, about 7 million, about 7.5 million, about 8 million, about 8.5 million or about 9 million per 35 mm well, with about 3 million or so per 35 mm well being particularly preferred in certain aspects.

The isolated composition comprising the primordial germ cells is grown on a layer of feeder cells. The feeder cells provide a microenvironment conducive to the growth of the primordial germ cells. The feeder cells provide growth factors to the growing primordial germ cells, as well as providing an extracellular matrix. In certain aspects of the present invention, the feeder cell lines may be engineered to express selected growth factors. Thus in certain embodiments of the present invention, the feeder cells may comprise at least a first exogenous DNA sequence. Exemplary types of feeder cells preferred for use in the present invention are embryonic cell lines such as embryonic fibroblasts from selected animal species, such as murine, porcine or bovine. In certain aspects of the present invention, the feeder cells may be murine S1/S1$^4$ cells. In other embodiments, the feeder cells may be STO cells (mouse embryonic fibroblast cells), while in other particular aspects, the feeder cells may be S1$^4$-m220 cells. Mixed cultures of cells are also contemplated for use as feeder cells in certain aspects of the invention. Thus, in further aspects of the present invention, the feeder cells comprise at least a first cell type and at least a second distinct cell type. In certain aspects, the feeder cells are a mixture of STO and porcine embryonic fibroblasts.

The feeder cells are inactivated prior to use, preferably by X-irradiation or using mitomycin C. In preferred embodiments of the present invention, the feeder cells are inactivated with cobalt radiation or cesium radiation.

The present invention also provides for culturing the isolated primordial germ cells in an appropriate medium. As discussed above, the feeder cells provide growth factors to the growing primordial germ cells, however, the amount of endogenous growth factors provided may vary from preparation to preparation of feeder cells. Therefore, in certain aspects of the invention exogenously added growth factors may be added to supplement the endogenous supply.

A growth factor that is critical for growth of the primordial germ cells of the present invention is basic fibroblast growth factor. As is the case with each of the growth factors described herein, basic fibroblast growth factor can be utilized from a variety of mammalian sources, including, but not limited to, porcine, bovine, ovine, caprine, equine, murine or human. In particular aspects human basic fibroblast growth factor is preferred. In certain aspects the growth factors, such as basic fibroblast growth factor, is from the same species as the primordial germ cells, or in other aspects from a different species as the primordial germ cells.

In preferred embodiments, the culture medium may comprise human basic fibroblast growth factor at a concentration of between about 5 ng/ml and about 100 μg/ml. In more preferred embodiments, the medium comprises human basic fibroblast growth factor at a concentration of about 40 ng/ml. However, it will be understood that the range of concentrations may be between about 5 ng/ml and about 10 μg/ml, or between about 10 ng/ml and about 100 μg/ml. Equally, the range can be between about 10 ng/ml and about 50 μg/ml, between about 10 ng/ml and about 1 μg/ml or between about 20 ng/ml and about 250 ng/ml.

It is also understood that about 5 ng/ml includes about 6 ng/ml, about 7 ng/ml, about 8 ng/ml and the like, while about 100 μg/ml includes about 99 μg/ml, about 98 μg/ml, about 97 μg/ml and the like. Additionally, the values at the lower end of the range can be lower than the value provided, for example about 4 ng/ml, about 3 ng/ml and still be within the scope of the present invention. Similarly, the upper end of the range includes values such as about 101 μg/ml, about 102 μg/ml within the scope of the present invention. Optimization of the concentration of these or any other of the media components described below can be performed by those of skill in the art without undue experimentation, by testing different concentrations and measuring the effect on growth of primordial germ cell-derived colonies.

In certain aspects of the invention, other members of the fibroblast growth factor family may be used in addition to basic fibroblast growth factor. These members include, but are not limited to, FGF-1 (acidic fibroblast growth factor), FGF-3 (int-2), FGF-4 (hst/K-FGF), FGF-5, FGF-6, and FGF-7.

Other growth factors may be added to the medium in an amount effective to improve the growth characteristics of the primordial germ cells, or to help maintain the primordial germ cells in an undifferentiated state. Thus, in particular embodiments, the culture medium may also comprise an effective amount of leukemia inhibitory factor. In certain aspects, the culture medium comprises leukemia inhibitory factor at a concentration of between about 5 ng/ml and about 100 μg/ml. In more preferred embodiments, the culture medium comprises leukemia inhibitory factor at a concentration of between about 10 ng/ml and about 10 µg/ml. In more preferred embodiments, the culture medium comprises leukemia inhibitory factor at a concentration of between about 15 ng/ml and about 1 µg/ml. In especially preferred embodiments, the culture medium comprises leukemia inhibitory factor at a concentration of about 20 ng/ml. However, it will be understood that the range of concentrations may be between about 5 ng/ml and about 10 µg/ml, or between about 10 ng/ml and about 100 µg/ml. Equally, the range can be between about 10 ng/ml and about 50 µg/ml, between about 10 ng/ml and about 1 µg/ml or between about 20 ng/ml and about 250 ng/ml.

It is also understood that about 5 ng/ml includes about 6 ng/ml, about 7 ng/ml, about 8 ng/ml and the like, while about 100 µg/ml includes about 99 µg/ml, about 98 µg/ml, about 97 µg/ml and the like. Additionally, the values at the lower end of the range can be lower than the value provided, for example about 4 ng/ml or about 3 ng/ml and still be within the scope of the present invention. Similarly, the upper end of the range includes values such as about 101 µg/ml or about 102 µg/ml within the scope of the present invention.

In other embodiments, the culture medium may also comprise an effective amount of uteroferrin. In certain embodiments, the culture medium comprises uteroferrin at a concentration of between about 1 ng/ml and about 100 µg/ml. In certain embodiments, the culture medium comprises uteroferrin at a concentration of between about 10 ng/ml and about 5 µg/ml or between about 20 ng/ml and about 500 ng/ml. In certain aspects of the present invention, the culture medium comprises uteroferrin at a concentration of about 40 ng/ml. In additional embodiments, the culture medium may also comprise an effective amount of soluble stem cell factor. In particular aspects, the culture medium comprises soluble stem cell factor at a concentration of between about 1 ng/ml and about 100 µg/ml. In other embodiments, the culture medium comprises soluble stem cell factor at a concentration of between about 10 ng/ml and about 5 µg/ml. In still more preferred embodiments, the culture medium comprises soluble stem cell factor at a concentration of between about 20 ng/ml and about 250 ng/ml. In exemplary embodiments, the culture medium comprises soluble stem cell factor at a concentration of about 40 ng/ml. However, it will be understood that the range of concentrations of these factors can be between about 1 ng/ml and about 10 µg/ml, or between about 10 ng/ml and about 100 µg/ml. Equally, the range can be between about 10 ng/ml and about 50 µg/ml, between about 10 ng/ml and about 1 µg/ml or between about 20 ng/ml and about 250 ng/ml.

It will be understood by those of skill in the art that about 1 ng/ml includes about 2 ng/ml, about 3 ng/ml, about 4 ng/ml and the like, while about 100 µg/ml includes about 99 µg/ml, about 98 µg/ml, about 97 µg/ml and the like. Additionally, the values at the lower end of the range can be lower than the value provided, for example about 0.8 ng/ml, about 0.5 ng/ml and still be within the scope of the present invention. Similarly, the upper end of the range includes values such as about 101 µg/ml, about 102 µg/ml within the scope of the present invention.

In further embodiments, the culture medium may also comprise an effective amount of α2-macroglobulin. In particular aspects, the culture medium comprises α2-macroglobulin at a concentration of between about 10 ng/ml and about 10 µg/ml. In other embodiments, the culture medium comprises soluble stem cell factor at a concentration of between about 50 ng/ml and about 5 µg/ml. In still more preferred embodiments, the culture medium comprises soluble stem cell factor at a concentration of between about 100 ng/ml and about 2.5 µg/ml. In exemplary embodiments, the culture medium comprises soluble stem cell factor at a concentration of about 1 µg/ml. However, it will be understood that the range of concentrations of these factors can be between about 10 ng/ml and about 2.5 µg/ml, or between about 100 ng/ml and about 10 µg/ml. Equally, the range can be between about 100 ng/ml and about 5 µg/ml, between about 250 ng/ml and about 2.5 µg/ml or between about 500 ng/ml and about 1 µg/ml.

It will be understood by those of skill in the art that about 10 ng/ml includes about 11 ng/ml, about 12 ng/ml, about 13 ng/ml, about 14 ng/ml and the like, while about 10 µg/ml includes about 9 µg/ml, about 8 µg/ml, about 7 µg/ml and the like. Additionally, the values at the lower end of the range can be lower than the value provided, for example about 8 ng/ml, about 5 ng/ml and still be within the scope of the present invention. Similarly, the upper end of the range includes values such as about 11 µg/ml or about 12 µg/ml within the scope of the present invention.

The present invention provides certain embodiments wherein the culture medium may also comprise an effective amount amino acids non-essential to the particular non-rodent animal. In further embodiments, the culture medium comprises amino acids non-essential to the particular non-rodent animal at a concentration of between about 10 nM and about 250 nM. In additional aspects, the culture medium comprises amino acids non-essential to the particular non-rodent animal at a concentration of between about 50 nM and about 150 nM. In still other embodiments, the culture medium comprises amino acids non-essential to the particular non-rodent animal at a concentration of about 100 nM. However, it will be understood that the range of concentrations can be between about 10 nM and about 100 nM, or between about 20 nM and about 250 nM. Equally, the range can be between about 20 nM and about 150 nM, between about 50 nM and about 125 nM or between about 75 nM and about 110 nM.

It is also understood that about 10 nM includes about 11 nM, about 12 nM, about 13 nM and the like, while about 250 nM includes about 249 nM, about 248 nM, about 247 nM and the like. Additionally, the values at the lower end of the range can be lower than the value provided, for example about 9 nM, about 8 nM and still be within the scope of the present invention. Similarly, the upper end of the range includes values such as about 251 nM or about 252 nM that fall within the scope of the present invention.

In preferred embodiments of the present invention, the culture medium may also comprise an effective amount of L-glutamine. In particular aspects, the culture medium comprises L-glutamine at a concentration of between about 0.1 mM and about 50 mM. In more preferred embodiments, the culture medium comprises L-glutamine at a concentration of between about 1 mM and about 20 mM. In still more preferred embodiments, the culture medium comprises L-glutamine at a concentration of about 2 mM. However, it will be understood that the range of concentrations can be between about 0.1 mM and about 10 mM, or between about 0.5 mM and about 50 mM. Equally, the range can be between about 0.7 mM and about 10 mM, between about 1 mM and about 5 mM or between about 1.5 mM and about 2.5 mM.

It is also understood that about 0.1 mM includes about 0.2 mM, about 0.3 mM, about 0.4 mM and the like, while about 50 mM includes about 49 mM, about 48 mM, about 47 mM and the like. Additionally, the values at the lower end of the range can be lower than the value provided, for example about 0.09 mM or about 0.08 mM and still be within the scope of the present invention. Similarly, the upper end of the range includes values such as about 51 mM or about 52 mM that still fall within the scope of the present invention.

In other preferred embodiments of the present invention, the culture medium may also comprise an effective amount of β-mercaptoethanol. In certain aspects, the culture medium comprises β-mercaptoethanol at a concentration of between about 1 μM and about 1 mM. In further embodiments, the culture medium comprises β-mercaptoethanol at a concentration of between about 25 μM and about 250 μM. In exemplary embodiments, the culture medium comprises β-mercaptoethanol at a concentration of about 100 μM. However, it will be understood that the range of concentrations can be between about 1 μM and about 500 μM, or between about 5 μM and about 1 mM. Equally, the range can be between about 20 μM and about 250 μM, between about 50 μM and about 125 μM or between about 75 μM and about 110 μM.

It is also understood that about 1 μM includes about 0.9 μM, about 0.8 μM, about 0.7 μM and the like, while about 1 mM includes about 2 mM, about 3 mM, about 4 mM and the like. Additionally, the values at the lower end of the range can be lower than the value provided, for example about 0.9 μM or about 0.8 μM and still be within the scope of the present invention. Similarly, the upper end of the range includes values such as about 2 mM or about 3 mM within the scope of the present invention. As discussed above, optimization of the concentration of this or other media components can be performed by those of skill in the art without undue experimentation by testing different concentrations and measuring the effect on growth of primordial germ cell-derived colonies.

In certain embodiments, the culture medium may also comprise an effective amount of Dulbecco's modified Eagle's media. The Dulbecco's modified Eagle's media may be either low sodium Dulbecco's modified Eagle's media or high sodium Dulbecco's modified Eagle's media. In exemplary embodiments, the culture medium comprises Dulbecco's modified Eagle's media at about 50% volume/volume. In other embodiments, the culture medium may also comprise Ham's F10 media. In more preferred embodiments, the culture medium comprises Ham's F10 media at about 50% volume/volume. In exemplary embodiments of the present invention, the culture medium comprises Dulbecco's modified Eagle's media at about 50% volume/volume and Ham's F10 media at about 50% volume/volume. It is understood that the amount of Dulbecco's modified Eagle's media or Ham's F10 media can be about 40% volume/volume, about 30% volume/volume and the like. Additionally, about 50% volume/volume includes about 49%, about 48%, and the like, as well as about 51%, about 52% and about 53% while remaining within the scope of the invention.

Culture media comprising combinations of different growth factors are also contemplated for use in the present invention. Thus, in certain aspects of the present invention, the culture medium comprises an effective amount of basic fibroblast growth factor and an effective amount of at least one of uteroferrin, α2-macroglobulin, leukemia inhibitory factor, soluble stem cell factor, amino acids non-essential to said non-rodent animal, L-glutamine, β-mercaptoethanol, Dulbecco's modified Eagle's media or Ham's F10 media. In further aspects, the culture medium comprises an effective amount of basic fibroblast growth factor and a combined effective amount of at least two of uteroferrin, α2-macroglobulin, leukemia inhibitory factor, soluble stem cell factor, amino acids non-essential to said non-rodent animal, L-glutamine, β-mercaptoethanol, Dulbecco's modified Eagle's media or Ham's F10 media.

In preferred aspects of the present invention, the culture medium comprises an effective amount of basic fibroblast growth factor and a combined effective amount of at least three of uteroferrin, α2-macroglobulin, leukemia inhibitory factor, soluble stem cell factor, amino acids non-essential to said non-rodent animal, L-glutamine, β-mercaptoethanol, Dulbecco's modified Eagle's media or Ham's F10 media. In further aspects of the present invention, the culture medium comprises an effective amount of basic fibroblast growth factor and a combined effective amount of uteroferrin, α2-macroglobulin and leukemia inhibitory factor. In particular embodiments, the culture medium comprises basic fibroblast growth factor at a concentration of between about 5 ng/ml and about 100 μg/ml, uteroferrin at a concentration of between about 1 ng/ml and about 100 μg/ml, α2-macroglobulin at a concentration of between about 10 ng/ml and about 10 μg/ml and leukemia inhibitory factor at a concentration of between about 5 ng/ml and about 100 μg/ml.

In certain embodiments of the present invention, the medium comprises between about 5 ng/ml and about 100 μg/ml of basic fibroblast growth factor, between about 1 ng/ml and about 100 μg/ml of uteroferrin, between about 10 ng/ml and about 10 μg/ml of α2-macroglobulin, between about 5 ng/ml and about 100 μg/ml of leukemia inhibitory factor, between about 1 ng/ml and about 100 μg/ml of soluble stem cell factor, between about 10 nM and about 250 nM of non-essential amino acids, between about 0.1 mM and about 50 mM of L-glutamine, between about 1 μM and about 1 mM of 13-mercaptoethanol, about 50% volume/volume of Dulbecco's modified Eagle's media, and about 50% volume/volume of Ham's F10 media.

In exemplary embodiments of the present invention, the medium comprises about 40 ng/ml of basic fibroblast growth factor, about 40 ng/ml of uteroferrin, about 1 μg/ml of α2-macroglobulin, about 20 ng/ml of leukemia inhibitory factor, about 40 ng/ml of soluble stem cell factor, about 100 nM of non-essential amino acids, about 2 mM of L-glutamine, about 0.1 mM of β-mercaptoethanol, about 50% volume/volume of Dulbecco's modified Eagle's media, and about 50% volume/volume of Ham's F10 media.

The instant invention also provides methods wherein the plated primordial germ cells are maintained in an undifferentiated state for about 2 passages, about 3 passages, about 4 passages, about 5 passages, about 6 passages, about 7 passages, about 8 passages, about 9 passages, about 10 passages, about 11 passages, about 12 passages, about 13 passages or about 14 passages. In other embodiments of the present invention, the plated primordial germ are maintained in an undifferentiated state for about 20 passages, about 30 passages, about 50 passages or about 100 passages.

As used herein, the term "non-rodent animal" will be understood to include all vertebrate animals, except rodents and humans. In certain embodiments of the present invention, the non-rodent animal species is bovine. In other embodiments, the non-rodent animal species is ovine. In still other embodiments, the non-rodent animal species is porcine. In yet other embodiments, the non-rodent animal species is caprine. Other non-rodent animals contemplated for use in the present invention include, but are not limited to, horses (equine), buffaloes and rabbits.

The present invention provides a primordial germ cell from a non-rodent animal species that may be prepared by a process comprising plating a composition comprising primordial germ cells on a stock of feeder cells at a density of between about $1.5\times10^5$ cells/cm$^2$ and about $10^6$ cells/cm$^2$, in a culture medium comprising an effective amount of basic fibroblast growth factor. In particular embodiments, the invention provides a primordial germ cell colony from a non-rodent animal species that may be prepared by a process comprising the steps of plating a composition comprising primordial germ cells on a stock of feeder cells at a density of between about $1.5\times10^5$ cells/cm$^2$ and about $10^6$ cells/cm$^2$, in a culture medium comprising an effective amount of basic fibroblast growth factor for an amount of time sufficient to obtain a primordial germ cell colony. In preferred aspects, the primordial germ cell colony is in an undifferentiated state.

Additionally, the present invention provides a method of preparing a primordial germ cell-derived cell line from a non-rodent animal species, that may comprise plating a composition comprising primordial germ cells on a stock of feeder cells at a density of between about $1.5\times10^5$ cells/cm$^2$ and about $10^6$ cells/cm$^2$, in a culture medium comprising an effective amount of basic fibroblast growth factor, and culturing the plated primordial germ cells for a period of time effective to provide a primordial germ cell-derived cell line.

Thus, the instant invention provides a primordial germ cell-derived cell line from a non-rodent animal species, that may be prepared by a process comprising plating a composition comprising primordial germ cells on a stock of feeder cells at a density of between about $1.5\times10^5$ cells/cm$^2$ and about $10^6$ cells/cm$^2$, in a culture medium comprising an effective amount of basic fibroblast growth factor, and culturing the plated primordial germ cells for an effective period of time to provide a primordial germ cell-derived cell line.

Additionally, the present invention provides a method of preparing primordial germ cells of a non-rodent animal species that contain a selected DNA segment, that may comprise introducing a selected DNA segment into a composition comprising primordial germ cells from the non-rodent animal species to obtain candidate primordial germ cells that contain the selected DNA segment, and plating the candidate primordial germ cells of the non-rodent animal species that contain the selected DNA segment on feeder cells at a density of between about $1.5\times10^5$ cells/cm$^2$ and about $10^6$ cells/cm$^2$, in a culture medium comprising an effective amount of basic fibroblast growth factor, to obtain the primordial germ cells of the non-rodent animal species that contain the selected DNA segment.

In particular aspects, the method may comprise the steps of introducing a selected DNA segment into a composition comprising primordial germ cells from the non-rodent animal species to obtain candidate primordial germ cells that contain the selected DNA segment, screening said candidate primordial germ cells of the non-rodent animal species for the presence of the selected DNA segment, and plating the candidate primordial germ cells of the non-rodent animal species that contain the selected DNA segment on feeder cells at a density of between about $1.5\times10^5$ cells/cm$^2$ and about $10^6$ cells/cm$^2$, in a culture medium comprising an effective amount of basic fibroblast growth factor, for an amount of time sufficient to obtain a colony comprising the primordial germ cells of the non-rodent animal species that contain the selected DNA segment.

In further aspects of the present invention, the method may comprise the steps of plating a composition comprising primordial germ cells on feeder cells at a density of between about $1.5\times10^5$ cells/cm$^2$ and about $10^6$ cells/cm$^2$, in a culture medium comprising an effective amount of basic fibroblast growth factor, for a period of time sufficient to obtain at least a first passage, introducing a selected DNA segment into the composition comprising primordial germ cells from the non-rodent animal species to obtain candidate primordial germ cells that contain the selected DNA segment, and plating the candidate primordial germ cells of the non-rodent animal species that contain the selected DNA segment on feeder cells at a density of between about $1.5\times10^5$ cells/cm$^2$ and about $10^6$ cells/cm$^2$, in a culture medium comprising an effective amount of basic fibroblast growth factor, to obtain the primordial germ cells of the non-rodent animal species that contain the selected DNA segment.

In particular methods of the present invention, the primordial germ cells of the non-rodent animal species that contain the selected DNA segment are cultured for between about 2 and about 14 passages. In other preferred methods, the primordial germ cells of the non-rodent animal species that contain the selected DNA segment are cultured for about 3, about 4, about 5, about 6, about 7, about 8, about 9, about 10, about 11, about 12 or about 13 passages.

In exemplary methods of the present invention, the selected DNA segment is introduced into the primordial germ cell by electroporation. In other methods, the selected DNA segment is introduced into the primordial germ cell by particle bombardment, calcium phosphate transformation or by viral transformation.

In certain embodiments, the selected DNA segment may comprise at least a first coding region encoding a selected protein, wherein the coding region is expressed in one or more of the primordial germ cells. In further embodiments, the first coding region encodes a selected disease resistance, carcass composition, weight gain, coat composition or milk component protein. In other embodiments, the first coding region encodes a selected marker protein. In exemplary embodiments, the first coding region encodes green fluorescent protein that has been adapted to increase expression in the non-rodent animal species. A protein is "adapted to increase expression in" a non-rodent animal species by altering the coding sequence of the protein to use codons that are preferred for use in the particular non-rodent animal species desired for use. In still other embodiments, the first coding region encodes a neomycin resistance protein. In further embodiments, the first coding region encodes GP63, myelin basic protein, hCD59, Factor IX, α-antitrypsin, α-casein, an interleukin or Bcl-2.

In exemplary embodiments of the present invention, the selected DNA segment may also comprises a second coding region encoding a selected protein. In particular embodiments of the present invention, the first coding region may encodes a selected non-marker protein and the second coding region encodes a selected marker protein.

In embodiments wherein expression of the selected DNA segment is desired, the DNA segment is operatively positioned under the control of a promoter, exemplified by, but not limited to, the CMV promoter, the Oct-4 promoter or the pgk promoter, that expresses the DNA segment in the primordial germ cells. In other embodiments of the present invention, the selected DNA segment is operatively positioned in reverse orientation under the control of the promoter, wherein the promoter directs the expression of an antisense product.

In still other embodiments of the instant invention, the DNA segment comprises two selected DNA regions that flank the coding region, thereby directing the homologous recombination of the coding region into the genomic DNA of a non-rodent animal species. In more preferred embodiments, the selected DNA regions correspond to distinct sequences in the genomic DNA of the non-rodent animal species. In exemplary embodiments, the isolated DNA regions correspond to the Oct-4 gene, or regions that flank the Oct-4 gene.

In still other embodiments of the present invention, the DNA segment comprises two selected DNA sequences that flank the DNA segment and allow for excision of the DNA segment under appropriate conditions. In particularly preferred embodiments, the DNA sequences are loxP sites.

In certain preferred methods of the present invention, the non-rodent animal species is bovine, ovine, porcine, caprine or equine. In other preferred methods, the non-rodent animal is a buffalo or a rabbit.

The present invention thus provides primordial germ cells of a non-rodent animal species that contain a selected DNA segment that may be prepared by a process comprising the steps of introducing the selected DNA segment into a composition comprising isolated primordial germ cells from a non-rodent animal species to obtain candidate primordial germ cells of the non-rodent animal species that contain the selected DNA segment, and plating the candidate primordial germ cells of the non-rodent animal species that contain the selected DNA segment on feeder cells at a density of between about $1.5 \times 10^5$ cells/cm$^2$ and about $10^6$ cells/cm$^2$, in a culture medium comprising an effective amount of basic fibroblast growth factor, to obtain the primordial germ cells of the non-rodent animal species that contain the selected DNA segment.

The invention also provides primordial germ cells of a non-rodent animal species that contain a selected DNA segment that may be prepared by a process comprising the steps of plating a composition comprising primordial germ cells on feeder cells at a density of between about $1.5 \times 10^5$ cells/cm$^2$ and about $10^6$ cells/cm$^2$, in a culture medium comprising an effective amount of basic fibroblast growth factor, introducing the selected DNA segment into the composition comprising isolated primordial germ cells from a non-rodent animal species to obtain candidate primordial germ cells of the non-rodent animal species that contain the selected DNA segment, and plating the candidate primordial germ cells on feeder cells at a density of between about $1.5 \times 10^5$ cells/cm$^2$ and about $10^6$ cells/cm$^2$, in a culture medium comprising an effective amount of basic fibroblast growth factor, to obtain the primordial germ cells of the non-rodent animal species that contain the selected DNA segment.

In further aspects of the present invention, primordial germ cells of a non-rodent animal species that contain a selected DNA segment are provided that may be prepared by a process comprising the steps of plating a composition comprising primordial germ cells on feeder cells at a density of between about $1.5 \times 10^5$ cells/cm$^2$ and about $10^6$ cells/cm$^2$, in a culture medium comprising an effective amount of basic fibroblast growth factor, introducing the selected DNA segment into the composition comprising isolated primordial germ cells from a non-rodent animal species to obtain candidate primordial germ cells of the non-rodent animal species that contain the selected DNA segment, plating the candidate transformed primordial germ cells on feeder cells at a density of between about $1.5 \times 10^5$ cells/cm$^2$ and about $10^6$ cells/cm$^2$, in a culture medium comprising an effective amount of basic fibroblast growth factor, and screening the candidate primordial germ cells of a non-rodent animal species for the presence of the selected DNA segment, to obtain the primordial germ cells of the non-rodent animal species that contain the selected DNA segment.

The present invention also provides a method of producing a transgenic non-rodent animal comprising introducing a selected DNA segment into a composition comprising primordial germ cells from said non-rodent animal to obtain candidate primordial germ cells that contain said selected DNA segment, plating said candidate primordial germ cells that contain said selected DNA segment on feeder cells, said feeder cells at a density of between about $1.5 \times 10^5$ cells/cm$^2$ and about $10^6$ cells/cm$^2$, in a culture medium comprising an effective amount of basic fibroblast growth factor, to obtain said primordial germ cells of said non-rodent animal that contain said selected DNA segment, and generating a transgenic non-rodent animal from said primordial germ cells of a non-rodent animal that contain said selected DNA segment, wherein said selected DNA segment is contained and expressed in somatic and germ cells of said non-rodent animal.

The present invention additionally provides a method of producing a transgenic pig comprising introducing a selected DNA segment into a composition comprising porcine primordial germ cells to obtain candidate porcine primordial germ cells that contain said selected DNA segment, plating said candidate porcine primordial germ cells that contain said selected DNA segment on feeder cells, said feeder cells at a density of between about $2 \times 10^5$ cells/cm$^2$ and about $10^6$ cells/cm$^2$, in a culture medium comprising an effective amount of basic fibroblast growth factor, to obtain porcine primordial germ cells of said non-rodent animal that contain said selected DNA segment, and generating a transgenic pig from said primordial germ cells that contain said selected DNA segment, wherein said selected DNA segment is contained and expressed in somatic and germ cells of said transgenic pig.

The present invention further provides a method of producing a transgenic non-rodent animal comprising plating a composition comprising primordial germ cells on feeder cells, said feeder cells at a density of between about $1.5 \times 10^5$ cells/cm$^2$ and about $10^6$ cells/cm$^2$, in a culture medium comprising an effective amount of basic fibroblast growth factor, introducing a selected DNA segment into said composition comprising primordial germ cells from said non-rodent animal to obtain candidate primordial germ cells that contain said selected DNA segment, plating said candidate primordial germ cells that contain said selected DNA segment on feeder cells, said feeder cells at a density of between about $1.5 \times 10^5$ cells/cm$^2$ and about $10^6$ cells/cm$^2$, in a culture medium comprising an effective amount of basic fibroblast growth factor, to obtain said primordial germ cells of said non-rodent animal that contain said selected DNA segment, and generating a transgenic non-rodent animal from said primordial germ cells of a non-rodent animal that contain said selected DNA segment, wherein said selected DNA segment is contained and expressed in somatic and germ cells of said non-rodent animal.

Additionally, the present invention provides a method of producing a transgenic non-rodent animal comprising introducing a selected DNA segment into a composition comprising primordial germ cells from said non-rodent animal to obtain candidate primordial germ cells that contain said selected DNA segment, plating said candidate primordial germ cells that contain said selected DNA segment on feeder cells, said feeder cells at a density of between about $1.5 \times 10^5$ cells/cm$^2$ and about $10^6$ cells/cm$^2$, in a culture medium comprising an effective amount of basic fibroblast growth factor, screening said candidate primordial germ cells for said selected DNA segment, to obtain said primordial germ cells of said non-rodent animal that contain said selected DNA segment, and generating a transgenic non-rodent animal from said primordial germ cells of a non-rodent animal that contain said selected DNA segment, wherein said selected DNA segment is contained and expressed in somatic and germ cells of said non-rodent animal.

In certain embodiments, the composition comprising primordial germ cells contains cultured cells from a primordial germ cell-derived cell line.

In particular embodiments of the present invention, the transgenic non-rodent animal is generated by a method comprising injecting the primordial germ cells of the non-rodent animal species that contain said selected DNA segment into a blastocyst from said non-rodent animal species. In certain aspects, the transgenic non-rodent animal is generated by a method comprising injecting the primordial germ cells of the non-rodent animal species that contain the selected DNA segment into a blastocyst from the non-rodent animal species, transferring the blastocyst into a synchronized recipient female of the non-rodent animal species to produce a pregnant non-rodent animal, and allowing gestation in the pregnant non-rodent animal to proceed for a period of time sufficient to allow the development of a viable transgenic non-rodent animal. In further embodiments, the viable transgenic non-rodent animal is obtained by natural birth, while in other embodiments, the viable transgenic non-rodent animal is obtained by surgically removing the viable transgenic non-rodent animal from the recipient female.

In other aspects of the present invention, the transgenic non-rodent animal is generated by a method comprising isolating a nucleus from the primordial germ cells of the non-rodent animal that contain the selected DNA segment and injecting the nucleus into an enucleated oocyte from the non-rodent animal. In particular embodiments, the transgenic non-rodent animal is generated by a method comprising, isolating a nucleus from the primordial germ cells of the non-rodent animal that contain the selected DNA segment and injecting the nucleus into an enucleated oocyte from said non-rodent animal species, transferring the oocyte into a synchronized recipient female of the non-rodent animal species to produce a pregnant non-rodent animal, and allowing gestation in the pregnant non-rodent animal to proceed for a period of time sufficient to allow the development of a viable transgenic non-rodent animal.

In still other embodiments of the present invention, the transgenic non-rodent animal is generated by a method comprising aggregating the primordial germ cells of the non-rodent animal species that contain the selected DNA segment with an early stage embryo of the non-rodent animal species. In certain aspects, the transgenic non-rodent animal is generated by a method comprising aggregating the primordial germ cells of the non-rodent animal species that contain the selected DNA segment with an early stage embryo of the non-rodent animal species, transferring the embryo into a synchronized recipient female of the non-rodent animal species to produce a pregnant non-rodent animal, and allowing gestation in the pregnant non-rodent animal to proceed for a period of time sufficient to allow the development of a viable transgenic non-rodent animal.

The present invention also provides a transgenic non-rodent animal that may be prepared by a process comprising the steps of introducing a selected DNA segment into a composition comprising primordial germ cells from the non-rodent animal to obtain candidate primordial germ cells that contain the selected DNA segment, plating the candidate primordial germ cells that contain the selected DNA segment on feeder cells, the feeder cells at a density of between about $1.5 \times 10^5$ cells/cm$^2$ and about $10^6$ cells/cm$^2$, in a culture medium comprising an effective amount of basic fibroblast growth factor, to obtain the primordial germ cells of the non-rodent animal species that contain the selected DNA segment, and generating a transgenic non-rodent animal from the primordial germ cells of the non-rodent animal that contain the selected DNA segment, wherein the selected DNA segment is contained and expressed in somatic and germ cells of the non-rodent animal. In particular aspects of the present invention, the transgenic non-rodent animal is a cow, sheep, pig, horse, buffalo, rabbit or a goat.

The invention also provides a composition comprising primordial germ cells from a non-rodent animal species, feeder cells sufficient to achieve a density of between about $1.5 \times 10^5$ and about $10^6$ feeder cells/cm$^2$, and basic fibroblast growth factor in an amount effective to promote the growth and continued proliferation of said primordial germ cells.

In certain aspects of the invention, the primordial germ cells comprise at least a first exogenous DNA segment. In other aspects, the feeder cells are STO cells. In particular embodiments of the invention, the composition may further comprise one or more of uteroferrin, α2-macroglobulin, leukemia inhibitory factor, soluble stem cell factor, amino acids non-essential to the non-rodent animal species contemplated for use, L-glutamine, β-mercaptoethanol, Dulbecco's modified Eagle's media and/or Ham's F10 media in an amount effective to promote the growth and continued proliferation of said primordial germ cells.

In further aspects of the present invention, the primordial germ cell is a bovine, ovine, porcine, caprine, equine, buffalo or rabbit primordial germ cell. In preferred embodiments, the primordial germ cell is porcine primordial germ cell.

The invention also provides for the use of any of the disclosed compositions in the preparation of a primordial germ cell-derived cell line. Thus, the instant compositions are contemplated for use in the preparation of a primordial germ cell-derived cell line. Further, the invention provides for the use of any of the disclosed compositions comprising an exogenous DNA segment in the preparation of a transgenic non-rodent animal. Therefore, the compositions comprising an exogenous DNA segment of the present invention are contemplated for use in the preparation of a transgenic non-rodent animal.

The present invention also provides a variety of kits for use in the practice of certain of the methods disclosed and/or claimed herein. The invention provides for the use of any of the disclosed compositions comprising primordial germ cells in the preparation of a kit. Thus, any of the primordial germ cell compositions are contemplated for use in the preparation of a kit. In particular aspects, the kit may comprise, in suitable container means, primordial germ cells from a non-rodent animal species, feeder cells sufficient to achieve a density of between about $1.5 \times 10^5$ and about $10^6$ feeder cells/cm$^2$, and basic fibroblast growth factor in an amount effective to promote the growth and continued proliferation of said primordial germ cells.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
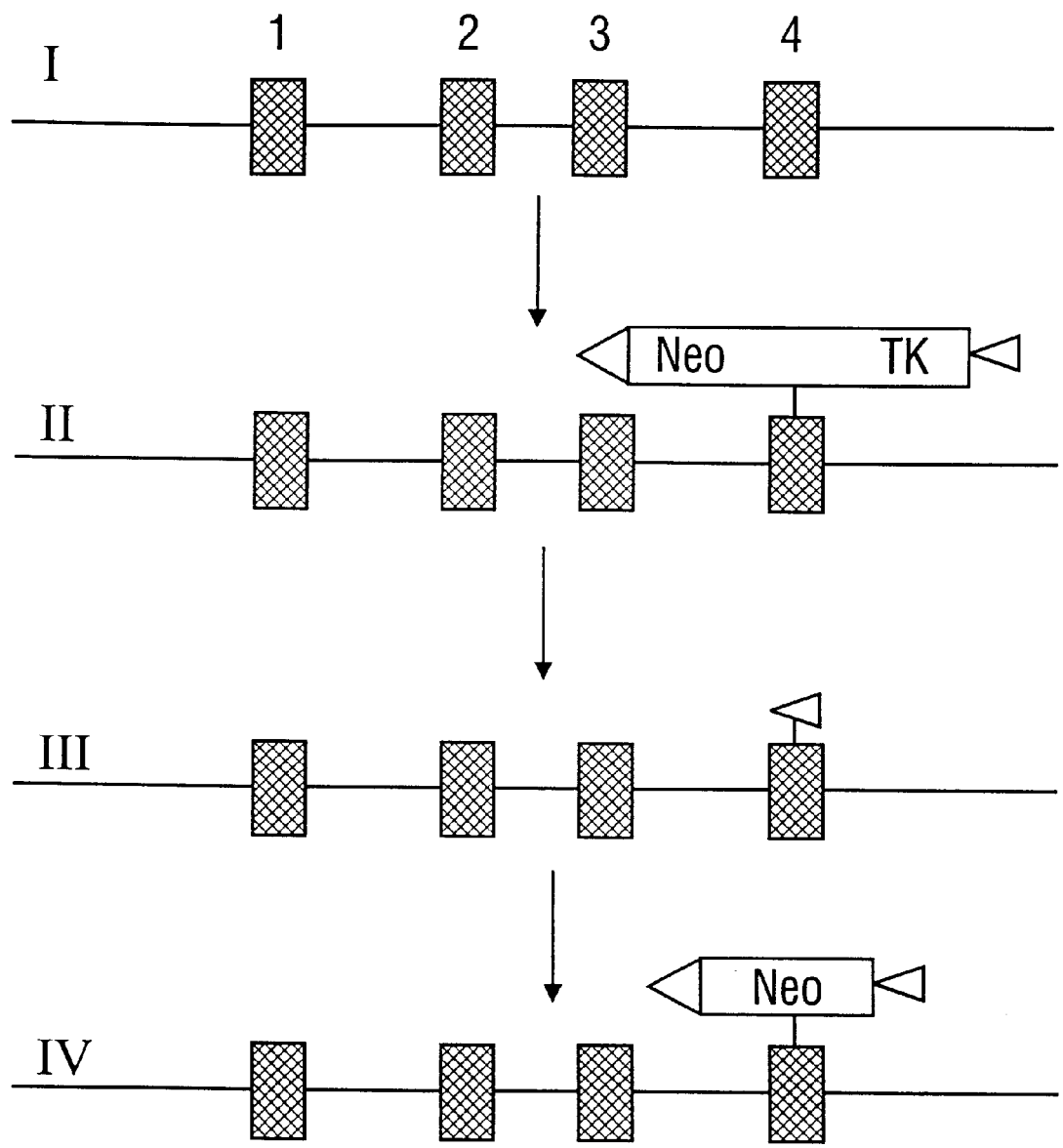
FIG. 1. Schematic of the strategy used for the introduction of a loxP site into the WAP locus of mouse ES cells. All four exons of WAP are shown, although exon size and relative distances to each other are not to scale. Initially, a WAP allele is targeted by homologous recombination with a loxP-flanked neo-TK cassette placed in the exon 4 of the targeting construct. Targeted ES cells are then exposed to Cre recombinase to delete the marker cassette leaving a single loxP site in the genome. These modified ES cells can be used to introduce a loxP containing construct through a Cre-mediated insertion event specifically into the WAP locus. A selection process is performed during each treatment to enrich for the isolation of the desired modification.

The terms "animal" and "non-rodent animal", as used herein, include all vertebrate animals, except rodents and humans. It also includes individual animals in all stages of development, including embryonic and fetal stages. A "transgenic animal" is any animal containing one or more cells bearing genetic information received, directly or indirectly, by deliberate genetic manipulation at the subcellular level. The genetic manipulation can be performed by any method of introducing genetic material to a cell, including, but not limited to, microinjection, infection with a recombinant virus, particle bombardment or electroporation. The term is not intended to encompass classical crossbreeding or in vitro fertilization, but rather is meant to encompass animals in which one or more cells receive a recombinant DNA molecule. This molecule may be integrated within a chromosome, or it may be extrachromosomally replicating DNA. The genetic information may be foreign to the species of animal to which the recipient belongs, foreign only to the individual recipient, or genetic information already possessed by the recipient expressed at a different level, a different time, or in a different location than the native gene.

Transgenic animals have a wide and growing variety of uses, including, but not limited to, production of recombinant proteins in the milk of mammalian hosts, creation of animal models for studying human and animal diseases, creation of disease and pest resistant animals, improved animal growth characteristics, improved carcass composition, and the generation of animals that can be used as human blood and tissue donors. In spite of the potential applications of large animal transgenesis in agriculture, and human and veterinary medicine, progress has been slow. This is due to both the drawbacks of existing technology for generating large animal transgenics, as well as the costs associated with their generation.

At present, all techniques available in domestic animals rely on the introduction of a transgene into a random location of the chromosome by pronuclear injection or viral vectors. Ideally, in the transgenic animal, transgene expression should be regulated in such a way as to mimic the endogenous patterns of expression with respect to the tissue, developmental and temporal specificity of the promoter being utilized. That, however, is rarely the case. The metallothionein promoter, an inducible liver-specific promoter, resulted in the highest transgene levels in the liver analogous to the endogenous promoter (Palmiter et al., 1983), but promoter "leakiness" caused ectopic expression in the kidneys and intestines as well.

Moreover, due to problems associated with random insertion of the transgene, transgenic animals produced with the same construct can be radically different. Another problem associated with random insertion is insertional inactivation, whereby the transgene inserts within a critical gene, thereby disrupting it. This effect can prove deleterious or even lethal to the developing embryo (Schnieke et al., 1983).

Of greater concern is the so called "positional effect", wherein transgenes inserting into different areas of the chromosome result in vastly different levels of transcript expression. In the context of proximal DNA sequences the transgene can be effectively silenced by inactivation of localized chromatin structures. The practical result of this positional effect is that, due to the effect of the neighboring regions, the appropriateness of gene regulation can be drastically affected. Thus, utilizing the same construct, transgenic animals can be obtained with a pattern of transgene expression mimicking the endogenous promoter, aberrant patterns of expression, or reduced expression or even no expression (Klintworth, 1990).

As the resulting phenotype of the transgenic animal can not be determined a priori, more than one founder animal needs to be generated to evaluate the effects of the transgene. Recently, several cis-acting elements have been included in transgenic constructs to promote a position-independent expression pattern. These elements include: LCRs (locus control regions), insulators and MAR (matrix attachment regions) (Reitman et al., 1993; McKnight et al., 1992; Krnacik et al., 1995). Although some progress has been made in this area, the general applicability of LCRs and MARs for generating position-independent transgenic animals still remains to be determined.

Additionally, the efficiency of transgene integration can be an infrequent event, especially when working with larger domestic species. Schindler and Ebert reported a low efficiency for the production of transgenic farm animals (porcine, ovine, bovine, caprine), with a range of 0.0% to 4.0% (Ebert and Schindler, 1993). This compares with a transgenic efficiency of 10–40% in mice (Palmiter and Brinster, 1986). Moreover, in swine, 60% of the transgenic founders expressed the c-ski transgene, but only 38% demonstrated the phenotype (Ebert and Schindler, 1993). The most prevalent concern to the commercial use of transgenics is the low efficiency of generating transgenic offspring. Thus, the production of transgenic animals by pronuclear injection is hindered by its low efficiency and its variable transcript regulation.

The technique of homologous recombination in ES cells overcomes most of the inherent problems of pronuclear injection. Unfortunately, at this time there are two barriers to its broad application: the low efficiency of recombination, and the unavailability of the required ES cells for any species but mice. One of the problems with homologous recombination is the low efficiency at which foreign DNA is inserted into the host chromosome. The human β-globin gene in mouse erythroleukemia cells was targeted at a frequency of $1\times10^{-7}$ (Smithies et al., 1985). Targeting the apoE locus with a neomycin-containing construct gave a frequency of about $6.3\times10^{-7}$ (Piedrahita et al., 1992). As a results of the low frequency, it is not practical to attempt homologous recombination by pronuclear injection. Brinster et al. (1989) reported that homologous recombination following direct pronuclear injection of DNA into mouse embryos occurred at a very low frequency; a single mutant MHC class II Eα gene was targeted by pronuclear injection after injecting more than 10,000 embryos (Brinster et al., 1989).

Thus, to successfully modify genes by homologous recombination a carrier cell line must be isolated. As mentioned above, carrier cell lines necessary for the creation of transgenic animals have been described for mice. The cell lines used to date are ES cells and PGC or EG cells, as they allow manipulation and selection in vitro followed by the generation, by ES- or EG-blastocyst injection, of a transgenic animal carrying those changes. ES cells have been isolated from murine embryos using either murine primary embryonic fibroblasts (Wobus et al., 1984) or a continuous cell line of murine embryonic fibroblasts (STO; Ware and Axelrad, 1974) as feeder cells. Once ES cell lines are isolated, they can be maintained in the undifferentiated state by culture on feeder layers (Martin, 1981), in medium containing Buffalo rat liver (BRL) cell conditioned media (Smith and Hooper, 1987), or in medium containing leukemia inhibitory factor (LIF; Smith et al., 1988; Williams et al., 1988). Additionally, it has been shown that it is possible not only to maintain, but to isolate mouse ES cell lines in the absence of a feeder layer by the addition of LIF to the culture system (Pease et al., 1990).

PGC-derived cell lines have been described in mice (Matsui et al., 1992; Labosky et al., 1994), which behave similarly to ES cell lines and are capable of contributing to the germ line. While the isolation of these cells is different from the isolation of ES cells, the cultures are maintained in the same manner as ES cells, by culture on inactivated mouse embryo fibroblasts in the presence of LIF.

In mice, the key development in this technology was the identification of embryo derived cell lines or ES cells that could be genetically manipulated in vitro and then reintroduced into a developing embryo for contribution to the formation of all tissues including the germ cells references. Unfortunately, in spite of substantial efforts by many investigators it has not been possible to isolate any ES cells lines with germ line characteristics from any species other than mice (Stice and Strelchenko, 1995).

Attempts at developing the ES and PGC technology in other mammalian species have been reported. Doetschman et al. (1988) showed that ES cell lines can be isolated from hamster embryos using feeders composed of murine primary embryonic fibroblasts. The isolated hamster ES cells had morphology and in vitro differentiation characteristics indistinguishable from mouse ES cells. However, in spite of repeated attempts, none of the hamster ES cell lines tested was capable of contributing to the formation of a chimera after injection into the blastocyst of a host embryo. This is despite confirmation of the ability of isolated ICM to contribute to chimera formation in the same strain combination used to test the ES cells (Piedrahita et al., 1992).

Sukoyan et al. (1992) reported ES-like cell lines from mink, that when injected into host blastocysts did not produce chimeric offspring. However, since teratoma assays using these same cells resulted in only fibroblastic cell types, the potency of these cells appears to have been limited. Unfortunately, a later study (Sukoyan et al., 1993) which produced varied cell type teratomas was not followed up with blastocyst injection studies.

ES-like cell lines have been described in the rabbit (Graves and Moreadith, 1993; Giles et al., 1993). ICM cells freshly isolated or cultured for less than three days contributed to the chimeric progeny, while those cultured beyond three days did not (Giles et al., 1993). Recently, Du et al. (1995) have reported the development of embryos to the blastocyst stage after nuclear transfer utilizing rabbit ES-like cells. It is generally accepted, however, that blastocyst formation is not a good indicator of the ability of a nucleus to produce live progeny.

The inventors and others (Piedrahita et al., 1990; Evans et al., 1990; Stice and Strelchenko, 1996), using STO as feeder layers, have reported the isolation of porcine embryo-derived cell lines with ES-like morphology and a limited ability to differentiate in vitro. Others have also reported porcine ES-like cell lines (Strojek et al., 1990; Notarianni et al., 1990; Talbot et al., 1993; Anderson et al., 1994; Wheeler, 1994; Gerfen and Wheeler, 1995). Like the study in rabbits, Anderson et al. (1994) showed production of chimeras using freshly isolated ICM cells, but not with cultured ICMs. Wheeler (1994) reported successful chimera production. However, not only was the degree of reported chimerism low to non-existent, but to date there has been no report of germ line transmission of the ES genotype. In addition, the results were cast in doubt when the same group was unable to repeat this result (Gerfen and Wheeler, 1995).

Wheeler (U.S. Pat. No. 5,523,226) disclose methods for obtaining embryonic stem cells for incorporation into a swine embryo to form a chimeric swine, comprising culturing embryonic stem cells in conditioned stem cell medium in the presence or absence of a layer of feeder cells, and verifying that the embryonic stem cells can form a tumor in an SCID mouse. However, the embryonic stem cells described by Wheeler are not the same as PGC cells, and have not been shown to be capable of germline transmission of the desired phenotype.

Hogan (U.S. Pat. No. 5,453,357) disclose compositions and methods involving PGCs, with the inclusion of fibroblast growth factor, leukemia inhibitory factor, soluble steel factor and membrane-bound steel factor being critical to the maintenance of the PGCs. However, germline transmission of the PGC phenotype was not shown.

Perhaps the greatest difficulty associated with the interpretation of the literature related to porcine ES cells is the heterogeneous nature of the cell lines isolated which are capable of some in vitro reorganization. Piedrahita et al. (1990) reported the isolation of porcine ES cells with a limited ability to differentiate in vitro. Although structures were obtained which resembled cystic embryoid bodies, light and electron microscope histological analysis indicated that the morphological changes were more indicative of a reorganization than true differentiation.

Yet the majority of reports since this time have utilized cyst formation as an indication of pluripotential differentiation without any substantial evidence supporting these claims. In addition, the appearance of cells such as muscle and neuron-type cells from the cultured cell lines has been interpreted as indicative of the pluripotency of the cell lines and their resemblance to ES cells. The problem with this interpretation is that even non-ES cell-like cell lines derived from early embryos have the same ability. Moreover, cells obtained from porcine primary ectoderm, a stage that in the mouse cannot give rise to ES cells, are capable of undergoing extensive differentiation in vitro. Additionally, even if the cell lines being tested are indeed ES cells, no reports have demonstrated a relationship between the ability of a cell line to differentiate in vitro and the ability to colonize the germ line of a chimera.

The inventors and others (Shim and Anderson, 1995) have initially utilized the conditions suitable for murine EG isolation with porcine primordial germ cells obtained from day 25 fetuses and have been able to isolate several cell lines that maintain the typical ES morphology and express alkaline phosphatase, a marker of undifferentiated ES cells, for as long as 14 passages and 4 months. Although at this time the ability of these cells to generate a chimera is unknown, studies by the inventors indicate that the morphological appearance and the pattern of alkaline phosphatase activity (Examples 2, 3) is closer to that seen in mouse ES cells than any other porcine ES cell line previously described. From work done on mice, the morphological appearance of the cell is a good indicator of the ability of a cell to contribute to the germ line.

Attempts at isolating ovine ES cells by culturing embryos on ovine skin fibroblasts in the presence (Handyside et al., 1987) or absence (Piedrahita et al., 1990) of Buffalo rat liver (BRL) conditioned media have been unsuccessful. Notarianni et al. (1991) reported an ovine ES-derived cell line with limited ability to differentiate in vitro, and Campbell et al. (1995) reported sheep nuclear transfer experiments with early passage embryonic disc cells which were capable of directing development to progeny.

The cell described by Campbell et al. (1995) does not resemble an ES cell. The morphology is epithelial in nature and they do not express alkaline phosphatase. Notwithstanding the apparent ability to produce progeny, it is unclear whether a similar methodology would work in other species, for example porcine. This is because cells from sheep retain their nuclear totipotency (even in non-ES cells) for a longer period of time than do cells from pigs. The cells isolated by Campbell et al. (1995) produce pregnant animals at a very low efficiency, which indicates that there may be a limit to the usefulness of these cells. In mice, ES and EG cell lines can be maintained for prolonged periods of time without affecting their ability to generate germ line chimeras.

Recently, Wilmut et al. (1997) have used adult mammalian cells (mammary gland epithelium) to produce a viable offspring lamb. However, the efficiency of the process was very low.

Similarly, using unmanipulated STO as feeder cells, only limited success at isolating bovine embryo-derived cell lines with ES-like morphology has been reported (Evans et al., 1990; Stice and Strelchenko, 1996) although several epithelial-like cell lines with the ability to contribute to the formation of the developing fetus after nuclear transfer have been reported (Stice and Strelchenko, 1996). However, none of these cell lines were capable of producing a live offspring. Other reports of ES-like cell lines from cattle have been published (Saito et al., 1992; Stice et al., 1994). Sims and First (1993) reported the ability to obtain live offspring by nuclear transfer using as nuclear donors embryo-derived cell lines isolated in suspension culture in the absence of feeder layers. Unfortunately, neither the original investigators nor others have been able to repeat these results despite considerable effort.

One group of investigators reported in two abstracts the isolation of colonies from bovine PGCs plated for 7 days, which positively stain for alkaline phosphatase activity and have an ES-like morphology (Chemy et al. 1994; Stokes et al., 1994). Furthermore, injection of FITC labeled cells into a host blastocyst indicated the ability of the injected cells to aggregate with the cells of the ICM. However, no further reports have been published, and no information regarding the ability of the cells to participate in chimera formation is known. Notwithstanding these somewhat dubious reports, to date, there have been no reports on the generation of undifferentiated transgenic cell lines of embryo-derived or PGC-derived cell lines in any non-rodent animal species.

The inventor's studies with the isolation of ES cells in bovine and porcine species have determined conditions that allow maintenance of the ES cells in an undifferentiated state for short periods of time, but have been unable to maintain the cell lines in an undifferentiated state long enough to attempt genetic modifications (Moore and Piedrahita, 1996, 1997).

The next important step in the production of a transgenic animal is the transformation of pluripotential cells with a selected gene. Once these transformed cells have been generated, they can be analyzed for the ability to pass the selected transgene to progeny animals. However, despite numerous reports of apparently pluripotent ES and PGC-derived cell lines, transformation of non-rodent ES- or PGC-derived cells or cell lines has not been reported.

To test for the ability of the transformed cell lines to contribute to the germ line two technologies are available; blastocyst injection for chimera generation and nuclear transfer. In pigs it has been demonstrated that injection of ICM into the blastocoele of a developing blastocyst results in chimeric pigs (Onishi et al., 1994; Anderson et al., 1994). Additionally, there have been unconfirmed reports of the ability of cultured ES-like cell to contribute to the generation of a chimeric pig. (Wheeler, 1994; Gerfen and Wheeler, 1995). Without germ line transmission any genetic changes that have been introduced into the ES cell can not carry to the next generation and as a result the animals have little if any practical value. However, the fact that ICM can contribute to the germ line indicates that if the isolated cell lines can be maintained in an undifferentiated state, they should be able to behave as ICM and carry the genetic changes through the germ line.

Problems of the isolated embryonic cell lines to contribute to the formation of a ES-blastocyst germ line chimera, a prerequisite for generation of a transgenic line of animals, can be overcome by bypassing chimera formation, using nuclear transfer. In the nuclear transfer procedure, nuclei from the correctly modified cells are transferred into an enucleated oocyte, and the embryo is allowed to develop to term following transfer to a suitable recipient. While nuclear transfer with nuclei from blastocyst stage embryos or ES cells has not resulted in any live offspring or mid-term pregnancies in mice (Barnes et al., 1987; Robl et al., 1986), a similar approach may be more successful in cattle and small ruminants since nuclei from cattle and sheep remain totipotent at least until the blastocyst stage. This has been demonstrated by the ability to obtain live offspring after transfer of ICM nuclei into an enucleated oocyte in both cattle and sheep (Smith and Wilmut, 1989; Keefer et al., 1994). Moreover, in cattle it has been demonstrated that embryo-derived cell lines can be used as nuclear donors, although resulting pregnancies are lost during the last third of gestation (Stice et al., 1996; Strelchenko, 1996).

As detailed above, it has not been possible to isolate non-rodent animal ES cells that permit the same manipulations that can be carried out in mice. The availability of PGC or EG cells and cell lines which are amenable to transformation while remaining in an undifferentiated state will allow the precise manipulation of the genomic material followed by the generation of a living animal carrying those changes.

The present invention provides novel methods for the generation of transgenic non-rodent animal species. As detailed herein, in certain preferred embodiments, the present invention concerns methods for growing isolated primordial germ cells, wherein the primordial germ cells are amenable to transformation, and remain in an undifferentiated state.

In further preferred embodiments, isolated primordial germ cells are transformed prior to culturing, and the transformed cells are used after 1–3 passages to produce transgenic non-rodent animals. In other preferred embodiments, the transformed primordial germ cells are cultured, wherein the transformed cells remain in an undifferentiated state.

In still frrther preferred embodiments, the primordial germ cells are transformed with a DNA segment that provides for homologous recombination. In certain other preferred embodiments, the selected transgene is flanked by DNA sequences that promote the excision of the incorporated transgene under appropriate conditions.

I. Embryonic Cells

Embryonic stem cells isolated from the inner cell mass of the preimplantation embryo possess the ability to proliferate indefinitely in an undifferentiated state, are capable of differentiating in vitro and in vivo, and can contribute to the formation of normal tissues and organs of a chimeric individual when injected into a host embryo. Differentiation can be stimulated in vitro by modifying culture conditions, and in vivo by injection of ES cells into athymic mice (Doetschman et al., 1985). When allowed to differentiate in vitro, ES cells form structures known as embryoid bodies, which closely resemble the embryo-proper portion of the 5-day mouse embryo (Doetschman et al., 1985).

The ability to colonize the germ line following culture and genetic manipulation has made ES cells a powerful tool for the modification of the genome in the mouse species. Chimeras produced between genetically modified ES cells and normal embryos have been used to study in vivo gene regulation (Stewart et al., 1985) as well as germ-line transmission of introduced genes (Smithies, 1991). In addition, ES cells have been used to study targeted modification of genes by homologous recombination (Smithies, 199 1; Piedrahita et al., 1992).

Although the majority of the research on ES cells has been done in the mouse, attempts at developing the ES technology in other mammalian species have been reported by several investigators. Doetschman et al. (1988), showed that ES cells can be isolated from hamster embryos using feeders composed of murine primary embryonic fibroblasts. Several investigators using STO as feeder layers, have reported the isolation of porcine embryo-derived cell lines with ES-like morphology and a limited ability to differentiate in vitro and in vivo (Evans et al., 1990; Notarianni et al., 1990; Piedrahita et al., 1990; Strojek et al., 1990; Gerfen and Wheeler, 1995). In pigs, not only has it been demonstrated that injection of ICM into the blastocoele of a developing blastocyst results in chimeric pigs (Anderson et al., 1994; Onishi et al., 1994) but, additionally, there have been reports of the ability of cultured ICM-derived ES-like cells to contribute to the generation of a chimeric pig (Wheeler, 1994). However, not only the degree of reported chimerism was low, but to date there has been no report of germ line transmission of the ES genotype (Wheeler, 1994; Gerfen and Wheeler, 1995). Without germ line transmission, any genetic changes that have been introduced into the ES cell can not be passed to the next generation and as a result the animals have little, if any, practical value.

Recently, it has been reported that murine cell lines derived from primordial germ cells behave similarly to ES cells and are capable of contributing to the germ line (Labosky et al., 1994). These cells, referred to as EG cells or PGC-derived cells (Labosky et al., 1994; Strelchenko, 1996), are similar from ES cells in terms of markers of the undifferentiated state, as well as in their ability to colonize the germ line following injection into a host blastocyst (Labosky et al., 1994; Stewart et al., 1994). Thus, even though the starting tissue source or cellular phenotype differs from the ICM-derived cell lines, once established they have similar properties. Shim et al. (1997) have reported the ability of PGC-derived cell lines to contribute to the formation of a porcine chimera, demonstrating the pluripotential characteristics of these cell lines. The inventors have extended this observation by demonstrating the ability of genetically transformed PGCs to contribute to chimera formation, indicating that the cells of the present invention have pluripotential characteristics, and that the genetic transformation and selection procedure does not interfere with the ability of the cells to participate in chimera formation.

Results obtained with PGC (EG) derived cell lines indicate that they have a greater chance of being useful for transgenic modifications than embryo-derived ES cells. The reasons include: the ability to isolate 10,000 to 20,000 primordial germ cells from a single fetus (Shim and Anderson, 1995; Piedrahita and Bazer, present disclosure), versus an average of 12–15 cells per embryo for ES cell isolation; the ability to obtain colonies with morphology and cellular markers typical of undifferentiated pluripotential cell lines at high frequency from the PGCs; the ability to maintain and passage the PGC colonies for a sufficient time that genetic modifications are permitted; the ability of PGC cell lines to contribute to the germ line of chimeras; and the potential use of EG cells as nuclear donors for embryo cloning studies.

Preliminary results with porcine inner cell mass indicates that injection of pluripotential EG cells into the blastocoele of the developing embryo have a good chance of transferring genetic changes through the germ line. The use of nuclear transfer with EG cell lines in ruminant species is based upon the technological advantages of using these embryos for nuclear transfer studies. To date is has not been possible to obtain any offspring from nuclear transfer studies in pigs beyond the 8-cell stage (Niemann and Reichelt, 1993). Nor, with few exceptions (Machaty et al., 1996), has it been possible to develop an in vitro oocyte maturation (IVM) system that can be used to generate oocytes suitable as nuclear recipients for nuclear transfers.

In contrast, studies in the bovine have indicated that nuclei from the inner cell mass of day 7 embryos are still capable of developing into a complete organism following nuclear transfer (Keefer et al., 1994). Additionally, the technology for IVM, IVF is well developed in bovine. Similarly, Campbell et al., (1996) recently reported that ability to generate live offspring from sheep embryo-derived cell lines after 13 passages in culture. As nuclear transfer studies have indicated that sheep and cattle are similar with respect to their timing of loss of totipotency (Smith and Wilmut, 1989; Keefer et al., 1994), it seems that cultured cattle embryo-derived cells will behave similarly to those from sheep.

A. Embryo Isolation

Embryos are collected from pregnant female animals of the selected non-rodent species. The animals are either anesthetized, and the uterus is removed, or the embryos can be collected after slaughter. The embryos are usually collected very early in the gestational period. For example, porcine embryos are collected at day 25 of gestation, bovine embryos are collected at day 35–40 of gestation, and ovine and caprine embryos are collected on day 6 or 7 after estrus.

B. Isolation and Culturing of Primordial Germ Cells

Once embryos have been collected, the primordial germ cells (PGCs) are isolated. Primordial germ cells are pluripotent cells that have the ability to differentiate into all three primary germ layers. In mammals, the PGCs migrate from the base of the allantois, through the hindgut epithelium and dorsal mesentery, to colonize the gonadal anlague (Eddy et al., 1981). The PGC-derived cells have a characteristically low cytoplasm/nucleus ratio, usually with prominent nucleoli. The PGCs are isolated from the embryos by removing the genital ridge of the embryo, dissociating the PGCs from the gonadal anlague, and collecting the PGCs. There are reports that the PGCs can be cryopreserved, with 60% viability 24 hours after thawing and culture (Leichthammer and Brem, 1990). Cryopreserved porcine PGCs are also capable of nuclear transfer (Liu et al., 1995).

For use in the present invention, the primordial germ cells are used upon collection, or within 24 hours of thawing cryopreserved PGCs. The PGCs can be used directly for transformation, or can be plated under appropriate conditions for culturing of the cells. The present invention discloses modified culture conditions that increase the number of PGC colonies by 5–10-fold over existing systems. Even after repeated passages, the morphology of the colonies and their expression of alkaline phosphatase closely resembles that of the freshly plated inner cell mass. Such inhibition of differentiation has never been observed with ICM-derived cell lines (Piedrahita et al., 1990).

1. Feeder Cells

The isolated primordial germ cells are grown on a layer of feeder cells. Types of feeder cells that may be used in the present invention are embryonic cell lines such as murine $S1/S1^4$ or embryonic fibroblasts from selected animal species, such as porcine or bovine. More preferred for use in the present invention are STO cells (mouse embryonic fibroblast cells; Ware and Axelrad, 1972). In certain aspects of the invention, $S1^4$-m220 cells, which express only the membrane associated form of stem cell factor, may be used. The feeder cells provide growth factors to the growing primordial germ cells, but the amount of endogenous growth factors provided is variable from preparation to preparation. Therefore, exogenously added growth factors may be added to supplement the endogenous supply. Additionally, in particular aspects of the invention, the inventors contemplate engineering feeder cell lines to express selected growth factors, for example membrane-associated stem cell factor and basic fibroblast growth factor.

The feeder cells are inactivated prior to use, preferably by X-irradiation with agents such as cobalt or cesium, or using mitomycin C. The inactivated feeder cells are allowed to culture prior to use in culturing PGCs, preferably for 24 hours, but longer and shorter culture times are possible.

The density of inactivated feeder cells is critical to the success of the instant invention. Densities of between about $1.5\times10^5$ and $10^6$ cells/cm$^2$ are preferred for use in the present invention, with densities of between about $2-4\times10^5$ cells/cm$^2$ more preferred. Additionally preferred for use in certain aspects of the present invention is the addition of $1-1.5\times10^6$ fresh feeder cells per 35 mm well every 3 to 5 days.

2. Media composition

The present invention provides compositions for primordial germ cell growth media. The PGCs can be grown on inactivated feeder cells in media directly after isolation, upon thawing from cryopreservation, or after transformation. Preferred media for use in the present invention is low glucose Dulbecco's modified Eagle's media. Also preferred is Ham's F10 media. More preferred is a combination of low glucose Dulbecco's modified Eagle's media (about 50% v/v) and Ham's F10 media (about 50% v/v). Preferably, the media is supplemented with L-glutamine. Additional preferred media is supplemented with β-mercaptoethanol, and still other preferred media is supplemented with 100 nM of non-essential amino acids (L-alanine, L-asparagine, L-aspartic acid, L-glutamine, glycine, L-proline and L-serine; GIBCO). More preferred for use in the present invention is fully supplemented media, additionally comprising one or more of the following growth factors.

a. bFGF

An essential component of the media compositions for use in the present invention is basic fibroblast growth factor (bFGF). bFGF is a member of the FGF family, currently composed of nine related mitogenic proteins that show 35–55% amino acid conservation. bFGF, unlike most of the other members of the family, lacks a signal peptide and is apparently secreted by mechanisms other than the classical protein secretory pathway. bFGF has been isolated from a number of sources, including neural tissue, pituitary, adrenal cortex, corpus luteum and placenta. bFGF contains four cysteine residues but reduced bFGF retains full biological activity. Several reports indicate that a variety of forms of bFGF are produced as a result of N-terminal extensions. These extensions apparently affect localization of bFGF in cellular compartments but do not affect biological activity. Recent studies indicate that binding of FGF to heparin or cell surface heparin sulfate proteoglycans is necessary for binding of FGF to high affinity FGF receptors.

bFGF stimulates the proliferation of all cells of mesodermal origin, and many cells of neuroectodermal, ectodermal and endodermal origin. The cells include fibroblasts, endothelial cells, astrocytes, oligodendrocytes, neuroblasts, keratinocytes, osteoblasts, smooth muscle cells and melanocytes. bFGF is chemotactic and mitogenic for endothelial cells in vitro. bFGF induces neuron differentiation, survival and regeneration. bFGF has also been shown to be crucial in modulating embryonic development and differentiation. These observed in vitro functions of bFGF suggest that bFGF may play a role in vivo in the modulation of such normal processes as angiogenesis, wound healing and tissue repair, embryonic development and differentiation and neuronal function and neural degeneration. Additionally, bFGF may participate in the production of a variety of pathological conditions resulting from excessive cell proliferation and excessive angiogenesis.

The N-terminally truncated, 146 amino acid isoform of human bFGF has been cloned (Abraham et al., 1986). Recombinant human basic fibroblast growth factor expressed in E. coli is commercially available from R & D Systems (catalog #233-FB). The inventors also contemplate cloning basic fibroblast growth factor from selected animal species, for use in the present invention (Section VIII).

b. Uteroferrin

Uteroferrin is a purple colored, progesterone-induced glycoprotein containing two molecules of iron which is secreted by uterine endometrial epithelium of pigs (Bazer and Roberts, 1983; Roberts and Bazer, 1984). Uteroferrin exists as a 35,000 $M_r$ polypeptide having a purple color, and as a heterodimer ($M_r=80,000$) with one of three "uteroferrin-associated proteins" which have high amino acid sequence homology with serine protease inhibitors (Murray et al., 1989). The heterodimer has a rose color, but the biochemical and biological significance of the rose-form of uteroferrin and the uteroferrin-associated proteins is not known. Uteroferrin carries high mannose carbohydrate with the mannose-6-$PO_4$ recognition marker for lysosomal enzymes (Baumbach et al., 1984) and has acid phosphatase activity (Schlosnagle, et al., 1974). During pregnancy, uteroferrin is transported from uterine secretions into the fetal-placental circulation by specialized placental structures called areolae (Renegar et al., 1982). The mannose residues on uteroferrin are responsible for uteroferrin being targeted to reticuloendothelial cells of the fetal liver, the major site of hematopoiesis in fetal pigs (Saunders, et al., 1985).

Administration of radiolabelled iron to pigs results in endometrial secretion of uteroferrin carrying radiolabelled iron and incorporation of radiolabelled iron into fetal erythrocytes and cells of liver, spleen and bone marrow (Ducsay et al., 1982, 1984). Uteroferrin gives up its iron to fetal transferrin in allantoic fluid with a half-life of 12 to 24 hours (Buhi et al., 1982). Further, administration of iron dextran to pregnant pigs on days 50, 60 and 70 (term is at 115 days), the period of maximum secretion of uteroferrin by the endometrium, results in a 20% increase in iron stores in neonatal piglets (Ducsay et al., 1982, 1984). These results suggest a role for uteroferrin in transplacental transport of iron. However, after Day 75 of gestation, translation of mRNA for uteroferrin decreases rapidly (Simmen et al., 1988), secretion of uteroferrin by endometrial explant cultures declines (Basha et al., 1979), and the amount of uteroferrin in allantoic fluid decreases dramatically (Bazer etal, 1975). This suggests that an alternate mechanism for transplacental iron transport becomes operative between Days 75 and term when fetal/placental demands for iron are increasing (Ducsay et al., 1982, 1984).

Uteroferrin from pig uterus is a tartarate-resistant acid phosphatase with many properties in common with the Type 5 acid phosphatase in human placenta (Ketcham et al., 1985), chondrocytes of humans with osteoclastic bone tumors and spleens of humans with hairy cell leukemia, Gaucher's disease and Hodgkin's disease. In addition, uteroferrin has characteristics similar to those for purple acid phosphatases from bovine, rat, mouse, and pig spleen, as well as bovine milk, bovine uterine secretions, equine uterine secretions, and rat bone (Ketcham et al., 1985).

Uteroferrin and uteroferrin rose have been shown to aid in the stimulation of the proliferation of hematopoietic cells (Bazer and Gross, U.S. Pat. No. 5,258,367, which is incorporated herein in its entirety by reference). Uteroferrin and uteroferrin rose effect differentiation of primitive nonadherent hematopoietic stem cells in a non-species specific manner.

Uteroferrin and rose may be obtained by a variety of different methods. These substances may be obtained from uterine flushings of pigs (Baumbach et al., 1984; Murray et al., 1989) or allantoic fluid of pseudopregnant pigs (Baumbach et al., 1986). Human uteroferrin, also referred to as human placental Type V acid phosphatase, can be purified as described by C. M. Ketcham et al. (1986). Uteroferrin has also been produced by recombinant techniques (Simmen et al., 1988; Ketcham et al., 1989).

C. Membrane-associated SCF

It is believed that the inactivated feeder cells supply the primordial germ cell culture with membrane-associated stem cell factor (SCF). Membrane-associated SCF lacks exon 6, which encodes a protease cleavage site. Feeder cells which provide membrane-associated SCF may be used in certain aspects of the present invention. Also preferred for use in certain aspects are feeder cells which have been engineered to overexpress membrane-associated SCF, or to solely express membrane-associated SCF.

d. Soluble SCF

Soluble stem cell factor (SCF) is another growth factor that may be used in particular embodiments of the present invention. SCF is a cytokine known to favor PGC survival and/or proliferation in vitro. SCF drastically reduces the incidence of apoptosis (programmed cell death) during the first hours of PGC culture (Pesce et al., 1993). C-kit ligand, the recently identified ligand for the kit tyrosine kinase receptor, is mapped to the mouse SI locus. This pleiotropic cytokine, alternately known as stem cell factor (SCF), mast cell growth factor (MGF) and steel-factor (SLF), plays essential roles in gametogenesis, melanogenesis and early stages of hematopoiesis. In vitro and in vivo, SCF can stimulate the proliferation of mature, as well as the proliferation and maturation of immature, mast cells. On purified primitive human and mouse hematopoietic precursors, SCF acts in a synergistic manner with various growth factors, such as IL-1, IL-3, IL-6, IL-7, and Epo, to induce myeloid, erythroid and lymphoid lineage colony formation. The finding that SCF is also expressed in the nervous system suggests a possible role for SCF in the development of the nervous system.

The cDNA sequences for human, mouse and rat SCF encode transmembrane proteins which are composed of a signal peptide, a 189 amino acid extracellular domain, a hydrophobic transmembrane domain and an intracellular domain. Native SCF can exist either as the membrane bound form or as a soluble form consisting of the first 164 or 165 amino acids of the extracellular domain. The soluble form is believed to be a proteolytic cleavage product of the transmembrane protein. Both the soluble and the transmembrane form of SCF have growth factor activities. Native soluble SCF is a heavily N- and O-glycosylated protein which exists as a non-covalently associated dimer in solution. All four cysteine residues of SCF monomers are involved in intramolecular disulfide bonds. Recombinant soluble SCF produced in E. coli is biologically active in in vitro bioassays, suggesting that glycosylation of the soluble form is not required for bioactivity in vitro. Murine or rat soluble SC is highly homologous to human soluble SCF (approximately 80%). Whereas both rat and mouse SCF are active on human cells, the human protein is much less active on mouse or rat cells.

The DNA sequence encoding the mature human SCF protein has been cloned (Martin et al., 1990). Recombinant human SCF from E. coli is available from R & D Systems (catalogue number 255-SC).

e. LIF

An additional growth factor that may be used in certain embodiments of the present invention is leukemia inhibitory factor (LIF). LIF is another cytokine that has also been shown to promote PGC survival by reducing apoptosis (Pesce et al., 1993). Leukemia inhibitory factor (LIF) was initially identified as a factor that inhibited the proliferation and induced the differentiation to macrophages of the murine myeloid leukemic cell line Ml. Subsequent to its purification and molecular cloning, LIF was recognized to be a pleiotropic factor with multiple effects on both hematopoietic and non-hematopoietic cells. LIF has overlapping biological functions with OSM, IL-6, IL-11 and CNTF. All these cytokines utilize gp130 as a component in their signal transducing receptor complexes.

Human LIF cDNA encodes a 202 amino acid residue polypeptide with a 22 amino acid residue signal peptide that is cleaved to yield a 180 amino acid residue mature human LIF. Native human and mouse LIF are highly glycosylated monomeric proteins. Both human and murine LIF protein sequences have multiple potential N- and O-linked glycosylation sites and six conserved cysteine residues that are involved in three intramolecular disulfide bridges. The non-glycosylated, *E. coli*-expressed, recombinant human LIF is indistinguishable from native LIF in its biological activities in vitro. Human and murine mature LIF exhibit a 78% sequence identity at the amino acid level. Whereas human LIF is equally active on both human and mouse cells, murine LIF is approximately 1000 fold less active on human cells.

Recombinant human LIF, expressed in *E. coli* as a fusion protein with glutathione S-transferase (GST), cleaved from GST and HPLC purified, is commercially available from R & D Systems (catalogue number 250-L). The inventors contemplate cloning LIF from cognate animal species (Section VIII). Towards the end of using cognate LIF from the selected animal species for the growth of PGCs, the inventors have optimized the known porcine LIF sequence for expression in yeast (SEQ ID NO:7; Section V).

f. Inhibitors of Apoptosis

A number of proteins have been shown to inhibit apoptosis, or programmed cell death. Since it has been shown that growth factors which inhibit apoptosis promote primordial germ cell survival (Pesce et al., 1993), this class of proteins is particularly preferred for use in the present invention. α2-macroglobulin is a particularly preferred example of an apoptosis inhibitor for use in certain aspects of the present invention. Also representative of this class are oncogenic proteins such as bcl-2 and family members including Bcl-x1, Mcl-1, Bak, A1, A20, and inhibitors of interleukin-1β-converting enzyme and family members. Preferred for use is bcl-2 (distinct from bcl-1, cyclin D1; GenBank Accession No. M14745, X06487). Overexpression of this oncogene was first discovered in T-cell lymphomas. It functions as an oncogene by binding and inactivating bax, a protein in the apoptotic pathway.

A number of additional factors are contemplated for use in the media compositions of the present invention, based on their ability to block, prevent, or reduce apoptosis. The calcium ionophore A23187 has been shown to block apoptosis in certain systems, such as when interleukin-3 (IL-3) is withdrawn from IL-3 dependent cells. N-Acetyl-L-cysteine has been shown to prevent apoptotic death of neuronal cells (Ferrari et al., 1995) and TNF-α induced apoptosis in U937 cells (Cossarizza et al., 1995). Nakajima et al. (1994) showed that actinomycin D, while a potent inducer of apoptosis in many cell lines, has been shown to suppress programmed cell death of PC12 cells induced by etoposide, an inhibitor of topoisomerase II These studies also showed that cycloheximide, nerve growth factor and epidermal growth factor also rescued PC12 cells from etoposide-induced death. Insulin-like growth factor-I (IGF-1) and the IGF-1 receptor were also shown to inhibit etoposide-induced apoptosis in BALB/c 3T3 cells (Sell et al., 1995).

3-Aminobenzamide has been shown to be an inhibitor of UV-induced apoptosis (Malorni et al., 1995). Aphidocolin potentiates apoptosis induced by arabinosyl nucleosides in leukemia cell lines, and inhibits vincristine-induced apoptosis in the p53-negative human prostate cancer cell line PC-3 (Borner et al., 1995). L-Ascorbic acid (vitamin C), catalase, follicle stimulating hormone, N-acetyl-L-cysteine, vasoactive intestinal peptide, cyclic GMP, hCG, interleukin-1β (IL-1β) and superoxide dismutase have all been shown to inhibit or suppress apoptosis in cultured rat ovarian follicles (Flaws et al., 1995; Tilly and Tilly 1995; Chun et al., 1995). Aurintricarboxylic acid has been shown to inhibit apoptotic cell death in various cell types induced by a variety of factors (Benchokroun et al., 1995).

BAPTA/AM [1,2,-bis(o-Aminophenoxy)ethane-N,N,N', N'-tetraacetic acid tetra (acetoxymethyl)ester] inhibits thapsigargin-induced apoptosis in rat thymocytes (Jiang et al., 1994). Caffeine has been shown to prevent apoptosis and cell cycle effects induced by camptothecin and topotecan in HL-60 cells (Traganos et al., 1993). Calpain inhibitor I inhibits apoptosis in thymocytes and metamyelocytes (Squier et al., 1994), while leupeptin, calpain inhibitor II and the E64 class of serine protease inhibitors have also been shown to inhibit activation-induced programmed cell death (Sarin et al., 1994). Cyclosporin A has been shown to prevent anti-IgM and ionomycin-induced apoptosis in BLB cell lines.

The general serine protease inhibitor 3,4-dichloroisocoumarin and the specific thiol reagent N-ethyl maleimide were shown to block apoptotic internucleosomal DNA cleavage in thymocytes without the involvement of endonucleases (Cain et al., 1994). The cysteine protease inhibitors E64 and leupeptin, the calpain selective inhibitor acetyl-leucyl-leucyl-normethional, and the serine protease inhibitors diisopropylfluorophosphate and phenylmethylsulfonyl fluoride were all shown to selectively block T-cell receptor-triggered programmed cell death in murine T-cell hybridoma and in activated peripheral T-cells (Sarin et al., 1993). Tetrodotoxin, nimodipine, verapamil, flunarizine and R56865 all protect bovine chromaffin cells from veratridine-induced cell death (Maroto et al., 1994).

Forskolin and insulin growth factor-1 (IGF-1) both have been shown to inhibit apoptosis in cerebellar granule cells, although by distinct mechanisms (Galli et al., 1995). The protein tyrosine kinase inhibitors genistein and herbimycin A have both been shown to prevent anti-CD3 monoclonal antibody-induced thymic apoptosis (Migita et al., 1994). Interleukin-6 (IL-6) inhibits constitutive, protein synthesis-independent apoptosis of murine B-cell hybridoma 7TD1 (Liu et al., 1994). The protein phosphatase inhibitors calyculin A and okadaic acid inhibit glucocorticoid-induced apoptosis in T-cell hybridomas (Gjertsen et al., 1994), and calyculin A is known to prevent γ-radiation induced apoptosis in Burkitt's lymphoma cell line BM13674.

The protein kinase C activator phorbol-12-myristate-13-acetate inhibits apoptosis induced by the Fas antigen (Tepper et al., 1995). 1-Pyrrolidinecarbodithioic acid prevents apoptosis in human promyeolocytic leukemia HL-60 cells and in thymocytes (Bessho et al., 1994). The calcium-channel blockers nifedipine and nisoldipine, as well as the endonuclease inhibitor aurintricarboxylic acid have been shown to block apoptosis in cultured human endothelial cells (Escargueil-Blanc et al., 1997). Spermine has been shown to inhibit morphological apoptosis, and the antioxidant thioredoxin inhibits apoptosis in Jurkat T-cells and human PBL blasts (Sata et al., 1995). Additionally, the protease inhibitors $N^\alpha$-Tosyl-L-Phe chloromethyl ketone, $N^\alpha$-Tosyl-L-Lys chloromethyl ketone, and to a lesser extent $N^\alpha$-Tosyl-L-Arg methyl ester inhibit apoptosis in thymocytes (Bruno et al., 1992).

3. Culture conditions

Optimization of conditions such as pH, percent $CO_2$, $pO_2$ and temperature for maximum growth of primordial germ cell cultures are well known to those of skill in the art. The preferred primordial germ cell culture conditions are about 5% $CO_2$ at about 38° C. in a humidified atmosphere.

C. Analysis of Primary Cultured Cells

For use in the present invention, the cultured primordial germ cells must be maintained in an undifferentiated state. There are a number of methods for determining whether cells are in an undifferentiated state. At present these methods are based on cellular morphology, or the expression of certain markers unique to either the undifferentiated state (positive screening) or the differentiated state (negative screening). The cellular morphology of undifferentiated cells is typically tightly packed cells, with a high nuclear/ cytoplasm ratio. Also, prominent nucleoli are often present in undifferentiated cells.

Screening methods are also preferred for use in the present invention. A preferred method for screening for the presence of undifferentiated cells is by screening for alkaline phosphatase activity. Studies have shown a good correlation between expression of alkaline phosphatase and stage of differentiation (Talbot et al., 1993a, 1993b). Also preferred for use in the present invention is screening for stage specific embryonic antigen 1 (SSEA-1), which is a positive screen characteristic of PGCs (Donovan et al., 1986) and undifferentiated ES and EC cells (Solter and Knowles, 1978). A negative screen preferred for use in the present invention is screening for cytokeratin 18, which is indicative of cells in the differentiated state (Piedrahita et al., 1990; Van Stekelenburg-Haers et al., 1995).

II. Transformation of Primordial Germ Cell-Derived Cell Lines

In certain preferred embodiments of the invention, the nucleic acid encoding the transgene may be stably integrated into the genome of the cell. In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the transgenic construct is delivered to a cell and where in the cell the nucleic acid remains is dependent on the type of transgenic construct employed.

A. Methods of Transformation

In order to effect expression of a gene construct, the expression construct must be delivered into a primordial germ cell. As described below, the preferred mechanism for delivery is via electroporation, calcium phosphate transformation or particle bombardment. However, several other methods for the transfer of transgenic constructs into primordial germ cells also are contemplated by the present invention. In one embodiment of the present invention, the transgenic construct may consist only of naked recombinant DNA or plasmids. Transfer of the construct may be performed by any of the methods mentioned which physically or chemically permeabilize the cell membrane.

1. Electroporation

In certain preferred embodiments of the present invention, the transgenic construct is introduced into the primordial germ cells via electroporation. Electroporation involves the exposure of a suspension of cells and DNA to a high-voltage electric discharge.

Transfection of eukaryotic cells using electroporation has been quite successful. Mouse pre-B lymphocytes have been transfected with human kappa-immunoglobulin genes (Potter et al., 1984), and rat hepatocytes have been transfected with the chloramphenicol acetyltransferase gene (Tur-Kaspa et al., 1986) in this manner.

It is contemplated that electroporation conditions for primordial germ cells from different sources may be optimized. One may particularly with to optimize such parameters as the voltage, the capacitance, the time and the electroporation media composition. The execution of other routine adjustments will be known to those of skill in the art.

Both primary porcine primordial germ cells and secondary (cultured) porcine primordial have been successfully transformed using electroporation (Example 3).

2. Particle Bombardment

One of the preferred embodiments of the invention for transferring a naked DNA construct into cells involves particle bombardment. This method depends on the ability to accelerate DNA-coated microprojectiles to a high velocity allowing them to pierce cell membranes and enter cells without killing them (Klein et al., 1987). The microprojectiles used have consisted of biologically inert substances such as tungsten, platinum or gold beads.

It is contemplated that in some instances DNA precipitation onto metal particles would not be necessary for DNA delivery to a recipient cell using particle bombardment. It is contemplated that particles may contain DNA rather than be coated with DNA. Hence it is proposed that DNA-coated particles may increase the level of DNA delivery via particle bombardment but are not, in and of themselves, necessary.

Several devices for accelerating small particles have been developed. One such device relies on a high voltage discharge to generate an electrical current, which in turn provides the motive force (Yang et al., 1990). Another method involves the use of a Biolistic Particle Delivery System, which can be used to propel particles coated with DNA through a screen, such as stainless steel or Nytex screen, onto a filter surface covered with cells in suspension. The screen disperses the particles so that they are not delivered to the recipient cells in large aggregates. It is believed that a screen intervening between the projectile apparatus and the cells to be bombarded reduces the size of projectile aggregates and may contribute to a higher frequency of transformation by reducing the damage inflicted on the recipient cells by projectiles that are too large.

For the bombardment, cells in suspension are preferably concentrated on filters, or alternatively on solid culture medium. The cells to be bombarded are positioned at an appropriate distance below the macroprojectile stopping plate. If desired, one or more screens are also positioned between the acceleration device and the cells to be bombarded.

In bombardment transformation, one may optimize the prebombardment culturing conditions and the bombardment parameters to yield the maximum numbers of stable transformants. Both the physical and biological parameters for bombardment are important in this technology. Physical factors are those that involve manipulating the DNA/ microprojectile precipitate or those that affect the flight and velocity or either the macro- or microprojectiles. Biological factors include all steps involved in manipulation of cells before and immediately after bombardment, the osmotic adjustment of target cells to help alleviate the trauma associated with bombardment, and also the nature of the transforming DNA, such as linearized DNA or intact supercoiled plasmids. It is believed that pre-bombardment manipulations are especially important for successful transformation of primordial germ cells.

Accordingly, it is contemplated that one may wish to adjust various of the bombardment parameters in small scale studies to fully optimize the conditions. One may particularly wish to adjust physical parameters such as gap distance, flight distance, tissue distance and helium pressure. One may also optimize the trauma reduction factors by modifying conditions which influence the physiological state of the recipient cells and which may therefore influence transformation and integration efficiencies. For example, the osmotic state, tissue hydration and the subculture stage or cell cycle of the recipient cells may be adjusted for optimum transformation. The execution of other routine adjustments will be known to those of skill in the art.

3. Viral Transformation a. Adenoviral Infection

One method for delivery of the transgenic constructs involves the use of an adenovirus expression vector. Although adenovirus vectors are known to have a low capacity for integration into genomic DNA, this feature is counterbalanced by the high efficiency of gene transfer afforded by these vectors. "Adenovirus expression vector" is meant to include those constructs containing adenovirus sequences sufficient to (a) support packaging of the construct and (b) to ultimately express a transgenic construct that has been cloned therein.

The vector comprises a genetically engineered form of adenovirus. Knowledge of the genetic organization or adenovirus, a 36 kb, linear, double-stranded DNA virus, allows substitution of large pieces of adenoviral DNA with foreign sequences up to 7 kb (Grunhaus and Horwitz, 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification.

Adenovirus is particularly suitable for use as a gene transfer vector because of its mid-sized genome, ease of manipulation, high titer, wide target-cell range and high infectivity. Both ends of the viral genome contain 100–200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off (Renan, 1990). The products of the late genes, including the majority of the viral capsid proteins, are expressed only after significant processing of a single primary transcript issued by the major late promoter (MLP). The MLP, (located at 16.8 m.u.) is particularly efficient during the late phase of infection, and all the mRNA's issued from this promoter possess a 5'-tripartite leader (TPL) sequence which makes them preferred mRNA's for translation.

In a current system, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and examine its genomic structure.

Generation and propagation of the current adenovirus vectors, which are replication deficient, depend on a unique helper cell line, designated 293, which was transformed from human embryonic kidney cells by Ad5 DNA fragments and constitutively expresses E1 proteins (Graham et al., 1977). Since the E3 region is dispensable from the adenovirus genome (Jones and Shenk, 1978), the current adenovirus vectors, with the help of 293 cells, carry foreign DNA in either the E1, the D3 or both regions (Graham and Prevec, 1991). In nature, adenovirus can package approximately 105% of the wild-type genome (Ghosh-Choudhury et al., 1987), providing capacity for about 2 extra kb of DNA. Combined with the approximately 5.5 kb of DNA that is replaceable in the E1 and E3 regions, the maximum capacity of the current adenovirus vector is under 7.5 kb, or about 15% of the total length of the vector. More than 80% of the adenovirus viral genome remains in the vector backbone.

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the preferred helper cell line is 293.

Recently, Racher et al. (1995) disclosed improved methods for culturing 293 cells and propagating adenovirus. In one format, natural cell aggregates are grown by inoculating individual cells into 1 liter siliconized spinner flasks (Techne, Cambridge, UK) containing 100– 200 ml of medium. Following stirring at 40 rpm, the cell viability is estimated with trypan blue. In another format, Fibra-Cel microcarriers (Bibby Sterlin, Stone, UK) (5 g/l) is employed as follows. A cell inoculum, resuspended in 5 ml of medium, is added to the carrier (50 ml) in a 250 ml Erlenmeyer flask and left stationary, with occasional agitation, for 1 to 4 h. The medium is then replaced with 50 ml of fresh medium and shaking initiated. For virus production, cells are allowed to grow to about 80% confluence, after which time the medium is replaced (to 25% of the final volume) and adenovirus added at an MOI of 0.05. Cultures are left stationary overnight, following which the volume is increased to 100% and shaking commenced for another 72 h.

Other than the requirement that the adenovirus vector be replication defective, or at least conditionally defective, the nature of the adenovirus vector is not believed to be crucial to the successful practice of the invention. The adenovirus may be of any of the 42 different known serotypes or subgroups A–F. Adenovirus type 5 of subgroup C is the preferred starting material in order to obtain the conditional replication-defective adenovirus vector for use in the present invention. This is because Adenovirus type 5 is a human adenovirus about which a great deal of biochemical and genetic information is known, and it has historically been used for most constructions employing adenovirus as a vector.

As stated above, the typical vector according to the present invention is replication defective and will not have an adenovirus E1 region. Thus, it will be most convenient to introduce the transforming construct at the position from which the E1-coding sequences have been removed. However, the position of insertion of the construct within the adenovirus sequences is not critical to the invention. The polynucleotide encoding the gene of interest may also be inserted in lieu of the deleted E3 region in E3 replacement vectors as described by Karlsson et al. (1986) or in the E4 region where a helper cell line or helper virus complements the E4 defect.

Adenovirus growth and manipulation is known to those of skill in the art, and exhibits broad host range in vitro and in vivo. This group of viruses can be obtained in high titers, e.g., $10^9$–$10^{11}$ plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus (Couch et al., 1963; Top et al., 1971), demonstrating their safety and therapeutic potential as in vivo gene transfer vectors.

Adenovirus vectors have been used in eukaryotic gene expression (Levrero et al., 1991; Gomez-Foix et al., 1992) and vaccine development (Grunhaus and Horwitz, 1992; Graham and Prevec, 1992). Recently, animal studies suggested that recombinant adenovirus could be used for gene therapy (Stratford-Perricaudet and Perricaudet, 1991; Stratford-Perricaudet et al., 1990; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993) and stereotactic inoculation into the brain (Le Gal La Salle et al., 1993).

b. AAV Infection

Adeno-associated virus (AAV) is an attractive vector system for use in the present invention as it has a high frequency of integration and it can infect nondividing cells, thus making it useful for delivery of genes into mammalian cells in tissue culture (Muzyczka, 1992). AAV has a broad host range for infectivity (Tratschin, et al., 1984; Laughlin, et al., 1986; Lebkowski, et al., 1988; McLaughlin, et al., 1988), which means it is applicable for use with the present invention. Details concerning the generation and use of rAAV vectors are described in U.S. Pat. No. 5,139,941 and U.S. Pat. No. 4,797,368, each incorporated herein by reference.

Studies demonstrating the use of AAV in gene delivery include LaFace et al. (1988); Zhou et al. (1993); Flotte et al. (1993); and Walsh et al. (1994). Recombinant AAV vectors have been used successfully for in vitro and in vivo transduction of marker genes (Kaplitt, et al., 1994; Lebkowski, et al., 1988; Samulski, et al., 1989; Shelling and Smith, 1994; Yoder, et al., 1994; Zhou, et al., 1994; Hermonat and Muzyczka, 1984; Tratschin, et al., 1985; McLaughlin, et al., 1988) and genes involved in human diseases (Flotte, et al., 1992; Luo, et al., 1994; Ohi, et al., 1990; Walsh, et al., 1994; Wei, et al., 1994). Recently, an AAV vector has been approved for phase I human trials for the treatment of cystic fibrosis.

AAV is a dependent parvovirus in that it requires coinfection with another virus (either adenovirus or a member of the herpes virus family) to undergo a productive infection in cultured cells (Muzyczka, 1992). In the absence of coinfection with helper virus, the wild type AAV genome integrates through its ends into human chromosome 19 where it resides in a latent state as a provirus (Kotin et al., 1990; Samulski et al., 1991). rAAV, however, is not restricted to chromosome 19 for integration unless the AAV Rep protein is also expressed (Shelling and Smith, 1994). When a cell carrying an AAV provirus is superinfected with a helper virus, the AAV genome is "rescued" from the chromosome or from a recombinant plasmid, and a normal productive infection is established (Samulski, et al., 1989; McLaughlin, et al., 1988; Kotin, et al., 1990; Muzyczka, 1992).

Typically, recombinant AAV (rAAV) virus is made by cotransfecting a plasmid containing the gene of interest flanked by the two AAV terminal repeats (McLaughlin et al., 1988; Samulski et al., 1989; each incorporated herein by reference) and an expression plasmid containing the wild type AAV coding sequences without the terminal repeats, for example pIM45 (McCarty et al., 1991; incorporated herein by reference). The cells are also infected or transfected with adenovirus or plasmids carrying the adenovirus genes required for AAV helper function. rAAV virus stocks made in such fashion are contaminated with adenovirus which must be physically separated from the rAAV particles (for example, by cesium chloride density centrifugation). Alternatively, adenovirus vectors containing the AAV coding regions or cell lines containing the AAV coding regions and some or all of the adenovirus helper genes could be used (Yang et al., 1994a; Clark et al., 1995). Cell lines carrying the rAAV DNA as an integrated provirus can also be used (Flotte et al., 1995).

c. Retroviral Infection

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding a transgene of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

Concern with the use of defective retrovirus vectors is the potential appearance of wild-type replication-competent virus in the packaging cells. This can result from recombination events in which the intact sequence from the recombinant virus inserts upstream from the gag, pol, env sequence integrated in the host cell genome. However, new packaging cell lines are now available that should greatly decrease the likelihood of recombination (Markowitz et al., 1988; Hersdorffer et al., 1990).

d. Other Viral Vectors

Other viral vectors may be employed as constructs in the present invention. Vectors derived from viruses such as vaccinia virus (Ridgeway, 1988; Baichwal and Sugden, 1986; Coupar et al., 1988) and herpesviruses may be employed. They offer several attractive features for various mammalian cells (Friedmann, 1989; Ridgeway, 1988; Baichwal and Sugden, 1986; Coupar et al., 1988; Horwich et al., 1990).

With the recent recognition of defective hepatitis B viruses, new insight was gained into the structure-function relationship of different viral sequences. In vitro studies showed that the virus could retain the ability for helper-dependent packaging and reverse transcription despite the deletion of up to 80% of its genome (Horwich et al., 1990). This suggested that large portions of the genome could be replaced with foreign genetic material. Chang et al. recently introduced the chloramphenicol acetyltransferase (CAT) gene into duck hepatitis B virus genome in the place of the polymerase, surface, and pre-surface coding sequences. It was cotransfected with wild-type virus into an avian hepatoma cell line. Culture media containing high titers of the recombinant virus were used to infect primary duckling hepatocytes. Stable CAT gene expression was detected for at least 24 days after transfection (Chang et al., 1991).

In still further embodiments of the present invention, the nucleic acids to be delivered are housed within an infective virus that has been engineered to express a specific binding ligand. The virus particle will thus bind specifically to the cognate receptors of the target cell and deliver the contents to the cell. A novel approach designed to allow specific targeting of retrovirus vectors was recently developed based on the chemical modification of a retrovirus by the chemical addition of lactose residues to the viral envelope. This modification can permit the specific infection of hepatocytes via sialoglycoprotein receptors.

Another approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

4. Calcium Phosphate Co-Precipitation or DEAE-Dextran Treatment

In other preferred embodiments of the present invention, the transgenic construct is introduced to the cells using calcium phosphate co-precipitation. Mouse primordial germ cells have been transfected with the SV40 large T antigen, with excellent results (Watanabe et al., 1997). Human KB cells have been transfected with adenovirus 5 DNA (Graham and Van Der Eb, 1973) using this technique. Also in this manner, mouse L(A9), mouse C127, CHO, CV-1, BHK, NIH3T3 and HeLa cells were transfected with a neomycin marker gene (Chen and Okayama, 1987), and rat hepatocytes were transfected with a variety of marker genes (Rippe et al., 1990).

In another embodiment, the expression construct is delivered into the cell using DEAE-dextran followed by polyethylene glycol. In this manner, reporter plasmids were introduced into mouse myeloma and erythroleukemia cells (Gopal, 1985).

5. Direct Microinjection or Sonication Loading

Further embodiments of the present invention include the introduction of the transgenic construct by direct microinjection or sonication loading. Direct microinjection has been used to introduce nucleic acid constructs into Xenopus oocytes (Harland and Weintraub, 1985), and LTK⁻ fibroblasts have been transfected with the thymidine kinase gene by sonication loading (Fechheimer et al., 1987).

6. Liposome Mediated Transformation

In a further embodiment of the invention, the transgenic construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated is a transgenic construct complexed with Lipofectamine (Gibco BRL).

Liposome-mediated nucleic acid delivery and expression of foreign DNA in vitro has been very successful (Nicolau and Sene, 1982; Fraley et al., 1979; Nicolau et al., 1987). Wong et al. (1980) demonstrated the feasibility of liposome-mediated delivery and expression of foreign DNA in cultured chick embryo, HeLa and hepatoma cells.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1.

7. Adenoviral Assisted Transfection

In certain embodiments of the present invention, the transgenic construct is introduced into the cell using adenovirus assisted transfection. Increased transfection efficiencies have been reported in cell systems using adenovirus coupled systems (Kelleher and Vos, 1994; Cotten et al., 1992; Curiel, 1994), and the inventors contemplate using the same technique to increase transfection efficiencies.

8. Receptor Mediated Transfection

Still further constructs that may be employed to deliver the transgenic construct to the target cells are receptor-mediated delivery vehicles. These take advantage of the selective uptake of macromolecules by receptor-mediated endocytosis that will be occurring in the target cells. In view of the cell type-specific distribution of various receptors, this delivery method adds a degree of specificity to the present invention. Specific delivery in the context of another mammalian cell type is described by Wu and Wu (1993; incorporated herein by reference).

Certain transgenic delivery constructs comprise a cell receptor-specific ligand and a DNA-binding agent. Others comprise a cell receptor-specific ligand to which the DNA construct to be delivered has been operatively attached. Several ligands have been used for receptor-mediated gene transfer (Wu and Wu, 1987; Wagner et al., 1990; Ferkol et al., 1993; Perales et al., 1994; Myers, EPO 0273085), which establishes the operability of the technique.

In other embodiments, the DNA delivery vehicle component may comprise a specific binding ligand in combination with a liposome. The nucleic acids to be delivered are housed within the liposome and the specific binding ligand is functionally incorporated into the liposome membrane. The liposome will thus specifically bind to the receptors of the target cell and deliver the contents to the cell. Such systems have been shown to be fimctional using systems in which, for example, epidermal growth factor (EGF) is used in the receptor-mediated delivery of a nucleic acid to cells that exhibit upregulation of the EGF receptor.

In still further embodiments, the DNA delivery vehicle component of the delivery vehicles may be a liposome itself, which will preferably comprise one or more lipids or glycoproteins that direct cell-specific binding. For example, Nicolau et al. (1987) employed lactosyl-ceramide, a galactose-terminal asialoganglioside, incorporated into liposomes and observed an increase in the uptake of the insulin gene by hepatocytes. It is contemplated that the transgenic constructs of the present invention can be specifically delivered into the target cells in a similar manner.

B. Vector Construction

Vectors for use in the present invention have at least one coding sequence encoding a selected transgene. The selected transgene can be a marker gene encoding a marker protein, or another transgene of interest (Sections D and E below). Additionally preferred are vectors that contain a marker gene and one or more additional transgenes. The transgenes are preferably operatively positioned with a promoter, to drive transcription of the transgene(s). Enhancers may be included in the vectors to further increase transcription.

Further embodiments of the vectors for use in the present invention include sequences which flank the transgene and promote homologous recombination of the transgene into the genome of the host animal. In certain embodiments, the vector will contain a cellular transforming construct (for example an oncogene), which will immortalize the cell lines to allow complex genetic manipulation. In these embodiments, the transforming transgene will be flanked by sequences which allow for excision of the transgene under appropriate conditions. By removing the transforming construct, the cells can return to their normal state, and be used in the production of transgenic animals. In other embodiments, the sequences which promote excision of the transgene can be used with non-cellular transforming transgenes, when the eventual removal of the transgene from the genome of the host animal is desired.

C. Promoters

The promoters and enhancers that control the transcription of protein encoding genes in eukaryotic cells are composed of multiple genetic elements. The cellular machinery is able to gather and integrate the regulatory information conveyed by each element, allowing different genes to evolve distinct, often complex patterns of transcriptional regulation.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7–20 bp of DNA, and containing one or more recognition sites for transcriptional activator proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV 40 late genes, a discrete element overlying the start site itself helps to fix the place of initiation.

Additional promoter elements regulate the frequency of transcriptional initiation. Typically, these are located in the region 30–110 bp upstream of the start site, although a number of promoters have recently been shown to contain functional elements downstream of the start site as well. The spacing between elements is flexible, so that promoter function is preserved when elements are inverted or moved relative to one another. In the tk promoter, the spacing between elements can be increased to 50 bp apart before activity begins to decline. Depending on the promoter, it appears that individual elements can function either co-operatively or independently to activate transcription.

Enhancers were originally detected as genetic elements that increased transcription from a promoter located at a distant position on the same molecule of DNA. This ability to act over a large distance had little precedent in classic studies of prokaryotic transcriptional regulation. Subsequent work showed that regions of DNA with enhancer activity are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Aside from this operational distinction, enhancers and promoters are very similar entities.

Promoters and enhancers have the same general function of activating transcription in the cell. They are often overlapping and contiguous, often seeming to have a very similar modular organization. Taken together, these considerations suggest that enhancers and promoters are homologous entities and that the transcriptional activator proteins bound to these sequences may interact with the cellular transcriptional machinery in fundamentally the same way.

In any event, it will be understood that promoters are DNA elements which when positioned functionally upstream of a gene leads to the expression of that gene. Most transgene constructs of the present invention are functionally positioned downstream of a promoter element.

1. Promoters Specific for Undifferentiated Cells

Preferred for use in the present invention are promoters which are active in undifferentiated cells. Studies have shown that the CMV promoter is not optimized for expression in undifferentiated cells (Example 3). Promoters that lead to high levels of expression in undifferentiated cells include the phosphoglycerate kinase (pgk) promoter and the octamer binding transcription factor 4 (Oct-4) promoter. The pgk promoter is known to lead to high levels of expression in undifferentiated mouse ES cells.

Transgenic experiments have identified a regulatory region upstream of the Oct-4 gene that is capable of targeting high level expression to the undifferentiated inner cell mass and the primordial germ cells (Yeom et al., 1996). By using the Oct-4 promoter, expression would be limited to highly undifferentiated cells and PGCs, thereby allowing for selection of the cells with the highest probability of contributing to the germ line by measurement of the expression levels of a selected marker protein, preferably green fluorescent protein. Use of the Oct-4 promoter also allows for early screening of putative transgenic animals, saving considerable time and expense, by not requiring that chimeras be saved until breeding age for testing, and by not requiring expensive and prolonged breeding tests.

The inventors contemplate cloning of the Oct-4 gene from a variety of animal species (Section V), for use in the present invention.

2. Eukaryotic and Viral Promoters and Enhancers

Preferred for use in the present invention is the cytomegalovirus (CMV) promoter. This promoter is commercially available from Invitrogen in the vector pcDNAIII, which is preferred for use in the present invention. Below are a list of additional viral promoters, cellular promoters/enhancers and inducible promoters/enhancers that could be used in combination with the present invention. Additionally any promoter/enhancer combination (as per the Eukaryotic Promoter Data Base EPDB) could also be used to drive expression of structural genes encoding oligosaccharide processing enzymes, protein folding accessory proteins, selectable marker proteins or a heterologous protein of interest.

TABLE 1

Inducible Elements

| Element | Inducer | References |
|---|---|---|
| MT II | Phorbol Ester (TFA) Heavy metals | Palmiter et al., 1982; Haslinger and Karin, 1985; Searle et al., 1985; Stuart et al., 1985; Imagawa et al., 1987; Karin ®, 1987; Angel et al., 1987b; McNeall et al., 1989 |
| MMTV (mouse mammary tumor virus) | Glucocorticoids | Huang et al., 1981; Lee et al., 1981; Majors and Varmus, 1983; Chandler et al., 1983; Lee et al., 1984; Fonta et al., 1985; Sakai et al., 1986 |
| β-Interferon | poly(rI)X poly(rc) | Tavernier et al., 1983 |
| Adenovirus 5 E2 | E1a | Imperiale and Nevins, 1984 |
| Collagenase | Phorbol Ester (TPA) | Angle et al., 1987a |
| Stromelysin | Phorbol Ester (TPA) | Angle et al., 1987b |
| SV40 | Phorbol Ester (TFA) | Angel et al., 1987b |
| Murine MX Gene | Interferon, Newcastle Disease Virus | |
| GRP78 Gene | A23187 | Resendez et al., 1988 |
| α-2-Macroglobulin | IL-6 | Kunz et al., 1989 |
| Vimentin | Serum | Rittling et al., 1989 |
| MHC Class I Gene H-2κb | Interferon | Blanar et al., 1989 |
| HSP70 | E1a, SV40 Large T Antigen | Taylor et al., 1989; Taylor and Kingston, 1990a,b |
| Proliferin | Phorbol Ester-TPA | Mordacq and Linzer, 1989 |
| Tumor Necrosis Factor | FMA | Hensel et al., 1989 |
| Thyroid Stimulating Hormone α Gene | Thyroid Hormone | Chatterjee et al., 1989 |

TABLE 2

Other Promoter/Enhancer Elements

| Promoter/ Enhancer | References |
|---|---|
| Immunoglobulin Heavy Chain | Hanerji et al., 1983; Gilles et al., 1983; Grosschedl and Baltimore, 1985; Atchinson and Perry, 1986, 1987; Imler et al., 1987; Weinberger et al., 1988; Kiledjian et al., 1988; Porton et al., 1990 |
| Immunoglobulin Light Chain | Queen and Baltimore, 1983; Picard and Schaffner, 1984 |
| T-Cell Receptor | Luria et al., 1987, Winoto and Baltimore, 1989; Redondo et al., 1990 |
| HLA DQ α and DQ β | Sullivan and Peterlin, 1987 |
| β-Interferon | Goodbourn et al., 1986; Fujita et al., 1987; Goodbourn and Maniatis, 1985 |
| Interleukin-2 | Greene et al., 1989 |
| Interleukin-2 Receptor | Greene et al., 1989; Lin et al., 1990 |
| MHC Class II 5 | Koch et al., 1989 |
| MHC Class II HLA-DRα | Sherman et al., 1989 |
| β-Actin | Kawamoto et., 1988; Ng et al., 1989 |
| Muscle Creatine Kinase | Jaynes et al., 1988; Horlick and Benfield, 1989; Johnson et al., 1989a |
| Prealbumin (Transthyretin) | Costa et al., 1988 |
| Elastase I | Omitz et al., 1987 |
| Metallothionein | Karin et al., 1987; Cullotta and Hamer, 1989 |
| Collagenase | Pinkert et al., 1987, Angel et al., 1987 |
| Albumin Gene | Pinkert et al., 1987, Tronche et al., 1989, 1990 |
| α-Fetoprotein | Godbout et al., 1988; Campere and Tilghman, 1989 |
| t-Globin | Bodine and Ley, 1987; Perez-Stable and Constanini, 1990 |
| β-Globin | Trudel and Constantini, 1987 |
| e-fos | Cohen et al., 1987 |
| c-HA-ras | Triesman, 1986; Deschamps et al., 1985 |
| Insulin | Edlund et al., 1985 |
| Neural Cell Adhesion Molecule (NCAM) | Hirsch et al., 1990 |
| $a_{1\text{-Antitrypain}}$ | Latimer et al., 1990 |
| H2B (TH2B) Histone | Hwang et al., 1990 |
| Mouse or Type I Collagen | Ripe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |
| Troponin I (TN I) | Yutzey et al., 1989 |
| Platelet-Derived Growth Factor | Pech et al., 1989 |
| Dochenne Muscular Dystrophy | Klamut et al., 1990 |
| SV40 | Banerji et., 1981; Moreau et al., 1981; Sleigh and Lockett, 1985; Firak and Subramanian, 1986; Herr and Clarke, 1986; Imbra and Karin, 1986; Kadesch and Berg, 1986; Wang and Calame, 1986; Ondek et al., 1987; Kuhl et al., 1987 Schaffner et al., 1988 |
| Polyoma | Swartzendruber and Lehman, 1987; Vasseur et al., 1980; Katinka et al., 1980, 1981; Tyndell et al., 1981; Dandolo et al., 1983; deVilliers et al., 1984; Hen et al., 1986; Satake et al., 1988; Campbell and Villareal, 1988 |
| Retroviruses | Kriegler and Botchan, 1982, 1983; Levinson et al., 1982; Kriegler et al., 1983, 1984a,b, 1988; Bosze et al., 1986; Miksicek et al., 1986; Celander and Haseltine, 1987; Thiesen et al., 1988; Celander et al., 1988; Chol et al., 1988; Reisman and Rotter, 1989 |
| Papilloma Virus | Campo et al., 1983; Lusky et al., 1983; Spandidos and Wilkie, 183; Spalholz et al., 1985; Lusky and Botchan, 1986; Cripe et al., 1987; Gloss et al., 1987; Hirochika et al., 1987, Stephens and Hentschel, 1987; Glue et al., 1988 |
| Hepatits B Virus | Bulla and Siddiqui, 1986; Jameel and Siddiqui, 1986; Shaul and Ben-Levy, 1987; Spandau and Lee, 1988; Vannice and Levinson, 1988 |
| Human Immunodeficiency Virus | Muesing et al., 1987; Hauber and Cullan, 1988; Jakobovits et al., 1988; Feng and Holland, 1988; Takebe et al., 1988; Rowen et al., 1988; Berkhout et al., 1989; Laspia et al., 1989; Sharp and Marciniak, 1989; Braddock et al., 1989 |
| Cytomegalovirus | Weber et al., 1984; Boshart et al., 1985; Foecking and Hofstetter, 1986 |

TABLE 2-continued

Other Promoter/Enhancer Elements

| Promoter/Enhancer | References |
|---|---|
| Gibbon Ape Leukemia Virus | Holbrook et al., 1987; Quinn et al., 1989 |

D. Marker Genes and Proteins

The present invention also provides recombinant candidate screening and selection methods which are based upon whole cell assays and which, preferably, employ a reporter gene that confers on its recombinant hosts a readily detectable phenotype that emerges only under conditions where a general DNA promoter positioned upstream of the reporter gene is functional. Generally, reporter genes encode a polypeptide (marker protein) not otherwise produced by the host cell which is detectable by analysis of the cell culture, e.g., by fluorometric, radioisotopic or spectrophotometric analysis of the cell culture.

1. Screening

Exemplary enzymes include esterases, phosphatases, proteases (tissue plasminogen activator or urokinase) and other enzymes capable of being detected by their activity, as will be known to those skilled in the art. More preferred for use in the present invention is green fluorescent protein (GFP) as a marker for transgene expression (Chalfie et al., 1994). The use of GFP does not need exogenously added substrates, only irradiation by near UV or blue light, and thus has significant potential for use in monitoring gene expression in living cells. As the previously existing selection procedures for identifying correctly modified cells required culture of the manipulated cells for 10–14 days in a chemical known as G418, it was necessary to pass the cells to fresh feeders during the selection procedure. However, the use of the green fluorescent protein (GFP) as an identification marker allows for identification of transgenic colonies without the need for passage or addition of selectable media. As a results the cells remain healthier and, since are not passaged repeatedly, maintain their ability to generate a living offspring after nuclear transfer or blastocyst injection.

Other preferred examples are the enzyme chlorarnphenicol acetyltransferase (CAT) which may be employed with a radiolabelled substrate, firefly and bacterial luciferase, and the bacterial enzymes β-galactosidase and β-glucuronidase. Other marker genes within this class are well known to those of skill in the art, and are suitable for use in the present invention.

2. Selection

Another class of reporter genes which confer detectable characteristics on a host cell are those which encode polypeptides, generally enzymes, which render their transformants resistant against toxins. Examples of this class of reporter genes are the neo gene (Colberre-Garapin et al., 1981) which protects host cells against toxic levels of the antibiotic G418, the gene conferring streptomycin resistance (U.S. Pat. No. 4,430,434), the gene conferring hygromycin B resistance (Santerre et al., 1984; U.S. Pat. Nos. 4,727,028, 4,960,704 and 4,559,302), a gene encoding dihydrofolate reductase, which confers resistance to methotrexate (Alt et al., 1978), the enzyme HPRT, along with many others well known in the art (Kaufman, 1990).

E. Transgenes of Interest

As discussed above, transgenic animals have a wide variety of uses. This utility is realized through the introduction of different classes of genes, the class of gene introduced depending upon the desired goal. Tables 3 and 4 below, while not limiting in any way, are exemplary of some of the types of transgenes that can be introduced into non-rodent animals using the methods of the present invention.

TABLE 3

ORAL IMMUNOGENS

| Disease | Antigen | Reference |
|---|---|---|
| Amoebic dysentery | SREHP | Zhang et al., 1995 |
| Leishmaniasis | GP63 | Xu et al., 1995 |
| Respiratory tract infection (pigs) | Actinobacillus pleuropneumoniae | Hensel et al., 1995 Jain and Michael, 1995 |
| Respiratory tract infection (pigs) | pseudomonas aeruynosa OprF | |
| Hepatitis | | |

AUTOIMMUNE

| | | |
|---|---|---|
| Multiple sclerosis | Myelin Basic protein | Weiner et al., 1995 |
| Diabetes (auto-immune type) | Insulin | Weiner et al., 1995 |

ANTIBODY PRODUCTION

| Transplantation | Protein | Reference |
|---|---|---|
| | hCD59 | Kroshus et al., 1996 |
| | DAF (CD55) | van Denderen et al., 1996 |
| | Modification of class I and II MHC protein | |

BIOPHARMACEUTICALS

| | | |
|---|---|---|
| Hemophilia | Factor IX | Clark et al., 1989 |
| | Urokinase | Meade et al., 1990 |
| Emphysema | α-antitrypsin | Archibald et al., 1990 |
| Stroke | Tissue plasminogen activator | Gordon et al., 1987 |
| Cancer | Interleukins | Buhler et al., 1989 |
| Burns | Collagen | |
| Cancer | Interferons | Houdebine, 1994 |
| Heart Attack | Protein C | Houdebine, 1994 |
| Growth | | Pursel and Rexroad, 1993 |
| Disease resistance | | Brem, 1993; Clements et al., 1994; Lo et al., 1991; Weidle et al., 1991 |
| Wood characteristics | | Bullock et al., 1995 |

MILK COMPOSITION
(Adapted from Clark, 1992; Yom and Bremel, 1993; Houdebine, 1994)

| Change | Consequence |
|---|---|
| Increase α- and β-caseins | Enhanced curd firmness for cheese-making, improved thermal stability, increased calcium content |
| Increase phosphorylation sites in caseins | Increased calcium content, improved emulsification |
| Introduce proteolytic sites in caseins | Increased rate of textural development (improved cheese ripening) |
| Increase κ-casein concentration | Enhanced stability of casein aggregates, decreased micelle size, decreased gelation and coagulation |
| Eliminate β-lactoglobulin | Decreased high temperature gelatin, improved digestibility, decreased allergenic response, decreased primary source of cysteine in milk |
| Decrease α-lactalbumin | Decreased lactose, increase market potential of fluid milk, decreased ice crystal formation, compromise osmotic regulation of mammary gland |

TABLE 3-continued

| | |
|---|---|
| Add human lactoferrin | Enhanced iron absorption, protect against gut infections |
| Add proteolytic sites to κ-casein | Increased rate of cheese ripening |
| Decrease expression of acetyl CoA carboxylase | Decreased fat content, improved nutritional quality, reduce milk production costs |
| Express immunoglobulin genes | Protection against pathogens such as salmonella and listeria |
| Replace bovine milk proteins genes with human equivalents | mimic human breast milk |

| Other Protein Classes | Individual Members |
|---|---|
| blood proteins | clotting factors VIII and IX, complement factors or components, hemaglobins |
| hormones | insulin, growth hormone, thyroid hormone, catecholamines gonadotrophins, PMSG, trophic hormones, prolactin, oxytocin, dopamine |
| growth factors | EGF, PDGF, NGF, IGF |
| cytokines | interleukins, CSF, GMCSF, TNF-α, TGF-α and TGF-β |
| enzymes | tissue plasminogen activator, streptokinase, cholesterol biosynthetic or degradative, digestive, steroidogenic, kinases, phophodiesterases, methylases, de-methylases, dehydrogenases, cellulases, proteases, glycosolases, lipases, phospholipases, aromatase, cytochromes, adenylate or guyanylate cyclases |
| hormone or other receptors | LDL, HDL, steroid, protein, peptide, lipid or prostaglandin |
| binding proteins | steroid, growth hormone or growth factor binding proteins |
| immune system proteins | antibodies, SLA or MHC genes |
| antigens | bacterial, parasitic, viral, allergens |
| muscle proteins | myosin, tropomyosin |

TABLE 4

Selected Cloned Structural Genes

| Gene | Clone Type* | Reference |
|---|---|---|
| activin | porcine-cDNA | Mason AJ, Nat, 318:659, 1985 |
| adenosine deaminase | h-cDNA | Wiginton DA, PNAS, 80:7481, 1983 |
| angiotensinogen I | r-cDNA | Ohkubo H, PNAS, 80:2196, 1983 |
| | r-gDNA | Tanaka T, JBC, 259:8063, 1984 |
| antithrombin III | H-cDNA | Bock SC, NAR 10:8113, 1982 |
| | h-cDNA and gDNA | Prochownik EV, JBC, 258:8389, 1983 |
| antitrypsin, alpha I | h-cDNA | Kurachi K, PNAS, 78:6826, 1981 |
| | h-gDNA | Leicht M, Nat, 297:655, 1982 |
| | RFLP | Cox DW, AJHG, 36:134S, 1984 |
| apolipoprotein A-I | h-cDNA, h-gDNA | Shoulders CC, NAR, 10:4873, 1982 |
| | RFLP | Karathanasis SK, Nat, 301:718, 1983 |
| | h-gDNA | Kranthanasis SK, PNAS, 80:6147, 1983 |
| apolipoprotein A-II | h-cDNA Chr | Sharpe CR, NAR, 12:3917, 1984 Sakaguchi, AY, AJHB, 36:207S, 1984 |
| | h-cDNA | Knott TJ, BBRCm 120:734, 1984 |
| apolipoprotein C-I | h-cDNA | Knott TJ, NAR, 12:3909, 1984 |
| apolipoprotein C-II | h-cDNA | Jackson CL, PNAS, 81:2945, 1984 |
| | h-cDNA | Mykelbost O, JBC, 249:4401, 1984 |
| | h-cDNA | Fojo SS, PNAS, 81:6354, 1984 |
| | RFLP | Humphries SE, C Gen, 26:389, 1984 |
| apolipoprotein C-III | h-cDNA and gDNA | Karanthanasis SK, Nat, 304:371, 1983 |
| | h-cDNA | Sharpe CR, NAR, 12:3917, 1984 |
| apolipoprotein E | h-cDNA | Brewslow JL, JBC, 257:14639, 1982 |
| atrial natriuetic factor | h-cDNA | Oikawa S, Nat, 309:724, 1984 |
| | h-cDNA | Nakayama K, Nat, 310:699, 1984 |
| | h-cDNA | Zivin RA, PNAS, 81:6325, 1984 |

TABLE 4-continued

Selected Cloned Structural Genes

| Gene | Clone Type* | Reference |
|---|---|---|
| | h-gDNA | Seidman CE, Sci, 226:1206, 1984 |
| | h-gDNA | Nemer M, Nat, 312:654, 1984 |
| | h-gDNA | Greenberg BI, Nat, 412:665, 1984 |
| chorionic gonadotropin, alpha chain | h-cDNA | Fiddles JC, Nat, 281:351, 1981 |
| | RFLP | Boethby M, JBC, 256:521,1981 |
| chorionic gonadotropin, beta chain | h-cDNA | Fiddles JC, Nat, 286:684, 1980 |
| | h-gDNA | Boorsetin WR, Nat, 300:419, 1982 |
| | h-gDNA | Talmadge K, Nat, 307:37, 1984 |
| chymosin, pro (rennin) | bovine-cDNA | Harris TJR, NAR, 10:2177, 1982 |
| complement, factor B | h-cDNA | Woods DE, PNAS, 79:521, 1982 |
| | h-cDNA and h-gDNA | Duncan R, PNAS, 80:664, 1983 |
| complement, C2 | h-cDNA | Bentley DR, PNAS, 81:1212, 1984 |
| | h-gDNA (C2, C4, and B) | Carroll MC, Nat, 307:237, 1984 |
| complement C3 | m-cDNA | Domdey H, PNAS, 79:7619, 1983 |
| | h-gDNA | Whitehead AS, PNAS, 79:5021, 1982 |
| complement C4 | h-cDNA and gDNA | Carroll MC, PNAS, 80:264, 1983 |
| | h-cDNA | Whitehead AS, PNAS, 79:5021, 1982 |
| complement C9 | h-cDNA | DiScipio RC, PNAS, 81:7298, 1984 |
| corticotropin releasing factor | sheep-h-cDNA | Furutani Y, Nat, 301:537, 1983 |
| | h-gDNA | Shibahara S, EMBO J, 2:775, 1983 |
| epidermal growth factor | m-cDNA | Gray A, Nat, 303:722, 1983 |
| | m-cDNA | Scott J, Sci, 21:236, 1983 |
| | h-gDNA | Brissenden JE, Nat, 310:781, 1984 |
| epidermal growth factor receptor, oncogene c-erb-B | h-cDNA and Chr | Lan CR, Sci, 224:843, 1984 |
| epoxide dehydratase | r-cDNA | Gonzlalez FJ, JBC, 256:4697, 1981 |
| erthropoietin | h-cDNA | Lee-Huang S, PNAS, 81:2708, 1984 |
| esterase inhibitor, C1 | h-cDNA | Stanley KK, EMBO J, 3:1429, 1984 |
| factor VIII | h-cDNA and gDNA | Gitschier J, Nat, 312:326, 1984 |
| | h-cDNA | Toole JJ, Nat, 312:342, 1984 |
| factor IX, Christmas factor | h-cDNA | Kutachi K, PNAS, 79:6461, 1982 |
| | h-cDNA | Choo KH, Nat, 299:178, 1982 |
| | RFLP | Camerino G, PNAS, 81:498, 1984 |
| | h-gDNA | Anson DS, EMBOO J, 3:1053, 1984 |
| factor X | h-cDNA | Leytus SP, PNAS, 81:3699, 1984 |
| fibrinogen A Alpha, B beta, gamma | h-cDNA | Kant JA, PNAS, 80:3953, 1983 |
| | h-cDNA (gamma) | Fornace AJ, Sci, 224:161, 1984 |
| | h-cDNA (alpha gamma) | Imam AMA, NAR, 11:7427, 1983 |
| | h-gDNA (gamma) | Fornace AJ, JBC, 259:12826, 1984 |
| gastrin releasing peptide | h-cDNA | Spindel ER, PNAS, 81:5699, 1984 |
| glucagon, prepro | hamster c-DNA | Bell GI, Nat, 302:716, 1983 |
| | h-gDNA | Bell GI, Nat, 304:368, 9183 |
| growth hormone | h-cDNA | Martial JA, Sci, 205:602, 1979 |
| | h-gDNA | DeNoto FM, NAR, 9:3719, 1981 |
| | GH-like gene | Owerbach, D, Sci, 209:289,1980 |
| growth hormone, RF, somatocrinin | h-cDNA | Gubler V, PNAS, 80:3411,1983 |
| | h-cDNA | Mayo KE, Nat, 306:86:1983 |
| hemopexin | h-cDNA | Stanley KK, EMBO J, 3:1429, 1984 |
| inhibin | porcine-cDNA | Mason AJ, Nat, 318:659, 1985 |
| insulin, prepro | h-gDNA | Ullrich a, Sci, 209:612, 1980 |
| insulin-like growth factor I | h-cDNA | Jansen M, Nat, 306:609, 1983 |
| | h-cDNA | Bell GI, Nat, 310:775, 1984 |
| | Chr | Brissenden JE, Nat, 310:781, 1984 |

TABLE 4-continued

Selected Cloned Structural Genes

| Gene | Clone Type* | Reference |
|---|---|---|
| insulin-like growth factor II | h-cDNA | Bell GI, Nat, 310:775, 1984 |
| | h-gDNA | Dull TJ, Nat, 310:777, 1984 |
| | Chr | Brissenden JE, Nat, 310:781, 1984 |
| interferon, alpha (leukocyte), multiple | h-cDNA | Maeda S, PNAS, 77:7010, 1980 |
| | h-cDNA (8 distinct) | Goeddel DV, nat, 290:20, 1981 |
| | h-gDNA | Lawn RM, PNAS, 78:5435, 1981 |
| | h-gDNA | Todokoro K, EMBO J, 3:1809, 1984 |
| | h-gDNA | Torczynski RM, PNAS, 81:6451, 1984 |
| interferon, beta (fibroblast) | h-cDNA | Taniguchi T, Gene, 10:11, 1980 |
| | h-gDNA | Lawn RM, NAR, 9:1045, 1981 |
| | h-gDNA (related) | Sehgal P, PNAS, 80:3632, 1983 |
| | h-gDNA (related) | Sagar AD, Sci, 223:1312, 1984 |
| interferon, gamma (immune) | h-cDNA | Gray PW, Nat, 295:503, 1982 |
| | h-gDNA | Gray PW, Nat, 298:859, 1982 |
| interleukin-1 | m-cDNA | Lomedico PT, Nat, 312:458, 1984 |
| interleukin-2, T-cell growth factor | h-cDNA | Devos R, NAR, 11:4307, 1983 |
| | h-cDNA | Taniguchi T, Nat, 302:305, 1983 |
| | h-gDNA Chr | Hollbrook NJ, PNAS, 81:1634, 1984 Siegel LF, Sci, 223:175, 1984 |
| interleukin-3 | m-cDNA | Fung MC, Nat, 307:233, 1984 |
| kininogen, two forms | bovine-cDNA | Nawa H, PNAS, 80:90, 1983 |
| | bovine-cDNA and gDNA | Kitamura N, Nat, 305:545, 1983 |
| leutinizing hormone, beta subunit | h-gDNA and Chr | Talmadge K, Nat, 207:37, 1984 |
| leuteinizing hormone releasing hormone | h-cDNA and gDNA | Seeburg PH, Nat, 311:666, 1984 |
| lymphotoxin | h-cDNA and gDNA | Gray PW, Nat, 312:721, 1984 |
| mast cell growth factor | m-cDNA | Yokoya T, PNAS, 81:1070, 1984 |
| nerve growth factor, beta subunit | m-cDNA | Scott J, Nat, 302:538, 1983 |
| | h-gDNA | Ullrich A, Nat, 303:821, 1983 |
| | Chr | Franke C, Sci, 222:1248, 1983 |
| ibcogene, c-sis, PGDF chain A | h-gDNA | Dalla-Favera R, Nat, 295:31, 1981 |
| | h-cDNA | Clarke MF, Nat, 208:464, 1984 |
| pancreatic polypeptide and icosapeptide | h-cDNA | Boel E, EMBO J, 3:090, 1984 |
| parathyroid hormone, prepro | h-cDNA | Hendy GN, PNAS, 78:7365, 1981 |
| | h-gDNA | Vasicek TJ PNAS, 80:2127, 1983 |
| plasminogen | h-cDNA and gDNA | Malinowski DP, Fed P, 42:1761, 1983 |
| plasminogen activator | h-cDNA | Edlund T, PNAS, 80:349, 1983 |
| | h-cDNA | Pennica D, Nat, 301:214, 1983 |
| | h-gDNA | Ny T, PNAS, 81:5355, 1984 |
| prolactin | h-cDNA | Cook NE, JBC, 256:4007, 1981 |
| | h-gDNA | Cooke NE, Nat, 297:603, 1982 |
| proopiomelanocortin | h-cDNA | DeBold CR, Sci, 220:721, 1983 |
| | h-gDNA | Cochet M, Nat, 297:335, 1982 |
| protein C | h-cDNA | Foster D, PNAS, 81:4766, 1984 |
| prothrombin | bovine-cDNA | Mac Gillivray RA, PNAS, 77:5153, 1980 |
| relaxin | h-gDNA | Hudson, P, Nat, 301:628, 1983 |
| | h-cDNA (2 genes) | Hudson, P, EMBO J, 3:2333, 1984 |
| | Chr | Crawford, RJ, EMBO, J, 3:2341, 1984 |
| renin, prepro | h-cDNA | Imai T, PNAS, 80:7405, 1983 |
| | h-gDNA | Hobart PM, PNAS 81:5026, 1984 |
| | h-gDNA | Miyazaki H, PNAS, 81:5999, 1984 |
| | Chr | Chirgwin JM, SCMG, 10:415, 1984 |
| somatostatin | h-cDNA | Shen IP, PNAS, 79:4575, 1982 |
| | h-gDNA and Ri-IP | Naylot SI, PNAS, 80:2686, 1983 |
| tachykinin, prepro, substances P & K | bovine-cDNA | Nawa H, Nat, 306:32, 1983 |
| | bovine-gDNA | Nawa H, Nat, 312:729, 1984 |
| urokinase | h-cDNA | Verde P, PNAS, 81:4727, 1984 |
| vasoactive intestinal peptide, prepro | h-cDNA | Itoh N, Nat, 304:547, 1983 |
| vasopressin | r-cDNA | Schmale H, EMBO J, 2:763, 1983 |

Key to Table 4:
*cDNA—complementary DNA;
Chr—chromosome;
gDNA—genomic DNA;
RFLP—restriction fragment polymorphism;
h—human;
m—mouse;
r—rat 1. Oral Vaccines This class of proteins are of immunological value when produced in the mammary glands or other target organs of transgenic animals. These proteins can then be purified and given orally in conjunction with specific immunogens for the production of oral vaccines. Some of the candidate proteins for use in the present invention are hepatitis and rabies antigens.

2. Oral Tolerance

This class of proteins is similar to the one above except the protein produced by the transgenic mammary gland or organ is given with compounds that stimulate tolerance instead of immunity. This has been postulated as being of potential benefit for the treatment of autoimmune diseases such as multiple sclerosis and diabetes. Proteins in these category preferred for use in the present invention include myelin basic protein for the treatment of multiple sclerosis and insulin for the treatment of diabetes.

3. Biopharmaceuticals

This refers to the production of compounds of medical and veterinary interest in transgenic mammary glands, as well as other organs. Proteins in these category can be used to treat burn patients, heart disease patients, hemophiliacs and stroke patients. Proteins in this category preferred for use in the present invention include a-1 antitrypsin, collagenase, factor VIII, factor IX and tissue plasminogen activator.

4. Transplantation

One of the greatest potential applications of the homologous recombination technology in non-rodent animals would be the generation of universal donors animals. These animals would have genes involved in the tissue rejection inactivated thus allow the transplantation of the tissue into the human body on a temporary basis. This would drastically reduce the present shortage of donor organs. Some of the genes involved in the rejection process suitable for use in the present invention are hCD59, DAF (CD55) as well as modifications of the class I and class II MHC molecules.

5. Animal Models of Human Disease

By the use of homologous recombination in ES cells it has been possible to create a host of animals with medical conditions that mimic human diseases. Examples of these models are atherosclerosis, cystic fibrosis and Alzheimer disease. Unfortunately, in some cases, the mouse is not an ideal animal model. The present invention allows for the generation of large animal models of human disease that can be used by the academic community and private industry for the development of new therapeutics, and for increasing the understanding of particular diseases. For instance, one use of the present invention is the generation of an apolipoprotein E deficient pig. The inventors have previously demonstrated that apoE deficient mice develop spontaneous premature atherosclerosis (Piedrahita et al., 1992; Zhang et al., 1992). A similar model in a larger animal, such as the pig, would be a great asset for the development of therapies, including gene therapy, to treat the human condition.

6. Agricultural Traits

In the agricultural field, a vast number of uses have been described for the transgenic animals which can be produced using the methods of the present invention. A non-inclusive list of uses includes generation of animals that are resistant to certain diseases and pests, modification of milk composition to increase shelf life, cheese yield and to permit lactose intolerant individuals to safely consume the modified milk, alteration of the growth rate, nutritional efficiency and carcass composition of animals, as well as items such as effecting wool composition. Some of the genes involved in, for example, milk modification are $\alpha$-, $\beta$-, and $\kappa$-casein, lactoglobulin and lactalbumin. A preferred gene for use in alteration of muscle mass is GDF-8 (McPherron et al., 1997).

Another trait contemplated for use in the present invention is the creation of cows that are devoid of prion protein (PrP). Recent studies have shown that mice lacking PrP are resistant to scrapie (Bueler et al., 1992, 1993; Brandner et al., 1996; Fischer et al., 1996; Blattler et al., 1997). The bovine spongiform encephalitis (BSE) agent is thought to be composed largely, if not entirely, of $PrP^{Sc}$, the abnormal isoform of the normal cellular $PrP^{C}$, therefore cattle lacking PrP may be resistant to BSE. The gene encoding the bovine PrP is known (Goldmann et al., 1991; Inoue et al., 1997).

7. Antisense

Antisense methodology takes advantage of the fact that nucleic acids tend to pair with "complementary" sequences. By complementary, it is meant that polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. Antisense polynucleotides, when introduced into a target cell, specifically bind to their target polynucleotide and interfere with transcription, RNA processing, transport, translation and/or stability. Antisense RNA constructs, or DNA encoding such antisense RNAs, may be employed to inhibit gene transcription or translation or both within the transformed primordial germ cells and resultant transgenic animals of the present invention.

Antisense constructs may be designed to bind to the promoter and other control regions, exons, introns or even exon-intron boundaries of a selected gene. It is contemplated that effective antisense constructs will often include regions complementary to intron/exon splice junctions. Thus, antisense constructs with complementarity to regions within 50–200 bases of an intron-exon splice junction of a selected gene are contemplated for use herewith. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether the expression of other genes having complementary sequences is affected.

"Antisense" or "complementary" means polynucleotide sequences that are substantially complementary over their entire length and have very few base mismatches. For example, sequences of fifteen bases in length may be termed complementary when they have complementary nucleotides at thirteen or fourteen positions. Naturally, sequences which are completely complementary will be sequences which are entirely complementary throughout their entire length and have no base mismatches. Other sequences with lower degrees of homology also are contemplated. For example, an antisense construct which has limited regions of high homology, but also contains a non-homologous region (e.g., ribozyme) could be designed. These molecules, though having less than 50% homology, would bind to target sequences under appropriate conditions.

It may be advantageous to combine portions of genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence.

8. Ribozymes

Although proteins traditionally have been used for catalysis of nucleic acids, another class of macromolecules has emerged as useful in this endeavor. Ribozymes are RNA-protein complexes that cleave nucleic acids in a site-specific fashion. Ribozymes have specific catalytic domains that possess endonuclease activity (Kim and Cech, 1987; Gerlach et al., 1987; Forster and Symons, 1987). For example, a large number of ribozymes accelerate phosphoester transfer reactions with a high degree of specificity, often cleaving only one of several phosphoesters in an oligonucleotide substrate (Cech et al., 1981; Michel and Westhof, 1990; Reinhold-Hurek and Shub, 1992). This specificity has been attributed to the requirement that the substrate bind via specific base-pairing interactions to the internal guide sequence ("IGS") of the ribozyme prior to chemical reaction.

Ribozyme catalysis has primarily been observed as part of sequence-specific cleavage/ligation reactions involving nucleic acids (Joyce, 1989; Cech et al., 1981). For example, U.S. Pat. No. 5,354,855 reports that certain ribozymes can act as endonucleases with a sequence specificity greater than that of known ribonucleases and approaching that of the DNA restriction enzymes. Thus, sequence-specific ribozyme-mediated inhibition of gene expression may be particularly suited to therapeutic applications (Scanlon et al., 1991; Sarver et al., 1990; Sioud et al., 1992). Recently, it was reported that ribozymes elicited genetic changes in some cells lines to which they were applied; the altered genes included the oncogenes H-ras, c-fos and genes of HIV. Most of this work involved the modification of a target mRNA, based on a specific mutant codon that is cleaved by a specific ribozyme.

Several different ribozyme motifs have been described with RNA cleavage activity (Symons, 1992). Examples that are expected to function equivalently for the down regulation of low $K_m$ hexokinases include sequences from the Group I self splicing introns including Tobacco Ringspot Virus (Prody et al, 1986), Avocado Sunblotch Viroid (Palukaitis et al., 1979 and Symons, 1981), and Lucerne Transient Streak Virus (Forster and Symons, 1987). Sequences from these and related viruses are referred to as hammerhead ribozyme based on a predicted folded secondary structure.

Other suitable ribozymes include sequences from RNase P with RNA cleavage activity (Yuan et al., 1992, Yuan and Altman, 1994), hairpin ribozyme structures (Berzal-Herranz et al., 1992 and Chowrira et al., 1993) and Hepatitis Delta virus based ribozymes. The general design and optimization of ribozyme directed RNA cleavage activity has been discussed in detail (Haseloff and Gerlach, 1988, Symons, 1992, Chowrira et al., 1994, and Thompson et al., 1995).

The other variable on ribozyme design is the selection of a cleavage site on a given target RNA. Ribozymes are targeted to a given sequence by virtue of annealing to a site by complimentary base pair interactions. Two stretches of homology are required for this targeting. These stretches of homologous sequences flank the catalytic ribozyme structure defined above. Each stretch of homologous sequence can vary in length from 7 to 15 nucleotides. The only requirement for defining the homologous sequences is that, on the target RNA, they are separated by a specific sequence which is the cleavage site. For hammerhead ribozyme, the cleavage site is a dinucleotide sequence on the target RNA is a uracil (U) followed by either an adenine, cytosine or uracil (A,C or U) (Perriman et al., 1992 and Thompson et al., 1995). The frequency of this dinucleotide occurring in any given RNA is statistically 3 out of 16. Therefore, for a given target messenger RNA of 1000 bases, 187 dinucleotide cleavage sites are statistically possible.

Designing and testing ribozymes for efficient cleavage of a target RNA is a process well known to those skilled in the art. Examples of scientific methods for designing and testing ribozymes are described by Chowrira et al., (1994) and Lieber and Strauss (1995), each incorporated by reference. The identification of operative and preferred sequences for use in selected gene-targeted ribozymes is simply a matter of preparing and testing a given sequence, and is a routinely practiced "screening" method known to those of skill in the art.

F. Analysis of Transformants

The initial identification of transformed cells is generally performed by detection of the expression of the selected marker protein. In examples where GFP is the marker protein, analysis is performed by fluorescent microscopy using FITC filters. Following initial identification of transformant colonies, the colonies can be expanded by pick passing. A single colony from the resulting passage can be analyzed by PCR. This technique has been used successfully in mice for detection of homologous recombinants (Smithies, 1991) The primers to be used in each case are dependent on the transgene introduced.

G. Homologous Recombination

Modification of the genome of selected domestic species has been the focus of intense research effort for the past 15 years. At present, the only techniques available for the generation of transgenic domestic animals are pronuclear injection or viral vectors. Production of transgenic pigs by pronuclear injection has demonstrated the difficulty and inefficiency of the procedure (Wall, 1996). This is in part due to the nature of the pronuclear injection technique itself, which leads to the random integration of the introduced DNA with unpredictable and, in some cases, undesirable results (Pursel et al., 1989), and in part due to the high cost associated with generation of transgenic pigs. Although viral transformation tends to be more efficient than pronuclear injection, it is also accompanied by problems associated with random insertion, mosaicism due to multiple integrations, and technical difficulties associated with generation of replication defective recombinant viral vectors. Thus, in domestic animals, the lack of complete information on the regulatory sequences required for proper expression and regulation of the transgene are compounded by the technical disadvantages associated with generation of transgenic animals.

Some of the drawbacks of pronuclear injection and viral vectors can be overcome by the utilization of a technique known as homologous recombination (Koller and Smithies, 1992). This technique allows the precise modification of existing genes, overcomes the problems of positional effects and insertional inactivation, and allows the inactivation of specific genes, as well as the replacement of one gene for another. Unfortunately the efficiency of the procedure is so low that it can not be utilized directly on embryos, but must make use of a carrier cell line. The cell line used to date is the embryonic stem (ES) cell as it allows easy manipulation and selection in vitro followed by the generation, by ES-blastocyst injection, of a transgenic animal carrying those changes. Until the present invention, homologous recombination could only be done in mice as it had not been possible to isolate domestic animals ES cells that permit the same genetic manipulations. The instant compositions and methods allow the culture and genetic manipulation of domestic animal cell lines with ES-like qualities.

Thus a preferred method for the delivery of transgenic constructs involves the use of homologous recombination, or "knock-out technology". Homologous recombination relies, like antisense, on the tendency of nucleic acids to base pair with complementary sequences. In this instance, the base pairing serves to facilitate the interaction of two separate nucleic acid molecules so that strand breakage and repair can take place. In other words, the "homologous" aspect of the method relies on sequence homology to bring two complementary sequences into close proximity, while the "recombination" aspect provides for one complementary sequence to replace the other by virtue of the breaking of certain bonds and the formation of others.

Put into practice, homologous recombination is used as follows. First, the target gene is selected within the host cell. Sequences homologous to the target gene are then included in a genetic construct, along with some mutation that will render the target gene inactive (stop codon, interruption, and the like). The homologous sequences flanking the inactivating mutation are said to "flank" the mutation. Flanking, in this context, simply means that target homologous sequences are located both upstream (5') and downstream (3') of the mutation. These sequences should correspond to some sequences upstream and downstream of the target gene. The construct is then introduced into the cell, thus permitting recombination between the cellular sequences and the construct.

As a practical matter, the genetic construct will normally act as far more than a vehicle to interrupt the gene. For example, it is important to be able to select for recombinants and, therefore, it is common to include within the construct a selectable marker gene. This gene permits selection of cells that have integrated the construct into their genomic DNA by conferring resistance to various biostatic and biocidal drugs. In addition, a heterologous gene that is to be expressed in the cell also may advantageously be included within the construct. The arrangement might be as follows:
. . . vector-5'-flanking sequence•heterologous gene•selectable marker gene•flanking sequence-3'•vector . . .

Thus, using this kind of construct, it is possible, in a single recombinatorial event, to (i) "knock out" an endogenous gene, (ii) provide a selectable marker for identifying such an event and (iii) introduce a transgene for expression.

Another refinement of the homologous recombination approach involves the use of a "negative" selectable marker. This marker, unlike the selectable marker, causes death of cells which express the marker. Thus, it is used to identify undesirable recombination events. When seeking to select homologous recombinants using a selectable marker, it is difficult in the initial screening step to identify proper homologous recombinants from recombinants generated from random, non-sequence specific events. These recombinants also may contain the selectable marker gene and may express the heterologous protein of interest, but will, in all likelihood, not have the desired "knock out" phenotype. By attaching a negative selectable marker to the construct, but outside of the flanking regions, one can select against many random recombination events that will incorporate the negative selectable marker. Homologous recombination should not introduce the negative selectable marker, as it is outside of the flanking sequences. Examples of processes that use negative selection to enrich for homologous recombination include the disruption of targeted genes in embryonic stem cells or transformed cell lines (Mortensen, 1993; Willnow and Herz, 1994) and the production of recombinant virus such as adenovirus (Imler et al., 1995).

Since the frequency of gene targeting is heavily influence by the origin of the DNA being used for targeting, it is beneficial to obtain DNA that is as similar (isogenic) to the cells being targeted as possible. One way to accomplish this is by isolation of the region of interest from genomic DNA from a single colony by long range PCR. Using long range PCR it is possible to isolate fragments of 7–12 kb from small amounts of starting DNA. To accomplish this the inventors have determined the conditions required for successfuil passage of primary PGC-derived colonies. As can be seen in Example 3, it is possible to obtain a 10–20 fold increase in colony number after each passage. This is accomplished by trypsinization and plating in fresh feeder layers at a high density. In some cases, however, the region of interest is conserved enough that non-isogenic DNA can be used. This is the case for the apoE locus of mice which the inventors were able to target at a high frequency with non-isogenic DNA.

Gene trapping is a useful technique suitable for use with the present invention. This refers to the utilization of the endogenous regulatory regions present in the chromosomal DNA to activate the incoming transgene. In this way expression of the transgene is absent or minimized when the transgene inserts in a random location. However, when homologous recombination occurs the endogenous regulatory region are placed in apposition to the incoming transgene, which results in expression of the transgene.

H. Excision of Transgenes

Members of the integrase family are proteins that bind to a DNA recognition sequence, and are involved in DNA recognition, synapsis, cleavage, strand exchange, and religation. Currently, the family of integrases includes 28 proteins from bacteria, phage, and yeast which have a common invariant His-Arg-Tyr triad (Abremski and Hoess, 1992). Four of the most widely used site-specific recombination systems for eukaryotic applications include: Cre-loxP from bacteriophage P1 (Austin et al., 1981); FLP-FRT from the $2\mu$ plasmid of *Saccharomyces cerevisiae* (Andrews et al., 1985); R-RS from *Zygosaccharomyces rouxii* (Maeser and Kahmann, 1991) and gin-gix from bacteriophage Mu (Onouchi et al., 1995). The Cre-loxP and FLP-FRT systems have been developed to a greater extent than the latter two systems. The R-RS system, like the Cre-loxP and FLP-FRT systems, requires only the protein and its recognition site. The Gin recombinase selectively mediates DNA inversion between two inversely oriented recombination sites (gix) and requires the assistance of three additional factors: negative supercoiling, an enhancer sequence and its binding protein Fis.

The present invention contemplates the use of the Crel-Lox site-specific recombination system (Sauer, 1993, available through Gibco/BRL, Inc., Gaithersburg, Md.) to rescue specific genes out of a genome, and to excise specific transgenic constructs from the genome. The Cre (causes recombination)-lox P (locus of crossing-over(x)) recombination system, isolated from bacteriophage P1, requires only the Cre enzyme and its loxP recognition site on both partner molecules (Sternberg and Hamilton, 1981). The loxP site consists of two symmetrical 13 bp protein binding regions separated by an 8 bp spacer region, which is recognized by the Cre recombinase, a 35 kDa protein. Nucleic acid sequences for loxp (Hoess et al., 1982) and Cre (Sternberg et al., 1986) are known. If the two lox P sites are cis to each other, an excision reaction occurs; however, if the two sites are trans to one another, an integration event occurs. The Cre protein catalyzes a site-specific recombination event. This event is bidirectional, i.e., Cre will catalyze the insertion of sequences at a LoxP site or excise sequences that lie between two LoxP sites. Thus, if a construct for insertion also has flanking LoxP sites, introduction of the Cre protein, or a polynucleotide encoding the Cre protein, into the cell will catalyze the removal of the construct DNA. This technology is enabled in U.S. Pat. No. 4,959,317, which is hereby incorporated by reference in its entirety.

An initial in vivo study in bacteria showed that the Cre excises loxP-flanked DNA extrachromosomally in cells expressing the recombinase (Abremski et al., 1983). A major question regarding this system was whether site-specific recombination in eukaryotes could be promoted by a bacterial protein. However, Sauer (1987) showed that the system excises DNA in *S. cerevisiae* with the same level of efficiency as in bacteria.

Further studies with the Cre-loxP system, in particular the ES cells system in mice, has demonstrated the usefulness of the excision reaction for the generation of unique transgenic animals. Homologous recombination followed by Cre-mediated deletion of a loxP-flanked neo-tk cassette was used to introduce mutations into ES cells. This strategy was repeated for a total of 4 rounds in the same line to alter both alleles of the rep-3 and mMsh2 loci, genes involved in DNA mismatch repair (Abuin and Bradley, 1996). Similarly, a transgene which consists of the 35S promoter/luciferase gene/loxP/35S promoter/hpt gene/loxP ($luc^+hyg^+$) was introduced into tobacco. Subsequent treatment with Cre causes the deletion of the hyg gene ($luc^+hyg^s$) at 50% efficiency (Dale and Ow, 1991). Transgenic mice which have the Ig light chain K constant region targeted with a loxP-flanked neo gene were bred to Cre-producing mice to remove the selectable marker from the early embryo (Lakso et al., 1996). This general approach for removal of markers stems from issues raised by regulatory groups and consumers concerned about the introduction of new genes into a population.

An analogous system contemplated for use in the present invention is the FLP/FRT system. This system was used to target the histone 4 gene in mouse ES cells with a FRT-flanked neo cassette followed by deletion of the marker by FLP-mediated recombination. The FLP protein could be obtained from an inducible promoter driving the FLP or by using the protein itself (Wigley et al., 1994).

The present invention also contemplates the use of recombination activating genes (RAG) 1 and 2 to excise specific transgenic constructs from the genome, as well as to rescue specific genes from the genome. RAG-1 (GenBank accession number M29475) and RAG-2 (GenBank accession numbers M64796 and M33828) recognize specific recombination signal sequences (RSSs) and catalyze V(D)J recombination required for the assembly of immunoglobulin and T cell receptor genes (Schatz et al., 1989; Oettinger et al., 1990; Cumo and Oettinger, 1994). Transgenic expression of RAG-1 and RAG-2 proteins in non-lymphoid cells supports V(D)J recombination of reporter substrates (Oettinger et al., 1990). For use in the present invention, the transforming construct of interest is engineered to contain flanking RSSs. Following transformation, the transforming construct that is internal to the RSSs can be deleted from the genome by the transient expression of RAG-1 and RAG-2 in the transformed cell.

I. Immortalization of PGCs

To date there has only been one description of a conditionally immortalized urogenital ridge-derived cell. The described behavior of the cell lines in culture differed little form non-immortalized cell lines, suggesting that it may be possible to conditionally immortalize the cells lines to grow, maintain, and genetically manipulate them, while retaining their ability to contribute to chimera formation. The concept that interfering with programmed cell death by immortalization of primordial germ cells with transforming constructs is derived from the observations that: Bcl-2 inhibits retinoic acid-induced apoptosis during differentiation of embryonic stem cells (Okazawa et al., 1996); apoptosis is responsible for death of primordial germ cells in culture (Pesce and Felici, 1994); and stem cell factor and leukemia inhibitory factor promote germ cell survival by suppressing programmed cell death (Pesce et al., 1993). Therefore, interference with the pathway of programmed cells death by conditional transformation should increase the ability to maintain and genetically manipulate PGCs in culture.

Exemplary transforming genes and constructs are listed below. These genes fall into different functional categories, such as those that perturb signal transduction, affect cell cycle, alter nuclear transcription, alter telomere structure or function, inhibit apoptosis, or that exert pleiotropic activities. It will be understood that the genes listed are only exemplary of the types of oncogenes, mutated tumor suppressors and other transforming genetic constructs and elements that may be used in this invention. Further transforming genes and constructs will be known to those of ordinary skill in the art.

A number of proteins have been shown to inhibit apoptosis, or programmed cell death. Representative of this class are bcl-2 and family members including Bcl-xl, Mcl-1, Bak, A1, A20, and inhibitors of interleukin-1β-converting enzyme and family members. Since it has been shown that growth factors which inhibit apoptosis promote primordial germ cell survival (Pesce et al., 1993), this class of proteins is particularly preferred for use in the present invention. Preferred for use is bcl-2 (distinct from bcl-1, cyclin D1; GenBank Accession No. M14745, X06487). Overexpression of this oncogene was first discovered in T cell lymphomas. It functions as an oncogene by binding and inactivating bax, a protein in the apoptotic pathway.

In addition to proteins which inhibit apoptosis, a large number of proteins have been reported which fail to promote apoptosis. Among these are p53, retinoblastoma gene (Rb), Wilm's tumor (WT1), bax alpha, interleukin-1b-converting enzyme and family, MEN-1 gene (chromosome 11q13), neurofibromatosis, type 1 (NF1), cdk inhibitor p16, colorectal cancer gene (DCC), familial adenomatosis polyposis gene (FAP), multiple tumor suppressor gene (MTS-1), BRCA1, BRCA2.

Preferred are p53 and the retinoblastoma gene. Most forms of cancer have reports of p53 mutations. Inactivation of p53 results in a failure to promote apoptosis. With this failure, cancer cells progress in tumorgenesis rather than be destined for cell death. A short list of cancers and mutations found in p53 is: ovarian (GenBank Accession No. S53545, S62213, S62216); liver (GenBank Accession No. S62711, S62713, S62714, S67715, S72716); gastric (Gen Bank Accession No. S63157); colon (GenBank Accession No. S63610); bladder (GenBank Accession No. S85568, S85570, S85691); lung (GenBank Accession No. S41969, S41977); glioma (GenBank Accession No. S85807, S85712, S85713).

There are a number of known oncogenes and mutant tumor suppressors which act by perturbing signal transduction. Representative members of this class are tyrosine kinases, both cytoplasmic and membrane-associated forms, such as the Src family, Jak/Stats, Ros, Neu, Fms, Ret, Abl and Met. Other members of this class are serine/threonine kinases, such as Mos, Raf, protein kinase C (PKC) and PIM-1. Another family of proteins which fall into this class are the growth factors and receptors, such as platelet derived growth factor (PDGF), insulin-like growth factor (IGF-1), insulin receptor substrate (IRS-1 and IRS-2), the Erb family, epidermal growth factor (EGF), growth hormone, hepatocyte growth factor (HGF) basic fibroblast growth factor (bFGF), as well as the corresponding growth factor receptors. Small GTPases or G proteins also belong to this class, and are represented by the ras family, rab family, and Gs-alpha. Receptor-type tyrosine phosphatase IA-2 is also a member of this class of proteins.

Exemplary of the members preferred for use in the present invention are Neu, also known as Her2, also known as erbB-2 (GenBank accession numbers Ml 1730, X03363, U02326 and S57296). Discovered as an oncogene in breast cancer, found also in other forms of cancer as well. This seems to be a member of the receptor tyrosine kinase family. Also preferred is hepatocyte growth factor receptor (HGFr; GenBank accession number U 11813), also known as scatter factor receptor. This can be an example of a receptor, either endogenously present or expressed from a recombinant adenovirus, that is used to stimulate proliferation of a target cell population. Other preferred members are insulin-like growth factor 1 receptor (GenBank accession number X04434 and M24599), and GTPase Gs alpha (GenBank accession numbers X56009, X04409). Gs alpha is associated with pituitary tumors that secrete growth hormone, but not other neuroendocrine or endocrine tumors.

Transforming genes have also been described which affect the cell cycle. Proteins which belong to this class are the cyclin-dependent protein kinases (cdk), classes A–E; and members of the cyclin family such as cyclin D. Exemplary for use in the present invention is cyclin D1, also known as PRAD, also known as bcl-1 (GenBank accession numbers M64349 and M73554). This is associated as an oncogene primarily with parathyroid tumors.

A number of transforming genes have been described which assert their effect through an alteration of nuclear transcription. This class includes the Myc family members including c-myc, N-myc, and L-myc; the Rel family members including NF-kappaB; c-Myb, Ap-1, fos, and jun, insulinoma associated cDNA (IA-1), Erbb-1, and the PAX gene family. Exemplary for use in the present invention is c-myc (GenBank accession numbers J00120, K01980, M23541, V00501, X00364.

A protein which has recently been implicated in cellular transformation is telomerase. Telomerase is involved in the assembly and maintenance of telomeres, which are at the end of chromosomes. It is presently unknown how telomerase functions as in transformation.

Some transforming genes have pleiotropic effects. Among these proteins are viral proteins such as SV40 and polyoma large T antigens, SV40 temperature sensitive large T antigen, adenovirus ElA and EIB proteins, and papilomavirus E6 and E7 proteins. Preferred from this class is SV40 large T antigen (TAG; GenBank accession number J02400). Also preferred is temperature sensitive large T antigen.

III. Production of Transgenic Non-Rodent Animals

As described above, the conditions for producing transgenic rodents is not suitable for the production of other transgenic species. The methods of the present invention allow for the first time rapid, reliable and cost-efficient production of non-rodent transgenic animals from a variety of species.

A. Animal Species

The present invention can be used to produce transgenic animals from any non-rodent animal species. Preferred for use in the present invention are mammals, and more preferred are animals from the porcine, bovine, ovine and caprine species.

B. Nuclear transfer

Current methods of nuclear transfer in domestic species are derived from the method developed by McGrath and Solter (1983). The donor embryos and unfertilized recipient oocytes are treated with cytoskeletal inhibitors, a micropipette is inserted into the oocyte, and the metaphase chromosomes are removed in a portion of membrane-bounded cytoplasm. Successful enucleation is monitored by observing the removal of the chromosomes directly (Stice and Robl 1988), by indirect staining using the DNA-specific fluorescent dye bisbenzimide (Tsunoda et al. 1988; Prather and First 1990a; Westhusin et al. 1990), or by mounting a portion of the enucleated oocytes and assuming an equal efficiency of enucleation in the remaining eggs (Willadsen 1986; Prather et al. 1987; Smith and Wilmut 1989). A single blastomere from the donor embryo (or portions thereof) is then aspirated into the micropipette and expelled into the perivitelline space, adjacent to the enucleated oocyte. The next step is the fusion of the two cells within the perivitelline space. This can be accomplished in some species with Sendai virus (Graham 1969) or with electrofusion (Berg 1982).

The efficiencies of the enucleation procedures can reach 100% when the chromosomes are directly or indirectly observed (Tsunoda et al. 1988; Stice and Robl 1988; Prather and First 1990a), whereas the percentage of enucleated oocytes is lower when chromosomal removal is based solely on the location of the first polar body (Willadsen 1986; Prather et al. 1987, 1989a).

Activation is thought to occur coincident with electrofusion. It has been known for many years that electrical pulses are an effective parthenogenetic agent in the mouse (Whittingham 1980). The specific mechanism of electrical activation is not known, but it may be related to membrane depolarization and calcium leakage after electrically induced pore formation (Whittingham 1980). As with fusion, electrically induced activation varies greatly from study to study. Factors that affect activation rates are many and include age and species of oocyte, type of chamber and medium in which the pulse is given, and type of pulse (Collas et al. 1989; Ozil 1990).

An inherent problem when working with species such as pigs, cattle, sheep and goats is the length of time required to test and obtain germ line transmission when producing chimeras using normal diploid host embryos. In order to determine whether the ES or EG contribution to the offspring can be increased, two approaches can be utilized: nuclear transfer and the generation of chimeras using tetraploid host embryos. In the case of nuclear transfer the totipotentiality of the cell is being tested, while with tetraploid embryos the pluripotentiality of the cells is tested.

The basic procedure for nuclear transfer consists of obtaining single cells and fusing them to enucleated recipient ovum. This effectively transfers the nucleus of the donor cell into the recipient cytoplasm where, if successfuil, it is reprogrammed and subsequently instructs development of a new embryo which is genetically identical to that from which the cell was acquired. The most drastic example of the potential of this technology has been reported by Wilmut et al. (1997), indicating that nuclei from embryonic fibroblast as well as adult mammary epithelial cell can direct normal development in the sheep. Although the nuclear transfer technique is much less advanced in pigs, there have been reports of successful births using nuclei from 4 cell embryos (Prather et al., 1989).

PGCs collected from fetal tissue have also been successfully utilized as donors for nuclear transplantation (Chemy and Merei, 1994; Delhaise et al., 1995; Lavoir et al., 1997; Strelchenko, 1986). In pigs it has been demonstrated that previously cryopreserved PGCs can be used successfully as nuclear donors, giving rise to nuclear reprogramming and cleavage to the 4-cell stage (Liu et al., 1995). Additionally, Ouhibi et al. (1996) reported nuclear reprogramming in cultured ICM-derived pig cells after nuclear transfer. Unfortunately, ability of the embryos to participate in normal development was not studied.

In a recent study in cattle, Lavoir et al. (1997) reported 9–13% of cleaved nuclear transplant embryos developing to the blastocyst stage when oogonia collected from female fetuses (50–70 days gestation) were utilized as nuclei donors. Although no live calves were produced, an abnormal conceptus developed in one animal which had received 4 embryos. This conceptus was recovered by induced abortion at day 43 after failing to detect a heartbeat, and genetic analysis showed the fetus to be genetically identical to the donor oogonia. Similar results using bovine PGCs from both male and female fetuses have been reported by Moens et al. (Moens et al., 1996). The observation by Strelchenko (1986) that nuclei from cultured bovine PGCs can direct development up to day 60 with no significant fetal abnormalities reported suggests that, when PGCs are placed in culture, nuclear changes occur that increase the nuclear potency of the cells when compared with freshly isolated PGCs.

An additional approach for increasing the contribution of the ES cell lines to the chimeric fetus has been the use of tetraploid embryos as hosts for the injection of ES cells. Using this approach, the developing tetraploid cells are restricted to the placental tissue while the diploid ES cells form the majority, if not all, of the fetus proper. While the original mouse cell lines used produced term offspring that died soon after birth (Nagy et al., 1990), use of other ES cell lines have resulted in chimeras with 100% ES contribution that survive to adulthood and breed normally (Ueda et al., 1995). In pigs, the ability of tetraploid embryos to form chimeric blastocysts when aggregated with diploid blastomeres has been demonstrated (Prather et al., 1996).

C. Blastocyst injection

In this technique, blastocyst stage embryos are removed from pregnant females. The PGC-derived colonies are dissociated into single cells, and incubated with 2–5 blastocyst stage embryos. The mixture is then injected into the blastocoele of a developing embryo. After injection, the embryos are placed in an incubator and allowed to recuperate. The embryos are then returned to a recipient in an estrus stage 24 hours behind (later) than the donor embryo. An example is the use of day 6 donor embryos and day 5 recipients. Following transfer, the animals are monitored daily. Pregnancy is determined by non-return to estrus and ultrasound.

D. Aggregation with Earlier Stage Embryos

Another way of making chimeras is to aggregate PGC-derived cells with earlier stage embryos, in particular 8 cell pre-compacted embryos. This is accomplished by either injecting 10–12 PGC-derived cells into the perivitteline space of an 8 cell stage embryo, and culture to the blastocyst stage to confirm incorporation of the PGC cells into the ICM, or by removing the zona pellucida of the 8 cells embryo and placing the embryonic cells in close apposition with 8–12 PGC-derived cells. The embryos are allowed to develop to the blastocyst stage to confirm incorporation of the PGCs into the ICM and transferred to recipient at the proper stage of the estrus cycle.

E. Tetraploid Embryos

Another preferred approach for increasing the contribution of the PGC-derived cells to the chimeric fetus has been the use of tetraploid embryos as hosts for the injection of PGC-derived cells. Using this approach, the developing tetraploid cells are restricted to the placental tissue while the diploid PGC cells form the majority, if not all, of the fetus proper. Tetraploid embryos are produced as described by Prather et al., (1996). Essentially, two cell embryos are collected at surgery from the oviduct after estrus detection and mating. Embryos are equilibrated and fused. After fusion, embryos are placed in Whitten's media and incubated for 6 days at 39° C. At this stage the tetraploid embryos are used as host embryos. Following injection of 10–15 PGC-derived cells, embryos will be transferred to synchronized recipients and allowed to develop to term.

F. Analysis of Transgenic Animals

In a preferred embodiment of the present invention, fetuses are collected from early stage pregnant animals, and examined for expression of the transgene. In particularly preferred embodiments, GFP marker protein is included in a construct with at least one additional selected transgene. After initial examination under fluorescent light in an dissecting microscope to determine the extent of expression of the GFP, the embryos are dissected for removal of the gonadal ridge. The gonadal (genital) ridge is reexamined using a fluorescent microscope. Primordial germ cells that are GFP positive are identified, indicating the ability of the transformed cell lines being to contribute to the formation of a germ line chimera. The gonadal ridge is dissociated, and the PGCs are isolated and examined under a fluorescent microscope, and the proportion of GFP expressing cells calculated. After fluorescent analysis all remaining tissues are saved for DNA extraction and genetic analysis of the DNA by PCR and genornic Southern analysis to confirm the presence of the transgene.

Once fetuses containing transgenic PGCs are identified, remaining pregnant animals are allowed to carry the gestation to term. At term, placental tissues are collected and a sample of the umbilical cord taken from each of the piglets born for genomic analysis. Two to three days later a small tissue sample is collected for DNA isolation and Southern analysis to identify transgenic animals. The animals are allowed to continue development until wearing at which time a blood sample is collected for DNA isolation and identification of transgenic animals. All identified transgenic animals are kept for further study.

Animals remaining under observation will be kept until breeding age to determine the extent of germ line contribution of the PGC-derived cells. The germ line contribution will be determined by breeding as well as by collecting a semen sample (if the transgenic animals are male). The sample is processed to isolate a pure population of sperm, and DNA is isolated for PCR and Southern analysis to determine whether the transgene can be detected in the sperm, indicating the potential for germ line transmission.

Expression of the GFP transgene is detected by fluorescence, and confirmed by Northern. In all cases tissues are examined first by Southern to confirm the presence of the transgene, then by Northern to confirm the transcription of the gene, and then by fluoresce to confirm translation of the protein. In cases other than GFP the same order is followed except that for the final stage PAGE protein analysis followed by Westerns is performed, or bioassays are performed.

Heritability of the transgene is confirmed by mating the germ line chimera to test animals, sampling the litters born by Southern analysis of tissue and blood DNA. At this stage transgenic animals should be non-chimeric and hemizygous, so it is possible to detect the transgene if it is inherited. To confirm that the transgene can pass to an additional generation, confirmed hemizygous transgenes expressing the transgene in the appropriate manner are further bred and resulting litters analyzed for inheritance of the transgene.

IV. Growth Factor Genes

Further aspects of the present invention concern isolated DNA segments and recombinant vectors encoding bovine leukemia inhibitory factor (LIF), porcine ciliary neurotrophic factor (CNTF), and porcine apolipoprotein-E (Apo-E), and the creation and use of recombinant host cells through the application of DNA technology, that express bovine LIF, porcine CNTF and porcine Apo-E.

Additional aspects of the present invention concern isolated DNA segments encoding porcine leukemia inhibitory factor (LIF; SEQ ID NO:7) and porcine ciliary neurotrophic factor (CNTF; SEQ ID NO:8), which have been optimized for maximal expression in yeast. This was accomplished by changing the DNA sequence to reflect codon usage in yeast, without changing the amino acid sequence of the resultant protein products. The protein products from these sequences are capable of conferring the appropriate growth promoting activity to a primordial germ cell when incorporated into a recombinant host cell from which porcine LIF or porcine CNTF can be isolated.

The present invention concerns DNA segments, isolatable from bovine (LIF) and porcine (CNTF and Apo-E), that are free from total genomic DNA and are capable of conferring the appropriate growth promoting activity to a primordial germ cell when incorporated into a primordial germ cell, or a recombinant host cell from which bovine LIF, porcine CNTF and porcine Apo-E can be isolated, and then added to an appropriate growth medium. As used herein, the term "growth promoting activity" refers to the ability to permit the growth of primordial germ cells, in a manner that maintains the undifferentiated state of the cells, and renders them amenable to transformation, cryopreservation and long term culture.

As used herein, the term "DNA segment" refers to a DNA molecule that has been isolated free of total genomic DNA of a particular species. Therefore, a DNA segment encoding bovine LIF refers to a DNA segment that contains bovine LIF coding sequence yet is isolated away from, or purified free from, total genomic bovine DNA, and a DNA segment encoding porcine CNTF or Apo-E refers to a DNA segment that contains porcine CNTF or Apo-E coding sequences, yet is isolated away from, or purified free from, total genomic porcine DNA. Included within the term "DNA segment", are DNA segments and smaller fragments of such segments, and also recombinant vectors, including, for example, plasmids, cosmids, phage, viruses, and the like.

Similarly, a DNA segment comprising an isolated or purified bovine LIF, porcine CNTF or porcine Apo-E gene refers to a DNA segment including bovine LIF, porcine CNTF or porcine Apo-E gene coding sequences and, in certain aspects, regulatory sequences, isolated substantially away from other naturally occurring genes or protein encoding sequences. In this respect, the term "gene" is used for simplicity to refer to a functional protein, polypeptide or peptide encoding unit. As will be understood by those in the art, this fuinctional term includes both genomic sequences, cDNA sequences and smaller engineered gene segments that express, or may be adapted to express, proteins, polypeptides or peptides.

"Isolated substantially away from other coding sequences" means that the gene of interest, in this case the bovine LIF, porcine CNTF or porcine Apo-E gene, forms the significant part of the coding region of the DNA segment, and that the DNA segment does not contain large portions of naturally-occurring coding DNA, such as large chromosomal fragments or other functional genes or cDNA coding regions. Of course, this refers to the DNA segment as originally isolated, and does not exclude genes or coding regions later added to the segment by the hand of man.

In particular embodiments, the invention concerns isolated DNA segments and recombinant vectors incorporating DNA sequences that encode a bovine LIF, porcine CNTF or porcine Apo-E gene that includes within its amino acid sequence a contiguous amino acid sequence from SEQ ID NO:2 (bovine LIF), SEQ ID NO:4 (porcine CNTF) and SEQ ID NO:6 (porcine Apo-E) corresponding to bovine (LIF) or porcine (CNTF, Apo-E).

Naturally, where the DNA segment or vector encodes a full length bovine LIF, porcine CNTF or porcine Apo-E protein, or is intended for use in expressing the bovine LIF, porcine CNTF or porcine Apo-E protein, the most preferred sequences are those that are essentially as set forth in the full length contiguous sequence of SEQ ID NO:2 (bovine LIF), SEQ ID NO:4 (porcine CNTF) and SEQ ID NO:6 (porcine Apo-E), and that encode a protein that retains growth promoting activity to a primordial germ cell, e.g., as may be determined by the ability to grow primordial germ cells in culture.

Sequence of the present invention will substantially correspond to a contiguous portion of SEQ ID NO:2 (bovine LIF), SEQ ID NO:4 (porcine CNTF) and SEQ ID NO:6 (porcine Apo-E), and have relatively few amino acids that are not identical to, or a biologically functional equivalent of, the amino acids of SEQ ID NO:2 (bovine LIF), SEQ ID NO:4 (porcine CNTF) and SEQ ID NO:6 (porcine Apo-E). The term "biologically functional equivalent" is well understood in the art and is further defined in detail herein (Section X).

Accordingly, sequences that have between about 70% and about 80%; or more preferably, between about 81% and about 90%; or even more preferably, between about 91% and about 99%; of amino acids that are identical or functionally equivalent to the amino acids of SEQ ID NO:2 (bovine LIF), SEQ ID NO:4 (porcine CNTF) and SEQ ID NO:6 (porcine Apo-E) will be sequences that are "essentially as set forth in SEQ ID NO:2 (bovine LIF), SEQ ID NO:4 (porcine CNTF) and SEQ ID NO:6 (porcine Apo-E).

In certain other embodiments, the invention concerns isolated DNA segments and recombinant vectors that include within their sequence a contiguous nucleic acid sequence from SEQ ID NO:1 (bovine LIF), SEQ ID NO:3 (porcine CNTF), SEQ ID NO:5 (porcine Apo-E), "optimized" porcine leukemia inhibitory factor (LIF; SEQ ID NO:7) and "optimized" porcine ciliary neurotrophic factor (CNTF; SEQ ID NO:8),. This definition is used in the same sense as described above and means that the nucleic acid sequence substantially corresponds to a contiguous portion of SEQ ID NO:1 (bovine LIF), SEQ ID NO:3 (porcine CNTF), SEQ ID NO:5 (porcine Apo-E), SEQ ID NO:7 ("optimized" porcine leukemia inhibitory factor) and SEQ ID NO:8 ("optimized" porcine ciliary neurotrophic factor) and has relatively few codons that are not identical, or functionally equivalent, to the codons of SEQ ID NO:1 (bovine LIF), SEQ ID NO:3 (porcine CNTF), SEQ ID NO:5 (porcine Apo-E), SEQ ID NO:7 ("optimized" porcine leukemia inhibitory factor) and SEQ ID NO:8 ("optimized" porcine ciliary neurotrophic factor). Again, DNA segments that encode proteins exhibiting primordial germ cell growth promoting activity will be most preferred. The term "functionally equivalent codon" is used herein to refer to codons that encode the same amino acid, such as the six codons for arginine or serine, and also refers to codons that encode biologically equivalent amino acids. See Table 5 and Table 6 in Section VI below.

The genomic sequences for bovine LIF (SEQ ID NO:49), porcine CNTF (SEQ ID NO:50) and porcine Apo-E (SEQ ID NO:51) are also disclosed herein. The exons of bovine LIF correspond to nucleotides 1214–1298, 3010–3188 and 3949–4359 of SEQ ID NO:49. The exons of porcine CNTF correspond to nucleotides 392–505 and 1768–2256 of SEQ ID NO:50. The exons of porcine Apo-E correspond to nucleotides 832–858, 1663–1728, 2473–2662 and 3037–3879 of SEQ ID NO:51. The exons correspond to the coding region, and in some cases 5' and/or 3' untranslated regions.

It will also be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region or may include various internal sequences, i.e., introns, which are known to occur within genes.

Excepting intronic or flanking regions, and allowing for the degeneracy of the genetic code, sequences that have between about 70% and about 79%; or more preferably, between about 80% and about 89%; or even more preferably, between about 90% and about 99% of nucleotides that are identical to the nucleotides of SEQ ID NO:1 (bovine LIF), SEQ ID NO:3 (porcine CNTF), SEQ ID NO:5

(porcine Apo-E), SEQ ID NO:7 ("optimized" porcine leukemia inhibitory factor) and SEQ ID NO:8 ("optimized" porcine ciliary neurotrophic factor) will be sequences that are "essentially as set forth in SEQ ID NO:1 (bovine LIF), SEQ ID NO:3 (porcine CNTF), SEQ ID NO:5 (porcine Apo-E), SEQ ID NO:7 ("optimized" porcine leukemia inhibitory factor) and SEQ ID NO:8 ("optimized" porcine ciliary neurotrophic factor). Sequences that are essentially the same as those set forth in SEQ ID NO:1 (bovine LIF), SEQ ID NO:3 (porcine CNTF), SEQ ID NO:5 (porcine Apo-E), SEQ ID NO:7 ("optimized" porcine leukemia inhibitory factor) and SEQ ID NO:8 ("optimized" porcine ciliary neurotrophic factor) may also be functionally defined as sequences that are capable of hybridizing to a nucleic acid segment containing the complement of SEQ ID NO:1 (bovine LIF), SEQ ID NO:3 (porcine CNTF), SEQ ID NO:5 (porcine Apo-E), SEQ ID NO:7 ("optimized" porcine leukemia inhibitory factor) and SEQ ID NO:8 ("optimized" porcine ciliary neurotrophic factor) under relatively stringent conditions. Suitable relatively stringent hybridization conditions will be well known to those of skill in the art.

Naturally, the present invention also encompasses DNA segments that are complementary, or essentially complementary, to the sequence set forth in SEQ ID NO:1 (bovine LIF), SEQ ID NO:3 (porcine CNTF), SEQ ID NO:5 (porcine Apo-E), SEQ ID NO:7 ("optimized" porcine leukemia inhibitory factor) and SEQ ID NO:8 ("optimized" porcine ciliary neurotrophic factor). Nucleic acid sequences that are "complementary" are those that are capable of base-pairing according to the standard Watson-Crick complementarity rules. As used herein, the term "complementary sequences" means nucleic acid sequences that are substantially complementary, as may be assessed by the same nucleotide comparison set forth above, or as defined as being capable of hybridizing to the nucleic acid segment of SEQ ID NO:1 (bovine LIF), SEQ ID NO:3 (porcine CNTF), SEQ ID NO:5 (porcine Apo-E), SEQ ID NO:7 ("optimized" porcine leukemia inhibitory factor) and SEQ ID NO:8 ("optimized" porcine ciliary neurotrophic factor) under relatively stringent conditions.

The nucleic acid segments of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, nucleic acid fragments may be prepared that include a short contiguous stretch identical to or complementary to SEQ ID NO:1 (bovine LIF), SEQ ID NO:3 (porcine CNTF), SEQ ID NO:5 (porcine Apo-E), SEQ ID NO:7 ("optimized" porcine leukemia inhibitory factor) and SEQ ID NO:8 ("optimized" porcine ciliary neurotrophic factor) such as about 14 nucleotides, and that are up to about 10,000 or about 5,000 base pairs in length, with segments of about 3,000 being preferred in certain cases. DNA segments with total lengths of about 1,000, about 500, about 200, about 100 and about 50 base pairs in length (including all intermediate lengths) are also contemplated to be useful.

It will be readily understood that "intermediate lengths", in these contexts, means any length between the quoted ranges, such as 14, 15, 16, 17, 18, 19, 20, etc.; 21, 22, 23, etc.; 30, 31, 32, etc.; 50, 51, 52, 53, etc.; 100, 101, 102, 103, etc.; 150, 151, 152, 153, etc.; including all integers through the 200–500; 500–1,000; 1,000–2,000; 2,000–3,000; 3,000–5,000; 5,000–10,000 ranges, up to and including sequences of about 12,001, 12,002, 13,001, 13,002 and the like.

It will also be understood that this invention is not limited to the particular nucleic acid and amino acid sequences of SEQ ID NO:1 and SEQ ID NO:2 (bovine LIF), SEQ ID NO:3 and SEQ ID NO:4 (porcine CNTF), SEQ ID NO:5 and SEQ ID NO:6 (porcine Apo-E), SEQ ID NO:7 ("optimized" porcine leukemia inhibitory factor) and SEQ ID NO:8 ("optimized" porcine ciliary neurotrophic factor) respectively. Recombinant vectors and isolated DNA segments may therefore variously include the bovine LIF, porcine CNTF, porcine Apo-E and porcine LIF coding regions themselves, coding regions bearing selected alterations or modifications in the basic coding region, or they may encode larger polypeptides that nevertheless include bovine LIF, porcine CNTF, porcine Apo-E and porcine LIF-coding regions or may encode biologically functional equivalent proteins or peptides that have variant amino acids sequences.

The DNA segments of the present invention encompass biologically functional equivalent bovine LIF, porcine CNTF, porcine Apo-E and porcine LIF proteins and peptides. Such sequences may arise as a consequence of codon redundancy and functional equivalency that are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques, e.g., to introduce improvements to the antigenicity of the protein or to test bovine LIF, porcine CNTF, porcine Apo-E and porcine LIF mutants in order to examine primordial germ cell growth promoting activity at the molecular level.

If desired, one may also prepare fusion proteins and peptides, e.g., where the bovine LIF, porcine CNTF, porcine Apo-E and porcine LIF coding regions are aligned within the same expression unit with other proteins or peptides having desired functions, such as for purification or immunodetection purposes (e.g., proteins that may be purified by affinity chromatography and enzyme label coding regions, respectively).

V. Cloning Growth Factor and Growth Factor Receptor Genes

The present inventor contemplates cloning growth factor and growth factor receptor genes or cDNAs from non-rodent animal cells, and particularly, oncostatin M (OSM), glycoprotein 130 (GP130), octamer binding transcription factor 4 (Oct-4), leukemia inhibitory factor (LIF), ciliary neurotrophic factor (CNTF), apolipoprotein-E (Apo-E), ciliary neurotrophic factor receptor alpha (CNTFr-α) and leukemia inhibitory factor receptor (LIFr). The animal cells contemplated for use include, but are not limited to, bovine, porcine, ovine and caprine cells.

A technique often employed by those skilled in the art of protein production today is to obtain a so-called "recombinant" version of the protein, to express it in a recombinant cell and to obtain the protein from such cells. These techniques are based upon the "cloning" of a DNA molecule encoding the protein from a DNA library, i.e., on obtaining a specific DNA molecule distinct from other portions of DNA. This can be achieved by, for example, cloning a cDNA molecule, or cloning a genomic-like DNA molecule.

The first step in such cloning procedures is the screening of an appropriate DNA library, such as a genomic or cDNA library from selected non-rodent animal cells. The screening procedure may be an expression screening protocol employing antibodies directed against the protein, or activity assays. For example, antibody screening is very routinely employed. Alternatively, screening may be based on the hybridization of oligonucleotide probes, designed from a consideration of portions of the amino acid sequence of the protein, or from the DNA sequences of genes encoding related proteins. The operation of such screening protocols are well known to those of skill in the art and are described in detail in the scientific literature, for example, in Sambrook et al. (1989), incorporated herein by reference. Moreover, as the present invention encompasses the cloning of genomic segments as well as cDNA molecules, it is contemplated that suitable genomic cloning methods, as known to those in the art, may also be used.

VI. Altering Codon Usage to Maximize Expression of Genes

Changes in any of the transgenes to be expressed in the present invention can be made from changing the sequence of the transgene to correspond to the codon usage of the non-rodent host species selected. Information on codon usage in a variety of organisms is known in the art (Bennetzen and Hall, 1982; Ikemura, 1981a, 1981b, 1982; Grantham et al., 1980, 1981; Wada et al., 1990; each of these references are incorporated herein by reference in their entirety). As an example, and not a limitation, Table 5 and Table 6 provide important information regarding bovine, porcine and ovine codon preference in a format that is easily used. Table 5 provides a list of the codons that are preferred for use in the "bovanized," "porcinized," and "ovinized" constructs of the present invention. Table 6 is simply the same information that incorporates U (uridine) rather than T (thymine), for ready cross-reference.

TABLE 5

Preferred DNA Codons for Bovine, Porcine and Ovine Use

| Amino Acids | | Codons Preferred in Bovine, Porcine and Ovine Genes | | | | |
|---|---|---|---|---|---|---|
| Alanine | Ala A | GCC | GCT | GCA[1] | GCG | |
| Cysteine | Cys C | TGC | TGT | | | |
| Aspartic acid | Asp D | GAC | GAT | | | |
| Glutamic acid | Glu E | GAG | GAA | | | |
| Phenylalanine | Phe F | TTC | TTT | | | |
| Glycine | Gly G | GGC | GGG | GGA | GGT | |
| Histidine | His H | CAC | CAT | | | |
| Isoleucine | Ile I | ATC | ATT | ATA | | |
| Lysine | Lys K | AAG | AAA | | | |
| Leucine | Leu L | CTG | CTC | CTT[2] | TTG[2] | CTA TTA |
| Methionine | Met M | ATG | | | | |
| Asparagine | Asn N | AAC | AAT | | | |
| Proline | Pro P | CCC | CCT | CCA | CCG | |
| Glutamine | Gln Q | CAG | CAA | | | |
| Arginine | Arg R | CGC | AGG | CGG | AGA | CGA CGT |

TABLE 5-continued

Preferred DNA Codons for Bovine, Porcine and Ovine Use

| Amino Acids | | Codons Preferred in Bovine, Porcine and Ovine Genes | | | | |
|---|---|---|---|---|---|---|
| Serine | Ser S | TCC[3] | AGC[3] | TCT | AGT[3] | TCA[3] TCG |
| Threonine | Thr T | ACC | ACA[4] | ACT[4] | ACG | |
| Valine | Val V | GTG | GTC | GTT | GTA | |
| Tryptophan | Trp W | TGG | | | | |
| Tyrosine | Tyr Y | TAC | TAT | | | |

[1] - GCA is the least preferred alanine codon in ovine, and is very rarely used
[2] - TTG is the third, and CTT is the fourth most preferred leucine codon in porcine
[3] - Bovine prefers AGC first over TCC; Ovine prefers TCA third over AGT
[4] - Ovine prefers ACT second over ACA The codons at left are those most preferred for use, with usage decreasing towards the right. Double underlined codons represent those which are rarely used.

TABLE 6

Preferred RNA Codons for Bovine, Porcine and Ovine Use

| Amino Acids | | Codons Preferred in Bovine, Porcine and Ovine Genes | | | | |
|---|---|---|---|---|---|---|
| Alanine | Ala A | GCC | GCU | GCA[1] | GCG | |
| Cysteine | Cys C | UGC | UGU | | | |
| Aspartic acid | Asp D | GAC | GAU | | | |
| Glutamic acid | Glu E | GAG | GAA | | | |
| Phenylalanine | Phe F | UUC | UUU | | | |
| Glycine | Gly G | GGC | GGG | GGA | GGU | |
| Histidine | His H | CAC | CAU | | | |
| Isoleucine | Ile I | AUC | AUU | AUA | | |
| Lysine | Lys K | AAG | AAA | | | |
| Leucine | Leu L | CUG | CUC | CUU[2] | UUG[2] | CUA UUA |
| Methionine | Met M | AUG | | | | |
| Asparagine | Asn N | AAC | AAU | | | |
| Proline | Pro P | CCC | CCU | CCA | CCG | |
| Glutamine | Gln Q | CAG | CAA | | | |
| Arginine | Arg R | CGC | AGG | CGG | AGA | CGA CGU |
| Serine | Ser S | UCC[3] | AGC[3] | UCU | AGU[3] | UCA[3] UCG |
| Threonine | Thr T | ACC | ACA[4] | ACU[4] | ACG | |
| Valine | Val V | GUG | GUC | GUU | GUA | |
| Tryptophan | Trp W | UGG | | | | |
| Tyrosine | Tyr Y | UAC | UAU | | | |

TABLE 6-continued

Preferred RNA Codons for Bovine, Porcine and Ovine Use

| Amino Acids | Codons Preferred in Bovine, Porcine and Ovine Genes |
|---|---|

[1] - GCA is the least preferred alanine codon in ovine, and is very rarely used
[2] - UUG is the third, and CUU is the fourth most preferred leucine codon in porcine
[3] - Bovine prefers AGC first over UCC; Ovine prefers UCA third over AGU
[4] - Ovine prefers ACU second over ACA
The codons at left are those most preferred for use, with usage decreasing towards the right.
Double underlined codons represent those which are rarely used.

From studying the information in Table 5 and Table 6, one of skill in the art would readily discern that the ATA, CTA, TTA, CGT, TCG and GTA (or AUA, CUA, UUA, CGU, UCG or GUA) codons should be changed to a more preferred codon for use in bovine, porcine or ovine embodiments of the present invention. As a general guideline, those codons listed in columns 5 and 6 generally represent codons that one would prefer to change in creating a "bovanized," "porcinized," or "ovinized" gene; the codons listed in column 4 should also often be changed in creating a "bovanized," "porcinized," or "ovinized" gene; the codons listed in column 3 may or may not be changed, depending on the number of changes that one wishes to make in total and on the particular amino acid that is to be encoded. Those codons listed in columns 1 and 2, when occurring in the wildtype transgene sequence, will generally be appropriate and should not need changing, unless there is only a choice of two codons available. However, replacing a codon from column 2 with a codon from column 1 is certainly a useful option, particularly where there is only a choice of two codons. Given this information, it will now be understood that, when introducing changes into the transgene sequence, one would generally desire to introduce a codon of column 1 wherever possible.

In light of the foregoing discussion, it is contemplated that changing about 10% of the codons would produce a useful increase in expression levels and such gene sequences therefore fall within the scope of the present invention. Changing about 15%, 20%, 25% or 30% of the codons within the transgene sequence is also considered to be useful and the altered transgenes of this invention encompass those gene sequences that fall within the aforementioned ranges.

In certain embodiments, depending on the nature of the codon changes introduced, it may not be necessary to even make a 10% change in the codon usage of the transgene. For example, if each of the ten least favored codons were to be changed and replaced with those most preferred for use in genes of the selected non-rodent animal species, it is contemplated that the resultant sequence may achieve reasonable expression in cells of the selected non-rodent animal species. When making these changes along with a number of other changes, it is contemplated that changing at least about 7, 8 or 9 of these codons will be sufficient to result in a transgene with improved expression. As described above, leucine would preferably be encoded by CTG, CTC, CTT or TTG; valine would preferably be encoded by GTG; and isoleucine would preferably be encoded by ATC.

Although transgene sequences in which about 4–5, about 10, about 20 or about 30–35% of the codons have been changed will generally be preferred, there is no reason that further changes should not be made if so desired. Altered transgene sequences in accordance with the present invention may therefore be sequences that contain altered codons at about 40%, 50%, 60%, 70% or even about 80–90% of the codon positions within the full length codon region.

VII. Protein Purification

Further aspects of the present invention concern the purification, and in particular embodiments, the substantial purification, of a recombinant heterologous protein. The term "purified recombinant heterologous protein" as used herein, is intended to refer to a recombinant heterologous protein composition, isolatable from a transgenic host, wherein the recombinant heterologous protein is purified to any degree relative to its naturally-obtainable state, i.e., in this case, relative to its purity within a natural product (for example milk) or cell extract. A purified recombinant heterologous protein therefore also refers to a recombinant heterologous protein free from the environment in which it may naturally occur.

Generally, "purified" will refer to a recombinant heterologous protein composition which has been subjected to fractionation to remove various non-host cell components. Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite, lectin affinity and other affinity chromatography steps; isoelectric focusing; gel electrophoresis; and combinations of such and other techniques.

Methods exhibiting a lower degree of relative purification may have advantages in total recovery of protein product, or in maintaining the activity of an expressed protein. Inactive products also have utility in certain embodiments, such as, e.g., in antibody generation.

Partially purified recombinant heterologous protein fractions for use in such embodiments may be obtained by subjecting a transgenic host product (for example milk) or cell extract to one or a combination of the steps described above. Substituting certain steps with improved equivalents is also contemplated to be useful. For example, it is appreciated that a cation-exchange column chromatography performed utilizing an HPLC apparatus will generally result in a greater-fold purification than the same technique utilizing a low pressure chromatography system.

VIII. Biological Functional Equivalents

As mentioned above, modification and changes may be made in the structure of transgenic proteins and still obtain a molecule having like or otherwise desirable characteristics. For example, certain amino acids may be substituted for other amino acids in a protein structure without appreciable loss of oligosaccharide processing capabilities. Since it is the interactive capacity and nature of a protein that defines that protein's biological functional activity, certain amino acid sequence substitutions can be made in a protein sequence (or, of course, its underlying DNA coding sequence) and nevertheless obtain a protein with like (agonistic) properties. Equally, the same considerations may be employed to create a protein or polypeptide with countervailing (e.g., antagonistic) properties. It is thus contemplated by the inventors that various changes may be made in the sequence of transgenic proteins or peptides (or underlying DNA) without appreciable loss of their biological utility or activity.

In terms of functional equivalents, It is also well understood by the skilled artisan that, inherent in the definition of a biologically functional equivalent protein or peptide, is the concept that there is a limit to the number of changes that may be made within a defined portion of the molecule and still result in a molecule with an acceptable level of equivalent biological activity. Biologically functional equivalent peptides are thus defined herein as those peptides in which certain, not most or all, of the amino acids may be substituted. Of course, a plurality of distinct proteins/peptides with different substitutions may easily be made and used in accordance with the invention.

It is also well understood that where certain residues are shown to be particularly important to the biological or structural properties of a protein or peptide, e.g., residues in active sites, such residues may not generally be exchanged.

Conservative substitutions well known in the art include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine, glutamine, or glutamate; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

In making such changes, the hydropathic index of amino acids may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte & Doolittle, 1982, incorporated herein by reference). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with its immunogenicity and antigenicity, i.e. with a biological property of the protein. use this shorter portion for non-immunological stuff It is understood that an amino acid can be substituted for another having a similar hydrophilicity value and still obtain a biologically equivalent, and in particular, an immunologically equivalent protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making changes based upon similar hydrophilicity values, the substitution of amino acids whose hydrophilicity values are within ±2 is preferred, those which are within ±1 are particularly preferred, and those within ±0.5 are even more particularly preferred.

While discussion has focused on functionally equivalent polypeptides arising from amino acid changes, it will be appreciated that these changes may be effected by alteration of the encoding DNA; taking into consideration also that the genetic code is degenerate and that two or more codons may code for the same amino acid. A table of amino acids and their codons is presented herein for use in such embodiments, as well as for other uses, such as in the design of probes and primers and the like.

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Culture of Primordial Germ Cells

A. Preparation of the Feeder Layers

STO cells (Ware and Axelrad, 1972) were grown in Dulbecco's modified Eagle's media supplemented, 2 mM glutamine, 15% fetal bovine sera (selected batches, Summit Biotechnology), and 0.1 mM β-mercapthoethanol (PEG media). When cells were in the log-phase of growth they were collected by trypsinization, centrifuged, resuspended in 50 ml tubes at concentration not greater than 1 million per ml and subjected to 3.2 Krad of cobalt radiation for inactivation.

Following inactivation cells were plated onto tissue culture plates pre-coated with 0.1% porcine gelatin at a density of 2.5 million per 35 mm well. This density is several fold higher that the density used for mouse ES cells and has been determined to be critical for the isolation of porcine and bovine EG cell lines. Following overnight culture the feeders were ready for use.

1. Analysis of Feeder Density

In order to quantitate the effect of feeder density on porcine and bovine primordial germ cell culture, porcine and bovine primordial germ cells were grown on feeder cells at three different densities.

Genital ridges were isolated from day 25–27 porcine fetuses and 3–5 cm crown rump length bovine fetuses were isolated essentially as described below. An equal number of PGCs were plated on feeder layers of STO at densities of 0.5, 1.5, and 3.0 million per 35 mm well. Following 6–9 days of culture, colonies were fixed in 4% formaldehyde, stained for alkaline phosphatase, and counted. Additionally the morphology of the colonies was recorded by microphotography. Alkaline phosphatase (AP) activity was determined essentially as described by Moore and Piedrahita (1997). Briefly, culture plates were rinsed twice in phosphate buffered saline (PBS) and fixed in 4% formaldehyde in PBS for 15 m at room temperature. Fixed cells were washed twice with PBS and stained in naphtol AS-MX phosphate (200 μg/ml; Sigma) and Fast Red TR salt (1 mg/ml; Sigma) in 100 mM Tris buffer, pH 8.2 for 15 m at room temperature. Staining was terminated by washing cultures in PBS. Specificity of staining was determined by staining some wells in the presence of tetramisole (500 $\mu$M; Sigma), an inhibitor of AP.

Bovine and porcine PGCs plated on lower density feeders had an epithelial-like morphology and little if any remaining AP activity. In contrast colonies in high density feeders had the compact morphology and the high AP activity associated with undifferentiated ES and EG cells. Additionally the typical large nucleus and prominent nucleoli associated with ES and EG cells was seen. The number of colonies was also affected by the density of the feeder layer. Table 7 shows the effect of feeder density on the behavior of cultured porcine primordial germ cells (experiment performed in triplicate), and Table 8 shows the effect of feeder density on the behavior of cultured bovine primordial germ cells (experiment performed in duplicate). Only alkaline phosphatase positive colonies were counted.

TABLE 7

| Density (× $10^6$) | R1 | R2 | R3 | Mean |
|---|---|---|---|---|
| 3.0 | 402 | 410 | 526 | 446 |
| 1.5 | 305 | 276 | 390 | 324 |
| 0.5 | 114 | 88 | 123 | 108 |

TABLE 8

| Density (million) | R1 | R2 | Mean |
|---|---|---|---|
| 3.0 | 42 | 36 | 39 |
| 1.5 | 23 | 41 | 32 |
| 0.5 | 6 | 12 | 9 |

As previously indicated there is a beneficial effect of increased feeder density on the ability of PGCs to proliferate in culture in an undifferentiated state. In addition to growth factors that the STO cells may be releasing into the media, it is clear that direct attachment of the PGC to the STO cells is required for maintenance of the undifferentiated morphology. Any time a PGC was seen growing directly on plastic, even when surrounded by STO cells, it grew and proliferated as an epithelial sheet. Thus it is likely that extracellular matrix components supplied by the STO cells are required for the replication of PGC-derived cells in an undifferentiated state. Additionally, the inventors have shown that addition of $1-1.5 \times 10^6$ fresh feeder cells every 3 to 5 days improves the performance of the PGC cells.

2. Effect of Porcine Embryonic Fibroblasts on Performance of Feeder Layer

To test whether the number of PGC colonies could be increased when using substandard STO feeders, the use of porcine embryonic fibroblasts (PEF) was tested. To isolate the PEF day 25 day fetuses were obtained, all internal organs and the head regions were removed, and the remaining tissues were minced. The tissues were then incubated in trypsin for 10–20 minutes and the resulting cell suspension plated in PES media without growth factors. Cells were passed every 2–3 days and used for only two weeks.

For feeder experiments, the PEF cells were treated the same as the STO cells. The cells were trypsinized, collected, and inactivated by 3–10 kilorads of radiation. Following irradiation feeders were plated on gelatinized plates at a density of 0.5–3 million cells per 35 mm dish.

Freshly collected PGC's were plated in STO or STO+PEF (50:50 ratio) feeders in PES with growth factors. 10–12 days after electroporation colonies were examined. The number of colonies in the STO-PES wells was over twice the number in the STO alone (325 versus 128). Moreover, the colonies were larger and appeared sooner. Experiments are being conducted using PEF feeders alone. However, the inventors contemplate using the PEF to "stabilize" the STO feeder system, and make it more practical.

3. Effect of Basic Fibroblast Growth Factor on Performance of Feeder Layer

STO feeder cells were plated in PES media alone for 48 hours or in PES media containing 40 ng/ml bFGF for the same period of time. It has been determined that bFGF is an essential component for the isolation of porcine primordial germ cells. It is not presently known whether bFGF is acting directly on the proliferation rate of the PGCs or whether the effect is through a change in the physiology of the STO cells which then effects the PGCs. Since it has also been demonstrated that it is possible to isolate PGC-derived colonies in the absence of soluble stem cell factor and/or leukemia inhibitory factor, either bFGF can act both as a proliferation inducer and differentiation inhibitor of the PGCs, or more likely the bFGF is stimulating the STO feeder cells to produce growth factors involved in the isolation of PGCs. A drastic change is seen in the morphology of the feeder cells, in particular the fiber-like arrangement seen in the presence of bFGF.

4. Involvement of Extracellular Matrix/Matrix Attachment in Differentiation

The extracellular matrix has been implicated in survival of apoptosis (Meredith et al., 1993). The possible involvement of the extracellular matrix and/or matrix attachment in ES and EG differentiation is suggested by three different studies. Firstly, mouse cells were placed in feeder free system, comprising tissue culture plates covered with 0.1% gelatin. When LIF was added, the cells grew well, but not optimally. The cells were then trypsinized and split into two, with half passed to a new plate, and half returned to the old plate. The cells returned to the old plate performed much better, with the cells being more undifferentiated and healthier looking. The originals cells may have left something behind that the trypsin either did not remove or removed incompletely.

Secondly, rat ES cells have never been isolated unless co-cultured with mouse ES cells. Culturing the rat ES cells on different feeders has no effect. The use of conditioned media also has no effect. This suggests that the mouse ES cells are secreting something that allows the rat ES cells to proliferate in an undifferentiated state.

Thirdly, when low density feeders are used to culture porcine PGCs, very few colonies grow and the few that do grow are always in direct contact with the feeder cells. No colonies grow on the plastic, even if surrounded by STO cells. Thus it is unlikely that the STO's are producing a soluble factor. Additionally, to isolate porcine PGC-derived cells, it is an absolute requirement that bFGF be added to the feeders. The bFGF drastically changes the morphology of the feeder cells. Thus the bFGF may be acting on the feeder to promote/inhibit production of a matrix component versus acting directly on the PGC cells. Also, very few colonies are obtained when plating porcine PGCs on feeders made within 6 hours. However, feeders made 24 hours prior to plating yield much better results. Thus this period of time may be required for synthesis and secretion of some matrix component.

The effect of the extracellular matrix and/or matrix attachment in ES and EG differentiation is being currently studied by a number of different methods. Firstly, ES cells are plated, removed by trypsinization, and then porcine PGC-derived cells are be added. Secondly, PGCs are plated in matrigel. Thirdly, PGCs are plated in specific matrix components. Lastly, a healthy feeder is "extracted" so the cells are killed but the matrix is left behind, and then PGCs are plated in the "extracted" versus live controls.

B. Generation of Porcine, Bovine and Caprine PGC (EG) Cells

1. Porcine and Bovine PGCs

Uteri and ovaries of pigs at day 25 of pregnancy and cattle at day 35–40 of pregnancy were collected at surgery or slaughter. Each fetus in the pregnant uterus was surgically removed under sterile conditions and placed in collection media which is comprised of PBS containing 0.4% BSA and 1% penicillin-streptomycin level (Gibco #15140-015; 100×: 10,000 units of penicillin, 10,000 μg of streptomycin). Following collection the fetuses were rinsed twice in collection media and dissected individually under a stereomicroscope. The genital ridge of the developing fetus was identified and gently dissected with the help of forceps. The isolated genital ridges were placed in collection media until all fetuses were dissected. The genital ridges were then incubated in dissociation media (0.02% EDTA, 0.8% NaCl, 0.02% KCl, 0.115% anhydrous $Na_2PO_4$, 0.02% $KH_2PO_4$, 0.02% glucose and 0.001% phenol red) for 20 minutes to dissociate PGC's from the gonadal anlague. Following incubation, the ridge was punctured with a 27 gauge needle, and the PGCs gently released in culture media by squeezing with a set of forceps. The PGCs were collected in 3–5 ml of Dulbecco's modified Eagle's media:Ham's F10 supplemented with 0.01 mM non-essential amino acids, 2 mM L-glutamine, 15% fetal bovine serum (selected batches, Summit Biotechnology) and 0.1 mM β-mercaptoethanol (PES media). Remaining tissues were gently disrupted by pipetting, and the resulting cell suspension was spun at 250 g for 5 min. The supernatant was removed and centrifuged at 1,500 g for 5 minutes.

The pellet, containing PGCs, was resuspended in PES media. Following collection, the cells were rinsed 3 times by centrifugation and resuspended in PEG medium containing soluble recombinant human stem cells factor at 30 ng/ml, human basic fibroblast growth factor at 40 ng/ml, and LIF at 20 ng/ml and plated onto STO feeder layers. Additionally, the effect of the addition of 100 ng/ml of uteroferrin in the presence or absence of stem cell factor on the number of alkaline phosphatase positive colonies was determined.

The cell suspension at a density of 10,000 PGCs/ml were plated onto feeder layer of STO cells. Following 10–14 days of culture, colonies with ES-like morphology were passaged to fresh feeder layers for establishment of cell lines. Resulting colonies were passaged by trypsinization to fresh feeder layers at 6–9 day intervals. State of differentiation of isolated cell lines was determined by morphology and expression of alkaline phosphatase, a marker of undifferentiated embryonic cells (Talbot et al., 1993).

The feeder cells are perhaps the most critical component of the whole system. To obtain the largest possible number of EG colonies a density of 2.5 million per 35 mm plate is required. This is in contrast with mouse ES cells where a density of only 1 million per 35 ml plate is required. Moreover, any attempt to culture EG cells on freshly prepared feeders has failed. Instead when the feeders are allowed to plate for at least 24 hr prior to use the best results are obtained.

2. Caprine PGCs

A single day 25 goat fetus was obtained and the genital ridges isolated as described above. Using the original needle teasing isolation procedure, PGCs were isolated and plated on STO feeder layers in media containing Uteroferrin rose and LIF, SCF, and bFGF at the concentrations described above. The resulting colonies were maintained for two passages at which point cells were fixed and stained for alkaline phosphatase activity.

Caprine cultured PGC had essentially the same morphology as that seen for porcine and bovine cells. Moreover, the caprine cells stained strongly for alkaline phosphatase activity. The morphology and AP staining pattern of the caprine PGCs is similar to that shown above for porcine and bovine PGCs. Colonies cultured as described herein were passaged at least twice before morphology and alkaline phosphatase activity was recorded. In all cases the typical ES-like morphology with small cytoplasm, large nucleus, and prominent nucleoli was seen. Additionally, colonies remaining unattached after the first passage showed the ability to differentiate into simple embryoid bodies (Example 2 below). In the caprine case the embryoid bodies were seen developing 4 days after normal passage into fresh feeder layers from colonies remaining in suspension. In all cases the double layered appearance typical of simple embryoid bodies is evident and indicates the pluripotential characteristics of the isolated cell lines.

The similarity of behavior of porcine, bovine, and caprine PGCs when placed in the culture system described here indicates that it will be possible to utilize this system across a large number of species for the isolation of PGC-derived cell lines. Equally important it implies that advances made in one species can easily be applied to another species. At present the inventors are initiating studies to isolate, genetically transform, and test the pluripotential ability of goat PGC-derived cell lines.

3. PGCs From Other Species

In order to determine whether the instant methods could be used to isolate EG cells from other mammalian species, PGCs were isolated from rabbits and rats in culture, and their ability to develop into PGC-derived colonies with EG-like morphology was determined. Briefly, PGCs were isolated from day 15–18 New Zealand White rabbit fetuses and day 11–12 Sprague-Dawley rat fetuses. Mouse fetuses at 9.5–12.5 d of gestation were used as controls. PGC isolation was accomplished by removal of the genital ridge and enzymatic disruption of the tissues followed by plating on inactivated STO feeder layers. Culture media consisted of Dulbecco's modified Eagle's media:Ham's F10 media, supplemented with 0.01 mM non-essential amino acids, 2 mM glutamine, 15% fetal bovine sera (selected batches), 0.1 mM 2-mercaptoethanol along with human stem cell factor, human basic fibroblast growth factor and human LIF. For maintenance of the cells, colonies were passed to fresh feeders every 8–10 d.

The resulting colonies were characterized by their morphology, alkaline phosphatase (AP) staining, and ability to differentiate in vitro. In all cases colonies with EG-like morphology were obtained, although there were slight differences between species with the mouse colonies being more rounded and "grape-like" than the other species. Similarly, although AP activity was found in all species the intensity of the signal was drastically reduced in the rabbit. These results suggest that PGC derived cells can be isolated and cultured in vitro from rabbit and rats, thus providing the basis for analyzing their developmental potential and their use for the precise genetic modification of these species.

C. Effects of α-2 Macroglobulin on PGC Cultures

The addition of uteroferrin rose (Utr) to the culture media was shown to increase the number of resulting PGC colonies. While the addition of uteroferrin alone to the culture media resulted in some improvement, it was determined that the most effective molecule was not uteroferrin alone but uteroferrin bound to a serpin (serine protease inhibitor; Malathy et al., 1990). In order to determine the beneficial effect provided by the serpin alone, a broad range protease inhibitor called α2-macroglobulin was studied (Feige et al., 1996). This molecule is known to irreversibly inhibit a broad range of proteases (Feige et al., 1996), as well as bind and transport cytokines.

Without being bound to any particular explanation, the mode of action of α2-macroglobulin is believed to be that it is acting by inhibition of programmed cells death (PCD or apoptosis) in PGC. Programmed cell death has been recorded for both normal (in embryo; Pesce and Felici, 1994) and cultured PGCs (Pesce et al., 1993). Serine protease inhibitors have been implicated in inhibition of PCD (Tewari and Dixit, 1995).

As indicated above, collection of PGCs from the developing fetus is accomplished by preincubation of genital ridges in a EDTA/glucose solution for 20 min followed by teasing the ridges with a needle and allowing the PGCs to seep out. The inventors decided to study whether macerating the tissues right after collection had any advantages over preincubation and needle teasing, and whether α2-macroglobulin provides any benefits to either method.

Genital ridges from two day 25–27 pig fetuses were collected, divided into four groups (a 2×2 study), placed in PES media either with α2-macroglobulin at 1 μg/ml (2 groups) or without α2-macroglobulin (2 groups), and immediately either needle teased to allow colonies to seep out (2 groups) or macerated (2 groups) with the help of a syringe. Briefly, the ridges were broken into small pieces by pressing them against the bottom of a dish with the back of a syringe. The disrupted tissues were further broken up by passing them several times through a 20 gauge needle until all large tissue clumps had been disrupted. Following tissue disruption, samples were centrifuged for 3–5 minutes at 250×g to settle tissue fragments and supernatant containing mostly single cells collected and centrifuged at 1000×g for 5 min. The resulting pellet was resuspended in PES containing LIF, SCF, and bFGF with or without human α2-macroglobulin, cells counted, and plated in triplicate in feeder layers.

Six days later colonies were fixed, stained for alkaline phosphatase activity, and counted. Table 9 shows the results of the effect of the isolation procedure and addition of α2-macroglobulin to the media on the number of PGCs developing into alkaline phosphatase positive colonies.

TABLE 9

| Pig # | Isolation Method | Media | R1 | R2 | R3 | Cells plated (k) | Normalized* value |
|---|---|---|---|---|---|---|---|
| 1 | Teasing | PES | 2608 | 3640 | 2936 | 247 | 12399 |
| 1 | Macerate | PES | 4216 | 3856 | 3976 | 371 | 10842 |
| 1 | Teasing | MAC | 4688 | 4960 | 5424 | 277 | 18087 |
| 1 | Macerate | MAC | 4712 | 5176 | 4368 | 290 | 16395 |
| 2 | Teasing | PES | 3904 | 3776 | 5000 | 263 | 16104 |
| 2 | Macerate | PES | 3368 | 3488 | 2840 | 380 | 8532 |
| 2 | Teasing | MAC | 6200 | 6008 | 6864 | 170 | 37380 |
| 2 | Macerate | MAC | 8312 | 7872 | 8896 | 233 | 35865 |

*Normalized values are expressed as number of colonies per million cells.

It is clear that α2-macroglobulin has a beneficial effect on the ability of PGC to proliferate in culture. The effect seems to be greater when cells are collected by the harsher smashing system that by the gentler teasing system. It could be that the harsher system of collection results in a greater release of proteases that can induce programmed cell death and the binding of the α2-macroglobulin to these proteases results in a high level of protection. In contrast the gentler teasing system induces a lower level of PCD during the isolation procedure and that is why protection by α2-macroglobulin is proportionally lower. The difference between the two pigs, with pig #2 showing a greater response can be attributed to a longer time between uteri collection and germ cell isolation thus allowing for factors being released by the dying tissue to act longer on the PGCs. Regardless of the mechanism of action, it is clear from the data above that addition of α2-macroglobulin to the culture media has a beneficial effect on the number of alkaline phosphatase positive cells appearing during culture.

The effect of α2-macroglobulin on the ability to passage cells was also studied. To test the ability of α2-macroglobulin to protect against the losses normally observed when cultured PGCs are trypsinized, cells were passaged twice in the presence or absence of α2-macroglobulin, the colonies fixed, stained for alkaline phosphatase and the number of alkaline phosphatase positive colonies determined. PGCs were collected in PES and plated on feeder layers in the presence or absence of media containing 1 μg/ml (α2-macroglobulin. Colonies were allowed to grow for 7 days, trypsinized as described above and plated again in media with or without α2-macroglobulin. Samples were done in duplicate and corrected for the number of added cells.

The experimental design was as follows:

| 1st passage | PES | | MAC | |
|---|---|---|---|---|
| 2nd passage | PES | MAC | PES | MAC |

The addition of α2-macroglobulin to the culture media increased the number of first passage colonies (Table 10). Additionally, there was a protective effect of α2-macroglobulin upon second passage whether the cells had been cultured previously in the presence (+) or absence (−) of this molecule (Table 11). It appears, therefore, that addition of α2-macroglobulin or other protease or apoptosis inhibitors to the media will facilitate the ability to initially isolate colonies of cultured PGCs, and equally importantly it may increase the efficiency of establishment of long term stable EG cell lines.

TABLE 10

| Media | R1 | R2 | Cells Plated (k) | Normalized Value* |
|---|---|---|---|---|
| PES | 4728 | 1680 | 433 | 7401 |
| MAC | 8000 | 6304 | 325 | 22028 |

*Normalized values are expressed as number of colonies per million cells.

TABLE 11

| Media 1st Passage | Media 2nd Passage | R1 | R2 | Colonies Plated | Normalized Value* |
|---|---|---|---|---|---|
| + | + | 3680 | 3920 | 1850 | 2052 |
| + | − | 2120 | 3480 | 1850 | 1512 |
| − | + | 1000 | 1277 | 801 | 1422 |
| − | − | 877 | 857 | 801 | 1084 |

*Normalized values are expressed as number of colonies per 1000 colonies plated.

The ability of colonies cultured and passaged in the presence or absence of (α2-macroglobulin to survive in an undifferentiated state for multiple passages is currently being studied. In a preliminary study twice as many colonies were obtained from third passage bovine PGC's (22 versus 45) cultured in media with α2-macroglobulin than in media without the protease inhibitor. Moreover, the colonies appear on average 2–3 days earlier and are of larger size when cultured in the presence of α2-macroglobulin.

An additional study was performed to determine the optimal concentration of α2-macroglobulin. The ratio of AP positive colonies in samples containing either 1 µg/ml or 0.5 µg/ml as compared to control samples was determined for three trials. The ratios at 1 µg/ml were 0.81±0.37, 0.84±0.23 and 0.83±0.27, while at 0.5 µg/ml they were 1.98±0.36, 1.43±0.27 and 1.70±0.41. Therefore, the lower dose of α2-macroglobulin appears to be more effective in generating AP positive colonies by almost a factor of 2.

EXAMPLE 2

Assays of Cultured PGCs

A. Porcine PGCs

Porcine PGCs were plated in IO mm wells containing STO feeders and media containing basic fibroblast growth factor (bFGF), leukemia inhibitory factor (LIF), and either soluble stem cell factor (SCF) or porcine uteroferrin rose (pUTE). Studies were done in quadruplicate. After 10–12 days, colonies were stained for alkaline phosphatase and counted. Only colonies with ES-like morphology as well as alkaline phosphatase positive were included in the final analysis. The alkaline phosphatase staining was performed as follows (Donovan et al., 1986; Talbot et al. 1993b; Moore and Piedrahita, 1996). The colonies were rinsed twice in PBS, fixed in 4% formaldehyde in PBS for 15 minutes at room temperature, and then washed 3 times in PBS. The colonies were then stained in naphthol AS-MX phosphate (200 µg/ml; Sigma) and fast red TR salt (1 mg/ml; Sigma) in 100 mM Tris buffer (pH 8.2) for 20 minutes at room temperature. Staining was terminated by washing the colonies in PBS.

The ratio of colonies in pUTE over colonies in SCF were 5.0, 3.0, 3.6, and 2.0 for each of the four replicates, respectively. The mean number of colonies per 10 mm well was 4 in the SCF media and 18 in the pUTE treatment. Moreover, there was no effect on the overall morphology of the colonies nor on the intensity of alkaline phosphatase staining.

B. Bovine PGCs

Two fetuses collected at the slaughter house and determined to be between 30–40 day of gestation by crown-rump length were processed as described above. The isolated bovine PGCs were resuspended in PES media supplemented with bFGF, LIF and soluble SCF, and incubated on top of inactivated STO feeder layers. Resulting colonies were checked at 2–3 day intervals until colonies with the appropriate EG-like morphology (compact appearance and large nucleus to cytoplasm ratio) were detected. After approximately 30 days in culture selected wells were stained for alkaline phosphatase to determine the expression pattern of the EG-like colonies. When similar colonies were stained for alkaline phosphatase it was determined that the expressing levels ranged from very high for highly compact colonies to low for expanding epithelial-like colonies.

C. Differentiation of Porcine, Bovine and Caprine PGCs into Embryoid Bodies

One of the indicators of the ability of ES and EG cells to retain their pluripotential characteristics is their ability to differentiate in vitro when placed in suspension culture. This differentiation is quite unique and results in what is referred as simple and cystic embryoid bodies. In order to determine whether the cells the inventors had isolated from pigs, goats and cattle could form embryoid bodies, colonies were gently trypsinized so as to dislodge from the tissue culture plate and the cell clumps centrifuged and resuspended in conventional ES media (Piedrahita et al., 1992) lacking growth factors and with FBS replaced by calf sera. The cell clumps were placed in non-adhesive bacteriological petri plates and incubated at 39 C. Media was changed daily and the morphology of the differentiating colonies recorded at 24 hr intervals.

All three species demonstrated the ability to form simple embryoid bodies when placed in suspension culture. In the caprine case the embryoid bodies were seen developing 4 days after normal passage into fresh feeder layers from colonies remaining in suspension. In all cases the double layered appearance typical of simple embryoid bodies is evident and indicates the pluripotential characteristics of the isolated cell lines. In the bovine case, a cystic embryoid body was observed attached to the bottom of the plate. Although at this point the characterization of the embryoid bodies has not gone beyond recording the morphological changes, it reinforces the ability of the isolated cells to differentiate into several tissue types when plated upon the proper culture conditions.

EXAMPLE 3

Electroporation and Analysis of Primordial Germ Cell-Derived Colonies

PGC cells (50,000–500,000) soon after collection were resuspended in 0.8 ml of PES media containing 5 nM of linearized plasmid DNA and electroporesed under different voltage and resistance conditions in a BioRad electroporation cuvette (0.4 cm gap distance, catalog #165-2088). The plasmid consisted of the "humanized" green fluorescent protein (GFP, Clontech) attached to the cytomegalovirus (CMV) promoter in pcDNAIII (Invitrogen). The cuvette was placed in a BioRad Gene Pulser with capacitance extender electroporator and electroporated at voltages ranging from 300 to 400 V and capacitances ranging from 250 to 500 µFa. Following electroporation, cells were resuspended in culture media and plated at a density of 10,000 PGC/ml on fresh feeder layers of inactivated STO cells and cultured for 8–12 days. Colonies with ES-like morphology were passaged to fresh feeder layers for establishment of cell lines. Resulting colonies were passaged by trypsinization to fresh feeder layers at 6–9 day intervals. State of differentiation of isolated cell lines was determined by morphology and expression of alkaline phosphatase.

Fourteen days after electroporation, transgenic colonies were identified by detection of green fluorescent protein (GFP). Detection of GFP was accomplished by placing cells in an inverted fluorescent microscope and observed under ultraviolet light (FITC filters). Under these conditions transgenic cells are seen as green while non-transgenic colonies are not detected. The number of fluorescent colonies was recorded. In some plates colonies were also stained for alkaline phosphatase to demonstrate the co-expression of alkaline phosphatase and GFP. In the remaining plates, fluorescent colonies were picked and passed to fresh feeders for establishment of transgenic EG cells lines.

In addition to transformation of primary PGC (uncultured), colonies after 1 and 2 passages were transformed. Non-transgenic PGCs were collected and plated in PES media containing growth factors on STO feeder layers. Ten to fourteen days after plating ES-like colonies were trypsinized in 0.25% trypsin for 5 minutes at 37° C. and resuspended in PES media. Between 100–5000 PGC-derived colonies were electroporated as previously described with the GFP construct, and plated onto fresh feeders in PES media containing growth factors. Transgenic colonies resulting from these electroporations were identified 10–14 days later as described above and pick-passaged to fresh feeder layers. Pick-passage was accomplished by mechanically removing the fluorescent colony from the feeder layer by the use of a mouth operated glass pipette and placing the colony in 0.25% trypsin for 5 minutes for cell dissociation. Colonies were then broken down into smaller aggregates of cells and single cells, and passaged to fresh feeder layers in PES containing growth factors for establishment of cell lines.

A. Effect of Variation of Electroporation Conditions

Approximately 200,000 freshly isolated PGCs were divided into four groups, and electroporated at either 300 or 400 V, and 250 or 500 $\mu$Fa. Cells from each treatment were split into two 35 mm wells and cultured on feeders for 12 days at which time the number of alkaline phosphatase positive and GFP positive colonies was determined (Table 12).

TABLE 12

| TREATMENT | TRANSGENIC COLONIES | ALKALINE PHOSPHATASE COLONIES |
|---|---|---|
| 300 V, 250 $\mu$Fa - A | 6 | 320 |
| 300 V, 250 $\mu$Fa - B | 13 | 552 |
| 300 V, 500 $\mu$Fa - A | 13 | 1200 |
| 300 V, 500 $\mu$Fa - B | 22 | 1060 |
| 400 V, 250 $\mu$Fa - A | 19 | 960 |
| 400 V, 250 $\mu$Fa - B | 26 | 1072 |
| 400 V, 500 $\mu$Fa - A | 25 | 812 |
| 400 V, 500 $\mu$Fa - B | 28 | 896 |

B. Genetic Transformation of Primary Porcine PGCs

PGCs isolated as described above were electroporated at 300 V and 250 $\mu$FA with 5 nM GFP-CVM plasmid and plated on STO feeder in mSCF media. Ten-twelve days after electroporation colonies were observed under ultraviolet light to determine the number of colonies expressing the GFP protein indicative of genetic transformation by the plasmid. Consequently, colonies were stained for alkaline phosphatase, a marker of primordial germ cells and undifferentiated embryonic cells, and counted. From 300,000 cells electroporated 6,221 alkaline phosphatase positive colonies were obtained. Of these, 28 were also positive for expression of the GFP indicating that they were transgenic. The morphology of the transformed PGC-derived cells is indistinguishable from that seen in murine ES and EG colonies. In some instances only a portion of a colony is expressing GFP, indicating that the colony most likely originated from several cells, only one of which is genetically modified. However, the expression of alkaline phosphatase does not differ between the transgenic and the non-transgenic component of these colonies, indicating that the genetic transformation does not interfere with the normal physiology of the PGC cells.

Colonies transformed with the CMV-GFP construct ranged in intensity from strong to barely distinguishable. Initially this heterogeneity was attributed to the positional effects caused by random insertion of the transgene. However, it has become clear that those colonies that have the morphology most associated with ES and EG cells have the lowest intensity of fluorescence. In contrast, fibroblasts and epithelial-like colonies have intense staining. This effect is interpreted as being a result of differentiation on the activity of the CMV promoter. The outer ring of GFP expressing cells is morphologically indistinguishable from the differentiating endoderm seen in differentiating mouse ES and EG cells. This suggests that in otherwise non-GFP expressing cells (inner undifferentiated cells), the promoter is activated upon differentiation. That this lack of expression is not always the case is most probably due to a combination of the positional effect and the stage of differentiation. This implies that the CMV promoter may not be the optimal promoter for detecting transgenic PGCs.

C. Transformation of First and Second Passage Porcine PGC's

PGC-derived colonies at zero passage and first passage were trypsinized, and electroporated at 400V, 250 $\mu$Fa, and plated as described above. Following 12 days of culture fluorescent colonies were counted, and a representative sample selected for further passage by individual passaging. An average of 40 colonies were detected from each transformation. The starting number of PGC is difficult to calculate due to the presence of contaminating STO remaining after collection of PGCs by trypsinization.

From this non-primary transformations the inventors have several GFP positive colonies that have survived two more passages. Expansion of these cell lines allows DNA extraction and analysis to be performed.

The secondary porcine PGC-derived colonies have a similar morphology to primary porcine PGC-derived colonies. Colonies expressing the GFP after electroporation with the CMV-GFP construct were identified, removed from the feeder layer by pick passing and dissociated in 0.25% trypsin for 5 minutes. Following dissociation, colonies were plated on fresh feeders in 24-well plates and incubated. Ten days after transfer, multiple colonies could be seen in each plate. The morphology of the colonies is indistinguishable from that seen in primary PGC-derived colonies. This indicates that the culture system being used allows the culture of the transgenic porcine PGC-derived cells over several passages without differentiation. From a practical standpoint this means that is possible to passage primary colonies to increase the amount of material available for genetic analysis and for the generation of chimeras. That is, some of the colonies seen in secondary passages can be collected and analyzed by PCR™ to identify targeted versus non-targeted transgenic colonies. This allows the identification of porcine derived cells that have undergone homologous recombination.

Later passage PGC-derived colonies were dissociated by trypsinization, resuspended in media containing 5 nM CMV-GFP and electroporated at 300 V and 250 $\mu$Fa. Following plating and 7–10 days of culture the cultures were analyzed for the presence of AP-positive transgenic colonies with undifferentiated ES-like morphology. Transgenic colonies were dissociated by trypsin and passed to fresh feeder layers in individual 24 well plates for establishment of transgenic cell lines. The morphology and GFP expression of this secondary colonies did not differ from those of the original colony. However, changes in the expression of GFP upon colonies with a more differentiated morphology was noted. This change ranged from reduction of GFP expression to a substantial increase in expression. Additionally, some mixed colonies containing areas of GFP expression in juxtaposition with GFP-negative areas were observed.

D. Genetic Transformation of Bovine PGCs

Bovine PGCs cells collected from fetuses of 4–6 cm crown rump length were electroporated at 400 V and 250 $\mu$Fa in PES media. Following electroporation with 5 nM of a CMV-GFP construct identical to the one used above for the porcine PGC transformations, cells were plated on STO at a density of 3.0 million per 35 mm dish and cultured for 6–9 days. Starting on day 6, and daily until day 9, colonies were examined by fluorescent microscopy to identify GFP-positive colonies.

Several colonies were identified that express the green fluorescent protein. As with the porcine cells, the morphology of the transgenic colonies did not appear to differ from that seen in the non-transgenic controls. The ability of the transgenic cells to generate viable fetuses by both nuclear transfer and blastocyst injection is currently being studied.

The ability to genetically transform bovine PGC cells opens up the possibility of generating transgenic animals by direct manipulation of the germ followed by culture, and nuclear transfer or chimera formation, versus pronuclear injection. There are several advantages of PGC over pronuclear injection. Firstly, the ability to determine the sex of the donor PGC, by PCR™ or southern analysis, prior to testing for pluripotentiality, allows prediction in advance the sex of the resulting transgenic animals. Secondly, as several transgenic colonies can be obtained from a single fetus, it is possible to use a fetus of superior genetics as the PGC donor, and obtain transgenic cells from it. These cells can then be used for either nuclear transfer or pronuclear injection. The resulting transgenic animals, therefore, will not only be of the desired sex but it will have superior genetics obviating the need for further genetic improvements. With the present pronuclear injection technique the need for several thousand embryos for injection makes the use of superior genetics (both maternal and paternal) prohibitively expensive and logistically impractical.

Thirdly, if nuclear transfer is used to generate the offspring, the number of embryo/fetus donors and recipient animals needed will be drastically reduced as only a) one fetus is required to obtain several hundred transgenic cells; and b) only embryos developing to the blastocyst stage and confirmed transgenic by marker detection and/or PCR™ will be transferred. Even if pregnancy rates are as low as 10% after nuclear transfer with cultured cells (Stice et al., 1996), only 10 recipients will be required to obtain a single transgenic animal. Presently, greater than 250 embryos need to be injected and transferred to 250 recipients before a single transgenic animal is obtained (Wall, 1996). And lastly, as a transgenic colony is composed of 20–100 identical cells it will be possible to clone several transgenic animals that are basically identical. This may allow the freezing of several of the resulting embryos until the phenotype of one of the clones is determined by allowing it to go to term. If the phenotype is deemed advantageous, the frozen embryos can be thawed and multiple sets of identical animals made.

In a recent report the ability of embryo-derived cultures to participate in fetal development after nuclear transfer has been reported (Cibelli et al., 1997). The cell lines were derived from inner cell masses of developing embryos and had an epithelial-type morphology, a morphology that has been demonstrated to be associated with differentiation and loss of AP expression. Yet nuclei from these cell lines were able to participate in fetal development. However, all of the pregnancies from this type of cells have resulted in fetal loss by day 50 (Stice et al., 1996) thus indicating their inability to form a viable offspring.

In contrast the isolated cells of the present invention retain the morphology typical of ES and EG cells, and express AP. As it has been previously demonstrated that ICM-derived cells can take part in normal embryonic development (Keefer et al., 1994) and as the morphology and AP activity of the instant cells is similar to ICM, they should be able to produce viable offspring after nuclear transfer. Additionally, due to the similarity to the porcine cells described above they should be able, just as in the porcine, to participate in chimera formation.

EXAMPLE 4

Transgenic Cultured Porcine PGC Contribution to Formation of Chimera

Transgenic PGC isolated and transformed as described above were identified, dissociated by trypsinization and 10–15 cells injected into the blastocoele of the developing blastocyst or into the inner portion of compacted morulas. Injected embryos were transferred to synchronized recipients and fetuses collected at day 25 of pregnancy. For evaluation embryos were observed under fluorescent light for detection of the marker GFP. Following visual inspection embryos were minced and a fraction of the tissue used for DNA analysis. DNA analysis consisted of detection of the GFP construct by PCR™ or Southern DNA analysis.

DNA was isolated by the salting out procedure (Miller et al., 1988) using the Puragene DNA isolation kit (Gentra Systems, Minneapolis, Minn.). Following isolation DNA was resuspended in TE buffer, allowed to dissolve by overnight incubation at 55° C., and the optical density measured to determine concentration. For PCR™ analysis 100 ng of DNA was subjected to 30–35 cycles of PCR™ using either neo primers or GFP primers. Fragments were separated by agarose gel electrophoresis, stained with ethidium bromide, and photographed.

For Southern analysis, genomic DNA (5–10 $\mu$g), was digested overnight with the indicated enzyme (Boehringer Mannheim, Indianapolis, Ind.; Promega, Madison, Wis.; or New England Biolabs, Beverly, Mass.), samples were loaded onto a 0.7% agarose gel, and separated by electrophoresis in TAE buffer (0.04M Tris-acetate, 0.001M EDTA). The DNA was transferred to a N-Hybond membrane (Amersham, Arlington Heights, Ill.) by capillary transfer (Sambrook et al., 1989). The membrane was then dried and cross-linked with UV light before hybridization with a radioactive probe. Hybridization was performed using RapidHyb solution (Amersham, Arlington Heights, Ill.) following the manufacturer's protocol.

The probe (50 ng) was labeled with [$^{32}$P]-dCTP (Amersham, Buckinhamshire, England) and a commercial kit (High Prime, Boehringer Mannheim, Indianapolis, Ind.) following the manufacturer's instructions. The unincorporated nucleotides were removed by passing the reaction through a Sephadex G-50 column (Promega, Madison, Wis.) as described by the manufacturer's protocol. The radiolabeled probe was denatured by heat (95° C. for 10 min), the membrane was hybridized with $10^6$ cpm of radiolabeled probe per ml of hybridization solution, and the reaction was incubated for 2 hours at 65° C. on a rocking platform. After hybridization, the membranes were rinsed twice and then washed for 20 min at room temperature with a 2× SSC, 1% w/v SDS solution. After washing, filters were placed in seal-a-meal plastic bag, enclosed in an exposure cassette with intensifying screens and Kodak X-Omat AR film (Eastman Kodak Company, Rochester, N.Y.), and left at −70° C. for 1 to 4 days.

Out of 7 recipients receiving injected embryos, two were pregnant. From these two gilts 14 normal fetuses and one resorbed fetus were obtained. The fetuses were then analyzed for the presence of the GFP and neo transgenes by southern analysis. DNA was isolated from the developing fetuses and digested with HindIII restriction endonuclease. The fragments from the digest were separated by agarose gel electrophoresis and transferred to a nylon membrane. The membrane was then sequentially probed with GFP and neo probes.

Of 14 normal fetuses analyzed, one was strongly positive and one was weakly positive upon hybridization with both GFP and neo. Surprisingly. DNA isolated from the resorbed fetus did not show the presence of the transgene. The two fetuses that were positive for the transgenes were selected for further analysis, in order to rule out the possibility of plasmid contamination.

DNA isolated from the two positive fetuses was digested with restriction enzymes that can distinguish between a plasmid contaminant and DNA that is inserted in the genome. The DNA was digested with BstX1, which does not cut within the GFP/neo plasmid used in the transformation. The BstX1 digest showed a hybridizing band of 8 kb with both the GFP and neo probes. As the initial GFP/neo plasmid construct is only 6.2 kb it is not possible to obtain a larger hybridizing band unless the construct is embedded in the genomic DNA flanked by two BstX1 sites. Additionally, this indicates that only a single copy of the construct was inserted into the genomic DNA. Although it was not possible to estimate the percent contribution of the transgenic colony to the fetus, the fact that the transgene in one of the fetuses could easily be detected by genomic southern analysis indicates that the contribution was significant.

The study as described above was repeated, and three pregnant gilts were obtained. From two of these gilts 19 normal fetuses were obtained. The fetuses were then analyzed for the presence of the GFP and neo transgenes by southern analysis as described above. One of the recovered fetuses was verified as transgenic by genomic southern and PCR™ analysis. Fluorescent analysis of the genital ridge of this fetus showed the presence of fluorescent streaks indicating expression of the green fluorescent protein marker. The GFP expression indicates that the fetus contained transgenic cells in its genital ridge. This suggests that the transgene may be present in the germ cells of the fetus, and therefore capable of germ line transmission.

The remaining pregnant gilt was allowed to carry her progeny to term. The gilt gave birth to three piglets, one of which was confirmed to be chimeric by genomic southern analysis. Furthermore, the transgene was present in 70% of the tissues, including the testes and the epididimis, suggesting the possibility of germ line transmission (Table 13, below). Additionally, to confirm that the transgene was indeed incorporated into the chromosome, restriction digests with HindIII and BamHI were carried out. A 6.0 kb HindIII fragment and a 9.5 kb BamHI fragment was detected. Both sizes indicate that the signal was not due to plasmid contamination.

TABLE 13

Detection Of GFP In Tissues From A Stillborn Transgenic Chimera

| Tissue Type | S1* | S2 | S3 | S4 | S5 |
| --- | --- | --- | --- | --- | --- |
| Liver | + | − | − | − | − |
| Heart | ++ | +++ | + | | |
| Lung | +/− | +/− | +/− | +/− | + |
| Kidney | + | +++ | | | |
| Epididymis | +++ | +++ | | | |
| Testis | + | − | | | |
| Skin | − | − | + | ++ | − |
| Muscle | + | − | − | + | + |
| Placenta | +/− | +/− | ++ | | |
| Large Intestine | + | + | | | |

TABLE 13-continued

Detection Of GFP In Tissues From A Stillborn Transgenic Chimera

| Tissue Type | S1* | S2 | S3 | S4 | S5 |
| --- | --- | --- | --- | --- | --- |
| Small Intestine | + | +/− | | | |
| Thymus | − | − | | | |
| Femur-marrow | − | + | | | |
| Spleen | + | +/− | ++ | | |
| Pancreas | + | +/− | | | |
| Umbilical cord | + | | | | |
| Stomach | + | + | + | | |

Sample number. Larger tissues were randomly sampled multiple times depending on their size and complexity.
−, signal non-detected; +/−, signal barely detected; +, signal present; ++, strong signal present; +++, very strong signal present.

An additional study performed as described above used PGCs derived from Duroc pigs which have red skin and red hair. The crossbred used is black and white from crosses between Yorkshire, Landrace, and Hampshire. The Duroc-derived cell lines were injected into crossbred embryos with the expectation that if a chimera is born it will have some degree of red patching in its skin demonstrating contribution from the injected cells lines. Two coat-color chimeras were identified. Breeding of the coat color chimeras will determine if germline transmission of the PGCs has occurred.

The data presented above clearly indicates that transgenic porcine EG cells have the ability to contribute to the development of a fetus when injected into a host blastocyst. The studies also suggest that the chimeras may have a germ line contribution. The use of early passage cells is thus currently preferred of ruse in the present invention.

How the number of passages affect the ability of the cells to contribute to chimera formation is currently being studied. As the inventors have been able to maintain cells for up to 5 months and over 10 passages while still retaining the alkaline phosphatase activity and the normal morphology, it is expected that there will be little reduction in the pluripotential characteristics of cultured porcine PGCs. The recent report by Shim et al. (1997) indicating that non-transgenic PGC-derived cells can contribute to chimera formation after long term culture strongly reinforces the potential of these transgenic colonies and cells lines for the generation of transgenic pigs.

From these results it is clear that unlike embryo-derived cells, PGC-derived colonies can survive in culture in an undifferentiated state for prolonged periods of time, as determined by morphology and AP staining. Interestingly, the morphology of the EG colonies more closely resemble that of mouse ES cells than porcine ES-like cells isolated previously (Piedrahita et al., 1990; Gerfen and Wheeler, 1995). Previously reported porcine ES-like cells had a less compact appearance where most if not all cells were easily distinguishable. In contrast the EG cells described here had a very compact appearance where it was hard to distinguish individual cells unless the colony stared to differentiate into an epithelial monolayer. Although the difference may only be due to the vast difference in starting cells numbers between the two systems where PGC numbers are thousand fold higher, the differences may be related to differences in LIF and CNTF receptor expression.

The study to determine the effects of feeder density on the number of colonies was undertaken due to observations that colonies not in direct contact with the feeder layer tended to rapidly differentiate into epithelial monolayers. This suggested that an increase in the feeder density, thus assuring that all plated colonies were in direct contact with the STO cells, may be beneficial. The results herein support this observation but equally importantly suggest that the feeder effect is not through secretion of embryotrophic factors or removal of toxic factors from the media but requires cell-cell contacts. This suggests that the extracellular matrix components, acting through integrin receptors, may be modulating the growth and differentiation of the PGC cells. Plating of PGC-derived colonies in matrices composed of extracellular matrix components did not allow the maintenance of the undifferentiated state, suggesting that it is not simply a matter of cell attachment to a single extracellular matrix component. This, however, does support the observation that conditioned media did not have a beneficial effect on the isolation of porcine ES cells (Piedrahita et al., 1990).

With respect to the ability to differentiate in vitro, the isolated EG colonies produced the typical simple embryoid bodies that have been described previously (Martin and Lock, 1983; Piedrahita et al., 1990). However, they had a limited capacity to form cystic structures in suspension and were only able to accomplish the formation of large cysts when placed in collagen matrices. As the in vitro differentiation was induced by removing fetal bovine serum and growth factors it is possible that the reduced ability to from cysts was due to biochemical deficiencies in the media rather than the developmental deficiencies of the colonies. This is reinforced by the fact that the EG colonies were able to normally differentiate in vivo during chimera formation.

When analyzing and identifying the transgenic colonies, a wide range of levels and patterns of expression of the GFP was observed. Colonies where only a portion of the colony was GFP positive were common, indicating that either the colony had originated form more than one cell, only one of which was transgenic, or that incorporation of the transgene occurred in later cell division creating a mosaic colony. More troublesome than the mosaic colonies was the observation that in some cases, the activity of the GFP was modulated by cell differentiation. Several colonies expressed GFP in portions of the colony morphologically identified as being more differentiated.

A likely explanation for this GFP expression modulation is the high positional effect observed when using the CMV promoter. This promoter has the benefit of potentially very high levels of expression but the disadvantage of being heavily influenced by neighboring chromatin as evidenced by the range of GFP intensities in the transgenic colonies from barely above background to very high intensity. This was confirmed by transforming mouse ES cells with a vector containing the SV40 promoter driving the neo gene, and the CMV driving the GFP. Following electroporation, cells were placed in G418 selection for 8–10 d and surviving colonies examined under fluorescent microscopy. On average, the proportion of neo-resistant colonies that were GFP-positive ranged from 30–50%. This strongly suggests that the CVM promoter is easily silenced upon incorporation.

Once it was determined that it was possible to genetically transform PGC-derived cells while maintaining their undifferentiated morphological and AP expression characteristics the in vivo pluiripotentiality of the cells was tested by chimera generation. The results clearly indicated that some of the chimeras developing from the injected embryos had incorporated the transgene into their chromosome with an frequency of 3 transgenic chimeras identified among 35 total fetuses and ⅓ piglets. Although an attempt was made to semi-quantify the signal obtained from the genomic Southern from the transgenic chimeras by comparing in to a standard curve made by transgenic and non-transgenic mouse DNA probed with neo (0:100 to 100:0 transgenic:non-transgenic in 10% intervals), results have varied from a limit of detection of 10% to 30% depending on strength of probe and washing and hybridization conditions. Regardless, it is clear from the Southern results as well as from the GFP-expression detection in one transgenic fetus that the transgenic PGCs were able to participate in the formation of the developing fetus.

The results presented here indicate that PGCs can be isolated, cultured, and genetically manipulated without loss of developmental potential. Although germ line transmission remains to be confirmed preliminary indication suggest that the cells can reenter the gonad and may indicate the potential of germ line transmission. Thus, the development of this technology opens up the possibility of undertaking the process of homologous recombination in the porcine species.

EXAMPLE 5

Cre-Mediated Deletion and Integration

Transgenic animals produced by conventional pronuclear injection are subject to potential problems of insertional inactivation and inappropriate regulation due to inadequate regulatory regions and/or the positional effect where the neighboring chromatin affects the behavior of the transgene (Klintworth, 1990). While the positional effect can be ameliorated to some degree by the co-injection of MAR (matrix attachment region) insulators (McKnight et al., 1992) the insulation is neither complete nor has it been demonstrated to have general applicability to all loci.

While the problems associated with random insertion can be circumvented by the use of homologous recombination in embryonic stem cells, this technique is time consuming, expensive, and available only in the mouse species at this time (Gordon, 1993; Stice and Strelchenko, 1995). An alternative approach is to direct a transgene into a predetermined site by tagging the site with a DNA sequence that would direct any future incoming transgene to the same location. The integrated transgene, under the regulatory domain of the targeted locus, should have an expression profile similar to the endogenous gene.

The mouse whey acidic protein (mWAP) gene was chosen for these studies due to its high mRNA (15% total RNA) and protein (I mg/ml) levels in the lactating mammary gland (Henninghausen and Sippel, 1982a; Grabowski et al., 1991) and its potential importance in the generation of mammary gland bioreactors producing proteins of medical interest in the mammary gland (Houdebine, 1994; Yom and Bremel, 1993). Transgene expression from this locus should have a distinct tissue and developmental specific profile, while the encoded protein would theoretically be harvested from the milk at high levels in a non-invasive fashion (Houdebine, 1994).

Site-specific recombination systems, such as Cre-loxP and FLP-FRT, have been utilized to direct transgenes into the genome of yeast, plants, and mammalian cells including ES cells (Sauer and Henderson, 1989; 1990; Albert et al., 1995; Araki et al., 1997). This approach has also been used for the generation of tissue-specific knockouts, inducible knockouts, and modifications of multiple loci in a single ES cell line (Bradley and Liu, 1996). To utilize the Cre-loxP approach, a loxP recognition site in a predetermined chromosomal location would need to be introduced into mouse embryonic stem (ES) cells by homologous recombination at the WAP locus. A neo-TK cassette would allow for the positive-negative selection of the gene targeting and Cre-mediated deletion events. Following marker deletion by Cre protein, a single loxP site would remain which could serve as a tag for the introduction of loxP-containing transgenes.

A. Materials and Methods

1. Cloning the mWAP Gene

A 14-kilobase (kb) genomic WAP clone was screened from a X phage Charon 35 library prepared from the mouse ES cell line E14gT2a (obtained from Dr. Nobuyo Maeda of the University of North Carolina) using an exon 3-specific probe. PCR™ primers for the mouse WAP (forward primer (SEQ ID NO:9): 5' TTGGTGTTCCGAAAGCTGGCT-TCTG 3'; reverse primer (SEQ ID NO:10): 5' GGGTTAT-CACTGGCACTGGGGGTGTA 3') were used with mouse genomic DNA under PCR™ conditions consisting of 1 cycle at 94° C. (5 min); 35 cycles at 94° C. (1 min), 55° C. (30 sec), 72° C. (30 sec); 1 cycle at 72° C. (10 min). A 178 bp product was gel purified on a 2% agarose gel, spin column purified and used as template for the Random Primed Labeling Kit (Boehringer Mannheim, Indianapolis, Ind.) with [$^{32}$P]-dCTP. A 4.5 kb XhoI-EcoI fragment containing exons 1–4 was subcloned into Bluescript IIKS (pBS) (Stratagene, La Jolla, Calif.).

2. Plasmids

The WAP targeting plasmid (PWPNT) construction and general plasmids used are shown in Table 14. AM-1 cells (Invitrogen, San Diego, Calif.), which have a lacz-cre, were used to check the presence of functional loxP sites in floxed constructs. Plasmids containing DNA flanked by loxP sites were introduced into electrocompetent AM-1 cells using the E. coli Pulser (BioRad, Hercules, Calif.) and plated overnight at 37° C. on LB-Carbenicillin-IPTG (10 mM) plates. pWPNT was purified with the Wizard MaxiPrep columns (Promega, Madison, Wis.), linearized with XhoI, and stored in 30 μg aliquots at −20° C. for electroporation.

TABLE 14

| Plasmid | Components |
|---|---|
| pBS64 | loxP site |
| pBS185 | CMV promoter: cre gene: MT-I polyA |
| pKJ-1 | PGK promoter; r: neo gene: PGK polyA |
| pPGKCre | PGK promote: cre gene: MT-I polyA |
| pHSVCre | HSV-TK promoter: cre gene: MT-I polyA |
| pOG231 | CMV promoter: synthetic intron: cre gene: MT-I polyA |
| pBSNeo | PGK promoter: neo gene: PGK polyA |
| ploxpNeo | loxP: PGK promoter: new gene: PGK polyA |
| pBSNeoTK | PGK promoter: neo gene: PGK polyA | pBS185, pPGKCre, pHSVCre and pOG231 were used as sources for transient Cre expression. For the pPGKCre plasmid, the PGK (phosphoglycerol kinase) promoter was used from the pKJ-1 plasmid. A 2.7 kb XhoI-HindIII fragment from pBS185 which included the cre gene and MT-I polyA was subcloned into pCRII (Invitrogen, San Diego, Calif.) and designated pCRIICre. Subsequently, a 2.7 kb NsiI-HindIII fragment from this subclone was ligated into pKJ-1 digested with PstI-HindIII. Plasmid pBSNeo-TK was digested with PstI to remove the neo cassette, TK coding sequence and HSV-TK polyA signal. A 2.7 kb NsiI fragment from pCRIICre was ligated into pBSNeo-TK to give pHS-VCre.

pBSNeo was prepared from a 1.9 kb EcoRI-HindIII fragment from pKJ-1 containing the PGK promoter, neo gene, and PGK polyA cloned into pBS. Plasmid ploxPNeo was prepared by cloning a SacII-KpnI fragment from pBSNeo, which contained the neo gene, into ploxP2.

3. Cell Tissue Culture

The embryonic stem (ES) cell line AB1 cells (from Allen Bradley, Baylor College of Medicine) were used for all studies. Cells were cultured in ES medium containing Dulbecco's Modified Eagle's Medium (DMEM) supplemented with 15% (v/v) fetal bovine serum, 0.1 mM β-mercaptoethanol and 2 mM glutamine. Temperature was kept at a constant 37° C. in a humidified incubator supplemented with 5% $CO_2$. ES cells were maintained on mouse fibroblast STO cells inactivated by treatment with either mitomycin C or γ-irradiation (3400 rad using $^{137}$Cs). Recombinant murine LIF ESGRO, (GibCo BRL), or human recombinant LIF, obtained from transfected COS-7 cells, was added to the culture medium at approximately 1,000 units/ml.

ES cells were passaged every 2–3 days by splitting 1:4 to 1:10 into 100 mm sterile petri dishes. Cells were washed twice with 3 ml of PBS then treated with 0.04% trypsin for 5 min at 37° C. To the trypsinized cells, 3 ml ES medium was added and the cells dispersed to break up any clumps. Cells were pelleted and resuspended in 10 ml ES medium and aliquoted into STO-containing plates.

4. Electroporation of ES Cells a. Homologous Recombination with the WAP Targeting Plasmid An 0.8 ml aliquot of cells (1×107) was mixed with 30 μg linearized pWPNT, electroporated at 300 V/250 μF, and plated in fresh ES media at 0.5–2×10⁶/plate. After 24 h, ES medium containing G418 (200 μg/ml geneticin, Gibco BRL, Grand Island, NY) was added and replaced as necessary during the 10 day selection. On day 10 after electroporation, individual colonies were picked and transferred to sterile, gelatin-coated 24-well plates containing ES/G418 medium. Upon reaching confluency, the cells were trypsinized and aliquoted for both genomic DNA harvest and for storage in ES medium with 10% DMSO at −70° C.

b. Cre-Mediated Deletion with Cre-Encoding Plasmids

Targeted cell line F2C was electroporated with 30 μg of cre plasmid as described above. Due to the "bystander effect" often observed with gancyclovir selection, cells were seeded at 5×10⁵ cells per 100 mm plate after electroporation. On day 3, 2 gM gancyclovir was added and selection was carried out for three days, after which cells were fed with ES medium until day 12–14.

C. Cre-Mediated Insertion with Cre and loxP-Containing Plasmids

The deletion cell line D25, which contained a loxP site in one WAP allele, was used for targeting studies. Electroporations were performed with 1×10⁶ ES cells per 0.8 ml at 300 V/250 pF and plated in fresh ES media at 1×10⁶ per 60 mm plate. After 24 h, ES medium containing G418 (200 gg/ml) was added and replaced as necessary during the 10 day selection.

5. Detection of Recombination Events and DNA Sequencing

Genomic DNA isolated from ES cell clones was used for Southern blot analysis and/or PCR™ diagnostics. For Southern blot analysis, EcoRI-, NsiI- or SphI-digested DNA was transferred onto N-Hybond membranes (Amersham, Arlington Heights, Ill.). Probes were labeled with the Random Primed Labeling Kit (Boehringer Mannheim, Indianapolis, Ind.) using [$^{32}$p]-dCTP and purified over Sephadex G-50 columns. Following hybridization in RapidHyb solution (Amersham, Arlington Heights, Ill.) at 55° C., filters were washed 2×20 min at room temperature with 2×SSPE/0.1% (w/v) SDS and 1 wash for 15 min at 42° C. with 1×SSPE/0.1% (w/v) SDS. Labeled filters were placed with Kodak X-Omat AR film and left at −70° C. for 1–3 days.

LoxP-containing plasmids were purified with the Qiagen Plasmid Kit and sequenced with the PRISM™ Ready Reaction DyeDeoxy™ Terminator Sequencing Kit containing AmpliTaq DNA polymerase using either M13 forward or reverse primers. The PCR™ consisted of an initial denaturation at 96° C. for 2 min followed by 25 cycles of 96° C. (30 sec), 50° C. (15 sec) and 60° C. (4 min). PCR™ reactions were run over Centri-Sep columns (Princeton Separations, Inc.) and run on the Applied Biosystems Inc. 373A automated DNA sequencer.

B. Targeting of the mWAP Locus

Figure 2:
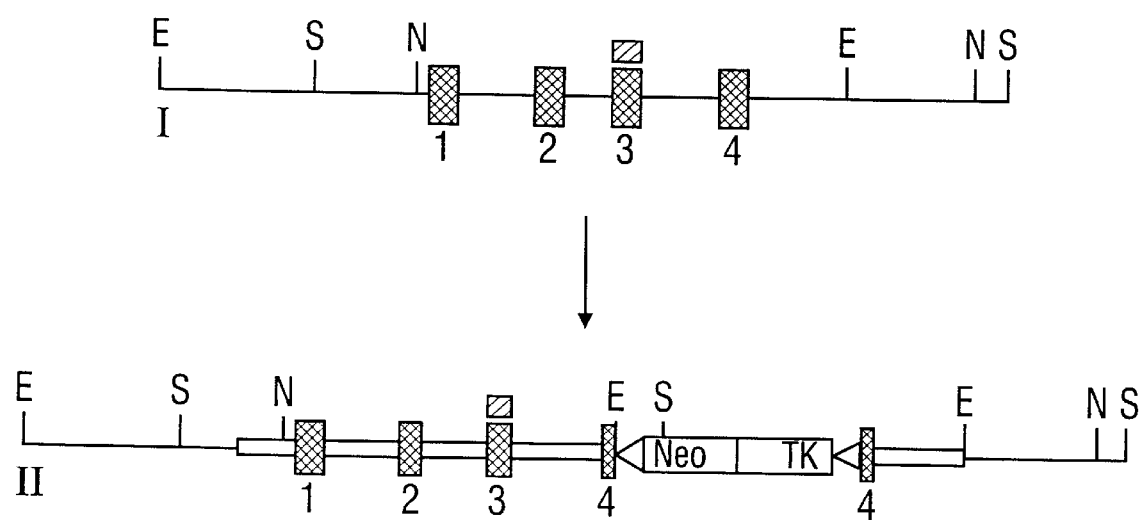
FIG. 2. Targeting of the mouse WAP gene in ES cells. Endogenous WAP locus and targeted WAP locus after homologous recombination with pWPNT. The region of homology between the endogenous locus and pWPNT targeting vector is delineated by a broadened line in the targeted WAP locus. Enzyme sites used for verification of the targeting event are as follows: E, EcoRI; N, NsiI; S, SphI. Predicted band sizes are given for both the endogenous and targeted alleles using an exon 3-specific probe. The loxP sites are represented as unfilled triangles.

The replacement-type targeting construct pWPNT consisted of the loxP-Neo-TK-loxP cassette positioned in exon 4 of WAP between the stop codon and polyadenylation signal (FIG. 1). The total amount of homology was 3.0 kb of 5' flanking and 1.5 kb of 3' flanking sequence. Genomic DNA from 199 clones was analyzed by Southern blotting to determine positively targeted clones. Predicted band sizes are shown in FIG. 2. Endogenous bands for EcoRI, NsiI and SphI digested DNA probed with exon 3 are 6.9 kb, 6.1 kb and 7.1 kb respectively. A targeted allele should have had corresponding bands of 5.4 kb, 10.1 kb and 3.9 kb, respectively. Out of 16 clones analyzed on a Southern blot with EcoRI-digested DNA from G418 resistant clones, 6 were correctly targeted with the 5.4 kb targeted allele. The targeted cell line F2C was verified with three separate enzymes.

The results of the WAP locus targeting study are summarized in Table 15. Out of 199 clones analyzed, 51 were targeted with the neo-TK cassette. The targeting frequency was determined to be $6.4 \times 10^{-5}$, while the ratio of homologous recombination to random integration was 1:4. There was additionally a slight variation in the targeting frequency dependent upon the day the colonies were harvested. Since targeted colonies have single copies of the neo gene, they grow slower under selection pressure than do colonies having multiple inserts. Therefore, harvesting colonies at later times gives these targeted clones time to grow. Colonies picked on day 8 were positive in 19.6% of the sarnples, day 10 clones in 27.6% and day 12 in 26.3%.

TABLE 15

Summary of Recombination at WAP Locus

| Recomb. type | # cells treated | Plasmid | Amount of DNA | # cells plated | G418$^r$ colonies | Ganc$^r$ colonies | Recomb./ Analyzed* |
|---|---|---|---|---|---|---|---|
| Homologous Recomb. | $1 \times 10^7$ | pWPNT | 5 nM | $2 \times 10^6$ | 2498 | — | 51/199 |
| Cre-Mediated Deletion | $1 \times 10^7$ | pBS185 | 30 µg | $5 \times 10^5$ | — | 1235 | 44/50 |
| | | | | $2.5 \times 10^5$ | — | 1002 | † |
| | $1 \times 10^7$ | pPGKCre | 30 µg | $5 \times 10^5$ | — | 1068 | 10/10 |
| | | | | $2.5 \times 10^5$ | — | 704 | † |
| | $1 \times 10^7$ | pHSVCre | 30 µg | $5 \times 10^5$ | — | 1023 | 10/10 |
| | | | | $2.5 \times 10^5$ | — | 735 | † |
| | $1 \times 10^7$ | No DNA | — | $5 \times 10^5$ | — | 140 | 0/10 |
| | | | — | $2.5 \times 10^5$ | — | 135 | † |
| Cre-Mediated Insertion | $1 \times 10^6$ | ploxPNeo + pOG231 | 1 µg 30 µg | $1 \times 10^6$ | 19 | — | 11/48‡ |
| | $1 \times 10^6$ | ploxPNeo + pOG231 | 1 µg 20 µg | $1 \times 10^6$ | 25 | — | 5/24‡ |
| | $1 \times 10^6$ | ploxPNeo + pOG231 | 1 µg 10 µg | $1 \times 10^6$ | 21 | — | 3/24‡ |
| | $1 \times 10^6$ | ploxPNeo + pOG231 | 1 µg 5 µg | $1 \times 10^6$ | 27 | — | 1/24‡ |
| | $1 \times 10^6$ | ploxPNeo | 1 µg | $1 \times 10^6$ | 33 | — | 0/10‡ |

All electroporations were performed at 200 µF and 300 V in ES medium. G418$^r$, G418-resistant; Ganc$^r$, Ganc-resistant.
*The number of positive colonies versus number analyzed as determined by PCR ™ and/or Southern blots.
† Not determined.
‡Summation of 3 electroporations with $1 \times 10^6$ cells used per treatment.

C. Cre-Mediated Deletion

The effect of the promoter to drive the cre gene was tested using the PGK, HSV-TK and CMV promoters to drive the cre gene (Table 15). At $2.5 \times 10^4$ cells plated, the treatment to control ratios for gancyclovir resistance were 8.8:1 (pBS185); 7.6:1 (pPGKCre); 7.3:1 (pHSVCre). At $5 \times 10^4$ cells plated the treatment to control ratios were 7.4:1 (pBS185); 5.2:1 (pPGKCre); 5.4:1 (pHSVCre). Since the relative amounts of gancyclovir-resistant colonies between cell seedings was approximately the same ($2.5 \times 10^4$ versus $5 \times 10^4$), the influence of the "bystander effect" can be reduced by plating cells at lower dilutions.

For PCR™ verification of the deletion event, primers were designed to amplify both the endogenous (166 bp) and modified (270 bp) alleles. A 0.7 kb BamHI-PstI WAP fragment which contained the 3' end of exon 4 and approximately 650 bases of downstream sequence was cloned into BluescriptIISK and sequenced with Sequenase Version 2.0 sequencing kit (U.S. Biochemical Corporation, Cleveland, Ohio) to find PCR™ primers (Forward primer (SEQ ID NO:11: 5'-AGCGACCAGCCCAAGTGTATACAG-3'; Reverse primer (SEQ ID NO:12): 5'-GCCTGCTTTGTCGTTCCTTCAG-3') which would flank the loxP site. PCR™ reaction conditions were 1 cycle at 94° C. (2 min); 33 cycles of 94° C. (30 sec), 54° C. (30 sec), 72° C. (30 sec); 1 cycle at 72° C. (10 min).

PCR™ analysis of 50 clones showed that 44 had the endogenous and modified alleles (88%). PCR™ and Southern blot analyses revealed that most clones contained the correct PCR™ product which was positive for the loxP site. The 166 bp and 270 bp bands were also positive for the WAP exon 4 sequence. The 270 bp PCR™ product was sequenced and found to have a wild-type loxP site. Southern analysis of deletion clones with SphI showed the loss of the 3.9 kb targeted band; the modified locus was the same size as the endogenous band of 7.1 kb.

D. Cre-Mediated Insertion

Co-electroporation of 1 gg loxPNeo and 30 μg pOG231 in loxP-tagged ES cells resulted in an average of 19 G418$^R$ colonies per electroporation over 3 electroporations, compared to 11 G418$^R$ colonies for the ploxPNeo control (Table 15). While varying the Cre-encoding plasmid, the total number of G418$^R$ colonies (both random and site-directed integrants) did not vary substantially over this range: using 5 μg gave an average of 27 G418$^R$ colonies; 10 μg gave 21 G418$^R$ colonies; 20 μg gave 25 G418$^R$ colonies; and the background control was 12 colonies. The ability of other Cre-expressing constructs to mediate the insertion event was tested. PCR™ analysis of G418$^R$ colonies with plasmids pBS185, pPGKCre, and pHSVCre indicated that none contained a site-specific insertion. Moreover, the number of G418$^R$ colonies was independent of co-electroporation of a Cre-encoding plasmid.

Site-specific integration of the ploxPNeo targeting plasmid at the WAP locus would result in a loxP-flanked PGK promoter, neo gene and PGK poly-adenylation signal cassette located in exon 4 of the mouse WAP gene. Targeting with ploxPNeo gives a PCR™ band of approximately 750 bp band with the WAP exon 4 and neo primers. A WAP exon 4-specific primer (SEQ ID NO:13: 5'-AGCGACCAGCCCAAGTGTATACAG-3') and neomycin-specific primer (SEQ ID NO:14: 5'-TGACCGCTTCCTCGTGCTTTAC-3') pair was used for PCR™ diagnostic of genomic DNA diagnostics under the following conditions: 1 cycle at 94° C. (2 min); 33 cycles of 94° C. (30 sec), 55° C. (30 sec), 72° C. (30 sec); 1 cycle at 72° C. (10 min).

From 48 G418$^R$ colonies analyzed from the ploxPNeo-pOG231 co-electroporations, 11 were site-specific integrants. Seven representative samples were positive with the correct 750 bp band from integration of the ploxPNeo plasmid. The frequency of insertion was found to vary directly with the amount of pOG231 electroporated. When expressed as a percentage, the frequency of site-specific integration was 22.9% for 30 μg pOG231, 20.8% for 20 μg, 12.5% for 10 μg, and 4.2% for 5 μg.

Integration of ploxPNeo into the WAP locus at exon 4 gave a predicted SphI band size of 4.8 kb compared to the endogenous WAP locus of 7.1 kb. Targeting the WAP locus by homologous recombination with pWPNT gave a band of 3.9 kb, since the neo genes for ploxPNeo and pWPNT were cloned in different orientations. As controls, the targeted cell line has a 3.9 kb allele, whereas the deletion cell line has a 7.1 kb allele. All of the PCR™-positive clones were confirmed by Southern blot except for one clone, perhaps mosaic for the insertion event.

The results discussed above illustrate the feasibility of utilizing the Cre-loxP system for the site-directed insertion of a DNA fragment into a predetermined chromosomal location. Although the locus chosen reflects the inventors' interest in the generation of transgenic animals that can serve as mammary gland bioreactors, the overall approach should be applicable to any locus of interest.

To date, this is the first report of targeting the WAP locus and also of Cre-mediated integration in ES cells at a predetermined loxP site. This work establishes that this event does occur at levels approximating those of homologous recombination. Transgenic animals made by blastocyst injection of this ES cell line can thus have a loxp target for Cre-mediated insertion of transgenes. Since the loxp site is positioned between the WAP termination codon and poly-adenylation signal, transgenes containing an internal ribosome entry site (IRES) could be employed for production of a WAP-transgene bicistronic message (Pelletier and Sonenberg, 1988). This approach would obviate any unpredictable problems which might arise from eliminating WAP expression altogether; in addition, transgenic animals with single-copy transgenes at the same location should give uniform expression patterns.

Most applications involving the Cre-loxP system in a mammalian setting are geared to utilize its efficiency at deleting loxP-flanked DNA sequences. Previous results from Cre-mediated deletion studies show that this event can occur at high frequencies in ES cells. In the inventors' case approximately 2.2% of targeted cells electroporated with pBS185 had undergone the deletion of the neo-TK cassette when seeded at 5×10$^5$ per plate. In a similar study, the $J_H$-$E_\mu$ region from the IgH locus in ES cells was targeted with a loxP-flanked neo-TK cassette. Cre-encoding vectors pIC-Cre and pMC-Cre, which contain enhanced translation and nuclear localization signals, respectively, gave comparable values of 2.0% and 4.0% at this seeding density (Gu et al., 1993). With FIAU selection, Abuin and Bradley (1996) found that 16% of targeted cells had undergone deletion of a loxP-flanked selection cassette, which questions the necessity of using selection pressures for the deletion event. In accordance with this, use of a recombinant adenovirus to express Cre results in nearly 100% of cultured cells having deleted out loxP-flanked sequences (Kanegae et al., 1995).

More importantly, however, the Cre-loxP and FLP-FRT systems have been shown to cause site-specific integration of DNA into the mammalian chromosome, although at frequencies much lower than those found for the deletion event. O'Gorman showed that FLP-mediated recombination in monkey kidney cells gave approximately 2-fold higher levels than random integration (O'Gorman et al., 1991). Baubonis and Sauer (1993) used Cre protein as a transient source of recombinase in a loxP-tagged human osteosarcoma cell line. Using a promoter trap system, they found a "position effect" as cell lines containing randomly integrated loxP site showed a 50-fold difference in targeting efficiency. Integration in ES cells using wild type loxP sites has been reported, although less than 0.5% of integrants were site-specific (Araki et al., 1997). Results from the inventors' studies have shown that site-specific integration at the WAP locus was 23% (11 of 48 G418$^R$ colonies) of random integration. Since the WAP locus was targeted by homologous recombination at a 1:4 HR:NHR ratio (homologous recombination:non-homologous recombination), the Cre-mediated event occurred at approximately the same level as homologous recombination.

Although the frequencies of Cre-mediated insertion and homologous recombination at the WAP locus in this study are similar with respect to random insertion, site-specific insertion has some added benefits. When designing constructs for Cre-based insertion the only homology needed is the 34 bp loxP site, compared to several kilobases for conventional gene targeting. In addition, mutation of the loxP sites can give increased insertion frequencies over that obtained with wild-type loxP sites (Albert et al., 1995) suggesting that it will be possible to increase the frequency of insertion events further. Moreover, complementary mutations in two loxP sites would result in a wild-type and double-mutant loxp site after the integration event. This double-mutant loxP site would not be bound by Cre and therefore can not participate in the excision reaction increasing the overall insertion frequency. As shown recently, use of this strategy in ES cells can give a 30-fold increase in Cre-mediated insertion at a randomly positioned loxp site (Araki et al., 1997).

Furthermore, as shown in Table 15, the ratio of transgene to the Cre-encoding plasmid affects the rate of recombination indicating that for maximal insertion frequency there needs to be an optimal ratio between the level of Cre and the loxP-tagged transgene. As an indication of the importance of the level of Cre on the insertion event, the only Cre-expressing plasmid that resulted in detectable integration events was plasmid pOG231. At higher amounts of pOG231, a higher level of integration is seen presumably due to the increased concentrations of pOG231 in each cell. Comparison of Cre-encoding plasmids for the deletion of the neo-TK cassette showed a 4-fold higher number of gancyclovir resistant colonies for pOG231 versus pBS185. The Cre gene is being placed under different promoters known to be active in ES cells to determine if this can result in an increased frequency of integration. Thus, there are several potential approaches that can increase the frequency of insertion over that reported here and would make this system, or a modification of it, a highly useful system for the generation of transgenic animals.

At present, no other alternative exists for direct use on embryos as conventional gene targeting in embryos is both highly inefficient and accompanied by changes in the incoming DNA (Brinster et al., 1989). Cre protein has been previously reported to work in one-cell stage mouse zygotes for the deletion of loxP-flanked sequences (Lakso et al., 1996). In mice, the efficiency of generating transgenic animals by pronuclear injection is 5–20% (transgenic pups born/total pups born). If the ratio of random integration to site-directed insertion is similar in embryos co-injected with a loxP-tagged transgene and the Cre enzyme as in cultured ES cells, between 1–5% of transgenic pups born would have a Cre-mediated insertion in the tagged locus. This would result in a form of targeted modification by pronuclear injection. At present the inventors are generating mice with a tagged WAP locus to study this effect.

This system has also been adapted to large animals by introducing stop signals into the WAP coding sequence. This way the bicistronic message is made, the protein of interest is produced from the IRES, but the WAP protein is not made. This is useful as the mouse WAP protein has been implicated in mammary gland damage in transgenic pigs.

EXAMPLE 6

Isolation and Characterization of The Porcine Apolipoprotein E Gene

Apolipoprotein E (apo-E), a constituent of various classes of plasma lipoproteins in mammals, serves several major functions including the transport and metabolism of cholesterol and lipids such as phospolipids and triglycerides (Mahley, 1988). In humans, the mature polypeptide composed of 299 amino acids (Rall et al., 1982), is synthesized as the preapo-E protein having an 18 amino acid signal peptide which is removed cotranslationally (Zannis et al., 1984). Apo-E is synthesized at multiple sites including the liver, brain, spleen, and kidney, with the liver being the largest producer (Mahley, 1988). Synthesis also occurs in peripheral cells such as macrophages (reviewed by Getz et al., 1988). Both the cDNA and genomic nucleotide sequences are known for a limited number of species, including human (Das et al., 1985; Paik et al., 1985), mouse (Rajavashisth et al., 1985), rat (Fukazawa et al., 1986) and baboon (Hixson et al., 1988).

The mechanism of action of apo-E in the metabolism of cholesterol and lipids is complex and appears to involve interactions with lipoprotein receptors such as the apo-B, E (LDL) receptor (Mahley and Innerarity 1983). A region rich in arginine and lysine in the vicinity of amino acids 140 to 160 is the receptor binding domain in human (Innerarity et al., 1883; Weisgraber et al., 1983). Single amino acid substitutions within this region result in genetic variation at the apo-E locus. Some of the naturally occurring variants exhibit deficiency in receptor binding and are associated with type III hyperlipoproteinemia and accelerated cardiovascular disease (Weisgraber et al., 1982). The apo-E3 and E4 isoforms which have cysteine and arginine at amino acid position 112, respectively, possess normal receptor binding ability (Weisgraber et al., 1982).

The role of apo-E in atherogenesis is complex and difficult to study in humans (Getz et al., 1988). As an omnivore with a similar cardiovascular and gastrointestinal physiology to that of humans, swine are well suited for the study of cardiovascular diseases (Hodson 1985; Armstrong and Heistad 1990). In fact, swine models already exist for various aspects of cardiovascular disease (See Swindle 1992). The development of porcine models that manifest aspects of atherosclerosis is very attractive to scientists researching this complex human disease. The isolation and characterization of the porcine apo-E gene brings this process one step closer to becoming a reality.

A. Cloning and Sequencing of the Porcine Apo-E Gene

A porcine genomic library constructed from partially digested Sau3Al fragments (8–22 kb) cloned into the BamHI site of the lambda vector EMBL3 Sp6/T7 (Clontech Laboratories Inc., Palo Alto, Calif.) was screened (Sambrook et al., 1989), using a $^{32}$P-labeled 700 bp SacI/BglI fragment from the mouse apo-E cDNA (Piedrahita et al., 1992). A single positive phage clone was isolated and contained a 10.7 Kb DNA insert after digestion with EcoRI/SalI. The 10.7 Kb DNA fragment was then cloned into the phagemid Bluescript (pBS) M13 using established methods (Sambrook et al., 1989).

A partial restriction enzyme map of this clone was generated in order to locate the position of the apo-E gene within the 10.7 kb insert, and to facilitate subcloning for sequencing. A 4.2 Kb XhoI/XhoI fragment containing the entire porcine apo-E gene and mapped at the 3' end of the 10.7 Kb insert was subcloned into pBS. Overlapping subclones were generated for sequencing from the XhoI/XhoI clone. Both strands of the subclones were sequenced using the M13-20 universal forward and the 17-mer reverse primers. Sequencing was carried out with the Dideoxy™ Dye Terminator/Sequenase™ kit (Applied Biosystems Division, Perkin-Elmer Cetus, Emeryville, Calif. USA) using an Applied Biosystems 377 DNA Sequencer. The MacVector™ and Assemblyline™ programmes were used to assimilate and align the sequence data.

A porcine genomic library was screened using a mouse apo-E-specific probe and a single positive phage clone was identified. The clone was isolated, and a 10.7 Kb insert was released by digestion with EcoRI and SalI. Restriction enzyme mapping and Southern analysis revealed that the insert contained the entire porcine apo-E gene at its 3' end within a 4.2 Kb XhoI/XhoI fragment. The nucleotide sequence (SEQ ID NO:5) and deduced amino acid sequence (SEQ ID NO:6) of the porcine apo-E gene was then determined.

The structure of the porcine apo-E gene is similar to that of human (Das et al., 1985; Paik et al., 1985), mouse (Rajavashisth et al., 1985), rat (Fukazawa et al., 1986) and baboon (Hixson et al., 1988) in that it consists of four exons separated by three introns. The sizes of exons 1 to 4 are 26 bp, 66 bp, 190 bp, and 843 bp, respectively. The sizes of the three introns are 804 bp, 744 bp, and 374 bp, respectively. Interestingly, exon 2 (66 bp) is the same size among the species that have been sequenced. The sizes of the other exons differ among the species.

The 4,266 bp XhoI/XhoI fragment was sequenced in its entirety (SEQ ID NO:5; GenBank accession number 470240). It contained 831 bp of 5' and 378 bp of 3' flanking regions in addition to the 3057 bp porcine apo-E gene. The exon/intron borders were identified by comparison of the porcine nucleotide sequence with that of the cDNA previously determined (Brzozowska et al., 1993a). Identification of the 5' GT and 3'AG intron splice-site consensus sequences (Breathnoch et al., 1978) confirmed the precise positions of the three introns within the gene.

The gene is comprised of 49 bp of 5' untranslated sequence encompassing exon 1 and part of exon 2 followed by the coding sequence spanning the remainder of exon 2 to exon 4 which codes for an 18 amino acid putative signal peptide, and a mature protein of 299 amino acids, and ends with a 3' untranslated sequence of 125 bp. The first exon and intron occur within the 5' untranslated region (positions G 1 and t 28, respectively). The second intron interrupts the codon for glycine at position −4 of the amino acid sequence for the signal peptide (G 897). The third intron interrupts the codon for threonine at position 60 of the mature protein (G 1831). An MRNA of 1125 bp is encoded by the porcine apo-E gene.

When both the nucleotide sequence of the exons and the inferred amino acid sequence were compared to that of the previously determined cDNA (Brzozowska et al., 1993a), differences at 17 nucleotides were found. However, 10 of the nucleotide substitutions had no effect on the inferred amino acid sequence of the mature protein. Of these, eight occurred outside the coding region at nucleotide positions 1, 2, 5, 8, 9, 252, 253 and 254 and two at positions 2470 and 2893 within exon 4. There were seven substitutions within the mature protein at amino acid positions 17 S to P, 142 N to K, 143 V to L, 148 V to L, 176 L to F, 233 D to E and 234 E to Q, corresponding to nucleotide positions 1701, 2455, 2456, 2470, 2471, 2728 and 2729, respectively. The inventors' sequence contains an additional CCC beginning at nucleotide position 2952 resulting in an mRNA of 1125 bp instead of 1122 found by Brzozowska et al. (1993a). It is unlikely that the differences found here were due to sequencing artifacts, since sequence data were obtained from both strands of overlapping clones.

The mature protein has glutamic acid as its $NH_2$-terminal residue, its codon begins at position 1653 of the nucleotide sequence. The canonical AATAAA, present within the 3' untranslated region of most eukaryotic genes (Benoist et al., 1980) is located 21 nucleotides upstream from the end of exon 4.

The MacVector™ program was used to align the inferred amino acid sequence for the primary translation product of the pig to that of human (Das et al., 1985; Paik et al., 1985), baboon (Hixson et al., 1988), monkey (Marotti et al., 1989), cow (Brzozowska et al., 1993b), mouse (Rajavashisth et al., 1985), rabbit (Hao et al., 1987) and rat (Fukazawa et al., 1986). For maximal alignment it was necessary to introduce gaps at positions where amino acids were lacking in some of the species. These gaps occur predominantly within the first 37 amino acids at the NH2-terminal end of the mouse, rabbit and rat apo-E. In addition, the rat sequence has six fewer amino acids at its COOH-terminal end.

The overall amino acid similarity between the pig apo-E and that of each of the other species is as follows: human 70.3%, baboon 72.3%, monkey 70.3%, cow 72.2%, rabbit 68%, mouse 65% and rat 60%. The amino acid sequence for each species mentioned above was aligned to each other. A higher degree of amino acid conservation was evident among closely related species with 93% amino acid similarity among human, baboon and monkey and 91% between mouse and rat.

The amino acid sequence of the pig diverged from that of some or all of the other species at 32 positions. Furthermore, close to 50% of these amino acid substitutions are non-conservative. There was a higher amount of amino acid similarity within the central portion of the protein (a.a. 41–211) than at its ends (a.a. 20–40 and a.a. 212–299) among the species. A range of 50% to 73% similarity exists within the 18 amino acid signal peptide among the species and only 19% to 36% within the first 22 amino acids of the mature protein. In contrast, a range of 75% to 90% similarity exists between residues 41 to 211.

Except for differences at 18 nucleotide positions, the sequence of the exons reported here matches that of the cDNA reported by Brzozowska et al. (1993a). In contrast, indirect evidence suggest that at least some of the differences may be attributable to misread bases within the sequence of Brzozowska et al. (1993a). For the genomic sequence here, the inferred amino acids at six of the seven positions that resulted in amino acid substitutions (amino acids 142, 143, 148, 176, 233 and 234) are identical to that of all or almost all of the seven species to which it was aligned. The seventh substitution has proline encoded by the genomic sequence and serine by the cDNA at inferred amino acid position 17 of the mature protein. This region has a much lower degree of conservation and only the bovine has proline at position 17-no species had serine at this position.

Furthermore, double mutations (at amino acid positions 142–143, 147–148 and 233–234) are uncommon, most amino acid substitutions in eukaryote genes are single amino acid substitutions (Mclean et al., 1984). Natural polymorphism is a less likely explanation for the differences between the two pig sequences. Furthermore, the additional CCC nucleotide triplet beginning at position 2952 of the genomic when compared to that of the cDNA sequence (Brzozowska et al., 1993a) is intriguing. This is within the 3' untranslated region and did not result in a translational frame-shift. Nevertheless, it appears that both the genomic sequence here and that of the cDNA (Brozozowska et al., 1993a) correspond to the apo-E4 isotype of the human gene (reviewed by Mahley, 1988), since both have arginine at position 111 and 157 of the mature protein. On the other hand, this comparison between human apo-E and that of other species may not be appropriate due to the critical role of arginine 61 (only found in human) in determining the E4 isotype (Dong et al., 1994).

The length of exon 1 in the pig is about 60% that of human (Das et al., 1985; Paik et al., 19985), baboon (Hixson et al.,, 1988), monkey (Marotti et al., 1989), mouse (Rajavashisth et al., 1985) and rat (Fukazawa et al., 1986). Apparently this is not critical in determining the length of the protein since it is not translated. In comparison, the conservation in length of exon 2 among species may be a common requirement to encode for most of the signal peptide. This may be ancestrally related, as alluded to by Paik et al. (1985) who found that other members of this gene family, namely apo-AI and apo-CIII, have nearly the same length exon 2 as apo-E. The first 18 inferred amino acids of pig apo-E conforms to that of the apo-E signal peptide in human (Zannis et al., 1984) and other mammalian species (Yang et al., 1991). This region is rich in hydrophobic amino acids, a characteristic of precursor peptides (Verner and Schatz 1988), and relatively conserved among species. A 73% identity exists between human and pig and 67% between human and rat. The mature apo-E protein in the pig is identical in length (299 amino acids) to that of human (Rall et al., 1982) and one amino acid longer than that of bovine (Brozowska et al., 1993b).

The human apo-E gene has been extensively analyzed for the presence of regulatory elements (Paik et al., 1988; Smith et al., 1988; Chang et al., 1990). Computer analysis of the 5' proximal region of the pig apo-E indicates that the regulation of expression of this gene is no doubt a complex process, not unlike that found for human apo-E (Smith et al., 1988). These workers found no less than 15 regions protected by DNA footprints. Smith et al. (1988) suggested that this complex form of regulation provides for the expression of apo-E within different tissue types, depending upon the intracellular cholesterol concentration, and other nutritional and hormonal factors. Simonet et al. (1991) found regulatory elements as far downstream as 14 kb that influence expression of apo-B within the liver in human.

A TATA box sequence found in most eukaryotic promoters occurs at the same position as that in humans (Paik et al., 1985). However, the putative transcription initiation site in pig apo-E is 20 bp downstream of that in human. This could account for the shorter exon 1 in the pig. Similar sequence motifs to all of the apo-E elements found in humans were also found in the rat apo-E gene (Smith et al., 1988). Computer analysis of the pig gene revealed some of the sequences within the 5' region that matches those found in the human apo-E gene (Smith et al., 1988).

Apart from the more common elements such as the TATA, and GC boxes found in most eukaryote genes, other putative regulatory sequences also mapped to the 5' proximal end of the pig apo-E gene. Apo-E is highly expressed in the liver (Mahley 1988), therefore, it is not surprising to find a TCATACTC sequence that binds to the liver specific enhancer protein C/EBP_cs2 (Costa et al., 1988). The apo-E gene is also expressed within the brain and is implicated to be a candidate Alzheimer disease-susceptibility gene (Pericak-Vance and Haines 1995). An enhancer regulatory consensus sequence, TCTGTCTC, that binds to two proteins that are specifically found in the brain (Khalili et al., 1988) is present beginning at position -435 in the pig apo-E. Because of the complex nature of apo-E regulation, additional regulatory sequences may be present within the pig gene as the survey for porcine upstream regulatory sequences here is by no means exhaustive, and the possible sequences found awaits confirmation by DNA footprinting studies.

Limited protease digestion of human apo-E generated two classes of peptide fragments with strikingly different physical and chemical properties. One class extending from amino acid 1 to 191 represented the amino terminal domain and the other from residue 216 to 299 the carboxy-terminal domain. The former and latter peptides contain the receptor and lipid binding-domains, respectively (reviewed by Mahley 1988). The alignment of the apo-E sequences of the seven above-mentioned species with that of the pig revealed a contrasting pattern of amino acid conservation between these two regions. The amino-terminal domain from residue 20 to 211 was highly conserved among the species with a 75 to 90% amino acid identity. The carboxy-terminal domain was much less conserved. In addition, amino acids 260 to 280 within the carboxy-terminal domain are highly conserved among species; this may also be related to function. The sequence between 140 to 160 is critical for receptor binding (Lalazar et al., 1988). The pig and human sequences within this region are identical except at two non-critical positions. Clay et al. (1995) found that the region from amino acids 141 to 149 has both cytostatic and cytotoxic effects on interleukin-2 dependent T lymphocyte proliferation. It would be interesting to determine whether these effects also extends to pig apo-E.

B. Determination of Polymorphism at the $(CG)_{13}$ Microsatellite Locus

A simple sequence repeat (microsatellite marker) was detected within intron 3 of the pig apo-E gene. Locus specific primers complementary to sequences flanking the repeat region were designed using the MacVector™ 5.0 program. The primers used were the forward primer (SEQ ID NO:15: 5'-AGCTGCTCAGCACCAAGGTCAC-3') and reverse primer (SEQ ID NO:16: 5'-CTGAGGGTCCAGACCACACGG-3'), respectively. Genomic DNA from 40 unrelated animals belonging to four pig breeds (Yorkshire, Landrace, Hampshire and Duroc; 10 animals per breed; obtained from Dr. Larry Shook, University of Minnesota) were amplified by PCR™ in order to determine the extent of polymorphism among breeds.

PCR™ conditions were: 50 ng of genomic DNA amplified in 50 pl containing 50 pmol of each primer, 3 mM $MgCl_2$, 200 µM of each dNTPs and 2.5 u/0.5µl Taq polymerase in standard PCR™ buffer (Promega, Madison Wis., USA). Cycling conditions were: 94° C. for 2 min, followed by 35 cycles of 94° C. for 30 sec, 61° C. for 30 sec, and 72° C. for 30 sec. A 194 nucleotide product was expected with this primer pair. The forward primer was 5' end labeled with [$\gamma$-$^{32}$P]-ATP prior to PCR. At the end of the PCR™ amplification 0.75 volume of gel loading buffer (95% formamide, 0.05% xylene cyanol, 0.05% bromophenol blue, 0.5 M EDTA) was added to each reaction which was then boiled at 90° C. for 5 min. Electrophoresis was performed on 6% denaturing polyacrylamide gels on a standard sequencing gel apparatus at 40 W and 45° C. for 2.5 h. After electrophoresis, gels were dried under vacuum at 80° C. for 2h and exposed for autoradiography.

A simple sequence repeat or $(CG)_{13}$ microsatellite was detected within intron 3 of the porcine apo-E gene beginning at position 1856 of the nucleotide sequence. This $(CG)_{13}$ microsatellite is moderately polymorphic. Four alleles having sizes of 190, 193, 194 and 199 bases were detected on the basis of electrophoretic mobility among the 40 animals from the four pig breeds tested. Four alleles were detected among eight animals from the Yorkshire breed of pig. The polymorphic information content (pic) value was 0.58 and the allelic frequencies were 0.38 (190), 0.13 (193), 0.44 (194) and 0.06 (199).

Three alleles were present among eight animals from the Hampshire breed. The pic value was 0.54 and the allelic frequencies were 0.31 (190), 0.50 (194) and 0.19 (199). The pic value for Duroc was 0.51 with allelic frequencies of 0.50 (190), 0.38 (194), and 0.13 (199). The pic value for Landrace was 0.35 and the allelic frequencies were 0.67 (190) 0.34 (194). Alleles 190 and 194 detected in all four breeds were the most frequently represented, while allele 193 was unique to the Yorkshire breed.

This is the first report of the presence of a $(CG)_{13}$ microsatellite marker within intron 3 of the pig apo-E gene. This microsatellite is unique to the pig among the species with known apo-E genomic sequence. The reason for the higher degree of polymorphism seen in the Yorkshire breed compared to the other three breeds tested is not clear. This outcome has no bearing on the number of animals tested, since eight unrelated animals per breed is a large enough representative sample size. Furthermore, this may not be unique to Yorkshire and may extend to other pig breeds not tested in this study. The importance of identifying new microsatellite markers within the genome of livestock species cannot be understated. Efforts are presently underway to develop a high-density linkage map in swine to search for loci affecting phenotypes of interest (Rohrer et al., 1994; Rettenberger et al., 1995; Robic et al., 1995).

C. Determination of the Porcine Apo-E Chromosome Location by FISH

Pig metaphase chromosomes were prepared from phytohemagglutinin stimulated lymphocytes following standard cytogenetic methods. The fluorescence in situ hybridization (FISH) procedure followed standard protocols (Pinkel et al., 1986) with slight modifications as previously described (Gallagher et al., 1993). Purified DNA from the X phage clone containing the entire apo-E gene (insert and vector) was labeled with biotin by nick translation. 200 ng of labeled probe and an excess of sheared total genomic DNA from pig were dissolved in 10 μl of hybridization solution. Hybridization suppression was overnight at 37° C. under a sealed coverslip. Following post hybridization washes the biotinylated probe was detected with FITC conjugated avidin. FISH preps were then mounted in antifade solution containing the counterstains propidium iodide and Hoechst 33258, each at 500–700 ng/ml. Photographs of metaphase showing PI counterstaining plus FITC probe signal and QFH-banding that resulted from the Hoechst counterstain were taken sequentially on color print film. The QFH banded chromosomes that showed probe hybridization were identified according to the domestic pig GTG-band standard karyotype (Committee for the Standardized Karyotype of the Domestic Pig 1988; Yerle et al., 1991).

Sequential FISH and QFH-banding were performed on porcine metaphase chromosome spreads using as probe a lambda phage clone containing the porcine apo-E gene. A total of 30 metaphase spreads were analysed and 21 showed strong specific centromeric hybridization signal on chromosome 6. Of these, 38% (8) showed symmetrical hybridization signals on both chromatids and chromosomes (two pairs of yellow dots); 14% (3) had three yellow dots (hybridization signal on three chromatids of the homologous chromosome pair); 29% (6) showed symmetrical signals on both chromatids of one chromosome (two yellow dots); and 19% (4) had a single dot on one chromatid. All yellow dots represented specific hybridization signal localized on chromosome 6 region cen→q2.1.

Arm length ratios were calculated for 20 metaphase chromosomes and 12 (60%) indicated that the pig apo-E gene is located on chromosome 6 (data from the other eight were unclear). Apo-E localization on chromosome 6 was confirmed by aligning QFH-banded FISH labeled chromosomes to the standard idiogram and G-banded chromosome 6 of the pig (Committee for the Standardized Karyotype of the Domestic Pig, 1988).

EXAMPLE 7

Isolation, Characterization, and Chromosomal Localization of the Porcine (CNTF) Gene Like other members of the hematopoietic cytokine family, ciliary neurotrophic factor (CNTF), first recognized as a survival factor for chick parasympathetic neurons (Barbin et al., 1984), has been shown to possess the ability to maintain murine embryonic stem (ES) cells in culture (Conover et al., 1993). By interacting with its receptor and forming a hexamer that includes a gp130/LifRβ heterodimer (Desirio et al., 1995), CNTF facilitates the activation of the gp130 signal transduction pathway (Ip et al., 1992; Stahl et al., 1993), which ultimately leads to the undifferentiated, proliferating phenotype of the ES cell (Yoshida et al., 1994). Since it has been shown that heterologous CNTF does not positively contribute to the isolation of a porcine embryo-derived cell line with characteristic ES cell morphology (Moore and Piedrahita, 1996), the inventors have cloned, sequenced, and mapped the porcine CNTF as a first step in determining whether the use of the homologous protein will be more conducive to the inhibition of differentiation of early porcine embryonic cells.

A. Cloning and Sequencing of the Porcine CNTF Gene

A porcine genomic library constructed in lambda EMBL3 SP6/T7 (Clontech) was screened with a 369 bp probe containing all of exon one and 253 bp of exon two of the porcine CNTF cDNA. The probe was generated by reverse transcription-polymerase chain reaction (RT-PCR™), of porcine activated macrophage mRNA. The 5' primer (SEQ ID NO:17; 5'-GGATGGCTTTCGCAGAGCAAACAC-3') and 3' primer (SEQ ID NO:18; 5'-GCTGGTAGGCAAAGGCAGAAACTTG-3'), were synthesized by identifying conserved regions in both the rat and human CNTF. Using this probe, seven positive plaques were identified and a single positive confirmed by secondary and tertiary screenings.

The positive plaque was grown in suspension and the DNA isolated using standard procedures (Sambrook et al., 1989), and subsequently digested with several restriction enzymes. After Southern blotting, a 6 kb Apa I fragment containing the complete CNTF gene was identified and cloned into pBluescript. From this clone, four smaller, overlapping subclones were made to facilitate cycle sequencing of porcine CNTF in its entirety. The subclones, their nomenclature, and the regions they span include: HindII 700 bp, containing the 5' untranslated region (UTR) and part of exon 1; HindIII 3 kb, containing the end of exon 1 through the 3' UTR; Xba 1 1.7 kb, containing less than 140 bp of intron 1, exon 2, and the 3' UTR; and Dra I 1 kb, containing approximately the last 50 bp of exon 2 and the 3' UTR. All four subclones were subjected to dye terminator cycle sequencing of both strands and any area with inconsistencies between the two strands was sequenced again to unequivocally confirm the correct sequence.

Sequencing was performed using the M13-20 and Reverse primers as well as other primers designed for regions not accessible with the M13 primers. DNA was prepared for sequencing using the QIAGEN Plasmid Kit. PCR™ reactions contained the following: 1 μg ds plasmid, 8 μl reaction mix with AmpliTaq® FS (Applied Biosystems, Foster City, Calif.), and 3.2 pmol primer in a total volume of 20 μl and were cycled 25 times after an initial 2 minute denaturation at 96° C. for 30 seconds, 50° C. for 15 seconds, and 60° C. for 4 minutes. Excess nucleotides and dye terminators were removed with Centri-Sep™ column, and the PCR™ reactions were analyzed with an ABI PRISM 377 automated DNA sequencer. Sequencing data was compiled and aligned using MacVector™ and AssemblyLine™.

The porcine CNTF gene includes two exons separated by a 1258 bp intron. Exon one is 114 bp in length and codes for 38 amino acids, while exon two is 486 bp and encodes the remaining 162 amino acids of the CNTF protein. Exon/intron borders were determined by comparison with human CNTF and confirmed by the location of 5'-GU and 3'-AT splice sites. Analysis of the promoter region revealed a TATA box at position −54 bp and a CAAT box at −120 bp. Though both vary somewhat from the reported consensus sequences for these elements, they are identical to those identified in the promoter of human CNTF and are in the same relative position (Negro et al., 1991). The TATA box is located at the exact same position in human CNTF, while the CAAT box shows a downstream shift of one basepair. The poly-A adenylation site, AAUAAA, was located 368 bp downstream of the stop codon (GenBank Accesion No.U57644).

The amino acid and cDNA nucleotide sequence of porcine CNTF was compared to sequences from rabbit (Lin et al., 1989), rat (Stockli et al., 1989), human (Negro et al., 1991), and mouse (GenBank accession No. U05342). The polypeptide with greatest similarity was that of the rabbit with 83%, while the rat, human, and mouse showed 82%, 82%, and 81% similarity, respectively. At the nucleotide level, porcine CNTF is most similar to the human cDNA (88%), while similarities for the other species were 87% for the rabbit, 84% for the rat, and 84% for the mouse.

Sequence alignments of the amino acids of the aforementioned species and the chicken (GenBank accession No. M80827) were also completed. Porcine CNTF differs from all five species in thirteen different positions. Moreover, the porcine amino acid sequence differs from four of the five species at seven additional locations. Of all these differences, seven positions represent non-conservative amino acid changes, according to MacVector™ groupings. These changes between the pig and other species are: glutamic acid to valine at position 96; aspartic acid to glycine or alanine at position 103; histidine to cysteine, glutamine, or serine at position 132; threonine to methionine or glutamic acid at position 142; glycine to aspartic acid or arginine at position 148, arginine to histidine at position 174, and alanine to either threonine, methionine, or proline at position 184. If these positions play critical roles in the functionality of the protein, the species differences might explain the apparent inability of a heterologous protein to activate the porcine gp130 signal transduction pathway. At present the inventors are in the process of expressing the porcine CNTF protein to determine its bioactivity when compared to heterologous CNTF.

The 5' promoter region of both the porcine and human CNTF was extensively analyzed for the presence of possible transcription factor binding sites. Several sites were found to be conserved in the same position between the two species, though exact sequences of particular motifs varied; yet, other sites were slightly shifted due to deletions in one or both species. Moreover, the 391 bp region immediately upstream of the start site of the human Lif (GenBank accession No. M63420, J05436), human IL-6 (GenBank accession No. M22111), and *Caenorhabditis elegans* Osm-3 (GenBank accession No. D14968) was analyzed for the subset of binding sites found within the porcine and human CNTF promoters.

Those sites of particular interest, conserved in all promoter sequences analyzed, included several binding motifs for activator protein one and two, AP-1 and AP-2. These are: one AP-1_CSI (STGACTMA), one AP-1_CS2 (TGAGTCAG), two AP-1_CS3 (TGANTMA), one AP-1_CS4 (TGASTMA), one AP-1-TRE-4/C (CTGAGTCAG), and three AP-2_CS6 (CCCMNSSS). AP-1 is ubiquitously expressed and composed of dimers between members of the Jun, Fos, and ATF families, while AP-2 is expressed mainly in the neural crest (Faisst and Meyer, 1992). AP-1 interacts with motifs containing TPA (12-O-tetradecanoyl-phorbol-13-acetate)-inducible enhancer elements known to activate protein kinase C (Lee et al., 1987), while AP-2 mediates transcriptional induction by two different pathways including phorbol ester activation of protein kinase C and cAMP-dependent protein kinase A (Imagawa et al., 1987).

Other sites include three gamma-IRE (CWKKANNY), conferring responsiveness to the lymphokine interferon γ (Yang et al., 1990), and two binding sites for granulocyte-macrophage colony-stimulating factor, GMCSF_CS (CATTW), a hematopoietic growth factor (Nimer et al., 1990). As well, there are potential binding sites for one 30S-rRNA.I (AGGT) involved in initiation factor IF3-30s binding (Ehresmann et al., 1986) and five TCF-1_CS sites (MAMAG), which are tissue specific for T cells (Faisst and Meyer, 1992). Two additional sites found only in the CNTF promoter are one alpha-INF (AARKGA) binding site, and one E2-A_CS site (RCAGNTG) related to E2-box factors which may be myocyte or B-cell specific (Faisst and Meyer, 1992). Although it is tempting to speculate the potential function of several of the conserved regions, elucidation of their exact role awaits transgenic analysis.

B. Determination of the Porcine CNTF Chromosome Location by FISH

Sequential R-banding and FISH were performed on porcine metaphase chromosome spreads to determine the precise chromosomal location of the porcine CNTF gene. Pig metaphase chromosomes were prepared from whole blood as described by Rønne et al. (1984). FISH was performed essentially as described by Niebergs et al. (1993). Briefly, a lambda bacteriophage clone containing 13 kb of genomic insert which included the entire CNTF gene was used as a probe. One microgram of phage DNA was labeled with digoxigenin-11-dUTP by nick translation. Repetitive sequences within the probe were suppressed with total porcine genomic DNA by denaturation at 70° C. for 5 min followed by incubation for 30 min in a 37° C. water bath.

The probe was then chilled on ice and transferred at a final concentration of 10 ng/ml to slides containing metaphase spreads denatured by immersing in freshly prepared 70% formamide/2×SSC for 2 min at 70° C. Coverslips were mounted onto the slides and the edges sealed with rubber cement. Slides were incubated in a humidified chamber at 37° C. for 18 h to allow for hybridization. Hybridization signal was detected by FITC-conjugated anti-digoxigenin antibody using the Chromosome In situ Kit (Oncor, Gaithersburg, Md.) according to the manufacturer's specifications. Chromosomes were counterstained with propidium Iodide/antifade (Oncor) and R-banded by mounting in Hoechst 33258/antifade (Oncor). Metaphase spreads were observed under an Olympus Varox-T fluorescence microscope and photographed with Kodak Ektachrome 100 color slide film.

A total of 95 metaphase spreads containing hybridization signals were analyzed. Of these, 27% (26) showed symmetrical hybridization signals on both chromatids and chromosomes; 20% (19) had hybridization signal on three chromatids of the homologous chromosome pair; 40% (38) showed symmetrical signals on both chromatids of one chromosome; and 13% (12) had a single signal on one chromatid. All of the specific hybridization signal localized on chromosome 2p, band 1.6. Arm length ratios were calculated for 40 early metaphase chromosomes and 32 (80%) indicated that the pig CNTF gene is located on chromosome 2p1.6. This was confirmed by aligning R-banded FISH labeled chromosomes to the standard idiogram and R-banded chromosome 2 of the pig (Committee for the standardized karyotype of the domestic pig, 1988).

EXAMPLE 8

Expression of GFP Using the Oct-4 Promoter and/or Enhancers

The expression regulated by the Oct-4 element is not controlled by the promoter alone but also by two enhancers located upstream of the gene. One is called the germ cell specific enhancer and the other the epiblast specific enhancer. Expression using both of these elements has been studied.

The Oct-4-GFP constructs were compared to the CMV-GFP or the PGK-GFP. There is a significant increase in the number of transgenic colonies from the Oct4 construct versus PGK and CMV constructs. Additionally, a "hybrid" construct combining the enhancer regions from Oct4 with the PGK promoter has been created. The Oct-4/$\mu$gK-GFP hybrid gives substantially higher expression of GFP than the PGK-GFP alone.

EXAMPLE 9

Development of an in vitro Differentiation Assay

An exogenous supply of hematopoietic cytokines is essential for maintaining murine embryonic stem (ES) cells in a proliferative yet undifferentiated state. Recently, it was demonstrated that hematopoietic cytokines utilize the gp130 signal transduction pathway to maintain this phenotype, yet their involvement towards maintaining porcine ES or PGC cell pluripotency has not been established. Isolation and maintenance of porcine ES cells have been hindered by the inability to inhibit differentiation of the porcine inner cell mass (PICM) in vitro. Optimizing culture conditions for the pICM is essential. Therefore, the objective of these studies were to determine the effectiveness of several heterologous hematopoietic cytokines and culture medium at maintaining PGC cells or the isolated porcine ICM in an undifferentiated state.

The inventors have developed a grading system to detect changes in the differentiation status of in vitro cultured PGC cells or the pICM. In the first study porcine ICMs (day 7) were isolated by immunosurgery and cultured 4 days in DMEM-based medium (D medium) or DMEM/Hams F-10 (1:1)-based medium (D/H medium) with or without human leukemia inhibitory factor (hLIF; 1000$\mu$/ml). For the second study pICMs were collected as above and cultured 4 days in one of six treatments: control medium, human leukemia inhibitory factor (hLIF; 1000$\mu$/ml), human interleukin-6 (hIL-6; 100 ng/ml), hIL-6+hIL-6 soluble receptor (hIL6+sR; 100 ng/ml+2.5 $\mu$g/ml), human oncostatin M (hOSM; 100 ng/ml), or rat ciliary neurotrophic factor (rCNTF; 100 ng/ml). All cytokines were prepared in Dulbecco's Modified Eagles Medium/Hams F-10 (1:1)-based medium. The colonies were photographed daily for morphological analysis.

pICMs were categorized into one of two types based on their morphological profile: type A, non-epithelial or type B, epithelial-like. The pICM differentiation was evaluated using standardized differentiation profiles. Each pICM series was graded on a scale of 1 (fully undifferentiated) to 5 (fully differentiated) for each time point. Differentiation was verified by alkaline phosphatase activity, cytokeratin staining, and scanning electron microscopy. In study 1, neither hLIF nor culture medium delayed differentiation of the developing pICM (p=0.08 and p=0.25, respectively). In study 2, differentiation was significantly lower on day two for rCNTF cultured pICMs versus hLIF cultured pICM (2.07±0.15 vs. 2.70±0.16; p<0.05). Furthermore, addition of rCNTF gave the lowest overall mean differentiation score (2.53±0.15). However, none of the cytokines significantly delayed differentiation over the control for the 4 day culture period (p>0.05). The grading system employed was thus an effective tool for detecting treatment effects on differentiation of the developing pICM.

Since these heterologous cytokines were unable to significantly inhibit differentiation, it is unlikely they will be beneficial towards isolating porcine ES cell lines under current conditions. Future work with homologous cytokines, protein half lives, and dose effects may prove more beneficial.

EXAMPLE 10

Development of an Animal Model for Atherosclerosis

Coronary heart disease is considered the major cause of death in the United States. From previous studies a strong correlation has been observed between elevated levels of low density lipoproteins (LDL) and the development of heart disease. Similarly, high levels of circulating HDL have been correlated with a decreased risk of developing atherosclerosis. Thus, environmental and genetic effects influencing the circulating levels of HDL and LDL appear to have an overall effect on the incidence of atherosclerosis. In general, any environmental or genetic effect influencing fat and cholesterol metabolism and transport would be expected to cause changes in the levels and proportions of circulating lipoprotein levels. As a result, it has been difficult to determine the association between a specific genetic or environmental component and its possible effect on the incidence of coronary heart disease.

Naturally occurring mutations in humans have demonstrated the existence of a genetic predisposition to some types of cardiovascular disease. For instance the apoE allele, E2, is strongly associated with type III hyperlipoproteinemia, a condition characterized by increased triglyceride and cholesterol levels, xanthomas, and atherosclerosis. Likewise, familial hypercholesterolemia has been associated with mutations in the LDL receptor gene. Unfortunately, not only are the identified mutations affecting atherosclerosis few in number, but when identified, the interrelationships between the genetic background and environmental influences are formidable to study. This is due in part to the difficulty in controlling environmental variables, difficulty in conducting some biochemical experimentation in humans, and the difficulty in conducting a comprehensive genetic analysis in humans (McCarrick et al., 1993).

Animal models of human diseases, on the other hand, permit careful control and manipulation of environmental factors, allow detailed biochemical and pathological studies at different stages of the disease process, and can be analyzed genetically more thoroughly than humans. The pig has been used extensively as a model of atherogenesis and thrombogenesis due to its similarities to the human in size, cardiovascular physiology, and omnivorous nature. Comprehensive studies have been performed on the effects of dietary fat and cholesterol on the incidence of heart disease in swine, and the results have shown the usefulness of the swine as a model for identifying factors affecting the development of atherosclerosis (Rapacz and Hasler-Rapacz, 1984).

Additionally, the pig provides a unique model for understanding thrombogenesis and the atherosclerotic process due to the feasibility of conducting detailed surgical and biochemical procedures. Thus, pigs have been used to study the correlation between the degree of thrombosis and the extent of vascular injury using carotid angioplasty, the role of shear stress in potentiation of thrombotic responses by use of extracorporeal perfusion system, and the role of Von Willenbrand factor in thrombogenesis and atherogenesis by analysis of cross-transplantation carotid thrombosis models (Fuster et al., 1991).

Rapacz, Hasler-Rapacz and collaborators have, during the past 22 years, established and characterized immunologically detectable genetic polymorphisms of lipoproteins in pigs, and more recently on the relationship of these polymorphisms to familial hypercholesterolemia associated with atherosclerosis. Applying immunogenetic technology to select breeders showing detectable qualitative and/or quantitative variations in cholesterol, lipoprotein, and apolipoproteins, they have established the immunogenetic project herd (IPH). Lines of swine in this herd show variations in blood plasma cholesterol from 60 to 400 mg/dl. One of the lines developed is characterized by inherited plasma hyper-LDL and hypercholesterolemia (IHLC; Rapacz and Hasler-Rapacz, 1984), referred to now as hypercholesterolemia or familial hyperlipidemia (FH; Hasler-Rapacz et al., 1995; Prescott et al., 1995; Rapacz and Hasler-Rapacz, 1989; Rapacz and Hasler-Rapacz, 1984; Rapacz et al., 1994).

Recently, with the utilization of gene targeting in ES cells it has been possible to generate mouse mutants lacking specific apolipoprotein genes (Piedrahita et al., 1992; Plump et al., 1992). Analysis of these animals has demonstrated the usefulness of the technique for generating animal models of atherosclerosis. One of the mutants generated by gene targeting in ES cells is an apoE-deficient mouse (Piedrahita et al., 1992; Plump et al., 1992; Zhang et al., 1992). ApoE-deficient mice have five times the normal plasma cholesterol levels and develop foam cell-rich depositions in their proximal aorta by 3 months of age. These spontaneous lesions can progress and cause severe coronary occlusion of the coronary artery ostium in older mice (Plump et al., 1992; Zhang et al., 1992). The mice, however, remain viable under normal dietary conditions for periods up to, and exceeding, one year. As a result of their viable phenotype and the progressive and spontaneous nature of their atherosclerotic process, they make useful animal models of atherogenesis and should be useful in helping elucidate some of the dietary and environmental factors affecting the incidence of the disease.

From the experience with the apoE mutant, it is expected that swine carrying deficient apoE genes will develop a similar phenotype to that observed in the apoE-deficient mouse; one that would not only complement the existing mouse mutant but that would, in itself, assist in elucidating some of the mechanisms of atherogenesis that are difficult to study in small animals or that are not evident in the mouse. Additionally, by working with the apoE locus, a simple locus known to be targetable at a high frequency, the resulting animal model will not only be a good model of premature atherosclerosis, but equally important that the chances of a successful inactivation are maximized by removing the variable of locus-specific effects on the frequency of homologous recombination. With the development of PGC-derived cell lines with pluripotential properties, coupled with the characterization of the porcine apoE gene, it is now possible to obtain apoE-deficient swine.

A. Characterization of the Developmental Competence of Transgenic PGC-Derived Cells For production of an apoE-deficient pig line, it is necessary that any genetic changes introduced into the PGC-derived cells be transmitted to the next generation. In spite of a recent report (Wilmut et al., 1997) of the ability of adult somatic cells in participating in the development of an adult organism, the present approach has several advantages over the use of somatic cells. Firstly, the PGCs have the potential to transmit the genetic modification to the next generation by both chimera formation and nuclear transfer. This is a very important advantage, as not only is the technique of nuclear transfer not well developed in pigs and there is the possibility that results may differ from those of sheep, but somatic cells cannot contribute to the formation of a chimeric animal. Secondly, somatic cells undergo homologous recombination at a lower rate than ES cells (Arbones et al., 1994, Thyagaraja et al., 1996). Assuming EG cells and ES cells have similar targeting frequencies, the cells of the present invention should target at a higher frequency than somatic cells. Thirdly, the efficiency of the nuclear transfer procedure, even in sheep, was higher with the early embryonic ectoderm than with the adult somatic cells. Thus, if nuclear transfer is successful, the efficiency should be higher using undifferentiated EG cells as the nuclear donor. Thus the PGC-derived cells have advantages over the somatic cell approach.

Therefore, to maximize the chances of germ line transmission in chimeras and to determine whether chimera formation can be bypassed, the degree of chimerism using tetraploid versus diploid embryos as host embryos, and determination of the totipotency of the PGC-derived cells by nuclear transfer are being studied.

1. Isolation of Primordial Germ Cells

Uteri of pregnant pigs are collected by hysterectomy, tissues are collected for DNA isolation for parental analysis, the fetuses are dissected, and germ cells are isolated as previously described (Labosky et al., 1994). For isolation of PGCs, the genital ridges of the developing fetus are removed and incubated in phosphate buffered saline (PBS) containing 10 mM EDTA for 20 min to dissociate PGCs from the gonadal ridge. Following incubation, the ridge is punctured and PGCs gently released into the medium. PGCs are collected in Dulbecco's modified Eagle's media:Ham's FIO, supplemented with 0.01 mM non-essential amino acids, 2 mM glutamine, 15% fetal bovine sera (selected batches, Summit Biotechnology), and 0.1 mM 2-mercapthoethanol (PEG medium). Following collection, cells are rinsed 3 times by centrifugation and resuspended in PEG medium preferably containing soluble recombinant human stem cell factor at 40 ng/ml, human basic fibroblast growth factor at 20 ng/ml, and human LIF at 20 ng/ml.

2. Culture of PGC Cells

The cell suspension at a density of 10,000 PGC/ml is plated onto a feeder layer of STO cells prepared as previously described (Piedrahita et al., 1990). Following 7–10 days of culture colonies with ES-like morphology are passaged to fresh feeder layers for establishment of cell lines. Resulting colonies are passaged by trypsinization to fresh feeder layers at 6–9 day intervals. State of differentiation of isolated cell lines is determined by morphology and expression of alkaline phosphatase, a marker of undifferentiated porcine ICMs (Moore and Piedrahita, 1996, Talbot et al., 1993).

3. Blastocyst Injection For Chimera Formation

The blastocyst injection technique is essentially as described herein. Briefly, porcine PGC-derived cells are dissociated into single cells by trypsinization and 12–15 transgenic cells injected into the blastocoele of blastocyst stage embryos. Following injection, 10–15 embryos are transferred per recipient pregnancies detected and periodically monitored by ultrasonography. Animals are allowed to carry the pregnancy to term and the degree of chimerism is determined by detection of the transgene by genomic southern analysis, as well as coat color and microsatellite markers.

4. Testing For Germ Line Transmission

All animals deemed to be chimeric are kept for germ line transmission testing. Briefly, the chimeric animals are mated to purebred Duroc animals and the PGC-derived genotype is identified by coat color and microsatellite markers unique to the PGC-derived cells. When transgenic PGCs are utilized, the offspring are analyzed for the presence of the transgene. When germ line transmission occurs, the offspring from this type of mating are purebred Durocs with their characteristic red pigmentation. When only the host embryo contribution is transmitted, the offspring are crossbred with their distinctive patchy appearance. At least 3 litters from each potential chimera are analyzed. If no germ line chimerism is detected, the chimeras are sacrificed and tissues obtained to determine the extent and distribution of the PGC-derived tissues.

5. Production of PGC-Blastocyst Chimeras Using Tetraploid Embryos

Tetraploid embryos are produced as described by Prather et al. (1996). Essentially, two cell embryos are collected at surgery from the oviduct of cross-bred (XB) gilts 52 hours after estrus detection and mating. Embryos are equilibrated in 0.3 M mannitol plus 5% HEPES buffered Tyrodes (HbT) and fused with a 5V/mm AC for 10 sec followed by 120 V/mm DC for 30 $\mu$sec. After fusion, embryos are placed in Whitten's media and incubated for 6 days at 39° C.

Transgenic and non-transgenic PGCs from purebred Durocs are isolated, cultured, and injected into the blastocoele of blastocyst stage embryos as described above. Tetraploid embryos prepared as previously described, in addition to diploid embryos collected at the 2-cell stage and cultured for 6 days, are used as host embryos. Following injection of 10–15 PGC-derived cells, embryos are transferred to synchronized recipients and allowed to develop to term. The degree and type of chimerism of the offspring and its placental tissues is determined by phenotypic markers, microsatellite markers, and karyotyping (XX;XY chimeras). For phenotypic markers, Duroc with their typical red pigmentation is used as the PGC-donor, and cross-bred (Yorkshire x Hampshire; XB) gilts are used as the host embryo donors. The XB animals used are mostly white with a few black spots. Although this system alone can not be used to identify weak chimeras due to the presence of spots in the cross-breeds, it is useful when combined with the other markers or when chimerism is as strong as is expected with the use of tetraploid embryos.

For microsatellite markers, several polymorphic markers are selected. DNA samples from potential chimeras, as well as the parents of the PGC donor and the host embryo, are analyzed by PCR™ as described previously (Piedrahita et al. 1997). The presence of the PGC-specific alleles in the offspring indicates participation of the PGCs in embryonic development. Animals deemed chimeric by coat color and microsatellite markers are kept for testing germ line transmission as described above.

A potential problem that can arise is the inability to establish pregnancies due to a high rate of early embryonic mortality after transfer. Gilts generally require 3–4 fetuses in the uterus for maintenance of pregnancy. When a high non-pregnancy rate is observed using the tetraploid embryos, additional non-manipulated embryos are introduced as "carriers". These extra embryos increase the number of piglets in the uterus so that, even if only one of the tetraploid embryos survive, it can be carried to term. By using XB as carrier embryos it is possible to identify the origin of the piglets as the XB component in the experimental group contains a tetraploid karyotype and should not be able to go to term without the injected PGCs. Thus any offspring with a Duroc-like phenotype originated from the injected cells. This phenotypic observation is confirmed by genetic analysis as described above.

6. Testing The Totipotency of PGC-Derived Cells by Nuclear Transfer

Nuclear transfer is performed using procedures previously described by Willadsen (Willadsen, 1989) with modifications by the inventors' laboratory (Westhusin et al., 1992) and others (Liu et al., 1995; Prather et al., 1989). Briefly oocytes are collected from pig ovaries obtained from the abattoir, or from females undergoing surgery for other purposes. The oocytes are matured in vitro for 20 hours at 39° C. in an atmosphere of 5% $CO_2$ and air as described by Kim et al. (1996). Maturation medium consists of BSA-free NCSU 23 (Petters and Wells, 1993) supplemented with 10% pig follicular fluid, 10 iu equine chorionic gonadotrophin per ml (Intervet America Inc., Millsboro, Del.) and 10 iu hCG per ml (Lypho Med Inc., Rosemont, Ill.).

Twenty hours after the initiation of maturation, oocytes are transferred into fresh wells (500 $\mu$l) of maturation medium without hormonal supplements and cultured for an additional 20 hour period. At the end of culture, oocytes are denuded by vortexing and a brief exposure to 0.05% pronase. Oocytes with visible polar bodies are selected and placed into a Petri dish containing TL Hepes medium (Bavister et al., 1993) supplemented with 5 $\mu$g/ml cytochalasin-B and 5 $\mu$g/ml Hoechst 33342 fluorochrome. The Petri dish containing the oocytes is placed on a heated microscope stage maintained at.37° C. and mounted on a Zeiss stereoscope equipped with Narshige micromanipulators. While the oocyte is held by suction on a holding pipette, a beveled enucleation pipette is used to remove the polar body and a small portion of the adjacent oocyte cytoplasm. Oocyte enucleation is confirmed by viewing the aspirated cytoplasm under ultraviolet irradiation.

After enucleation, PGCs, collected and genetically transformed as described above, are exposed briefly to 20 $\mu$g/ml phytohemagglutinin to increase their stickiness, placed into the perivitelline space of the enucleated oocytes, and transferred into the oocyte cytoplasm by electrofusion. Fusion parameters consist of a single DC pulse of 1.6 KV/cm for 50 $\mu$sec. Following electrofusion, the embryos are transferred into 500 $\mu$l of fresh NCSU medium and cultured for 6 days at 39° C. in an atmosphere of 5% $CO_2$ and air. Blastocysts are transferred into synchronized recipients for production of offspring. Pregnancy is detected and monitored by ultrasonography. When ultrasonography indicates a large amount of early embryonic losses accompanied by loss of pregnancy, carrier embryos are co-transferred with the nuclear transfer embryos as described above. The piglets originating from the nuclear transfer study are easily identified as they are 100% Durocs.

When the nuclei from the PGC-derived cells direct development to term, any genetic changes introduced into the PGCs are carried quickly to the next generation without the need for chimera generation and germ line testing, a procedure requiring two generations.

B. Optimization of Parameters for the Detection, Analysis, and Maintenance of Transgenic Porcine PGC-Derived Cells Two complementary approaches are taken. First, a promoter that not only maximizes the number of transgenic colonies detected but equally important that can serve as an indicator of the differentiated state of the cells is identified. Secondly, components of the gp130 pathway in pig PGCs are identified and their role in the maintenance and proliferation of cultured PGCs in the presence of homologous cytokines is analyzed.

1. Testing Different Promoters Controlling Expression of GFP

Using the humanized GFP gene under the control of the CMV promoter, very weak fluorescence in transgenic undifferentiated PGC-derived cells followed by an increase in intensity during in vitro differentiation was observed. Therefore, the fluorescent signal of the CMV-GFP combination with the HSV-tk-GFP (HSV; herpes simplex virus), pgk-GFP (pgk; phosphoglycerate kinase), and Oct-4-GFP is studied. The HSV-tk and pgk promoters have been used extensively for the modification of undifferentiated ES cells (Koller and Smithies, 1992; Smithies, 1991), while the oct-4 promoter is functional in ES and PGC cells (Yeom et al., 1996). Moreover, the oct-4 promoter is quickly silenced upon differentiation of early embryonic cells or ES cells (Yeom et al., 1996).

Both the HSV and the pgk promoters were cloned into pBS and the GFP placed downstream of the promoter. The GFP was subcloned into a modified pBS and the GFP excised by a PstI digest. The GFP was then cloned into plasmid pPGK containing the pgk promoter in pBS. pPGK was made by digesting the pgk-neo cassette with PstI. The two fragments were ligated together and orinetation checked by NotI digestion. Plasmid HSV-GFP was constructed by isolating the GFP/polyA fragment from CMV-GFP plasmid (obtained from Steve Lacey). The GFP was subcloned into a modified pBS and excised by EcoRV/SpeI digest. The pHSV promoter was obtained from a HSV-neo cassette by removing the neo by BamHI/BglII digest, and self-ligating the remaining plasmid. The pHSV was then digested with SacI, blunt ended by Klenow fill-in, and digested by SpeI. The two fragments were ligated together to form HSV-GFP. Both the promoter and the structural gene are in the correct 5' to 3' orientation.

For the Oct-4 promoter a mouse genomic library was screened with a PCR™-generated Oct-4 probe and a positive clone mapped by restriction digestion and Southern analysis. The inventors have isolated and modified a 3 kb fragment containing the promoter region responsible for expression in germ cells and early embryonic cells (Yeom et al., 1996). The modification entailed introduction of an oligonucleotide containing a unique restriction site downstream of the start site. A unique MluI site was introduced immediatly adjacent to the initiaton codon of Oct-4 by in vitro mutagenesis. A multiframe cloning site (MCS) which provides three possible open reading frames (ORF), was also introduced into the MluI site. GFP is introduced into one of the cloning sites for in-frame fusion to Oct-4.

DNA from each of the above constructs is linearized and 5 nM introduced into the same number of PGCs by electroporation as described above. Resulting colonies are analyzed 7–10 days after electroporation and the number of transgenic colonies/total number of AP-positive colonies is determined. Intensity of signal is determined by digitizing 10 randomly selected colonies with the aid of an Olympus Vanox research microscope equipped for DIC and epifluorescent visualization. Gray-scale images are acquired with an integrated Optronics DEI-750 high resolution, low-light, 3-chip camera coupled to a Neotech 24-bit color digitizing card onboard a PowerMacintosh 8100 work station. Microdensitometric measurements and analysis are performed using the "NIH-image" or "Ultimate Pro" (Graftek Corp.) software. Parametric statistics to test differences in signal intensity are performed using the (Abacus) statistical package.

2. Role of gp130 Pathway and Homologous Cytokines on the Proliferation and Maintenance of PGC-Derived Cells In order to increase the efficiency of passage of porcine PGC-derived cells, the effect of activation of the gp130 pathway in pigs on the proliferation and survival of PGC-derived cells is analyzed.

a. Elucidation of the gp130 Pathway in Pigs

In mice, multiple hematopoietic cytokines (CNTF, OSM, IL-11, IL-6+IL-6 sR, and LIF) can inhibit the differentiation of ES cells by activating the gp130 pathway. Similar results have been reported with freshly isolated PGCs as well as EG cells lines. This family of molecules can act through specific receptors such as the LIF receptor (LIFR), the CNTF receptor (CNTFR), or the soluble IL-6 receptor (IL-6sR) and induce homodimerization or heterodimerization with gp130 (Yoshida et al., 1994). Furthermore, it has been shown that IL-6 and CNTF actually assemble into hexameric complexes, each containing two cytokine molecules, two α receptors, one gp130 and one LIFR molecule, or two gp130 molecules for CNTF and IL-6, respectively (Deserio et al., 1995; Ward et al., 1995). To date, however, the presence of these receptors or their message has not been studied in any species but mice.

In order to increase the efficiency of passage of cells in the undifferentiated phenotype, nested RT-PCR™ is utilized to detect the message for CNTFR, LIFR, IL-6 sR, and gp130. This procedure has been successfully used by Sharkey et al. (1995) for the elucidation of the gp130 pathway components in human embryos. A modification of this technique has even been shown to successfully amplify message obtained from a single mouse blastomere (Collins and Fleming, 1995).

Briefly, primary colonies of PGC-derived cells are gently trypsinized in 0.05% trypsin for 10 min to dissociate the colonies from the feeder layer. Colonies are individually picked with a mouth operated pipette, all STOs removed, and total RNA harvested using the Tri-reagent (MRC, Cincinnati, Ohio), a commercially available product similar to the acid phenol method previously described (Chomczynski, 1993; Chomczynski and Sacchi, 1987). Total RNA (1 μg) is reverse transcribed with oligo-dT primers at 42° C. for 1 hour with AMV reverse transcriptase. One-tenth of the reaction is used as cDNA template for nested PCR™ amplification as previously described by Sharkey et al. (1995). The presence of receptors for one or more of these molecules suggests that the homologous cytokines activate the porcine gp130 pathway and assist in the long term maintenance of the PGC-derived cell lines. The RT PCR™ primers for preparation of probes and nested PCR™ primers that are used to detect cytokine receptor expression are listed below in Tables 16 and 17.

TABLE 16

RT-PCR ™ Primers

| Gene | Primers | SEQ ID NO | Location | Tm (° C.) | Prod. Size |
|---|---|---|---|---|---|
| CNTF5' | GGATGGCTTTCGCAGAGCAAACAC | 19 | 76–99 | | |
| CNTF3' | GCTGGTAGGCAAAGGCAGAAACTT | 20 | 444–420 | 61.2 | 378 |
| CNTFR exon9 5' | CGACCAGCACCACCAGCTC | 21 | 557–575 | | |
| CNTFR exon9 3' | CCAGGATGATGGGACGCTG | 22 | 676–657 | 55.5 | 120 |
| LIFR5' | CCAGTGGCAGTGGCTGTCATTGTT | 23 | 2705–2728 | | |
| LIFR3' | CCTGAGGTCTGTAACCCGCAGTTTT | 24 | 3272–3248 | 60.6 | 568 |
| GP1305' | CCAAAGGACCTACTGTTCGGACAA | 25 | 1814–1837 | | |
| GP1303' | CAGGACCGACTATGGCTTCAA | 26 | 2128–2108 | 55.3 | 315 |
| OSM5' | TGCTCTGTGGATGAGAGGAACCATC | 27 | 627–651 | | |
| OSM3' | TTGCACCACCTGTCCTGATTTACAG | 28 | 1334–1310 | 59.0 | 708 |
| IL-65' | ATTCGGTACATCCTCGACGGCATC | 29 | 232–255 | | |
| IL-63' | TCGTCAGCAGGCTGGCATTTGT | 30 | 595–574 | 61.4 | 364 |
| IL-6R5' | ATCGGGCTGAACGGTCAAAG | 31 | 1207–1226 | | |
| IL-6R3' | AGCAACCAGGAATGTGGGCAGT | 32 | 1547–1526 | 56.4 | 341 |
| OCT-4 exon1 5' | TCAAGGCTAGAGGGTGGGATTG | 33 | 124–145 | | |
| OCT-4 exon1 3' | TCCAACCTGAGGTCCACAGTATG | 34 | 449–427 | 55.0 | 326 |
| APOE5' | CAGTCCCTGTCTGACCAAGTGC | 35 | 221–242 | | |
| APOE3' | TGCGGTAGAGCACCAAGCGG | 36 | 458–439 | 55.5 | 238 |

TABLE 17

Nested RT-PCR ™ Primers

| Gene | Primers | SEQ ID NO | Tm (° C.) | Prod. Size |
|---|---|---|---|---|
| β-Actin5'ext | GGGACATCAAGGAGAAGCTGTG | 37 | | |
| β-Actin3'ext | ATGGAGTTGAAGGTAGTTTCGTGG | 38 | 53 | 215 |
| β-Actin5'int | TGGACTTCGAGCAGAGATGG | 39 | | |
| β-Actin3'int | AGGATTCCATGCCCAGGAAG | 40 | 50 | 151 |
| GP1305'ext | CCAAAGGACCTACTGTTCGGACAA | 41 | | |
| GP1303'ext | CAGGACCGACTATGGCTTCAA | 42 | 52 | 315 |
| GP1305'int | TCTTAGAGTGGGACCAACTTCCTG | 43 | | |
| GP1303'int | CACCTTCATCTGTGTATGCTGCC | 44 | 52 | 192 |
| LIFR5'ext | TGGCAGTGGCTGTCATTGTTGG | 45 | | |
| LIFR3'ext | GGAGGTGCATCTGTGGCTTATAGC | 46 | 57 | 490 |

TABLE 17-continued

Nested RT-PCR ™ Primers

| Gene | Primers | SEQ ID NO | Tm (° C.) | Prod. Size |
|---|---|---|---|---|
| LIFR5'int | GCTTGTGAGGGAAGCAGTGCTC | 47 | | |
| LIFR3'int | GGACGCTCAGCTACTGGGGA | 48 | 55 | 137 | b. Expression of Homologous Cytokines

Artificial genes from pLIF and pCNTF for expression in yeast have been prepared. The biological activity of these proteins are tested essentially as described by Koshimizu et al. (1996). Briefly, freshly isolated porcine PGCs are plated on inactivated feeder layers in the presence of recombinant pLIF, and/or pCNTF, and/or pOSM. Treatments are done in triplicate. The choice of molecule depends on the RT-PCR™ results. Seven to 10 days after plating, the number of AP positive colonies is recorded in each treatment. As an increase in colony number can be due to increased proliferation or increased survival of the cells, both proliferation and apoptosis are analyzed.

The rate of proliferation is determined by 5-bromo-2'-deoxy-uridine incorporation using the 5-Bromo-2'-deoxy-uridine Labeling and Detection kit (Boehringer-Mannheim) following the manufacturer's recommendations. The effect on apoptosis is determined by two independent methods: the use of ApoAlert annexing kit (Clontech) based on the detection of phosphatidylserine, an indicator of the early stages of apoptosis, on the cell surface; and the use of TUNEL (TdT-mediated dUTP-x nick end labeling) staining, used to detect DNA fragmentation typical of later stages of apoptosis. All three methods have the advantage of being capable of quantitative analysis. Quantitation is based on either a calorimetric assay or by flow cytometry. For statistical analysis, each assay is done in triplicate and differences between samples evaluated by Student's t-test.

Results from these studies help increase the number of PGC-derived colonies that are obtained from a set number of PGCs as well as assist in the long term maintenance of the cell lines. Both factors facilitate the ability to inactivate the apoE gene by homologous recombination and to transfer that modification to the germ line by either chimera formation or nuclear transfer.

C. Demonstration of PGC-Derived Cells to Undergo Homologous Recombination

To demonstrate the ability of porcine PGCs to undergo homologous recombination, the GFP protein is targeted to the Oct-4 gene. The pattern of expression of Oct-4 is tightly restricted to early embryonic cells and germ cell (Yeom et al., 1996). In mice, Oct-4 is expressed in ES cells and EG cells (Yeom et al., 1996), as well as PGCs. Moreover, the gene is rapidly inactivated during differentiation of the ES cells.

To maximize the detectable targeted events, a gene trap approach is utilized. Briefly, the trap consists of a splice acceptor (SA), an internal ribosomal entry site (IRES), and a promoterless GFP with its own polyA signal. Correct insertion results in a exon 1-IRES-GFP dicistronic message thus placing the GFP under the control of the oct-4 promoter. Mountfourt et al. (1994) were able to target the Oct-4 gene in mouse ES cells with a promoterless β-galactosidase-IRES-neomicin cassette (IRES; internal ribosomal entry site). When colonies surviving G418 were analyzed, over 80% of them had undergone homologous recombination.

Thus, using a gene trap approach and a locus active at the ES, EG, and PGCs stages of development leads to enrichment for homologous recombinants. The GFP gene is used as the selectable marker, as preliminary results have indicated the inability of the PGC-derived cells to develop under G418 selection. The constructs consist of 4 kb of homology in the 5' region and 4 kb of homology in the 3' region.

As determined previously in mice, the frequency of homologous recombination is affected by the degree of homology between the target DNA and the endogenous gene. In mice this has not been a major problem as "isogenic" DNA, obtained from the same cell lines as the one to be modified can be easily obtained. In contrast, in swine there are no isogenic strains available. Thus the locus being targeted is likely to differ from the genomic clones available, as the inventors have shown for the apoE locus. The level of heterogeneity at any locus being targeted may be reduced by: a) The use of the NIH miniature pig. This line of pigs was originally developed from 2 founders. Thus a maximum of 4 alleles for each locus exists in the population: b) The use of a single boar to generate all of the PGCs being used for the targeting studies. If the genomic clone is isolated from the boar and used to develop a targeting construct, in at least 50% of the cells there will be a "isogenic" allele to the one present in the targeting construct: c) As it is very difficult to isolate genomic clones repeatedly depending on the boar/strain used, long range PCR™ may be used to develop the targeting constructs. Briefly, DNA isolated from the strain/boar of interest will be amplified using long range PCR™ conditions and primer sets designed using sequencing data generated by the inventors or available in GenBank. In the case of the Oct-4 and apoE, the inventors have isolated and sequenced genomic clones containing at least 8 kb of the gene in addition to flanking regions. This sequence information is used for designing and testing PCR™ primers for the long-range amplification.

Long-range PCR™ has been used previously for obtaining isogenic DNA for the generation of targeting constructs (Randolph et al., 1996). The technology is based on the combination of DNA polymerases and can produce amplicons as large as 35 kb (Barnes et al., 1994). More important than the length of homology is the remarkable fidelity of the enzymes with error rates as low as 1 bp in 100 kb (Barnes et al., 1994). Thus a conservative error rate would be 1 bp mismatch every 5–10 kb. Such a low level of mismatch should not affect the targeting frequency as has been demonstrated by Randolph et al. (1996) who indicated that the targeting frequency did not differ between constructs made the conventional way (cloning of the genomic sequence) versus targeting vectors prepared by long-range PCRTM.

PCR™ primers are made to selected regions, and the 5' and 3' homology regions are amplified separately and introduced into a cloning vector containing the promoterless Oct-4 gene. As described above, under ideal amplification conditions it is possible to amplify regions as large as 35 kb with high fidelity. In the present case regions of approximately 4 kb are amplified for each arm of homology. Thus, this is well within the capabilities of the long-range procedure.

Once the Oct-4 construct is completed, it is introduced into both Duroc and NIH miniature porcine PGCs as previously described. Following plating and culture, fluorescing cells are identified and expanded for PCR™ and genomic analysis. Using the gene trap approach, the majority of random insertion events result in lack of expression of GFP. Thus, the majority of fluorescent cells are targeted. As random insertions cannot be identified, the targeting efficiency is calculated as number of targeted colonies over total number of colonies.

Results from this study assist in designing the apoE knockout studies as it provides an indication of the ability of porcine PGC-derived cells to undergo homologous recombination and the relative efficiency of the procedure. Other genes expressed in PGCs that are used in the gene trap approach include β2-microglobulin, Rex-1, GAPDH, and actin.

D. Inactivation of the Apolipoprotein E Gene by Homologous Recombination

Inactivation of the apoE gene is accomplished by a homologous recombination event between the endogenous gene and exogenous DNA introduced into PGC-derived cells. The use of isogenic DNA targeting constructs by PCR™-based technologies, and enrichment for homologous events by polyA trapping maximize the ability to detect a targeting event.

Unlike the oct-4 gene that is highly expressed in ES and EG cells, apoE expression is undetectable in mouse or porcine undifferentiated PGC-derived cells. As a result it is possible to utilize a gene trap approach as with the Oct-4 gene. A less effective but still useful enrichment approach has been used by Danoff et al. (Danoff et al., 1997), for targeting the RANTES locus. Briefly, the targeting construct contains the regions of homology to the target sequence, a polyA-minus selectable marker under the control of its own promoter, and a diphtheria toxin (DT) under control of the pgk promoter attached to the 3' end of the construct. The selectable marker is either not expressed or inefficiently expressed if the targeting construct inserts randomly. Homologous recombination events, however, result in the selectable marker being able to utilize the target gene's polyA signal.

Thus, for the inactivation of the apoE gene a polyA trap approach, combined with screening by PCR and/or RT-PCR is used. Briefly, the trap consists of a polyA minus GFP under the control of the oct-4 promoter inserted in the partially deleted apoE exon 2. Additionally a TAG stop signal is introduced to make sure the remaining apoE message is not translated. Correct insertion of the targeting plasmid results in a bicistronic message containing the GFP, a mutated apoE and the apoE poly tail. Random integration events are detected with lower efficiency due to inappropriate processing of the GFP message as a result of the lack of a polyA signal. Targeted events are confirmed by PCR and/or RT-PCR.

This provides not only a polyA for proper processing of the message and maximal activity of the selectable marker, but in addition facilitates screening by allowing the use of RT-PCR™ to differentiate between targeted and non-targeted events. Additionally, the DT tail selects against random integration events as these events should incorporate the DT gene while homologous recombination events should delete the tail and lose the DT gene. This system is analogous to the TK negative selection system previously used to target the mouse apoE gene (Piedrahita et al., 1992). The DT gene is used in this case as it does not require addition of ganciclovir to the media. The DT gene has been used previously in this manner to target the mouse genome and obtain germ line transmission (McCarrick et al., 1993).

Inactivation of the apoe gene is accomplished by a homologous recombination event between the endogenous gene and exogenous DNA introduced into Duroc and NIH miniature porcine PGCs. The targeting event involves the replacement of the endogenous intact apoE with a copy of the same gene inactivated by insertion of the GFP gene within its coding sequence. The targeting plasmid is introduced by electroporation into PGCs and the cells are cultured for 7–12 days. Fluorescent colonies are expanded and their DNA is analyzed by RT-PCR™ for the presence of the diagnostic fragment indicative of homologous recombinants. In addition, DNA is isolated from PCR™-positive clones, digested with HindIII and/or EcoRI and fragments separated by agarose gel electrophoresis. Following separation, the DNA fragments are transferred to nylon filters and the filters probed for the apoE gene. Presence of the diagnostic fragment indicates targeting of the apoe gene.

PGC-derived cells containing a disrupted apoE allele are used to produce offspring by either chimera formation or by nuclear transfer. All transgenic offspring are allowed to reach maturity and tested for germ line transmission of the disrupted apoE allele by breeding to a test animal and analyzing the progeny for the presence of the transgene. This results not only in the development of apoE deficient pigs that can serve as valuable models of atherosclerosis, but equally important, it demonstrates the feasibility of doing gene targeting in swine. This leads to the utilization of this technology in many areas of biomedical research such as xenotransplantation and the development of new gene therapies.

EXAMPLE 11

Totipotency of Bovine PGC-Derived Cells

A. Embryo Production In vitro and In vivo

Cattle are maintained on pasture with supplemental feed provided to maintain good body condition. To obtain in vivo produced embryos for use as nuclei donors, cows are superovulated with a 4 day regimen of intramuscular injections of follicle-stimulating hormone twice a day (FSH, Super Ov). Total FSH administered varies from 28 mg to 37 mg, depending on the cow. Cows are administered 25 mg of prostaglandin (Lutalyse, Upjohn Co., Kalamazoo, Mich.) with the fifth and sixth injection of FSH-P to synchronize estrus. The cows are artificially inseminated and the embryos are collected non-surgically on day 5–7 after estrus.

For embryo production in vitro, bovine ovaries are collected from a local abattoir and transported to the laboratory, where immature oocytes are aspirated from follicles. Follicular aspirates are examined under a stereo microscope and the oocytes recovered and placed into fresh Tyrodes-Hepes (TL Hepes) medium (Bavister et al., 1993). Procedures for in vitro oocyte maturation are essentially as described by Crister et al. (1986). Once the oocytes are isolated, they are placed into 1 ml tissue culture wells containing 250 $\mu$l of maturation medium composed of TCM 199 supplemented with 10% fetal calf serum, 5 $\mu$g/ml FSH, 5 $\mu$g/ml LH (NOBL Inc., Sioux Center, Iowa) and 1% penicillin streptomycin. The oocytes are placed in an incubator at 39° C. in an atmosphere of 5% $CO_2$ and air for 20 hours. For in vitro fertilization, frozen semen is thawed, separated by centrifugation in a discontinuous percoll gradient (45%:95%) and used to inseminate mature oocytes at a concentration of 1.0×10⁶ cells per ml (Parrish et al., 1986). After fertilization, the embryos are cultured in vitro using a BRL cell co-culture system as described by Voelkel and Hu (1992) at 37° C. in an atmosphere of 5% $CO_2$ and air.

B. Nuclear Transplantation

Nuclear transplantation is performed using procedures previously described by Willadsen (1989) with modifications by Barnes et al. (1993b), Westhusin et al. (1992) and Lavoir et al. (1997). Briefly 20 hours after the initiation of maturation, oocytes are vortexed to remove the cumulus cells. Oocytes with visible polar bodies are selected and placed into a Petri dish containing TL Hepes medium supplemented with 5 µg/ml cytochalasin-B and 5 µg/ml Hoechst 33342 fluorochrome. The Petri dish containing the oocytes is placed on a heated microscope stage maintained at 37° C. and mounted on a Zeiss stereoscope equipped with Narshige micromanipulators. While the oocyte is held by suction on a holding pipette, a beveled enucleation pipette is used to remove the polar body and a small portion of the adjacent oocyte cytoplasm. Oocyte enucleation is confirmed by viewing the aspirated cytoplasm under ultraviolet irradiation.

After enucleation, oocytes are maintained in TL Hepes medium at 37° C. At approximately 24 hours post maturation, the enucleated oocytes are activated by a 4 minute incubation in 5 µM inomycin followed by a 3 hour culture period in 1.9 mM dimethylaminopurine (DMAP) (Lavoir et al., 1997). Alternatively, some oocytes are returned to culture at 37° C. following enucleation, then activated and utilized for nuclear transfer the following day (38–42 hours after initiation of maturation). Approximately 4 hours after activation, PGCs, collected and genetically transformed as described above, are exposed briefly to 20 µg/ml phytohemagglutinin to increase their stickiness, placed into the perivitelline space of the enucleated oocytes, and transferred into the oocyte cytoplasm by electrofusion (Westhusin et al., 1992). In some cases 5–6 day old embryos collected from cows or produced in vitro are used as nuclei donors to serve as controls. Following electrofusion, the embryos are cultured in vitro as described above. Blastocysts are transferred into synchronized recipient cows for production of offspring. Pregnancy is detected and monitored by ultrasonography.

C. Blastocyst Injection for Chimera Formation

The blastocyst injection technique is essentially as described herein. Briefly, transgenic bovine PGC derived cells are dissociated into single cells by trypsinization and 12–15 cells injected into the blastocoele of blastocyst stage embryos collected from superovulated cows. Following injection, two embryos are transferred per recipient and the pregnancy detected and periodically monitored by ultrasonography. Animals are allowed to carry the pregnancy to term and the degree of chimerism is determined by detection of the transgene by genomic Southerns, as well as microsatellite markers. Microsatellite markers are selected and detected under standard conditions (Piedrahita et al., 1997).

D. Fusion Parameters for Nuclear Transplantation

Lavoir et al. (1997) reported that the percentage of donor-cell cytoplast pairs in which fusion occurred was only 45% when fetal oogonia were used compared to 91% with blastomeres. This represents a decrease in efficiency approaching 50% due simply to the lack of optimum methods for electrofusion of enucleated oocytes with PGCs. Thus different fusion parameters for transferring PGCs into enucleated oocytes are used. Unfertilized oocytes are enucleated and activated as described above. Following insertion of PGCs into the perivitelline space, the cell-cytoplast pairs are assigned to 1 of 8 treatments in a 2×2×2 factorial study. Fusion parameters consist of either 1 or 3 pulses, at 1.5 or 2.0 kV/cm, for either 25 or 50 µsec, and are chosen based on the inventors' previous studies involving the use of ICM cells which are similar in size to PGCs. Following fusion treatment, the nuclear transfer embryos are cultured in vitro as described above. After 7 days, the embryos are removed from culture and evaluated for development to the blastocyst stage.

E. Effect of Age and Sex of Fetus on Totipotency of PGC-Derived Cells

As embryonic/fetal development proceeds, germ cells become more differentiated and diverge depending on their sex chromosome constitution with oogonia entering the meiotic phase at 65–80 days of gestation (Moens et al., 1996). While the stages of PGCs are prior to initiation of oogonial meiosis, some genetic and phenotypic divergence may occur prior to day 65. This may influence the ability of the PGCs to direct normal embryonic development following nuclear transplantation or chimera formation. To study this effect, PGCs are collected, transfected, and cultured as described above, from fetuses at 3 different ages of gestation as defined by crown-rump length; group A, 2.0–3.0 cm (35–44 d), group B, 3.1–5.3 cm (45–54 d), and group C, 5.4–7.5 cm (55–65 d). Each fetus is processed separately and the remaining tissues are used for DNA analysis to determine the sex of the fetus by PCR™. Procedures for nuclear transplantation are described above.

The percentage of nuclear transplant embryos developing to the blastocyst stage in each treatment group is recorded and data is analyzed by non-parametric statistics. In addition, blastocysts are transferred into synchronized recipient cows to compare pregnancy rates and the number of live births. Animals are allowed to carry the pregnancy to term and the presence of the transgene is determined by genomic Southerns in blood, skin, and muscle samples.

F. Effect of Passage Number on Totipotency of PGC-Derived Cells

Previous work with ICM-derived and PGC-derived cell lines indicate that cell morphology and/or marker expression change as culture time is extended and passage number increases (Piedrahita et al., 1990). These changes may effect the developmental potential of the cell lines following nuclear transplantation or injection into blastocysts. To study this effect, PGCs are collected, transfected, cultured and passaged as previously described. The age and sex of the fetal donors are selected as described above. Fresh cells, in addition to cells collected from the 5th, 10th and 20th passage, are utilized for nuclear transplantation and blastocyst injection. Procedures for nuclear transplantation, blastocyst injection, embryo culture and embryo transfer for the production of live calves, data collection, and data analysis, are as described above. Contribution of the cell line to the offspring is determined as previously described.

\* . . . \* . . . \*

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,430,434
U.S. Pat. No. 4,559,302
U.S. Pat. No. 4,727,028
U.S. Pat. No. 4,960,704
U.S. Pat. No. 5,354,855
EPO 0273085
Abraham, J. A. et al., *EMBO J* 5:2523–2528, 1986.
Abremski, Frommer, Wierzbicki, Hoess, "Properties of a mutant Cre protein that alters the topological linkage of recombinant products," *J. Mol. Biol.,* 202:59–66, 1988.
Abuin and Bradley, "Recycling selectable markers in mouse embryonic stem cells," *Mol. Cell. Biol.,* 16:1851–1856, 1996.
Adra et al., "Cloning and expression of the mouse pgk-1 gene and the nucleotide sequence of its promoter", *Gene,* 60:65:74, 1987.
Albert, Dale, Lee, Ow, *Plant J.,* 7:649–659, 1995.
Alt, Kellems, Bertino and Schimnke, *J. Biol. Chem.,* 253:1357, 1978.
Anderson, G. B., Choi, S. J. and BonDurant, R. H., "Survival of porcine inner cell masses in culture and after injection into blastocysts," *Theriogenology* 42:204–212, 1994.
Andrews, Proteau, Beatty, Sadowski, "The FLP recombinase of the 2 micron circle DNA of yeast: interaction wit its target sequences," *Cell,* 40:795–803, 1985.
Applewhite and Westhusin, "In vitro culture of bovine embryos in MBMOC and CR2", *Theriogenology,* 43:160–167, 1995.
Araki, Araki, Miyazaki, Vassali, "Site-specific recombination of a transgene in fertilized eggs by transient expression of cre recombinase," *Proc. Nat. Acad. Sci. USA,* 92:160–164, 1995.
Araki, Araki, Yamamura, *Nucl. Acids Res.,* 25:868–872, 1997.
Arbones et al., "Gene targeting in normal somatic cells: inactivation of the interferon-receptor in myoblasts," *Nature Genetics,* 6:90–97, 1994.
Archibald, McClenaghan, Hornsey, Simons, Clark, "Highlevel expression of biologically active human $\alpha_1$-antitrypsin in the milk of transgenic mice," *Proc. Natl. Acad Sci.,* 87:5178–5182, 1990.
Atamas and White, "Screening for homologous recombination in ES cells using RT-PCR," *BioTechniques,* 22:22–26, 1997.
Austin, Ziese, Sternberg, "A novel role for site-specific recombination in maintenance of bacterial replicons," *Cell,* 25:729–736, 1981.
Baichwal et al., "Vectors for gene transfer derived from animal DNA viruses: Transient and stable expression of transferred genes," In: Gene transfer, Kucherlapati R, ed., New York: Plenum Press, pp. 117–148, 1986.
Barbin, Manthorpe, Varon, "Purification of the chick eye ciliary neurotrophic factor," *Journal of Neurochemistry,* 43:1468–1478, 1984.
Barnes et al., "Embryo cloning in cattle: The use of in vitro matured oocytes", *J. Reprod. Fert.,* 97:317–323, 1993a.
Barnes et al., "Influences of recipient oocyte cell cycle stage on DNA synthesis, nuclear envelope breakdown, chromosome constitution, and development in nuclear transplant bovine embryos", *Mol. Reprod. Dev.,* 36:33–39, 1993b.
Barnes, "PCR amplification of up to 35-kb DNA with high fidelity and high yield from bacteriophage templates," *Proc. Natl. Acad. Sci. USA,* 91:2216–2220, 1994.
Barnes, Robl, First, "Nuclear transplantation in mouse embryos: Assessment of nuclear function," *Biol. Reprod.,* 36:1267–1272, 1987.
Basha, et al., *Biol Reprod.,* 20:431, 1979.
Baubonis and Sauer, *Nucl. Acids Res.,* 9:2025–2029, 1993.
Baumbach, et al., *J. Biol. Chem.,* 261:12869, 1986.
Baumbach, et al., *Proc. Natl. Acad. Sci. U.S.A.,* 81:2985, 1984.
Bavister et al., "Development of preimplantation embryos of the golden hamster in a defined culture medium", *Biol. Reprod.,* 28:237–242, 1993.
Bazer and Roberts, *J. Exp. Zool.,* 228:373, 1983.
Bazer et al., *J. Anim. Sci.,* 41:1112, 1975.
Behboodi et al., "Birth of large calves that developed from in vitro-derived bovine embryos", *Theriogenology,* 44:227, 1995.
Benchokroun, Y., Couprie, J. and Larsen, A. K., "Aurintricarboxylic acid, a putative inhibitor of apoptosis, is a potent inhibitor of DNA topoisomerase II in vitro and in Chinese hamster fibrosarcoma cells," *Biochem. Pharmacol.* 49:305–313, 1995.
Bennetzen and Hall, "Codon selection in yeast," *J. Biol. Chem.* 257:3026–3031, 1982.
Benoist et al., "The ovalbumin gene-sequence of putative control regions," *Nucl. Acid Res.,.* 8:127–140, 1980.
Berg, H., "Biological implications of electric field effects. V: Fusion of blastomeres and blastocysts of mouse embryos," *Bioelectrochem. Bioenerg.* 9:223, 1982.
Berzal-Herranz et al., *Genes and Devel.,* 6:129–134, 1992.
Bessho, R. et al., "Pyrrolidine dithiocarbamate, a potent inhibitor of nuclear factor kappa B (NF-kappa B) activation, prevents apoptosis in human promyelocytic leukemia HL-60 cells and thymocytes," *Biochem. Pharmacol.* 48:1883–1889, 1994.
Blattler, T. et al., "PrP-expressing tissue required for transfer of scrapie infectivity from spleen to brain," *Nature* 389:69–73, 1997.
Boggs et al., "Efficient transformation and frequent single site, single copy insertion of DNA can be obtained in mouse erythroleukemia cells transformed by electroporation", *Exp. Hematol.,* 14:988–994, 1986.
Bondioli et al., "Production of identical bovine offspring by nuclear transfer", *Theriogenology,* 33:165, 1990.
Bondioli et al., In: *Transgenic Animals,* First and Haseltine (eds.), Butterwort-Heinnemann, M A, pp. 265–273, 1991.
Bondioli, "Commercial cloning of cattle by nuclear transfer", In: *Symposium on Cloning Mammals by Nuclear Transplantation,* Seidel (ed), pp. 35–38, 1994.
Borner, M. M., Myers, C. E., Sartor, O., Sei, Y., Toko, T., Trepel, J. B. and Schneider, E., "Drug-induced apoptosis is not necessarily dependent on macromolecular synthesis or proliferation in the p53-negative human prostate cancer cell line PC-3,"*Cancer Res.* 55:2122–2128, 1995.
Bradley and Liu, *Nature Genetics,* 14:121–123, 1996.
Bradley, A., Evans, M., Kaufman, M. H. and Robertson, E., "Formation of germline chimaeras from embryo-derived teratocarcinoma cell lines," *Nature* 309:255–256, 1984.
Brandner, S. et al., "Normal host prion protein necessary for scrapie-induced neurotoxicity," *Nature* 379:339–343, 1996.

Breathnach and Chambon, "Organization and expression of eukaryotic split genes coding for proteins," *Ann. Rev. Biochem.,* 50:349–383, 1981.

Breathnach et al., "Ovalbumin gene: evidence for a leader sequence in mRNA and DNA sequences at the exon-intron boundaries," *Proc. Nat'l. Acad. Sci. USA,* 75:4853–4857, 1978.

Brem, "Inheritance and tissue-specific expression of transgenes in rabbits and pigs," *Mol. Reprod. Devel.,* 36:242–244, 1993.

Breslow, "Mouse models of atherosclerosis," *Science,* 272 (5262):685–888, 1996.

Brinster, "Cultivation of the mammalian egg", *In: Growth, nutrition and metabolism of cells in culture,* Vol. 11, Rothblat and Cristofalo (eds.), Academic Press, Inc., New York, pp. 251, 1972.

Brinster, Braun, Lo, Avarbock, Oran, Palmiter, *Proc. Natl. Acad. Sci. USA,* 86:7087–7091, 1989.

Bruno, S., Del Bino, G., Lassota, P., Giaretti, W. and Darzynkiewicz, Z., "Inhibitors of proteases prevent endonucleolysis accompanying apoptotic death of HL-60 leukemic cells and normal thymocytes," *Leukemia* 6:1113–1120, 1992.

Brzozowska et al., "Isolation, Sequencing, and expression analysis of a bovine apolipoprotein E (APOE) cDNA and chromosomal localization of the ApoE locus," *Mammalian Genome,* 4:53–57, 1993b.

Brzozowska et al., "The sequence of porcine apolipoprotein E (APOE) cDNA," *DNA Sequence,* 4:207–210, 1993.

Bueler, H. et al., "Normal development and behaviour of mice lacking the neuronal cell-surface PrP protein," *Nature* 356:577–582, 1992.

Bueler, H. et al., "Mice deviod of PrP are resistant to scrapie," *Cell* 73:1339–1347, 1993.

Buhi et al., *J. Biol. Chem.,* 257:1712, 1982.

Buhler, Bruyere, Went, Stranzinger, Burki, "Rabbit β-casein promoter directs secretion of human interleukin-2 into the milk of transgenic rabbis," *Biotechnology,* 8:140–143, 1989.

Bullock, Damak, Jay, Su, Barrell, "Improved wool production from transgenic sheep expressing insulin-like growth factor I driven by a keratin promoter. *In: Biotechnology's role in the genetic improvement of farm animals,*" Miller RH (ed.), Beltsville Symposium XX, P8(abstract), 1995.

Cain, K., Inayat-Hussain, S. H., Kokileva, L. and Cohen, G. M., "DNA cleavage in rat liver nuclei activated by $Mg^+$ or $Ca^{2+}+Mg^{2+}$ is inhibited by a variety of structurally unrelated inhibitors," *Biochem. Cell. Biol.* 72:631–638, 1994.

Campbell et al., "Improved development to blastocyst of bovine nuclear transfer embryos reconstructed during the presumptive S-phase of enucleated activated oocytes", *Biol. Reprod.,* 50:1385–1390, 1994.

Campbell, McWhir, Ritchie, Wilmut, "Production of live lambs following nuclear transfer of cultured embryonic disc cells," *Theriogenology* 43:181 (Abstr.), 1995.

Campbell, McWhir, Ritchie, Wilmut, "Sheep cloned by nuclear transfer from a cultured cell line," *Nature,* 380:64, 1996.

Cech et al., "In vitro splicing of the ribosomal RNA precursor of Tetrahymena: involvement of a guanosine nucleotide in the excision of the intervening sequence," *Cell,* 27:487–496, 1981.

Chalfie et al., *Science,* 263:802–805,1994.

Chang et al., "Characterization of a human apolipoprotein E gene enhancer element and its associated protein factors," *J. Biol. Chem.,* 265:9496–9504, 1990.

Chang et al., "Foreign gene delivery and expression in hepatocytes using a hepatitis B virus vector," *Hepatology,* 14:134A, 1991.

Chen and Okayama, "High-efficiency transfection of mammalian cells by plasmid DNA," *Mol. Cell Biol.,* 7:2745–2752, 1987.

Cheong et al., "Birth of mice after transplantation of early cell-cycle stage embryonic nuclei into enucleated oocytes", *Biol. Reprod.,* 48:958–965, 1993.

Chemy and Merei, "Evidence for pluripotency of bovine primordial germ cell-derived cell lines maintained in long-term culture", *Theriogenology,* 41:175, 1994.

Chomczynski and Sacchi, "Single-step method of RNA isolation by acid guanidinium thiocyanate-phenol-chloroform extraction," *Anal. Biochem.,* 162:156–159, 1987.

Chomczynski, "A reagent for the single-step simultaneous isolation of RNA, DNA and proteins from cell and tissue samples," *BioTechniques,* 15:532–536, 1993.

Chowrira et al., "In vitro and in vivo comparison of hammerhead, hairpin, and hepatitis delta virus self-processing ribozyme cassetyes," *J. Biol. Chem.,* 269:25856–25864, 1994.

Chowrira et al., *Biochemistry,* 32:1088–1095, 1993.

Chun, S. Y., Eisenhauer, K. M., Kubo, M. and Hsueh, A. J., "Interleukin-1 beta suppresses apoptosis in rat ovarian follicles by increasing nitric oxide production," *Endocrinology* 136:3120–3127, 1995.

Cibelli et al., "Production of germline chimeric bovine fetuses from transgenic embryonic stem cells", *Theriogenology,* 46:241, 1997.

Clark, "Prospects for the genetic engineering of milk," *J. Cell. Biochem.,* 49:121, 1992.

Clark, Bessos, Bishop, Brown, Harris, Lathe, McClenaghan, Prowse, Simons, Whitelaw, Wilmut, "Expression of human antihemophilic factor IX in the milk of transgenic sheep," *Biotechnology,* 7:487–492, 1989.

Clark, Voulgaropoulou, Fraley, Johnson, "Cell lines for the production of recombinant adeno-associated virus," *Human Gene Therapy,* 6:1329–1341, 1995.

Clay et al., "Localization of a domain in apolipoprotein E with both cytostatic and cytotoxic activity," *Biochemistry,* 34:11142–11151, 1995.

Elements Wall, Narayan, Hauer, Schoborg, Sheffer, Powell, Carruth, Zink, Rexroad, "Development of transgenic sheep that express the visna virus envelope gene," *Virology,* 200:370–380, 1994.

Coffin, "Retroviridae and their replication," *In: Virology,* Fields et al. (eds.), New York: Raven Press, pp. 1437–1500, 1990.

Colberre-Garapin et al., *J. Mol. Biol.,* 150:1, 1981.

Collas, P., Balise, J. J., Hofmann, G. A. and Robl, J. M., "Electrical activation of mouse oocytes," *Theriogenology* 32:835, 1989.

Collins and Fleming, "Specific mRNA detection in single lineage-marked blastomeres from preimplantation embryos," *Trends In Genetics,* 11:5–7, 1995.

Committee for the standardized karyotype of the domestic pig, *Hereditas,* 109:151–157, 1988.

Conover, Ip, Poueymirou, Bates, Goldfarb, DeChiara, Yancopoulos, "Ciliary neurtrophic factor maintains the pluripotentiality of embryonic stem cells," *Development,* 119:559–565, 1993.

Cossarizza, A., Franceschi, C., Monti, D., Salvioli, S., Bellesia, E., Rivabene, R., Biondo, L., Rainaldi, G., Tinari, A. and Malomi, W., "Protective effect of N-acetylcysteine in tumor necrosis factor-alpha-induced apoptosis in U937 cells: the role of mitochondria," *Exp. Cell Res.* 220:232–40, 1995.

Costa et al., "A liver-specific DNA-binding protein recognizes multiple nucleotide sites in regulatory regions of transthyretin, al-antitrypsin, albumin, and simian virus 40 gene," *Proc. Nat'l. Acad. Sci. USA* 85:3840–3844, 1988.

Cotten, Wagner, Zatloukal, Phillips, Curiel, "High efficiency receptor-mediated delivery of small and large (48 kilobase) gene constructs using the endosome disruption activity of defective or inactivated adenovirus particles," *P.N.A.S. USA*, 89:6094–6098, 1992.

Couch et al., "Immunization with types 4 and 7 adenovirus by selective infection of the intestinal tract," *Am. Rev. Resp. Dis.*, 88:394–403, 1963.

Coupar et al., "A general method for the construction of recombinant vaccinia virus expressing multiple foreign genes," *Gene*, 68:1–10, 1988.

Cripps, Dunkley, Taylor, Cousins, Clancy, "Immunity to *Pseudomonas aeruginosa* induced by OprF following intestinal immunization," *Advances in Nucosal Immunology*, J. Mestecky et al., ed. Plenum Press, New York, pp. 761–763, 1995.

Crister et al., "Influences of cumulus cell association during in vitro maturation of bovine oocytes on embryo development", *Biol. Reprod. Suppl.*, 134:192–198, 1986.

Cumo and Oettinger, "Analysis of regions of RAG-2 important for V(D)J recombination," *Nuc. Acids Res.*, 22(10):1810–1814, 1994.

Curiel, "Gene transfer mediated by adenovirus-polylysine DNA complexes," *In: Viruses in Human Gene Therapy*, J.-M. H. Vos (Ed.), Carolina Academic Press, Durham, N.C., pp.179–212, 1994.

Dale and Ow, "Gene transfer with subsequent removal of the selection gene from the host Egenome," *Proc. Natl. Acad. Sci. USA*, 88:10558–10562, 1991.

Danoff et al., "Screening for homologous recombination in ES cells using RT-PCR," *BioTechniques*, 22:22–26, 1997.

Das et al., "Isolation, characterization, and mapping to chromosome 19 of the human apolipoprotein E gene," *J. Biol. Chem.*, 260:6240–6247, 1985.

Delhaise et al., "Nuclear transplantation using bovine primordial germ cells from male fetuses," *Reprod. Fertil. Dev.*, 7:1217–1219, 1995.

Deng and Capecchi, "Reexamination of gene targeting frequency as a function of the extent of homology between the targeting vector and the target locus," *Mol. Cell. Biol.*, 12:3365–3371, 1992.

Deserio, Graziani, Laufer, Ciliberto, Paonessa, "In vitro binding of ciliary neurotrophic factor to its receptors-evidence for the formation of an IL-6 type hexameric complex," *J. Mol. Biol.*, 254:795–800, 1995.

Deursen and Wieringa, "Targeting of the creatine kinase M gene in embryonic stem cells using isogenic and nonisogenic vectors," *Nucl. Acid Res.*, 20:3815–3820, 1992.

Doetschman et al., "Targeted correction of a mutant HPRT gene in mouse embryonic stem cells," *Nature*, 330:576–578, 1987.

Doetschman et al., "The in vitro development of blastocyst-derived embryonic stem cell lines: Formation of visceral yolk sac, blood islands and myocardium", *J Embryol. Exp. Morph.*, 87:27–45, 1985.

Doetschman, Williams, Maeda, "Establishment of hamster blastocyst-derived embryonic stem (ES) cells," *Dev. Biol.*, 127:224–227, 1988.

Donavan, Stott, Cairns, Heasman, Wylie, "Migratory and postmigratory mouse primordial germ cells behave differently in culture," *Cell*, 44:831–838, 1986.

Dong et al., "Human apolipoprotein E: Role of argenine 61 in mediating the lipoprotein preferences of the E3 and E4 isoforms," *J. Biol. Chem.*, 269:22358–22365, 1994.

Ducsay et al., *Biol. Reprod.*, 26:729, 1982.

Ducsay et al., *J. Anim. Sci.*, 59:1303, 1984.

Eddy, Clark, Gong, Fenderson, "Origin and migration of primordial germ cells in mammals," *Gamete Res.*, 4:333–362, 1981.

Ehresmann, Moine, Mougel, Dondon, Grunberg-Manago, Ebel, Ehresmann, "Cross-linking of initiation factor IF3 to *Escherichia coli* 30S ribosomal subunit by trans-diamminedichloroplatinum(II): characterization of two cross-linking sites in 16S rRNA; a possible way of functioning for IF3," *Nucl. Acid Res.*, 14:4803–4821, 1986.

Escargueil-Blanc, I., Meilhac, O., Pieraggi, M. T., Arnal, J. F., Salvayre, R.and Negre-Salvayre, A., "Oxidized LDLs induce massive apoptosis of cultured human endothelial cells through a calcium-dependent pathway. Prevention by aurintricarboxylic acid," *Arterioscler. Thromb. Vasc. Biol.* 17:331–339, 1997.

Evans and Kaufman, "Pluripotential cells grow directly from normal mouse embryos", *Cancer Surveys*, 2:185–207, 1983.

Evans, Notarianni, Laurie, Moor, "Derivation and preliminary characterization of pluripotent cell lines from porcine and bovine blastocysts," *Theriogenology*, 33:125–128, 1990.

Evenson et al., "Flow cytometric evaluation of boar semen by the sperm chromatin structure assay as related to cryopreservation and fertility," *Theriogenology*, 41:637:651, 1994.

Faisst and Meyer, "Compilation of vertebrate-encoded transcription factors," *Nucl. Acid Res.*, 20:3–26, 1992.

Fechheimer et al., "Transfection of mammalian cells with plasmid DNA by scrape loading and sonication loading," *Proc. Nat'l Acad. Sci. USA,* 84:8463–8467, 1987.

Ferkol et al., *FASEB J.*, 7:1081–1091, 1993.

Ferrari G, Yan C Y and Greene L A, "N-acetylcysteine (D- and L-stereoisomers) prevents apoptotic death of neuronal cells," *J. Neurosci.* 15:2857–2866, 1995.

Fischer, M. et al., "Prion protein (PrP) with amino-proximal deletions restoring susceptibility of PrP knockout mice to scrapie," *EMBO J.* 15:1255–1264, 1996.

Flaws, J. A., DeSanti, A., Tilly, K. I., Javid, R. O., Kugu, K., Johnson, A. L., Hirshfield, A. N. and Tilly, J. L., "Vasoactive intestinal peptide-mediated suppression of apoptosis in the ovary: potential mechanisms of action and evidence of a conserved antiatretogenic role through evolution," *Endocrinology* 136:4351–4359, 1995.

Flotte, Afione, Conrad, McGrath, Solow, Oka, Zeitlin, Guggino, and Carter, "Stable in vivo expression of the cystic fibrosis transmembrane conductance regulator with an adeno-associated virus vector," *Proc. Natl. Acad Sci. USA,* 90:10613–10617, 1993.

Flotte, Barraza-Ortiz, Solow, Afione, Carter, and Guggino, "An improved system for packaging recombinant adeno-associated virus vectors capable of in vivo transduction," *Gene Therapy,* 2:29–37, 1995.

Flotte, Solow, Owens, Afione, Zeitlin, and Carter, "Gene expression from adeno associated virus vector in airway epithelial cells," *Am. J. Respir. Cell Mol. BioL,* 7:349–356, 1992.

Folger et al., "Patterns of integration of DNA microinjected into cultured mammalian cells: Evidence for homologous recombination between injected plasmid DNA molecules", *Mol. Cell Biol.*, 2:1372–1387, 1982.

Forster and Symons, "Self-cleavage of plus and minus RNAs of a virusoid and a structural model for the active sites," *Cell*, 49:211–220, 1987.

Fraley et al., "Entrapment of a bacterial plasmid in phospholipid vesicles: Potential for gene transfer," *Proc. Nat'l Acad. Sci. USA*, 76:3348–3352, 1979.

Friedmann, "Progress toward human gene therapy," *Science*, 244:1275–1281, 1989.

Fukazawa et al., "Complete nucleotide sequence of the gene encoding the rat apolipoprotein E," *Nucl. Acids Res.*, 14:9527–9528, 1986.

Fuster et al., "The porcine model for the understanding of thrombogenesis and atherogenesis," *Mayo Clin. Proc.*, 66:818–831, 1991.

Gallagher Jr. and Womack, "Chromosome conservation in the Bovidae," *J. Heredity*, 83:287–298, 1992.

Gallagher Jr. et al., "Chromosomal Localization of HSP70 genes in cattle," *Mammalian Genome* 4:388–390, 1993.

Galli, C., Meucci, O., Scorziello, A., Werge, T. M., Calissano, P. and Schettini, G., "Apoptosis in cerebellar granule cells is blocked by high KCl, forskolin, and IGF-1 through distinct mechanisms of action: the involvement of intracellular calcium and RNA synthesis," *J. Neurosci.* 15:1172–1179, 1995.

Gerfen and Wheeler, "Isolation of embryonic cell-lines from porcine blastocysts," *Anim. Biotech.* 6:1–14, 1995.

Gerlach et al., "Construction of a plant disease resistance gene from the satellite RNA of tobacco rinspot virus," *Nature (London)*, 328:802–805, 1987.

Getz et al., "Atherosclerosis and Apoprotein E: An enigmatic relationship," *Arch. Pathol. Lab. Med.* 112:1048–1055, 1988.

Ghosh-Choudhury et al., "Protein IX, a minor component of the human adenovirus capsid, is essential for the packaging of full-length genomes," *EMBO J.*, 6:1733–1739, 1987.

Ghosh and Bachhawat, "Targeting of liposomes to hepatocytes," *In: Liver diseases, targeted diagnosis and therapy using specific receptors and ligands*," Wu G. and C. Wu ed. New York: Marcel Dekker, pp. 87–104, 1991.

Gidoni et a!., "Multiple specific contacts between a mammalian transcription factor and its cognate promoters," *Nature* 312:409–413, 1984.

Giles, Yang, Mark, Foote, "Pluripotency of cultured rabbit inner cell mass cells detected by isozyme analysis and eye pigmentation of fetuses following injections into blastocysts or morulae," *Mol. Reprod. Dev.* 36:130, 1993.

Gjertsen, B. T., Cressey, L. I., Ruchaud, S., Houge, G., Lanotte, M. and Doskeland, S. O., "Multiple apoptotic death types triggered through activation of separate pathways by cAMP and inhibitors of protein phosphatases in one (IPC leukemia) cell line," *J. Cell Sci.* 107:3363–3377, 1994.

Goldmann, W. et al., "Different forms of the bovine PrP gene have five or six copies of a short, G-C rich element within the protein-coding exon," *J. Gen. Virol.* 72:201–204, 1991.

Gomez-Foix et al., "Adenovirus-mediated transfer of the muscle glycogen phosphorylase gene into hepatocytes confers altered regulation of glycogen," *J. Biol. Chem.*, 267:25129–25134, 1992.

Gopal, "Gene transfer method for transient gene expression, stable transfection, and cotransfection of suspension cell cultures," *Mol. Cell Biol.*, 5:1188–1190, 1985.

Gordon, Lee, Vitale, Smith, Westphal, Hennighausen, "Production of human tissue plasminogen activator in transgenic mouse milk," *Biotechnology*, 5:1183–1187, 1987.

Gordon, *Methods in Enzymol.*, 225:747–771, 1993.

Grabowski, Le Bars, Chene, Attal, Malienou-N'Gassa, Puissant, Houdebine, *J. Dairy Sci.*, 74:4143–4154, 1991.

Graham and Prevec, "Adenovirus-based expression vectors and recombinant vaccines," *Biotechnology*, 20:363–390, 1992.

Graham and Prevec, "Manipulation of adenovirus vector," *In: Methods in Molecular Biology: Gene Transfer and Expression Protocol*, E. J. Murray (ed.), Clifton, N.J.: Humana Press, 7:109–128, 1991.

Graham and van der Eb, "A new technique for the assay of infectivity of human adenovirus 5 DNA", *Virology*, 52:456–467, 1973.

Graham et al., "Characteristics of a human cell line transformed by DNA from human adenovirus type 5", *J. Gen. Virol.*, 36:59–72, 1977.

Graham, C. F., "The fusion of cells with one- and two-cell mouse embryos," *Wistar Inst. Symp. Monogr.* 9:19, 1969.

Grantham, Gautier, Gouy, Jacobzone, Mercier, "Codon catalog usage is a genome strategy modulated for gene expressivity," *Nuc. Acids Res.* 9:r43–r74, 1981.

Grantham, Gautier, Gouy, Mercier, and Pave, "Codon catalog usage and the genome hypothesis," *Nuc. Acids Res.* 8:r49–r62, 1980.

Graves and Moreadith, "Derivation and characterization of putative pluripotent embryonic stem cells from preimplantation rabbit embryos," *Mol. Reprod Dev.* 36:424, 1993.

Grunhaus and Horwitz, "Adenovirus as cloning vector," *Seminar in Virology*, 3:237–252, 1992.

Gu, Zou, Rajewski, *Cell*, 73:1155–1164, 1993.

Handyside, Hooper, Kaufman Wilmut, "Towards the isolation of embryonal stem cell lines from the sheep," *Roux's Arch. Dev. Biol.*, 196:185–190, 1987.

Harland and Weintraub, "Translation of mammalian MRNA injected into Xenopus oocytes is specifically inhibited by antisense RNA," *J. Cell Biol.*, 101:1094–1099, 1985.

Haseloff and Gerlach, "Simple RNA enzymes with new and highly specific endoribonuclease activities," *Nature*, 334:585–591, 1988.

Hasler-Rapacz et al., "Effects of simvastatin on plasma lipids and apolipoproteins in familiar hypercholesterolemic swine," *Arteriosclerosis, Thrombosis & Vascular Biology*, 16(1):137–143, 1996.

Hasler-Rapacz et al., "Elevated concentrations of plasma lipids and apolipoproteins B, C-III, and E are associated with the progression of coronary artery disease in familial hypercholesterolemic swine," *Arteriosclerosis, Thrombosis & Vascular Biology*, 15(5):583–592, 1995.

Hasty et al., "The length of homology required for gene targeting in embryonic stem cells," *Mol. Cell. Biol.*, 11:4509–4517, 1991.

Hennighausen and Sippel, *Eur. X Biochem.*, 125:131–141, 1982a.

Hensel, Delventahl, Windt, Stockhofe-Zurwieden, Pabst, Petzoldt, "Oral immunization with lung-pathogenic bacteria is protective against defined challenge in a pig aerosol infection model," *Advances in Mucosal Immunology*, J. Mestecky et al., ed., Plenum Press, New York, pp. 803–806, 1995.

Hermonat and Muzyczka, "Use of adeno-associated virus as a mammalian DNA cloning vector; transduction of neomycin resistance into mammalian tissue culture cells," *Proc. Natl. Acad. Sci. USA*, 81:6466–6470, 1984.

Hersdorffer et al., "Efficient gene transfer in live mice using a unique retroviral packaging line," *DNA Cell Biol.*, 9:713–723, 1990.

Herz and Gerard, "Adenovirus-mediated transfer of low density lipoprotein receptor gene acutely accelerates cholesterol clearance in normal mice," *Proc. Nat'l Acad. Sci. USA* 90:2812–2816, 1993.

Hill et al., "Production of transgenic cattle by pronuclear injection", *Theriogenology*, 37:222, 1992.

Hixson et al., "The baboon apolipoprotein Egene: Structure, expression, and linkage with the gene for apolipoprotein C-1," *Genomics*, 2:315–323, 1988.

Hodson et al., "Isolation and chromosomal assignment of 100 highly informative human simple sequence repeat polymorphism," *Genomics*, 13:622–629, 1992.

Hoess, Ziese, Sternberg, "P1 site-specific recombination: nucleotide sequence of the recombining sites,"*Proc. Natl. Acad. Sci. USA,* 79:3398–3402, 1982.

Horwich et al. "Synthesis of hepadenovirus particles that contain replication-defective duck hepatitis B virus genomes in cultured HuH7 cells," *J. Virol.,* 64:642–650, 1990.

Houdebine, "Production of pharmaceutical proteins from transgenic animals," *Journal of Biotechnology,* 34:269–287, 1994.

Ikemura, "Correlation between the abundance of *Escherichia coli* transfer RNAs and the occurance of the respective codons in its protein genes," *J. Mol. Biol.* 146:1–21, 1981 a.

Ikemura, "Correlation between the abundance of *Escherichia coli* transfer RNAs and the occurance of the respective codons in its protein genes: a proposal for a synonymous codon choice that is optimal for the *E. coli* translational system," *J. Mol. Biol.* 151:389–409, 1981b.

Ikemura, "Correlation between the abundance of yeast transfer RNAs and the occurance of the respective codons in protein genes: differences in synonymous codon choice patterns of yeast and *Escherichia coli* with reference to the abundance of isoaccepting transfer RNAs," *J. Mol. Biol.* 158:573–597, 1982.

Imagawa, Chiu, Karin, "Transcription factor AP-2 mediates induction by two different signal-transduction pathways: protein kinase C and cAMP," *Cell,* 51:251–260, 1987.

Innerarity et al., "The receptor-binding domain of human apolipoprotein E: Binding of apolipoprotein E fragments," *J. Biol. Chem.,* 258:12341–12347, 1983.

Inoue, S. et al., "Characterization of the bovine prion protein gene: the expression requires interaction between the promoter and intron,"*J. Vet. Med. Sci.* 59:175–183, 1997.

Ip, Nye, Boulton, Davis, Taga, Li, Birren, Yasukawa, Kishimoto, Anderson, Stahl, Yancopoulos, "CNTF and LIF act on neuronal cells via shared signaling pathways that involve the IL-6 signal transducing receptor component gp130*,*" *Cell,* 69:1121–1132, 1992.

Jain and Michael, "The influence of antigen digestion on orally induced immunity and tolerance," *Advances in Mucosal Immunology,* J. Mestecky et al., ed., Plenum Press, New York, pp. 1245–1250, 1995.

Jiang, S., Chow, S. C., Nicotera, P. and Orrenius, S., "Intracellular Ca2+signals activate apoptosis in thymocytes: studies using the Ca(2+)-ATPase inhibitor thapsigargin," *Exp. Cell Res.* 212:84–92, 1994.

Jones and Shenk, "Isolation of deletion and substitution mutants of adenovirus type 5,*" Cell,* 13:181–188, 1978.

Jones and Westhusin, "Effect of polyvinyl alcohol, bovine serum albumin fraction V, fetal calf serum, and fetal calf serum plus bovine serum albumin fraction V on bovine embryo development", *Theriogenology,* 45:205, 1996.

Joyce, "RNA evolution and the origins of life," *Nature,* 338:217–244, 1989.

Kaneda et al., "Increased expression of DNA cointroduced with nuclear protein in adult rat liver," *Science,* 243:375–378, 1989.

Kanegae, Gwang, Sato, Tanaka, Nakai, Sakaki, Sugano, Saito, Nucl. Acids Res., 23:3816–3821, 1995.

Kaplitt, Leone, Samulski, Siao, Pfaff, OMalley, During, "Long-term gene expression and phenotypic correction suing adeno-associated virus vectors in the mammalian brain," *Nature Genetics,* 8:148–154, 1994.

Karlsson et al, *EMBO J.,* 5:2377–2385, 1986.

Kato et al., "Expression of hepatitis β virus surface antigen in adult rat liver," *J. Biol. Chem.,* 266:3361–3364, 1991.

Kaufman, "Selection and Coamplification of Heterologous Genes in Mammalian Cells," *Methods in Enzymology,* 185:537–566,1990.

Keefer, Stice, Mathews "Bovine inner cell mass cells as donor nuclei in the production of nuclear transfer embryos and calves," *Biol. Reprod.,* 50:935–939, 1994.

Kelleher and Vos, "Long-term episomal gene delivery in human lymphoid cells using human and avian adenoviral-assisted transfection," *Biotechniques,* 17(6):1110–1117, 1994.

Ketcham et al., *J. Biol. Chem.,* 260:5768, 1985.

Ketcham et al., *J. Biol. Chem.,* 264:557, 1989.

Khalili et al., "Nuclear factors in human brain cells bind specifically to JCV regulatory region," *EMBO J.,* 7:1205–1210, 1988.

Kim and Cech, "Three dimensional model of the active site of the self-splicing rRNA precursor or Tetrahymena," *Proc. Natl. Acad. Sci. USA,* 84:8788–8792, 1987.

Kim et al., "Effects of oviductal fluid on sperm penetration and cortical granule exocytosis during fertilization of pig oocytes in vitro," *J. Reprod. Fertil.,* 107:79–86, 1996.

Klein et al., "High-velocity microprojectiles for delivering nucleic acids into living cells," *Nature,* 327:70–73, 1987.

Klintworth, *Adv. Pathol.,* 3:233–299, 1990.

Koller and Smithies, "Altering genes in animals by gene targeting", *Ann. Rev. Immun.,* 10:705–730, 1992.

Koshimizu et al., "Functional requirement of gpl 30-mediated signaling for growth and survival of mouse primordial germ cels in vitro and derivation of embryonic germ (EG) cells," *Development,* 122:1235–1242, 1996.

Kotin, Siniscalco, Samulski, Zhu, Hunter, McLaughlin, Muzyczka, Berns, "Site-specific integration by adeno-associated virus," *Proc. Natl. Acad. Sci. USA,* 87:2211–2215, 1990.

Kroshus, Bolman III, Dalmasso, Rollins, Guilmette, Williams, Squinto, Fodor, "Expression of human CD59 I transgenic pig organs enhances organ survival in an ex vivo xenogeneic perfuision model," *Transplantation,* 61(10):1513–21, 1996.

Kyte and Doolittle, "A simple method for displaying the hydropathic character of a protein," *J. Mol. Biol.,* 157:105–132, 1982.

Labosky, Barlow, Hogan, "Mouse embryonic germ (EG) cell lines: transmission through the germline and differences in the methylation imprint of insulin-like growth factor 2 receptor (Igf2r) gene compared with embryonic stem (ES) cell lines," *Development,* 120:3197–3204, 1994.

LaFace, Hermonat, Wakeland, Peck, "Gene transfer into hematopoietic progenitor cells mediated by an adeno-associated virus vector," *Virology,* 162:483–486, 1988.

Lakso, Pichel, Gorman, Sauer, Okamoto, Lee, Alt, Westphal, "Efficient in vivo manipulation of mouse genomic sequences at the zygote stage," *Proc. Nat. Acad. Sci. USA,* 93:5860–5865, 1996.

Lalazar et al., "Site-specific mutagenesis of human apolipoprotein E: Receptor binding activity of variants with single amino acid substitutions," *J. Biol. Chem.,* 263:3542–3545, 1988.

Laughlin, Cardellichio, Coon, "Latent Infection of KB Cells with Adeno-Associated Virus Type 2," *J. Virol.,* 60:515–524, 1986.

Lavoir et al., "Isolation and identification of germ cells from fetal bovine ovaries", *Molecular Reproduction and Development*, 37:413–424, 1994.

Lavoir et al., "Development of bovine nuclear transfer embryos made with oogonia", *Biol. Reprod.*, 56:194–199, 1997.

Le Gal La Salle et al., "An adenovirus vector for gene transfer into neurons and glia in the brain," *Science*, 259:988–990, 1993.

Lebkowski, McNally, Okarma, and Lerch, "Adeno-associated virus: a vector system for efficient introduction and integration of DNA into a variety of mammalian cell types," *Mol. Cell. Biol.*, *:3988–3996, 1988.

Lee, Mitchell, Tjian, "Purified transcription factor AP-1 interacts with TPA-inducible enhancer elements," *Cell* 49:741–752, 1987.

Leichthammer and Brem, "In vitro culture and cryopreservation of farm animals' primordial germ cells," *Theriogenology* 33:272, 1990.

Levrero et al., "Defective and nondefective adenovirus vectors for expressing foreign genes in vitro and in vivo," *Gene*, 101:195–202, 1991.

Lieber and Strauss, "Selection of efficient cleavage sites in target RNAs by using a ribozyme expression library." *Mol. Cell. Biol.*, 15: 540–551, 1995.

Lin, Mismer, Lile, Armes, Butler, III, Vannice, Collins, "Purification, cloning, and expression of ciliary neurotrophic factor (CNTF)," *Science*, 246:1023–1025, 1989.

Liu et al., "Nuclear remodelling and early development in cryopreserved, porcine primordial germ cells following nuclear transfer into in vitro-matured oocytes", *Int. J. Dev. Biol.*, 39:639–644, 1995

Liu, J., Li, H., de Tribolet, N., Jaufeerally, R., Hamou, M. F. and Van Meir, E. G., "IL-6 stimulates growth and inhibits constitutive, protein synthesis-independent apoptosis of murine B-cell hybridoma 7TD1," *Cell. Immunol.* 155:428435, 1994.

Lo, Pursel, Linton, Sandgren, Behringer, Rexroad, Palmitter, Brinster, "Expression of mouse IgA by transgenic mice, pigs and sheep," *Eur. J. Immunol.*, 21:1001–1006, 1991.

Luo, Zhou, Cooper, Munshi, Boswell, Broxmeyer, Srivastava, "Adeno-associated virus 2 mediated transfer and functional expression of a gene encoding the human granulocyte-macrophage colony-stimulating factor," *Blood*, 82 (Supp.): 1,303A, 1994.

Lusis, "Genetic factors affecting blood lipoproteins: The candidate gene approach," *J. Lipid Res.*, 29:397–429, 1988.

Machaty, Funahashi, Mayes, Day, Prather, "Effect of injecting calcium chloride into in vitro-matured porcine oocytes," *Biol. Reprod.*, 54:316–322, 1996.

Maeser and Kahmann, "The Gin recombinase of phage Mu can catalyze site-specific recombination in plant protoplasts," *Mol. Gen. Genetics*, 230:170–176, 1991.

Mahley and Innerarity, "Lipoprotein receptors and cholesterol homeostasis," *Biochem. Biophys. Acta.*, 737:197–222, 1983.

Mahley et al, "Plasma lipoproteins: apolipoprotein structure and function," *J. Lipid Res.*, 25:1277–1294, 1984.

Mahley, "Apolipoprotein E:Cholesterol transport protein with expanding role in cell biology," *Science*, 240:622–630, 1988.

Malorni, W., Rivabene, R., Straface, E., Rainaldi, G., Monti, D., Salvioli, S., Cossarizza, A. and Franceschi, C., "3-Aminobenzarnide protects cells from UV-B-induced apoptosis by acting on cytoskeleton and substrate adhesion," *Biochem. Biophys. Res. Commun.* 207:715–724, 1995.

Mann et al., "Construction of a retrovirus packaging mutant and its use to produce helper-free defective retrovirus," *Cell*, 33:153–159, 1983.

Markowitz et al., "A safe packaging line for gene transfer: Separating viral genes on two different plasmids," *J. Virol.*, 62:1120–1124, 1988.

Maroto, R., De la Fuente, M. T., Artalejo, A. R., Abad, F., Lopez, M. G., Garcia-Sancho, J. and Garcia, A. G., "Effects of Ca2+ channel antagonists on chromaffin cell death and cytosolic Ca2+ oscillations induced by veratridine," *Eur. J. Pharmacol.* 270:331–339, 1994.

Martin and Lock, "Pluripotent cell lines derived from early mouse embryos in medium conditioned by teratocarcinoma stem cells", *In: Teratocarcinoma Stem Cells*. Silver et al., (eds), Cold Spring Harbor Conference on Cell Proliferation, Vol 10, Cold Spring Harbor Laboratory, Cold Spring Harbor, N.Y. pp. 635–646, 1983.

Martin, "Isolation of a pluripotent cell line from early mouse embryos cultured in medium conditioned by teratocarcinoma stem cells," *Proc. Natl. Acad. Sci. USA*, 78:7634–7638, 1981.

Martin, F. et al., *Cell* 63:203–211, 1990.

Matsui et al., "Derivation of pluripotential embryonic stem cells from murine primordial germ cells in culture", *Cell*, 70:841–847, 1992.

McCarrick et al., "Positive-negative selective gene targeting with the diphtheria toxin A-chain gene in mouse embryonic stem cells," *Transgenic Res.*, 2:183–190, 1993.

McCarty, Christensen, Muzyczka, "Sequences Required for Coordinate Induction of Adeno-Associated Virus p19 and p40 Promoters by Rep Protein," *J. Virol.*, 65:2936–2945, 1991.

McGrath, J. and Solter, D., "Nuclear transplantation in the mouse embryo by microsurgery and cell fusion," *Science* 220:1300, 1983.

McKnight, Shamay, Sankaran, Wall, Hennighausen, *Proc. Natl. Acad. Sci USA*, 89:6943–6947, 1992.

McLaughlin, Collis, Hermonat, Muzyczka, "Adeno-Associated Virus General Transduction Vectors: Analysis of Proviral Structures," *J. Virol.*, 62:1963–1973, 1988.

McLean et al., "Human apolipoprotein E mRNA: cDNA cloning and nucleotide sequencing of a new variant," *J. Biol. Chem.*, 259:6498–6504, 1984.

McPherron, A. C., Lawler, A. M. and Lee, S. -J., "Regulation of skeletal muscle mass in mice by a new TGF-beta superfamily member," *Nature* 387:83, 1997.

Meade, Gates, Kacy, Lonberg, "Bovine $\alpha_{S1}$-casein gene sequences direct high level expression of active human urokinase in mouse milk," *Biotechnology*, 8:433–446, 1990.

Meredith, J. E., Fazeli, B. and Schwartz, M. A., "The extracellular matrix as a cell survival factor," *Mol. Biol. Cell* 4:953–961, 1993.

Michel and Westhof, "Modeling of the three-dimensional architecture of group I catalytic introns based on comparative sequence analysis," *J. Mol. Biol.*, 216:585–610, 1990.

Migita, K., Eguchi, K., Kawabe, Y., Mizokami, A., Tsukada, T. and Nagataki, S., "Prevention of anti-CD3 monoclonal antibody-induced thymic apoptosis by protein tyrosine kinase inhibitors," *J. Immunol.* 153:3457–3465, 1994.

Minucci et al., "Retinoic acid-mediated down-regulation of Oct3/4 coincide with the loss of promoter occupancy in vivo," *EMBO J.*, 15:888–889, 1996.

Moens et al., "Assessment of nuclear totipotency of fetal bovine diploid germ cells by nuclear transfer", *Theriogenology*, 46:871–880, 1996.

Moore and Piedrahita, "Effects of heterologous hematopoietic cytokines on in vitro differentiation of cultured porcine inner cell masses," *Mol. Reprod. Dev.,* 45:139–144, 1996.

Moore and Piedrahita, "The effects of human leukemia inhibitory factor (HLIF) and culture medium on in vitro differentiation of cultured porcine inner cell mass (PICM) ", *In vitro Cell Dev. Biol.—Animal,* 33:62–71, 1997.

Moreno and Westhusin, "A comparison of two systems for culture of bovine zygotes in vitro", *Biol. Reprod.,* 48(1):169, 1993.

Mountford et al., "Dicistronic targeting constructs: Reporters and modifiers of mammalian gene expression," *Proc. Natl. Acad. Sci. USA,* 91:4303–4307, 1994.

Mueller and Wold, "In vivo footprinting of a muscle specific enhancer by ligation mediated PCR," *Science,* 246:780–785, 1989.

Murray, et al., *J. Biol. Chem.,* 264:4143, 1989.

Muzyczka, "Use of Adeno-Associated Virus as a General Transduction Vector for Mammalian Cells," *Curr. Top. Microbiol. Immunol.,* 158:97–129, 1992.

Nagy et al., "Embryonic stem cells alone are able to support fetal development in the mouse," *Development,* 110:815–821, 1990.

Nakajima, M., Kashiwagi, K., Ohta, J., Furukawa, S., Hayashi, K., Kawashima, T. and Hayashi, Y., "Nerve growth factor and epidermal growth factor rescue PC12 cells from programmed cell death induced by etoposide: distinct modes of protection against cell death by growth factors and a protein-synthesis inhibitor," *Neurosci. Lett.* 176:161–4, 1994.

Negro, Tolosano, Skaper, Martini, Callegaro, Silengo, Fiorini, Altruda, "Cloning and expression of human ciliary neurtrophic factor," *European Journal of Biochemistry,* 201:289–294, 1991.

Neimman, and Reichelt, "Manipulating early pig embryos," *J. Reprod. Fertil.,* 48:75–94, 1993.

Nicolas and Rubinstein, "Retroviral vectors," *In: Vectors: A survey of molecular cloning vectors and their uses,* Rodriguez and Denhardt (eds.), Stoneham: Butterworth, pp. 494–513, 1988.

Nicolau and Sene, "Liposome-mediated DNA transfer in eukaryotic cells," *Biochem. Biophys. Acta,* 721:185–190, 1982.

Nicolau et al., "Liposomes as carriers for in vivo gene transfer and expression," *Methods Enzymol.,* 149:157–176, 1987.

Niebergs et al., "Physical mapping of inhibin B-A in domestic cattle", *Mamm Genome* 4:328–332, 1993.

Niebergs, Gallagher, Georges, Sargeant, Dietz, Womack, "Physical mapping of inhibin B-A in domestic cattle," *Mammalian Genome,* 4:328–332, 1993.

Nimer, Fraser, Richards, Lynch, Gasson, "The repeated sequence CATT(A/T) is required for granulocyte-macrophage colony-stimulating factor promoter activity," *Mol. Cell. Biol.,* 10:6084–6088, 1990.

Notarianni, Galli, Laurie, Moor, Evans, "Derivation of pluripotent, embryonic cell lines from pig and sheep," *J. Reprod. Fertil.* 43 (suppl.):255, 1991.

Notarianni, Laurie, Moor, Evans, "Maintenance and differentiation in culture of pluripotential embryonic cell lines from pig blastocysts," *J. Reprod. Fertil.* 41 (suppl.):51–56, 1990.

O'Gorman, Fox, Wahl, *Science,* 251:1351–1355,1991.

Oettinger, Schatz, Gorka, and Baltimore, "RAG-1 and RAG-2, adjacent genes that synergistically activate V(D)J recombination," *Science,* 248:1517–1523, 1990.

Ohi, Dixit, Tillery, and Plonk, "Construction and replication of an adeno-associated virus expression vector that contains human λ-globin cDNA," *Gene,* 89L:279–282, 1990.

Okazawa et al., "The Oct-3 gene, a gene for an embryonic transcription factor, is controlled by retinoic acid repressible enhancer," *EMBO J.,* 10:2997–3005, 1991.

Onishi et al., "Production of chimeric pigs and the analysis of chimerism using mitochondrial deoxyribonucleic acid as a cell marker", *Biol. Reprod,* 51:1069–1075, 1994.

Onouchi, Nishihama, Kudo, Machida, Machida, "Visualization of site-specific recombination catalyzed by a recombinase from *Zygo-saccharomyces rouxii* in *Arabidopsis thaliana,*" *Mol. Cell. Biol.,* 247:653–660, 1995.

Osborne et al., "Operator constituitive mutation of 3-Hydroxy-Methylglutaryl coenzyme A reductase promoter abolishes protein binding to sterol regulatory element," *J Biol. Chem.,* 263:3380–3387, 1988.

Ouhibi et al., "Nuclear transplantation of ectodermal cells in pig oocytes: ultrastructure and radiography," *Mol. Reprod. Dev.,* 44:533–539, 1996.

Ozil, J. P., "The parthenogenetic development of rabbit oocytes after repetitive pulsatile electrical stimulation," *Development* 10:117, 1990.

Paik et al., "Nucleotide sequence and structure of the human apolipoprotein E gene," *Proc. Nat'l. Acad. Sci. USA,* 82:3445–3449, 1985.

Palukaitis et al., "Characterization of a viroid associated with avacado sunblotch disease," *Virology,* 99:145–151, 1979.

Parrish et al., "Bovine in vitro fertilization with frozen-thawed semen", *Theriogenology,* 25:591–598, 1986.

Paskind et al., "Dependence of moloney murine leukemia virus production on cell growth," *Virology,* 67:242–248, 1975.

Pease, Braghetta, Gearing, Grail, Williams, "Isolation of embryonic stem (ES) cells in media supplemented with recombinant leukemia inhibitory factor (LIF)," *Dev. Biol.,* 141:344–52, 1990.

Pelletier and Sonenberg, *Nature,* 334:320–325, 1988.

Perales et al., *Proc. Natl. Acad. Sci. USA,* 91:4086–4090, 1994.

Pericak-Vance and Haines, "Genetic susceptibility to alzheimer disease," *Trends Genet.,* 11:504–508, 1995.

Perriman et al., "Extended target-site specificity for a hammerhead ribozyme," *Gene,* 113:157–163, 1992.

Perucho et al., "Genetic and physical linkage of exogenous sequences in transformed cells", *Cell,* 309–317, 1980.

Petters and Wells, "Culture of pig embryos," *J. Reprod Fert. Suppl.,* 48:61–73, 1993.

Piedrahita J A, Zhang S H, Hagaman J R, Clark P M, and Maeda N., "Generation of mice carrying a mutant apolipoprotein E gene inactivated by gene targeting in mouse embryonic stem cells," *Proc. Natl. Acad. Sci. USA* 89:4471–4475, 1992.

Piedrahita, Anderson, BonDurant, "On the isolation of embryonic stem (ES) cells: Comparative behavior of murine, porcine, and ovine embryos," *Theriogenology,* 34:879–901, 1990.

Piedrahita, Weaks, Petrescu, Derr, Shrode, Womack JE, "Genetic characterization of the bovine leukemia inhibitory factor: Cloning and sequencing, chromosome assignment, and microsatellite analysis",*Animal Genetics* 28:14–20, 1997.

Pinkel et al., "Cytogenetic analysis using quantative high sensitivity fluorescence hybridization," *Proc. Nat'l. Acad. Sci. USA,* 83:2934–2938, 1986.

Plump, Smith, Hayek, Aalto-Setala, Walsh, Verstuyft, Rubin, Breslow, "Severe hypercholesterolemia and atherosclerosis in apolipoprotein E-deficient mice created by homologous recombination in ES cells," *Cell,* 71:343–353, 1992.

Potter et al., "Enhancer-dependent expression of human k immunoglobulin genes introduced into mouse pre-B lymphocytes by electroporation," *Proc. Natl Acad. Sci. USA,* 81:7161–7165, 1984.

Prather, Hoffman, Schoenbeck, Stumpf, Li, "Characterization of DNA synthesis during the 2-cell stage and the production of tetraploid chimeric pig embryos," *Mol. Reprod. Develop.,* 45:38–42, 1996.

Prather, R. S. and First, N. L., "Cloning of embryos," *J. Reprod. Fertil.* 40 (suppl):227, 1990.

Prather, R. S., Barnes, F. L., Sims, M. M., Robl, J. M., Eyestone, W. H. and First, N. L., "Nuclear transplantation in the bovine embryo: Assessment of donor nuclei and recipient oocyte stage," *Biol. Reprod.* 37:859–368, 1987.

Prather, R. S., Sims and First, N. L., "Nuclear transplantation in pig embryos," *Biol. Reprod.* 41:414–418, 1989.

Prescott, Hasler-Rapacz, von Linden-Reed, Rapacz, "Familial hypercholesterolemia associated with coronary atherosclerosis in swine bearing different alleles for apolipoprotein B," *Annals NY Acad. Sci.,* 748:283–292, 1995.

Prody et al., "Autolytic processing of dimeric plant virus satellite RNA." *Science,* 231, 1577–1580, 1986.

Pursel and Rexroad Jr., "Status of research with transgenic farm animals," *J. Anim. Sci.,* 71 Suppl. 3:10–19, 1993.

Pursel et al., "Genetic engineering of livestock", *Science,* 244:1281–1288, 1989.

Rønne, "Fluorouracil synchronization of pig lymphocyte cultures. Induction of high resolution R-banding by in vitro exposure to 5-bromodeoxyuridine/Hoechst 33258, 6th European Colloquim on Cytogenetics in Domestic Animals,* 1980:189–196, 1984.

Racher et al., *Biotechnology Techniques,* 9:169–174, 1995.

Ragot et al., "Efficient adenovirus-mediated transfer of a human minidystrophin gene to skeletal muscle of mdx mice," *Nature,* 361:647–650, 1993.

Rajavashisth, Kaptein, Reue, Lusis, "Evolution of apolipoprotein E: Mouse sequence and evidence for an 11-nucleotide ancestral unit," *Proc. Nat'l. Acad. Sci. USA,* 82:8085–8089, 1985.

Rall et al., "Human apolipoprotein E: The complete amino acid sequence," *J. Biol. Chem.,* 257:4171–4178, 1982.

Randolph, Verbsky, Yang, Fang, Hakem, Fields, "PCR-based gene targeting of the inducible nitric oxide synthase (NOS2) locus in murine ES cells, a new and more cost-effective approach," *Transgenic Res.,* 5:413–420, 1996.

Rapacz and Hasler-Rapacz, "Animal models:the pig," *In: Genetic Factors in Atherosclerosis: Approaches and Model Systems,* Lusis and Sparkes, Basel, Karger, eds., pp. 139–169, 1989.

Rapacz and Hasler-Rapacz, "Investigations on the relationship between immunogenetic polymorphism of b-lipoproteins and the b-lipoprotein and cholesterol levels in swine," *In: Atherosclerosis & Cardiovascular Diseases,* Lenzi and Descovich, eds., Editrice, Bologna, Italy, pp. 99–108, 1984.

Rapacz, Hasler-Rapacz, Hu, Rapacz, Vogeli, Hojny, Janik, "Identification of new apolipoprotein B epitopes and haplotypes and their distribution in swine populations," *Animal Genetics,* 25(1):51–57, 1994.

Reinhold-Hurek, Shub, "Self-splicing introns in tRNA genes of widely divergent bacteria," *Nature,* 357:173–176, 1992.

Renan, "Cancer genes: current status, future prospects, and applicants in radiotherapy/oncology," *Radiother. Oncol.,* 19:197–218, 1990.

Renegar, et al., *Biol. Reprod.,* 27:1247, 1982.

Rettenberger et al., "Chromosomal assignment of seventeen porcine microsatellites and genes by use of a somatic cell hybrid mapping panel," *Animal Genetics,* 26:269–273, 1995.

Rich et al., "Development and analysis of recombinant adenoviruses for gene therapy of cystic fibrosis," *Hum. Gene Ther.,* 4:461–476, 1993.

Ridgeway, "Mammalian expression vectors," In: Rodriguez RL, Denhardt DT, ed. Vectors: A survey of molecular cloning vectors and their uses. Stoneham: Butterworth, pp. 467–492, 1988.

Rippe et al., "DNA-mediated gene transfer into adult rat hepatocytes in primary culture," *Mol. Cell Biol.,* 10:689–695, 1990.

Roberts and Bazer, *Bio Essays,* 1:8, 1984.

Robic et al., "Pig microsatellites isolated from cosmids revealing polymorphism and localized on chromosomes," *Animal Genetics,* 26:1–6, 1995.

Robl and Stice, "Prospects for the commercial cloning of animals by nuclear transplantation", *Theriogenology,* 31:75–81, 1989.

Robl, Gilligan, Critser, First, "Nuclear transplantation in mouse embryos: Assessment of recipient cell stage," *Biol. Reprod,* 43:733–738, 1986.

Rohrer et al., "A microsatellite linkage map of the porcine genome," *Genetics,* 136:231–245, 1994.

Rosenfeld et al., "Adenovirus-mediated transfer of a recombinant al-antitrypsin gene to the lung epithelium in vivo," *Science,* 252:431–434, 1991.

Rosenfeld et al., "In vivo transfer of the human cystic fibrosis transmembrane conductance regulator gene to the airway epithelium," *Cell,* 68:143–155, 1992.

Roux et al., "A versatile and potentially general approach to the targeting of specific cell types by retroviruses: Application to the infection of human cells by means of major histocompatibility complex class I and class II antigens by mouse ecotropic murine leukemia virus-derived viruses," *Proc. Natl. Acad. Sci. USA,* 86:9079–9083, 1989.

Russe, "Oogenesis in cattle and sheep", *Biblio. Anat.,* 24:77–92, 1983.

Saito, Strelchenko, Niemann, "Bovine embryonic stem cell-like cell lines cultured over several passages," *Roux's Arch. Dev. Biol.,* 201:134–140, 1992.

Sambrook, Fritsch, Maniatis, *Molecular Cloning A Laboratory Manual,* 2nd ed., pp. 2.69–2.81, Cold Spring Harbor Laboratory Press, Cold Spring Harbor, N.Y., 1989.

Samulski, Chang, Shenk, "Helper-free stocks of recombinant adeno-associated viruses: Normal integration does not require viral gene expression," *J. Virol.,* 63:3822–3828, 1989.

Samulski, Zhu, Xiao, Brook, Housman, Epstein, Hunter, "Targeted integration of adeno-associated virus (AAV) into human chromosome 19,"*EMBO J.,* 10:3941–3950, 1991.

Sanger, Nicklen, Coulson, "DNA sequencing with chain-terminating inhibitors," *Proc. Natl. Acad. Sci. U.S.A.,* 74:5463–5467, 1977.

Santerre, et al., *Gene,* 30:147, 1984.

Sarin, A., Adams, D. H. and Henkart, P. A., "Protease inhibitors selectively block T cell receptor-triggered programmed cell death in a murine T cell hybridoma and activated peripheral T cells," *J. Exp. Med.* 178:1693–1700, 1993.

Sarin, A., Clerici, M., Blatt, S. P., Hendrix, C. W., Shearer, G. M. and Henkart, P. A., "Inhibition of activation-induced programmed cell death and restoration of defective immune responses of HIV+ donors by cysteine protease inhibitors," *J. Immunol.* 153:862–872, 1994.

Sarver et al, "Ribozymes as potential anti-HIV-l therapeutic agents," *Science,* 247:1222–1225, 1990.

Sato, N., Iwata, S., Nakamura, K., Hori, T., Mori, K. and Yodoi, J., "Thiol-mediated redox regulation of apoptosis. Possible roles of cellular thiols other than glutathione in T cell apoptosis," *J. Immunol.* 154:3194–3203, 1995.

Sauer and Henderson, *New Biol.,* 2:441–449, 1990.

Sauer and Henderson, *Nucl. Acids Res.,* 17:147–161, 1989.

Sauer, "Functional expression of the cre-lox stie-specific recombination system in the yeast *Saccharoyces cerevisiae, Mol. Cell. Biol.,* 7:2087–2096, 1987.

Sauer, "Manipulation of transgenes by site-specific recombination: Use of Cre recombinase," *Methods in Enzymology,* 225:890–900, 1993.

Saunders et al., *J. Biol. Chem.,* 260:3658, 1985.

Scanlon et al., "Ribozyme-mediated cleavages of c-fos mRNA reduce gene expression of DNA synthesis enzymes and metallothionein," *Proc Natl Acad Sci USA,* 88:10591–10595, 1991.

Schatz, Oettinger, Baltimore, "The V(D)J recombination activating gene, RAG-1, *Cell,* 59:1035–1048, 1989.

Schlosnagle et al., *J. Biol. Chem.* 249:7574, 1974.

Schöler, "Octamania: the POU factors in murine development," *Trends Genet.,* 7:323–329, 1991.

Sell, C., Baserga, R. and Rubin, R., "Insulin-like growth factor I (IGF-I) and the IGF-I receptor prevent etoposide-induced apoptosis," *Cancer Res.* 55:303–306, 1995.

Sharkey, Dellow, Blayney, Macnamee, Charnock-Jones, Smith, "Stage-specific expression of cytokine and receptor messenger ribonucleic acids in human preimplantation embryos," *Biol. Reprod.,* 53:955–962, 1995.

Shelling and Smith, "Targeted integration of transfected and infected adeno-associated virus vectors containing the neomycin resistance gene," *Gene Therapy,* 1:165–169, 1994.

Shim and Anderson, "Putative porcine embryonic germ cells maintained in long-term culture," *Biol. Reprod.,* 52:136, 1995.

Shim, Gutiérrez-Adán, Chen, BonDurant, Anderson, "Isolation of pluripotent stem cells from cultured porcine primordial germ cells," *Theriogenology,* 46:245, 1997.

Simmen et al., *Mol. Endocrinol.* 2:253, 1988.

Simonet et al., "Multiple tissue-specific elements control the apolipoprotein E/C-I gene locus in transgenic mice," *J. Biol. Chem.,* 266:8651–8654, 1991.

Sims and First, "Production of calves by transfer of nuclei from cultured inner cell mass cells", *Proc. Natl. Acad. Sci. USA,* 91:6143–6147, 1994.

Sioud et al., "Preformed ribozyme destroys tumour necrosis factor mRNA in human cells," *J. Mol. Biol.,* 223:831–835, 1992.

Smith and Hooper, "Buffalo rat liver cells produce a diffusible activity which inhibits the differentiation of murine embryonal carcinoma and embryonic stem cells," *Dev. Biol.,* 121:1–9,1987.

Smith and Wilmut, "Influence of nuclear and cytoplasmic activity on the development in vivo of sheep embryos after nuclear transfer", *Biol. Reprod.,* 40:1027–1032, 1989.

Smith, Heath, Donaldson, Wong, Moreau, Stahl, Rogers, "Inhibition of pluripotential embryonic stem cell differentiation by purified polypeptides," *Nature,* 336:688–690, 1988a.

Smith, Melian, Leff, Breslow, "Expression of the human apolipoprotein E gene is regulated by multiple positive and negative elements," *J. Biol. Chem.,* 263: 8300–8308, 1988b.

Smithies, "Altering genes in animals and humans," *In: Etiology of Human Disease at the DNA Level,* J. Lindsten and U. Pettersson, eds, Nobel Symposium 80, Raven Press, N.Y., pp. 221–231, 1991.

Smithies, Gregg, Boggs, Koralewski, Kucherlapati, "Insertion of DNA sequences into the human chromosomal beta-globin locus by homologous recombination," *Nature,* 317:230–234, 1985.

Solter and Knowles, "Monoclonal antibody defining a stage-specific mouse embryonic antigen (SSEA-1)," *Proc. Natl. Acad. Sci. USA,* 75:5565–5569, 1978.

Squier, M. K., Miller, A. C., Malkinson, A. M. and Cohen, J. J., "Calpain activation in apoptosis," *J. Cell. Physiol.* 159:229–237, 1994.

Stahl, Davis, Wong, Taga, Kishimoto, Ip,Yancopoulos, "Cross-linking identifies leukemia inhibitory factor-binding protein as a CNTF receptor component," *J. Biol. Chem.,* 268:7628–7631, 1993.

Stemmer, Crameri, Ha, Brennan, Heyneker, "Single-step assembly of a gene and entire plasmid from large numbers of oligodeoxyribonucleotides," *Gene,* 164(1):49–53, 1995.

Sternberg and Hamilton, "Bacteriophage P1 site-specific recombination. 1. Recombination between lox P sites," *J. Mol. Biol.,* 150:467–486, 1981.

Sternberg, Sauer, Hoess, Abremski, "Bacteriophage P1 cre gene and its regulatory region," *J. Mol. Bio.,* 187:197–212, 1986.

Stewart, Gadi, Blatt, "Stem cells from primordial germ cells can reenter the germline," *Dev. Biol.,* 161:626–628, 1994.

Stewart, Vanek, Wagner, "Expression of foreign genes from retroviral vectors in mouse teratocarcinoma chimeras," *EMBO J.,* 4:3701–3709, 1985.

Stice and Strelchenko, "Domestic animal embryonic stem cells: Progress toward germ-line contribution," *In: Biotechnology's Role in the Genetic Improvement of Farm Animals,* Miller, Pursel, Norman, eds., Beltsville Symposia in Agricultural Research XX, Beltsville, Md. p. 189–201, 1995.

Stice, S. L. and Robl, J. M., "Nuclear reprogramming in nuclear transplant rabbit embryos," *Biol. Reprod.* 39:657–668, 1988.

Stice, Strelchenko, Betthauser, Scott, Jugella, Jackson, David, Keefer, Matthews, "Bovine pluripotent embryonic cells contribute to nuclear transfer and chimeric fetuses," *Theriogenology* 41:301 (Abstr.), 1994.

Stice, Strelchenko, Keefer, Matthews, "Pluripotent bovine embryonic cell lines direct embryonic development following nuclear transfer," *Biol. Reprod.,* 54:100–110, 1996.

Stockli, Lottspeich, Sendtner, Masiakowski, Carroll, Gotz, Lindholm, Thoenen, "Molecular cloning, expression, and regional distribution of rat ciliary neuruotrophic factor," *Nature,* 342:920–923, 1989.

Stokes et al., "Production of chimaeric bovine embryos", *Theriogenology,* 41:303–309, 1994.

Stratford-Perricaudet and Perricaudet, "Gene transfer into animals: the promise of adenovirus," *In: Human Gene Transfer,* Eds, O. Cohen-Haguenauer and M. Boiron, Editions John Libbey Eurotext, France, p. 51–61, 1991.

Stratford-Perricaudet et al., "Evaluation of the transfer and expression in mice of an enzyme-encoding gene using a human adenovirus vector," *Hum. Gene Ther.,* 1:241–256, 1990.

Strelchenko, "Bovine pluripotent stem cells," *Theriogenology,* 45:131–140, 1986.

Strojek, Reed, Hoover, Wagner, "A method for cultivating morphologically undifferentiated embryonic stem cells from porcine blastocysts," *Theriogenology* 33:901, 1990.

Sukoyan, Golubista, Zhelezova, Shilov, Vatolin, Maximovsky, Andreeva, McWhir, Pack, Bayborodin, Kerkis, Kizilova, Serov, "Isolation and cultivation of blastocyst-derived stem cell lines from American mink (Mustela vision)," *Mol. Reprod. Dev.,* 33:418, 1992.

Sukoyan, Vatolin, Golubista, Zhelezova, Seminova, Serov, "Embryonic stem cells derived from morulae, inner cell mass, and blastocyst of mink: Comparisons of their pluripotencies," *Mol. Reprod. Dev.,* 36:148, 1993.

Swindle, *Swine as Models in Biomedical Research*, Iowa State University Press, Ames, 1992.

Swindle, *Swine in Biomedical Research*, Iowa State University Press, Ames, 1989.

Symons, "Avacado sunblotch viroid: primary sequence and proposed secondary structure." *Nucl. Acids Res.,* 9:6527–6537, 1981.

Symons, "Small catalytic RNAs," *Annu. Rev. Biochem.,* 61:641–671, 1992.

Talbot, Rexroad, Pursel, Powell et al., "Alkaline phosphatase staining of pig and sheep epiblast cells in culture," *Mol. Reprod. Dev.,* 36:139–147, 1993b.

Talbot, Rexroad, Pursel, Powell, Nel, "Culturing the epiblast cells of the pig blastocyst," In vitro *Cell. Dev. Biol.,* 29A:543–550, 1993a.

Temin, "Retrovirus vectors for gene transfer: Efficient integration into and expression of exogenous DNA in vertebrate cell genome," *In: Gene Transfer*, Kucherlapati (ed.), New York, Plenum Press, pp. 149–188, 1986.

Tepper, C. G., Jayadev, S., Liu, B., Bielawska, A., Wolff, R., Yonehara, S., Hannun, Y. A. and Seldin, M. F., "Role for ceramide as an endogenous mediator of Fas-induced cytotoxicity," *Proc. Natl. Acad. Sci. USA* 92:8443–8447, 1995.

Thompson et al., "Ribozymes in gene therapy." *Nature Medicine,* 1:277–278, 1995.

Thyagaraja, McCormick-Graham, Romero, Campbell, "Characterization of homologous DNA recombination activity in normal and immortal mammalian cells," *Nucl. Acids Res.,* 24:4084–4091, 1996.

Tilly, J. L. and Tilly, K. I., "Inhibitors of oxidative stress mimic the ability of follicle-stimulating hormone to suppress apoptosis in cultured rat ovarian follicles," *Endocrinology* 136:242–252, 1995.

Toneguzzo et al., "Electric field-mediated DNA transfer: Transient and stable gene expression in human and mouse lymphoid cells", *Mol. Cell Biol.,* 6:703–706, 1986.

Toneguzzo et al., "Electric field-mediated gene transfer: Characterization of DNA transfer and patterns of integration in lymphoid cells", *Nucl. Acid. Res.,* 16:5515–5532, 1988.

Top et al., "Immunization with live types 7 and 4 adenovirus vaccines. II. Antibody response and protective effect against acute respiratory disease due to adenovirus type 7," *J. Infect. Dis.,* 124:155–160, 1971.

Traganos, F. Kapuscinski, J., Gong, J., Ardelt, B., Darzynkiewicz, R. J. and Darzynkiewicz, Z., "Caffeine prevents apoptosis and cell cycle effects induced by camptothecin or topotecan in HL-60 cells," *Cancer Res.* 53:4613–4618, 1993.

Tratschin, Miller, Smith, Carter, "Adeno-associated virus vector for high-frequency integration, expression and rescue of genes in mammalian cells," *Mol. Cell. Biol.,* 5:32581–3260, 1985.

Tratschin, West, Sandbank, Carter, "A human parvovirus, adeno-associated virus, as a eucaryotic vector: transient expression and encapsidation of the procaryotic gene for chloramphenicol acetyltransferase," *Mol. Cell. Biol.,* 4:2072–2081, 1984.

Tsunoda, Y., Shioda, Y., Onodera, M., Nakamura, K. and Uchida, T., "Differential sensitivity of mouse pronuclei and zygote cytoplasm to Hoescht staining and ultraviolet irradiation," *J. Reprod. Fertil.* 82:173, 1988.

Tur-Kaspa et al., "Use of electroporation to introduce biologically active foreign genes into primary rat hepatocytes," *Mol. Cell Biol.,* 6:716–718, 1986.

Ueda, Jishage, Kamada, Uchida, Suzuki, "Production of mice entirely derived from embryonic stem (ES) cell with many passages by coculture of ES cells with cytochalasin B induced tetraploid embryos," *Experimental Animals,* 44(3):205–210, 1995.

Van Denderen, Pearse, Katerelos, Nottle, Zminian, Adam, Shenoy-Scaria, Lublin, Shinkel, d'Apice, "Expression of functional decay-accelerating factor (CD5S) in transgenic mice protects against human complement-mediated attack," *Transplantation,* 61(4):582–8, 1996.

Van Stekelenburg-Hamers, Van Achterberg, Rebel, Flechon, Campbell, Weima, Mummery, "Isolation and characterization of permanent cell lines from inner cell mass cells of bovine blastocyst," *Mol. Reprod. Dev.,* 40:444–454, 1995.

Verner and Schatz, "Protein translocation across membranes," *Science,* 241:1307–1312, 1988.

Voelkel and Hu, "Effect of gas atmosphere on the development of one-cell bovine embryos in two culture systems", *Theriogenology,* 37:1117–1131, 1992.

Wada, Aota, Tsuchiya, Ishibashi, Gojobori, Ikemura, "Codon usage tabulated from the GenBank genetic sequence data," *Nucl. Acids Res.,* 18 (supl.):2367–2411, 1990.

Wagner et al., *Science,* 260:1510–1513, 1990.

Walker et al., "The production of unusually large offspring following embryo manipulation: Concepts and challenges", *Theriogenology,* 45(1):111, 1996.

Wall, "Transgenic livestock: Progress and prospects for the future", *Theriogenology,* 45:57–68, 1996

Wall, "Modification of milk composition in transgenic animals", *In: Biotechnology's Role in the Genetic Improvement of Farm Animals*, Miller et al. (eds.), Beltsville Symposia in Agricultural Research, Beltsville, Md. p. 165, 1995.

Walsh, Nienhuis, Samulski, Brown, Miller, Young, Liu, "Phenotypic correction of Fanconi anemia in human hematopoietic cells with a recombinant adeno-associated virus vector," *Proc. Natl. Acad. Sci. USA,* 89:7257–7261, 1994; *J. Clin. Invest.,* 94:1440–1448, 1994.

Ward, Howlett, Discolo, Yasukawa, Hammacher, Moritz, Simpson, "High affinity interleukin-6 receptor is an hexameric complex consisting of two molecules each of interleukin-6, interleukin-6 receptor, and gp-130," *J. Biol. Chem.,* 269:23286–23289, 1995.

Ware and Axelrad, "Inherited resistance to N- and B-tropic murine leukemia viruses in vitro:

Evidence that congenic mouse strains SIM and SIM.R differ at the Fv-1 locus, *Virology,* 50:339–348, 1972.

Watanabe, M., Shirayoshi, Y., Koshimizu, U., Hashimoto, S., Yonehara, S., Eguchi, Y., Tsujimoto, Y. and Nakatsuji, N., "Gene transfection of mouse primordial germ cells in vitro and analysis of their survival and growth control," *Exp. Cell Res.* 230:76–83, 1997.

Wei, Wei, Samulski, Barranger, "Expression of the human glucocerebrosidase and arylsulfatase A genes in murine and patient primary fibroblasts transduced by an adeno-associated virus vector," *Gene Therapy,* 1:261–268, 1994.

Weidle, Lenz, Brem, "Genes encoding a mouse monoclonal antibody are expressed in transgenic mice, rabbits and pigs," *Gene,* 98:185–191, 1991.

Weiner, Miller, Khoury, Zhang, Al-Sabbagh, Brod, Lider, Higgins, Sobel, Matsui, Sayegh, Carpenter, Eisenbarth, Nussenblatt, Hafler, "Treatment of autoimmune diseases by oral tolerance to autoantigens," *Advances in Mucosal Immunology*, J. Mestecky et al., ed., Plenum Press, New York, pp. 1217–1222, 1995.

Weisgraber et al., "Abnormal lipoprotein receptor-binding activity of the human E apoprotein due to cysteine-argenine interchange at a single site," *J. Biol. Chem.*, 257:2518–2521, 1982.

Weisgraber et al., "The receptor-binding domain of human apolipoprotein E: Monoclonal antibody inhibition of binding," *J. Biol. Chem.*, 258:12348–12354, 1983.

Westhusin et al., "Nuclear transfer in the bovine embryo: A comparison of 5-day, 6-day, frozen-thawed, and nuclear transfer donor embryos", *Mol. Reprod. Dev.*, 28:119–127, 1991.

Westhusin, Levanduski, Scarbrough, Looney, Bondioli, "Viable embryos and normal calves following nuclear transfer into hoechst stained enucleated bovine demi-oocytes," *J. Reprod. Fertil.*, 95:475, 1992.

Westhusin, M. E., Levanduski, M. J., Scarborough, R., Looney, C. R. and Bondioli, K. R., "Utilization of fluorescent staining to identify enucleated demi-oocytes for utilization in bovine nuclear transfer," *Biol. Reprod.* (suppl.) 42:176, 1990.

Wheeler, "Development and validation of swine embryonic stem cells—A review", *Reprod. Fertil. Dev.*, 6:563–570, 1994.

Whittingham, D. G., "Parthenogenesis in mammals," in *Oxford reviews in reproductive biology* (ed. C. A. Finn), vol. 2, p. 205, Oxford University Press, England. 1980.

Wigler et al., "Transformation of mammalian cells with genes from procaryotes and eurcaryotes", *Cell*, 16:777–785, 1979.

Wigley, Becker, Beltrame, Balke, Crocker, Harrison, Lyons, McKensie, Tearle, Crawford, Robins, "Site-specific transgene insertion: an approach," *Reprod. Fertil. Dev.*, 6:585–588, 1994.

Willadsen, "Cloning of sheep and cow embryos," *Genome*, 31:956, 1989.

Willadsen, S. M., "Nuclear transplantation in sheep embryos," *Nature* 320:63, 1986.

Williams, Hilton, Pease, Wilson, Steward, Gearing, Wagner, Metcalf, Nicola, Gough, "Myeloid leukemia inhibitory factor maintains the developmental potential of embryonic stem cells," *Nature*, 336:684–687, 1988.

Wilmut, Schuleke, McWhir, Kind, Campbell, "Viable offspring derived from fetal and adult mammalian cells," *Nature*, 385:810–813, 1997.

Wilson et al., "Comparison of birth weight and growth characteristics of bovine calves produced by nuclear transfer (cloning), embryo transfer and natural mating", *Animal Reprod. Sci.*, 38:73–83, 1995.

Wilson, Metcalf, Gough, "Cross-species comparison of the sequence of the leukemia inhibitory factor gene and its protein," *Eur. J Biochem.*, 204:21–30, 1992.

Wobus, Holzhausen, Jakel, Schoneich, "Characterization of a pluripotent stem cell line derived from a mouse embryo," *Exp. Cell Res.*, 152:212–219, 1984.

Wong et al., "Appearance of β-lactamase activity in animal cells upon liposome mediated gene transfer," *Gene*, 10:87–94, 1980.

Wu and Wu, "Evidence for targeted gene delivery to HepG2 hepatoma cells in vitro," *Biochemistry*, 27:887–892, 1988.

Wu and Wu, "Receptor-mediated in vitro gene transfections by a soluble DNA carrier system," *J. Biol. Chem.*, 262:4429–4432, 1987.

Wu and Wu, *Adv. Drug Delivery Rev.*, 12:159–167, 1993.

Xu, McSorley, Chatfield, Dougan, Liew, "Protection against Leishmania major infectin in genetically susceptible BALB/c mice by GP63 delivered orally in attenuated Salmonella typhimurium," *Immunology*, 85:1–7, 1995.

Yang et al., "Cloning and sequencing of bovine apolipoprotein E complementary DNA and molecular evolution of apolipoproteins E, C-I and C-II," *J. Mol. Evolution*, 32:469–475, 1991.

Yang et al., "In vivo and in vitro gene transfer to mammalian somatic cells by particle bombardment," *Proc. Nat'l Acad Sci. USA*, 87:9568–9572, 1990.

Yang, Chen, Trempe, "Characterization of cell lines that inducibly express the adeno-associated virus Rep proteins," *J. Virol.*, 68:4847–4856, 1994a.

Yang, Sugawara, Ponath, Wessendorf, Baneiji, Li, Strominger, "Interferon γ response region in promoter of the human DPA gene," *Proc. Natl. Acad. Sci. USA*, 87:9226–9230, 1990.

Yeom, Fuhrmann, Ovitt, Brehm, Ohbo, Gross, Hübner, Schöler, "Geimline regulatory element of Oct-4 specific for totipotent cycle of embryonal cells," *Development*, 122:881–894, 1996.

Yoder, Kang, Zhou, Luo, Srivastava, "In vivo gene transfer in murine hematopoietic reconstituting stem cells mediated by the adeno-associated virus 2-based vectors," *Blood*, 82 (Supp.): 1:347A, 1994.

Yom and Bremel, "Genetic engineering of milk composition: Modification of milk components in lactating transgenic animals", *Am. J. Clin. Nutri.*, 58:299–314, 1993.

Yoshida, Chambers, Nichols, Smith, Mikiyoshi, Yasukawa, Shoyab, Taga, Kishimoto, "Maintenance of the pluripotential phenotype of embryonic stem cells through direct activation of gp130 signalling pathways," *Mechanisms of Development* 45:163–171, 1994.

Yuan and Altman, "Selection of guide sequences that direct efficient cleavage of mRNA by human ribonuclease P," *Science*, 263:1269–1273, 1994.

Yuan et al., "Targeted cleavage of mRNA by human RNase P," *P.N.A.S.*, 89:8006–8010, 1992.

Zannis et al., "Synthesis intracellular processing and signal peptide of human apolipoprotein E," *J. Biol. Chem.*, 259:5495–5499, 1984.

Zhang S H, Reddick R L, Piedrahita J A, and Maeda N., "Spontaneous hypercholesterolemia and arterial lesions in mice lacking apolipoprotein E," *Science* 258:468–471, 1992.

Zhang, Li, Stanley Jr., "Oral immunization with the dodecapeptide repeat of the serine-rich *Entamoeba histolytica* protein (SREHP) fused to the cholera toxin B subunit induces a mucosal and systemic anti-SREHP antibody response," *Infection and Immunity*, 63(4):1349–1355, 1995.

Zhou, Broxmyer, Cooper, Harrington, Srivastava, "Adeno-associated virus 2 mediated gene transfer in murine hematopoietic cells, *Exp. Hematol. (NY)*, 21:928–933, 1993.

Zhou, Cooper, Kang, Ruggieri, Heimfeld, Srivastava, Broxmeyer, "Adeno-associated virus 2-mediated high efficiency gene transfer into immature and mature subsets of hematopoietic progenitor cells in human umbilical cord blood," *J. Exp. Med.*, 179:1867–1875, 1994.

SEQUENCE LISTING (1) GENERAL INFORMATION:

(iii) NUMBER OF SEQUENCES: 51

(2) INFORMATION FOR SEQ ID NO:1:

(i) SEQUENCE CHARACTERISTICS:
        (A) LENGTH: 675 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 67..672

(xi) SEQUENCE DESCRIPTION: SEQ ID NO:1:

```
GCATGAACCT CTGAAAACTG CCGGCATCTA AGGTCTCCTT CAAGGCCCTC TGGAGTGCAG        60

CCCATA ATG AAG GTC TTG GCG GCA GGA GTT GTG CCC TTG CTG CTG GTT         108
       Met Lys Val Leu Ala Ala Gly Val Val Pro Leu Leu Leu Val
         1               5                  10

CTC CAC TGG AAA CAC GGG GCC GGG AGC CCC CTT CCC ATC ACC CCG GTC         156
Leu His Trp Lys His Gly Ala Gly Ser Pro Leu Pro Ile Thr Pro Val
 15              20                  25                  30

AAC GCC ACC TGT GCC ACC CGC CAT CCC TGT CCC AGC AAC CTC ATG AAC         204
Asn Ala Thr Cys Ala Thr Arg His Pro Cys Pro Ser Asn Leu Met Asn
                 35                  40                  45

CAG ATC AGA AAC CAG CTG GGA CAA CTC AAC AGC AGT GCC AAC AGC CTC         252
Gln Ile Arg Asn Gln Leu Gly Gln Leu Asn Ser Ser Ala Asn Ser Leu
             50                  55                  60

TTT ATC CTC TAT TAC ACG GCC CAG GGG GAG CCC TTC CCC AAC AAC CTG         300
Phe Ile Leu Tyr Tyr Thr Ala Gln Gly Glu Pro Phe Pro Asn Asn Leu
         65                  70                  75

GAC AAG CTG TGC AGC CCC AAC GTG ACT GAC TTC CCG CCC TTC CAC GCC         348
Asp Lys Leu Cys Ser Pro Asn Val Thr Asp Phe Pro Pro Phe His Ala
     80                  85                  90

AAC GGC ACG GAG AAG GCC CGG CTG GTG GAG CTG TAC CGC ATC ATC GCG         396
Asn Gly Thr Glu Lys Ala Arg Leu Val Glu Leu Tyr Arg Ile Ile Ala
 95                 100                 105                 110

TAC CTG GGC GCC TCC CTG GGC AAC ATC ACG AGA GAC CAG AAG GTC CTC         444
Tyr Leu Gly Ala Ser Leu Gly Asn Ile Thr Arg Asp Gln Lys Val Leu
                115                 120                 125

AAC CCC TAC GCC CAC GGC CTG CAC AGC AAG CTG AGC ACC ACG GCC GAC         492
Asn Pro Tyr Ala His Gly Leu His Ser Lys Leu Ser Thr Thr Ala Asp
            130                 135                 140

GTC CTG CGG GGT CTG CTC AGC AAC GTG CTC TGC CGC TTG TGC AGC AAG         540
Val Leu Arg Gly Leu Leu Ser Asn Val Leu Cys Arg Leu Cys Ser Lys
        145                 150                 155

TAC CAC GTG AGC CAC GTG GAC GTG ACC TAC GGC CCC GAC ACC TCG GGC         588
Tyr His Val Ser His Val Asp Val Thr Tyr Gly Pro Asp Thr Ser Gly
    160                 165                 170

AAG GAC GTC TTC CAG AAG AAG AAG CTG GGC TGT CAG CTC CTG GGG AAG         636
Lys Asp Val Phe Gln Lys Lys Lys Leu Gly Cys Gln Leu Leu Gly Lys
175                 180                 185                 190

TAC AAG CAG GTC ATC GCC GTG CTG GCC CAG GCC TTC TAG                      675
Tyr Lys Gln Val Ile Ala Val Leu Ala Gln Ala Phe
                195                 200
```

(2) INFORMATION FOR SEQ ID NO:2:

(i) SEQUENCE CHARACTERISTICS:
        (A) LENGTH: 202 amino acids
        (B) TYPE: amino acid
        (D) TOPOLOGY: linear (ii) MOLECULE TYPE: protein (xi) SEQUENCE DESCRIPTION: SEQ ID NO:2:

Met Lys Val Leu Ala Ala Gly Val Val Pro Leu Leu Val Leu His
1               5                  10                  15

Trp Lys His Gly Ala Gly Ser Pro Leu Pro Ile Thr Pro Val Asn Ala
            20                  25                  30

Thr Cys Ala Thr Arg His Pro Cys Pro Ser Asn Leu Met Asn Gln Ile
            35                  40                  45

Arg Asn Gln Leu Gly Gln Leu Asn Ser Ser Ala Asn Ser Leu Phe Ile
    50                  55                  60

Leu Tyr Tyr Thr Ala Gln Gly Glu Pro Phe Pro Asn Asn Leu Asp Lys
65                  70                  75                  80

Leu Cys Ser Pro Asn Val Thr Asp Phe Pro Pro Phe His Ala Asn Gly
                85                  90                  95

Thr Glu Lys Ala Arg Leu Val Glu Leu Tyr Arg Ile Ile Ala Tyr Leu
            100                 105                 110

Gly Ala Ser Leu Gly Asn Ile Thr Arg Asp Gln Lys Val Leu Asn Pro
            115                 120                 125

Tyr Ala His Gly Leu His Ser Lys Leu Ser Thr Thr Ala Asp Val Leu
    130                 135                 140

Arg Gly Leu Leu Ser Asn Val Leu Cys Arg Leu Cys Ser Lys Tyr His
145                 150                 155                 160

Val Ser His Val Asp Val Thr Tyr Gly Pro Asp Thr Ser Gly Lys Asp
                165                 170                 175

Val Phe Gln Lys Lys Lys Leu Gly Cys Gln Leu Leu Gly Lys Tyr Lys
            180                 185                 190

Gln Val Ile Ala Val Leu Ala Gln Ala Phe
            195                 200

(2) INFORMATION FOR SEQ ID NO:3:

(i) SEQUENCE CHARACTERISTICS:
        (A) LENGTH: 603 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..600

(xi) SEQUENCE DESCRIPTION: SEQ ID NO:3:

ATG GCT TTT GCA GAG CAT TCA CCG CTG ACC CCT CAC CGC GGG GAC CTC      48
Met Ala Phe Ala Glu His Ser Pro Leu Thr Pro His Arg Arg Asp Leu
1               5                  10                  15

TGT AGC CGC TCT ATC TGG CTA GCA AGG AAG ATT CGT TCA GAC CTG ACT      96
Cys Ser Arg Ser Ile Trp Leu Ala Arg Lys Ile Arg Ser Asp Leu Thr
            20                  25                  30

GCT CTT ATG GAA GCT TAT GTG AAG CAT CAA GGT CTG AAT GAG AAC ATC     144
Ala Leu Met Glu Ala Tyr Val Lys His Gln Gly Leu Asn Glu Asn Ile
        35                  40                  45

AAC CTG GAC TCT GTG GAT GGT GTG CCA ATG GCA AGC ACT GAT CGA TGG     192
Asn Leu Asp Ser Val Asp Gly Val Pro Met Ala Ser Thr Asp Arg Trp
    50                  55                  60

```
AGT GAG CTG ACG GAG GCA GAG CGA CTC CAA GAG AAC CTC CGA GCT TAC         240
Ser Glu Leu Thr Glu Ala Glu Arg Leu Gln Glu Asn Leu Arg Ala Tyr
 65                  70                  75                  80

CGT ACC TTC CAT GTT ATG TTG GCC AGG CTG TTA GAA GAC CAG CGG GAA         288
Arg Thr Phe His Val Met Leu Ala Arg Leu Leu Glu Asp Gln Arg Glu
                 85                  90                  95

CAT TTT ACT CCA GCT GAA GAT GAC TTC CAT CAA GCA ATA CAC ACC ATT         336
His Phe Thr Pro Ala Glu Asp Asp Phe His Gln Ala Ile His Thr Ile
            100                 105                 110

GTC CTC CAA GTC GCT GCC TTT GCT TAC CAG CTG GAA GAA TTA ATG GTG         384
Val Leu Gln Val Ala Ala Phe Ala Tyr Gln Leu Glu Glu Leu Met Val
        115                 120                 125

CTC CTG GAG CAC AAG GTC CCC CCC AGT GAG GCT GAT GGT ACG CCC CTC         432
Leu Leu Glu His Lys Val Pro Pro Ser Glu Ala Asp Gly Thr Pro Leu
    130                 135                 140

AGC GTT GGA GGT GGT GGT CTC TTT GAG AAG AAG CTG TGG GGC CTG AAG         480
Ser Val Gly Gly Gly Gly Leu Phe Glu Lys Lys Leu Trp Gly Leu Lys
145                 150                 155                 160

GTG CTG CAA GAG CTT TCA CAG TGG ACA GTG AGG TCC ATC CGT GAC CTT         528
Val Leu Gln Glu Leu Ser Gln Trp Thr Val Arg Ser Ile Arg Asp Leu
                165                 170                 175

CGA GTC ATC TCC TCT CAT CAG GCT GGG GTC CCA GCA CAC GGG AGC CAT         576
Arg Val Ile Ser Ser His Gln Ala Gly Val Pro Ala His Gly Ser His
            180                 185                 190

CAT GTC GCT AAG GAC AAG AAA ATG TAG                                     603
His Val Ala Lys Asp Lys Lys Met
        195                 200

(2) INFORMATION FOR SEQ ID NO:4:

(i) SEQUENCE CHARACTERISTICS:
            (A) LENGTH: 200 amino acids
            (B) TYPE: amino acid
            (D) TOPOLOGY: linear (ii) MOLECULE TYPE: protein (xi) SEQUENCE DESCRIPTION: SEQ ID NO:4:

Met Ala Phe Ala Glu His Ser Pro Leu Thr Pro His Arg Arg Asp Leu
  1               5                  10                  15

Cys Ser Arg Ser Ile Trp Leu Ala Arg Lys Ile Arg Ser Asp Leu Thr
             20                  25                  30

Ala Leu Met Glu Ala Tyr Val Lys His Gln Gly Leu Asn Glu Asn Ile
         35                  40                  45

Asn Leu Asp Ser Val Asp Gly Val Pro Met Ala Ser Thr Asp Arg Trp
     50                  55                  60

Ser Glu Leu Thr Glu Ala Glu Arg Leu Gln Glu Asn Leu Arg Ala Tyr
 65                  70                  75                  80

Arg Thr Phe His Val Met Leu Ala Arg Leu Leu Glu Asp Gln Arg Glu
                 85                  90                  95

His Phe Thr Pro Ala Glu Asp Asp Phe His Gln Ala Ile His Thr Ile
            100                 105                 110

Val Leu Gln Val Ala Ala Phe Ala Tyr Gln Leu Glu Glu Leu Met Val
        115                 120                 125

Leu Leu Glu His Lys Val Pro Pro Ser Glu Ala Asp Gly Thr Pro Leu
    130                 135                 140

Ser Val Gly Gly Gly Gly Leu Phe Glu Lys Lys Leu Trp Gly Leu Lys
145                 150                 155                 160

Val Leu Gln Glu Leu Ser Gln Trp Thr Val Arg Ser Ile Arg Asp Leu
```

```
                   165                 170                 175
Arg Val Ile Ser Ser His Gln Ala Gly Val Pro Ala His Gly Ser His
               180                 185                 190

His Val Ala Lys Asp Lys Lys Met
           195                 200

(2) INFORMATION FOR SEQ ID NO:5:

(i) SEQUENCE CHARACTERISTICS:
         (A) LENGTH: 1126 base pairs
         (B) TYPE: nucleic acid
         (C) STRANDEDNESS: single
         (D) TOPOLOGY: linear (ix) FEATURE:
         (A) NAME/KEY: CDS
         (B) LOCATION: 51..1001

(xi) SEQUENCE DESCRIPTION: SEQ ID NO:5:

GAGGAAGGAG GAGGAGGAAG CAACCGGGTT GGCCAATCGC AAGCCAGAAG ATG AGG        56
                                                      Met Arg
                                                        1

GTT CTG TGG GTT GCT TTG GTG GTA ACC CTC CTC GCA GGA TGC CGG ACA     104
Val Leu Trp Val Ala Leu Val Val Thr Leu Leu Ala Gly Cys Arg Thr
          5                  10                  15

GAG GAC GAG CCG GGG CCG CCG CCG GAG GTG CAC GTG TGG TGG GAG GAG     152
Glu Asp Glu Pro Gly Pro Pro Pro Glu Val His Val Trp Trp Glu Glu
     20                  25                  30

CCC AAG TGG CAG GGC AGC CAG CCC TGG GAG CAG GCC CTG GGC CGC TTC     200
Pro Lys Trp Gln Gly Ser Gln Pro Trp Glu Gln Ala Leu Gly Arg Phe
 35                  40                  45                  50

TGG GAT TAC CTG CGC TGG GTG CAG TCC CTG TCT GAC CAA GTG CAG GAG     248
Trp Asp Tyr Leu Arg Trp Val Gln Ser Leu Ser Asp Gln Val Gln Glu
                 55                  60                  65

GAG CTG CTC AGC ACC AAG GTC ACC CAG GAA CTG ACG GAG CTG ATA GAG     296
Glu Leu Leu Ser Thr Lys Val Thr Gln Glu Leu Thr Glu Leu Ile Glu
             70                  75                  80

GAG AGC ATG AAG GAG GTG AAG GCC TAC CGC GAG GAG CTG GAG GCG CAG     344
Glu Ser Met Lys Glu Val Lys Ala Tyr Arg Glu Glu Leu Glu Ala Gln
         85                  90                  95

CTG GGC CCC GTG ACC CAG GAG ACG CAG GCG CGC CTG TCC AAG GAG CTG     392
Leu Gly Pro Val Thr Gln Glu Thr Gln Ala Arg Leu Ser Lys Glu Leu
    100                 105                 110

CAG GCG GCG CAG GCC CGC GTG GGC GCC GAC ATG GAG GAC GTG CGC AAC     440
Gln Ala Ala Gln Ala Arg Val Gly Ala Asp Met Glu Asp Val Arg Asn
115                 120                 125                 130

CGC TTG GTG CTC TAC CGC AGC GAG GTG CAC AAC ATG TTG GGC CAG ACC     488
Arg Leu Val Leu Tyr Arg Ser Glu Val His Asn Met Leu Gly Gln Thr
                135                 140                 145

ACC GAG GAG CTG CGG AGC CGC CTG GCT TCC CAC CTG CGC AAG CTG CGC     536
Thr Glu Glu Leu Arg Ser Arg Leu Ala Ser His Leu Arg Lys Leu Arg
            150                 155                 160

AAG CGG CTG CTC CGC GAC ACC GAG GAC CTG CAG AAG CGC CTG GCC GTG     584
Lys Arg Leu Leu Arg Asp Thr Glu Asp Leu Gln Lys Arg Leu Ala Val
        165                 170                 175

TAC CAG GCG GGG CTG CGC GAG GGC GCC GAG CGC AGC GTG AGC GCC CTC     632
Tyr Gln Ala Gly Leu Arg Glu Gly Ala Glu Arg Ser Val Ser Ala Leu
    180                 185                 190

CGC GAG CGC CTC GGG CCC CTG GTG GAG CAG GGC CGA TTG CGC GCC GCC     680
Arg Glu Arg Leu Gly Pro Leu Val Glu Gln Gly Arg Leu Arg Ala Ala
195                 200                 205                 210
```

```
ACC CTG AGT ACC AGG GCC GGC CAG CCG CTG CGC GAG CGC GCG GAA GCC    728
Thr Leu Ser Thr Arg Ala Gly Gln Pro Leu Arg Glu Arg Ala Glu Ala
                215                 220                 225

TGG GGC CAG AAG CTG CGC GGA CGG CTG GAG GAG ATG GGC AGC CGG ACC    776
Trp Gly Gln Lys Leu Arg Gly Arg Leu Glu Glu Met Gly Ser Arg Thr
                230                 235                 240

CGC GAC CGC CTG GAT GAG ATG CGT GAG CAG CTG GAG GAG GTG CGC ACC    824
Arg Asp Arg Leu Asp Glu Met Arg Glu Gln Leu Glu Glu Val Arg Thr
                245                 250                 255

AAA GTG GAG GAG CAG GGC AGC CAG TTG CGC CTG CAG GCC GAG GGA TTC    872
Lys Val Glu Glu Gln Gly Ser Gln Leu Arg Leu Gln Ala Glu Gly Phe
    260                 265                 270

CAC GCC CTC CTC AAA GGC TGG TTC GAG CCT CTG GTG GAA GAC ATA CGG    920
His Ala Leu Leu Lys Gly Trp Phe Glu Pro Leu Val Glu Asp Ile Arg
275                 280                 285                 290

CGC CAG TGG GCC GGG CTG GTG GAG AGG ATG CAG TCG GCC GTG AGC ATA    968
Arg Gln Trp Ala Gly Leu Val Glu Arg Met Gln Ser Ala Val Ser Ile
                295                 300                 305

AGC TCC TCC ACC TCT GCG CCC AGT GAT AAT CAG TGAGTGCCCT CTCATCCGGG  1021
Ser Ser Ser Thr Ser Ala Pro Ser Asp Asn Gln
                310                 315

CACCCCCTTC GGGGCCCCGT TCCTGCCCAA CTCCCCCGCC TCCCCCAGCC TTAGATGCCC  1081

TCTTGGTGGG CCCCTGCTTA ATAAAGATTC ATCAAGCTTC ACAGC                 1126
```

(2) INFORMATION FOR SEQ ID NO:6:

(i) SEQUENCE CHARACTERISTICS:
        (A) LENGTH: 317 amino acids
        (B) TYPE: amino acid
        (D) TOPOLOGY: linear (ii) MOLECULE TYPE: protein (xi) SEQUENCE DESCRIPTION: SEQ ID NO:6:

```
Met Arg Val Leu Trp Val Ala Leu Val Val Thr Leu Leu Ala Gly Cys
 1               5                  10                  15

Arg Thr Glu Asp Glu Pro Gly Pro Pro Val His Val Trp Trp
                20                  25                  30

Glu Glu Pro Lys Trp Gln Gly Ser Gln Pro Trp Glu Gln Ala Leu Gly
                35                  40                  45

Arg Phe Trp Asp Tyr Leu Arg Trp Val Gln Ser Leu Ser Asp Gln Val
    50                  55                  60

Gln Glu Glu Leu Leu Ser Thr Lys Val Thr Gln Glu Leu Thr Glu Leu
65                  70                  75                  80

Ile Glu Glu Ser Met Lys Glu Val Lys Ala Tyr Arg Glu Glu Leu Glu
                85                  90                  95

Ala Gln Leu Gly Pro Val Thr Gln Glu Thr Gln Ala Arg Leu Ser Lys
                100                 105                 110

Glu Leu Gln Ala Ala Gln Ala Arg Val Gly Ala Asp Met Glu Asp Val
            115                 120                 125

Arg Asn Arg Leu Val Leu Tyr Arg Ser Glu Val His Asn Met Leu Gly
    130                 135                 140

Gln Thr Thr Glu Glu Leu Arg Ser Arg Leu Ala Ser His Leu Arg Lys
145                 150                 155                 160

Leu Arg Lys Arg Leu Leu Arg Asp Thr Glu Asp Leu Gln Lys Arg Leu
                165                 170                 175

Ala Val Tyr Gln Ala Gly Leu Arg Glu Gly Ala Glu Arg Ser Val Ser
                180                 185                 190
```

```
Ala Leu Arg Glu Arg Leu Gly Pro Leu Val Gln Gly Arg Leu Arg
        195                 200                 205

Ala Ala Thr Leu Ser Thr Arg Ala Gly Gln Pro Leu Arg Glu Arg Ala
        210                 215                 220

Glu Ala Trp Gly Gln Lys Leu Arg Gly Arg Leu Glu Glu Met Gly Ser
225                 230                 235                 240

Arg Thr Arg Asp Arg Leu Asp Glu Met Arg Glu Gln Leu Glu Glu Val
                245                 250                 255

Arg Thr Lys Val Glu Glu Gln Gly Ser Gln Leu Arg Leu Gln Ala Glu
            260                 265                 270

Gly Phe His Ala Leu Leu Lys Gly Trp Phe Glu Pro Leu Val Glu Asp
        275                 280                 285

Ile Arg Arg Gln Trp Ala Gly Leu Val Glu Arg Met Gln Ser Ala Val
    290                 295                 300

Ser Ile Ser Ser Ser Thr Ser Ala Pro Ser Asp Asn Gln
305                 310                 315
```

(2) INFORMATION FOR SEQ ID NO:7:

(i) SEQUENCE CHARACTERISTICS:
        (A) LENGTH: 671 base pairs
        (B) TYPE: nucleic acid
        (C) STRANDEDNESS: single
        (D) TOPOLOGY: linear (xi) SEQUENCE DESCRIPTION: SEQ ID NO:7:

```
AGATGTTGAC GTTGCAGACT TGGGTAGTCG CGAAGGTTTT GGCTGCTGGT GTTGTTCCAT    60

TGTTGTTGGT TTTGCACTGG AAGCACGGTG CTGGTTCTCC ATTGTCTATC ACCCCAGTTA   120

ACGCTACCTG TGCTACCAGA CACCCATGTC ACTCTAACTT GATGAACCAA ATCTTGAACC   180

AATTGGCTCA CGTTAACTCT TCTGCTAACG CTTTGTTCAT CTTGTACTAC ACCGCTAACG   240

GTGAACCATT CCCAAACAAC TTGGACAAGT TGTGTGGTCC AAACGTTACC ACCTTCCCAC   300

CATTCCACGC TAACGGTACC GAAAAGGCTA GATTGGTTGA ATTGTACAGA ATCGCTTACT   360

TGGGTGCTTC TTTGGGTAAC ATCACCAGAG ACCAAAGATC TTTGAACCCA GGTGCTGTTA   420

ACTTGCACTC TAAGTTGAAC GCTACCGCTG ACTCTATGAG AGGTTTGTTG TCTAACGTTT   480

TGTGTAGATT GTGTAACAAG TACCACGTTG CTCACGTTGA CGTTGCTTAC GGTCCAGACA   540

CCTCTGGTAA GGACGTTTTC CAAAAGAAGA AGTTGGGTTG TCAATTGTTG GGTAAGTACA   600

AGCAAGTTAT CTCTGTTTTG GCTAGAGCTC CATAATAGGG ATCCCAGAGC CTACTTTCAA   660

GCCTGGAATC A                                                       671
```

(2) INFORMATION FOR SEQ ID NO:8:

(i) SEQUENCE CHARACTERISTICS:
        (A) LENGTH: 702 base pairs
        (B) TYPE: nucleic acid
        (C) STRANDEDNESS: single
        (D) TOPOLOGY: linear (xi) SEQUENCE DESCRIPTION: SEQ ID NO:8:

```
GGTGGTGCAG CTGCTTTCGC TGAACACTCT CCATTGACCC CACACAGAAG AGACTTGTGT    60

TCTCGTTCTA TCTGGTTGGC TAGAAAGATC CGTTCTGACT TGACCGCTTT GATGGAAGCT   120

TACGTTAAGC ACCAAGGTTT GAACGAAAAC ATCAACTTGG ACTCTGTTGA CGGTGTTCCA   180

ATGGCTTCTA CCGATCGATG GGCTGCTGGA TCCGGTGGTA TCGATGGAGT GAGCTGACGG   240
```

-continued

```
AGGCAGAGCG ACTCCAAGAG AACCTCCGAG CTTACCGTAC CTTCCATGTT ATGTTGGCCA        300

GGCTGTTAGA AGACCAGCGG GAACATTTTA CTCCAGCTGA AGATGACTTC CATCAAGCAA        360

TACACACCAT TGTCCTCCAA GTCGCTGCCT TTGCTTACCA GCTGGAAGAA TTAATGGTGC        420

TCCTGGAGCA CAAGGTCCCC CCCAGTGAGG CTGATGGTAC GCCCCTCAGC GTTGGAGGTG        480

GTGGTCTCTT TGAGAAGAAG CTGTGGGGCC TGAAGGTGCT GCAAGAGCTT TCACAGTGGA        540

CAGTGAGGTC CATCCGTGAC CTTCGAGTCA TCTCCTCTCA TCAGGCTGGG GTCCCAGCAC        600

ACGGGAGCCA TCATGTCGCT AAGGACAAGA AAATGTAGCA GTTACCTCCC TTCTTTCTTA        660

GTTGCCTTCT ATTCTAATGG AATAGACAGT TCTCTGAGGG GG                          702
```

(2) INFORMATION FOR SEQ ID NO:9:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:9:

```
TTGGTGTTCC GAAAGCTGGC TTCTG                                              25
```

(2) INFORMATION FOR SEQ ID NO:10:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:10:

```
GGGTTATCAC TGGCACTGGG GGTGTA                                             26
```

(2) INFORMATION FOR SEQ ID NO:11:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:11:

```
AGCGACCAGC CCAAGTGTAT ACAG                                               24
```

(2) INFORMATION FOR SEQ ID NO:12:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:12:

```
GCCTGCTTTG TCGTTCCTTC AG                                                 22
```

(2) INFORMATION FOR SEQ ID NO:13:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:13:

```
AGCGACCAGC CCAAGTGTAT ACAG                                              24

(2) INFORMATION FOR SEQ ID NO:14:

(i) SEQUENCE CHARACTERISTICS:
          (A) LENGTH: 22 base pairs
          (B) TYPE: nucleic acid
          (C) STRANDEDNESS: single
          (D) TOPOLOGY: linear (xi) SEQUENCE DESCRIPTION: SEQ ID NO:14:

TGACCGCTTC CTCGTGCTTT AC                                                22

(2) INFORMATION FOR SEQ ID NO:15:

(i) SEQUENCE CHARACTERISTICS:
          (A) LENGTH: 22 base pairs
          (B) TYPE: nucleic acid
          (C) STRANDEDNESS: single
          (D) TOPOLOGY: linear (xi) SEQUENCE DESCRIPTION: SEQ ID NO:15:

AGCTGCTCAG CACCAAGGTC AC                                                22

(2) INFORMATION FOR SEQ ID NO:16:

(i) SEQUENCE CHARACTERISTICS:
          (A) LENGTH: 21 base pairs
          (B) TYPE: nucleic acid
          (C) STRANDEDNESS: single
          (D) TOPOLOGY: linear (xi) SEQUENCE DESCRIPTION: SEQ ID NO:16:

CTGAGGGTCC AGACCACACG G                                                 21

(2) INFORMATION FOR SEQ ID NO:17:

(i) SEQUENCE CHARACTERISTICS:
          (A) LENGTH: 24 base pairs
          (B) TYPE: nucleic acid
          (C) STRANDEDNESS: single
          (D) TOPOLOGY: linear (xi) SEQUENCE DESCRIPTION: SEQ ID NO:17:

GGATGGCTTT CGCAGAGCAA ACAC                                              24

(2) INFORMATION FOR SEQ ID NO:18:

(i) SEQUENCE CHARACTERISTICS:
          (A) LENGTH: 25 base pairs
          (B) TYPE: nucleic acid
          (C) STRANDEDNESS: single
          (D) TOPOLOGY: linear (xi) SEQUENCE DESCRIPTION: SEQ ID NO:18:

GCTGGTAGGC AAAGGCAGAA ACTTG                                             25

(2) INFORMATION FOR SEQ ID NO:19:

(i) SEQUENCE CHARACTERISTICS:
          (A) LENGTH: 24 base pairs
          (B) TYPE: nucleic acid
          (C) STRANDEDNESS: single
          (D) TOPOLOGY: linear (xi) SEQUENCE DESCRIPTION: SEQ ID NO:19:

GGATGGCTTT CGCAGAGCAA ACAC                                              24
```

(2) INFORMATION FOR SEQ ID NO:20:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:20:

GCTGGTAGGC AAAGGCAGAA ACTT                                                     24

(2) INFORMATION FOR SEQ ID NO:21:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:21:

CGACCAGCAC CACCAGCTC                                                        19

(2) INFORMATION FOR SEQ ID NO:22:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:22:

CCAGGATGAT GGGGACGCTG                                                    20

(2) INFORMATION FOR SEQ ID NO:23:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:23:

CCAGTGGCAG TGGCTGTCAT TGTT                                               24

(2) INFORMATION FOR SEQ ID NO:24:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:24:

CCTGAGGTCT GTAACCCGCA GTTTT                                            25

(2) INFORMATION FOR SEQ ID NO:25:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:25:

CCAAAGGACC TACTGTTCGG ACAA                                               24

(2) INFORMATION FOR SEQ ID NO:26:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:26:

CAGGACCGAC TATGGCTTCA A                                          21

(2) INFORMATION FOR SEQ ID NO:27:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:27:

TGCTCTGTGG ATGAGAGGAA CCATC                                  25

(2) INFORMATION FOR SEQ ID NO:28:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:28:

TTGCACCACC TGTCCTGATT TACAG                                  25

(2) INFORMATION FOR SEQ ID NO:29:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:29:

ATTCGGTACA TCCTCGACGG CATC                                    24

(2) INFORMATION FOR SEQ ID NO:30:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:30:

TCGTCAGCAG GCTGGCATTT GT                                        22

(2) INFORMATION FOR SEQ ID NO:31:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:31:

ATCGGGCTGA ACGGTCAAAG                                            20

(2) INFORMATION FOR SEQ ID NO:32:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:32:

AGCAACCAGG AATGTGGGCA GT                                              22

(2) INFORMATION FOR SEQ ID NO:33:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:33:

TCAAGGCTAG AGGGTGGGAT TG                                              22

(2) INFORMATION FOR SEQ ID NO:34:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:34:

TCCAACCTGA GGTCCACAGT ATG                                             23

(2) INFORMATION FOR SEQ ID NO:35:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:35:

CAGTCCCTGT CTGACCAAGT GC                                              22

(2) INFORMATION FOR SEQ ID NO:36:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:36:

TGCGGTAGAG CACCAAGCGG                                                 20

(2) INFORMATION FOR SEQ ID NO:37:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:37:

GGGACATCAA GGAGAAGCTG TG                                              22

(2) INFORMATION FOR SEQ ID NO:38:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:38:

ATGGAGTTGA AGGTAGTTTC GTGG                                          24

(2) INFORMATION FOR SEQ ID NO:39:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:39:

TGGACTTCGA GCAGAGATGG                                               20

(2) INFORMATION FOR SEQ ID NO:40:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:40:

AGGATTCCAT GCCCAGGAAG                                               20

(2) INFORMATION FOR SEQ ID NO:41:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:41:

CCAAAGGACC TACTGTTCGG ACAA                                          24

(2) INFORMATION FOR SEQ ID NO:42:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:42:

CAGGACCGAC TATGGCTTCA A                                             21

(2) INFORMATION FOR SEQ ID NO:43:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:43:

TCTTAGAGTG GGACCAACTT CCTG                                          24

(2) INFORMATION FOR SEQ ID NO:44:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (xi) SEQUENCE DESCRIPTION: SEQ ID NO:44:

CACCTTCATC TGTGTATGCT GCC                                           23

(2) INFORMATION FOR SEQ ID NO:45:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (xi) SEQUENCE DESCRIPTION: SEQ ID NO:45:

TGGCAGTGGC TGTCATTGTT GG                                            22

(2) INFORMATION FOR SEQ ID NO:46:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (xi) SEQUENCE DESCRIPTION: SEQ ID NO:46:

GGAGGTGCAT CTGTGGCTTA TAGC                                          24

(2) INFORMATION FOR SEQ ID NO:47:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (xi) SEQUENCE DESCRIPTION: SEQ ID NO:47:

GCTTGTGAGG GAAGCAGTGC TC                                            22

(2) INFORMATION FOR SEQ ID NO:48:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:48:

GGACGCTCAG CTACTGGGGA                                               20

(2) INFORMATION FOR SEQ ID NO:49:

(i) SEQUENCE CHARACTERISTICS:
            (A) LENGTH: 4791 base pairs
            (B) TYPE: nucleic acid
            (C) STRANDEDNESS: single
            (D) TOPOLOGY: linear (xi) SEQUENCE DESCRIPTION: SEQ ID NO:49:

GGTACCCCTG GCAATTTTAG GGGCAGTGTG GTCTCAGATA TGTGCCTGGC TGGCACTCCC    60

CCACCTCTGT TTTTTCTTTT TTGAATGCTT TTTAATGGGA GGGGATGCCA AGCTCATTCT   120

CCCTAGTCCT CACCATTCCT TCCTGCCCCT CATTCATTTC TGAACCTACC TGCCGCCAAA   180

```
GACACCAGAA TCTGTGACTC TGCCTAAGAG GCTCCGGAAG TGCCTTTAGG GGGCCATCAC    240

CCTGCTCTGA GCCCCAAGGG CCCTCCAAGC CGCTTCTGTT CTCCCCAACC ATCTCTCCGC    300

ATCCAAGGA GCAAGCCCAG GTTCAGTTGG CTAAGTCTCT GCTTCAAATG TCCTTTCAAC     360

ATGGAAATGC AGGACCACCC TCCCTGGAAG GGAGCCGAGA GATCAGGCAA ACGCCAGACG    420

CACCACACTT TCCCCGAAGC TCCTCCCCAG CGAAGGCAGT CACAGCAGCC CCTCAGCTTT    480

CATCTTGCCA GCCCCTCCTG GGCCCACCG GTGGTCAGCA GTGCCGGCTT GCTGATGGCG     540

CTCAGGAGGC CTGACCGTGT GGGACCCTGG GCAACCTGTC CTCTTGGGAG CCCCGCTTTG    600

CCCGGTGGCA GCGGGCAGGA TGGAGGAGGC CATCCCTGTG GTGGCTTCCA GGGCCCACGT    660

TCAGTTTCGC TTTATTGCCG TCTAAAGTCC ACGCCAGGGC CCCAGCCCCT CTTCCTGGAA    720

CCTCCTTCTC AGCCAAGCCC CAGCCTGCCT CCTCCCCACT GCCCCCCTCC AAACCCCTTG    780

ACCAGGGGGC TGCAGGTGTC AGCTCCCATC TCCTTGCCTA GTTTCAAGCC ACCTCCCCAA    840

ACCCAGGTGA GTCAGGGTTG TCTGGGGTGC CCACTTCCCC GGGGGAGGGG GGACCCTGAT    900

GACTCGGGGA CCCTCCCTCC CCCCCATCTT CAAACAACTC CCAGGGCAAG CCGCTCAGGA    960

AAACCGCAGG GTGTTTTGTT GAAGAGTTCA TTATAATTTT ATCAATCAAA TTCTTAGAAG   1020

AGGGAAAAAG TCTGCTCTCC CCACCCTCCC CCCTCACTGC CCCCCCTCCA CTCTCACTTT   1080

CTTCCATTCA TAATTTCCTA TGATGCACCT CAAACAACTT CCTGGACCGG GGATCCCTGC   1140

TAAATATAGC TGTTTCTCTC TCTGTCTTAC AACACAGGCT CCAGTATATA AATCAGGCAA   1200

ATTCCCCATT TGAGCATGAA CCTCTGAAAA CTGCCGGCAT CTAAGGTCTC CTTCAAGGCC   1260

CTCTGGAGTG CAGCCCATAA TGAAGGTCTT GGCGGCAGGT AAATCCACCC GCCCCCTGCC   1320

CCGGGCTGGC TTCCGCCGGG AGCCCCGGCC GCGGGCGCCG CGGCAAACTT GGGGCCCCTG   1380

GCGATCGCGA GCGGGACACC CACCCGCCGC AGACACACGG ACACTTGGGG CGCCCGCGCA   1440

GCCGAGAGCC CGGGCCGCCG GAGGCGCCGG GTGGCGGCCG CCGCCGGGGG CGAGCGCGGG   1500

CACATGGTCC CCGCACCTCG CGCCCAGCCC GCCCGGGGCC CCGCAGGTTG GCGGGCCAGG   1560

CAGGGGGCGC CGCTGCCTTC CTCCTCCTCC TCCTCGCTCC TGAACTCTCG CCGCTGCTCT   1620

TCCCGCTCAG CTTTGTCCGG GATTCACCCT CCCTCTTTTC TTTCTTTTTC TTTCTTTCCG   1680

CTTTCTTTTC CAACCGCGTC CCCGGCTGCT CCCTGGGAGG GGCGCCGGCC GCCGGAGCAG   1740

CTCGCAAACT CCGGCCCGGG ACGGGAGCAG GTGCCGCCTC CATCTGCTAG AGCCCGGAAA   1800

GCTGTGGTCT GTGCTAGGTG AGCCCGGGGT GTGGGGCACC CCCCGCCCCC CCGCCAGCCA   1860

TCCTGGGGCC TGAGCCCTGC CTGGAGATGC TGGGAGGCAC AGGGGACCCA GAAGTGAAGT   1920

CGAGGCTGCA CTGTCCCAGC CGAGGAACGG GCTCCAGAGC GCCTCCCCTT CCTCCAGTCT   1980

CCTCGCTTCT CCAACTCTCA CAGGTCCCCC GACCCCAGCC CTTGCTGCAG GGTCATCTGG   2040

AACACAGAGA GGGGTGGGTG GCAAGCAGGG CCCCCCTGCC CTCCCTGCGG GGAGGGGTGC   2100

TCCTGGACAG GCCTGGACAG ATCTCCCCTC TCCCTCTCAC CTTTCACTTC CCTCCCTCCC   2160

CCGCCCACCT GGCTGCCTGC AACCTTTTCC CTTTTTTTCT TTCCTGGTTG CACCATTCCC   2220

TCTCCCTCTT GAAGGCTCTG AGGGCGTCTG TGGAACCCCA GGATTCTCCT TGTCCTAACC   2280

CGCAACCTGG GACGAGGACC AGTGAACAAG AGTGTGGGGG GTGGGGGGTG GAGCTCGGAG   2340

GCCAGGAGCA GCAAGGAGCC AGGAAGGGAG GTTCTGAAGG ATGCCCTGGC ACTGGAGAAG   2400

GGGGCAGAGT TGCAGCCCTG GGGTGGAGTC CAGGGTCCCA GAGAGGGGAC TGGCCACATC   2460

TGGAGGAGGA GGAGCACAGA GAAGCTGGGG AAAGGTGACA GGATCAGGGG GAAAAAGGCC   2520

CAGTGAGCCC ACATCACCGA GACAAGTTTG GGAGATGAGG GTCAGCAGAA ACCCCCGCTC   2580
```

```
CCCGTGGGCC TGGTGGGAGC CCACTCTGTG AGACAGGAGC ATGAAGTAAC ACTTAGGAAT    2640

CTGGACCTTC CTGGGGAGTT AAGGATCTTT TTCTTGAGAC CTGGGGCATC GTCCCCTCCT    2700

GGCAGAGGCC TGGAGGGTTG GTATCACTCT GAATCCGGTT CTCAGCTGAT AGGAACAGCT    2760

CATGTCCTGT GCCCCTTGGT CCCCCCAGGA GACAGCAGGG AGTGATAAAC AGGGAGATTT    2820

AGCCATCTGG GGAGGTAGAT GCAGGGACAT TGCGAAAATC AGAAACCGCC AGGTCTGGAG    2880

AAGAGAGAGC TGGAGCCTGA GAGGGGAACG TCCCTGCAGG ACCAGAGTCG CAGCCTCTCC    2940

CCTAAGCTGC TTGCCCGCTG CCCCCCACCC CGCCACCCCT GCTCATGGCT CCCCACCGCT    3000

TGTCTGCAGG AGTTGTGCCC TTGCTGCTGG TTCTCCACTG GAAACACGGG GCCGGGAGCC    3060

CCCTTCCCAT CACCCCGGTC AACGCCACCT GTGCCACCCG CCATCCCTGT CCCAGCAACC    3120

TCATGAACCA GATCAGAAAC CAGCTGGGAC AACTCAACAG CAGTGCCAAC AGCCTCTTTA    3180

TCCTCTATGT AAGCCTCCCC CTCAGGGTAC CGAGGAACGC GCAGGGAGGG CTGGGGTCTG    3240

CAAGCAGGGA CCTGGGCTGG TGCGGCTGGT CAGAGAAGGG AATGGTGTGT GGTTTTGTCC    3300

CACTGCACCC AGATCCCCCC AGCTTCCTCC CCATCCCGCG GCCGAGGCCC GGCCTCTTTC    3360

CCTTGGTGCC AAGGTAGATG GGGCGGGGGG GGGGGAGGCG GGCAGAGGCT CCTGGAGAAG    3420

AGGTGGCAGG CAGGGCTGGC ACTTGTAGCA TTGGGATTTG TCCACCTGGT GGAGGGAGGC    3480

AGATGACAGA GAGGGAGGCG GTGGAAGGGA CTGGGGAGGT GCTGTTGAAA GAGACAGCGG    3540

GCTGTGGGTG ACGGGGTGCG GAGCCGCCCA GGAAGAGGGT GAATGCGGTG GGTGAAAGGG    3600

CAAGTGTGTG TGGTGTACAA GGCTGGAGGT GAGACTGGGT GTTTCCCCCC CTCTCCCTTG    3660

TGGTCCTGAT GCGGGTGATG AGGAGGGTAC CTCCTTGCGT GGGATAGAGG CTGGATGCTT    3720

TAGCAAGTGC ATTCGCGCCC ACTGCTACTT CTGGCTCTCG GACAGTCCC  GAGATGCCTG    3780

CAGGGCAAGT GATTGGATTC TCAAGCCCCT GTGTGTGTGT GTGTGTGTGT GTGTGTATTG    3840

TGGGGGGGCG GCACTGACGC CCAAGGGCTG ACCACAGGCG GGGCAGCAGG GCTGGAGCAG    3900

CCGTCCCTGC CTCCCACTTC ACCACCCCTC TGCCCCTCTG CTCCTCAGTA CACGGCCCAG    3960

GGGGAGCCCT TCCCCAACAA CCTGGACAAG CTGTGCAGCC CAACGTGAC  TGACTTCCCG    4020

CCCTTCCACG CCAACGGCAC GGAGAAGGCC CGGCTGGTGG AGCTGTACCG CATCATCGCG    4080

TACCTGGGCG CCTCCCTGGG CAACATCACG AGAGACCAGA AGGTCCTCAA CCCCTACGCC    4140

CACGGCCTGC ACAGCAAGCT GAGCACCACG GCCGACGTCC TGCGGGGTCT GCTCAGCAAC    4200

GTGCTCTGCC GCTTGTGCAG CAAGTACCAC GTGAGCCACG TGGACGTGAC CTACGGCCCC    4260

GACACCTCGG GCAAGGACGT CTTCCAGAAG AAGAAGCTGG GCTGTCAGCT CCTGGGGAAG    4320

TACAAGCAGG TCATCGCCGT GCTGGCCCAG GCCTTCTAGA CGGGAGGTCT TAGATAGTAG    4380

GGGACTCTCC AACTGCAGCC GTGGCCCAGA GCACTGCCAG ACCCGAGTAG GGGCCGCTGG    4440

CAGACCCCTG AGGGGGTTCC TGGCCGGTCC ACTCCCCTCC AGGGTGGGCC GCCACGAAGC    4500

CGAGCAGAGC CAGAACTCCC AGAGGCAGAA CCTATACGTG GTGCCAACTA GAAAGGAAGG    4560

CGCCCCTTCT TCTGGGAGAC TACAGCCGGG CACGCAGTGT CGGGCTGGAG TTTGCCCCCT    4620

GACTCATCCC CTCAGCCAGG GTCTTTGTGA GCAAACCCCG AAAGTTGTCT CTGGCGACCC    4680

TGACCACGGG GTGAGACAGC AGGGGTCGGG GGCACTAACC CGCGACCCCC CAGCAGAATG    4740

ACCACCATCA GTGCCTTGGC TGACCTTGAA AGGTCTGGTT GGAGCTCCAG C             4791
```

(2) INFORMATION FOR SEQ ID NO:50:

(i) SEQUENCE CHARACTERISTICS:

-continued (A) LENGTH: 2680 base pairs
(B) TYPE: nucleic acid
(C) STRANDEDNESS: single
(D) TOPOLOGY: linear (ix) FEATURE:
(A) NAME/KEY: modified_base
(B) LOCATION: one-of(1000, 1064)
(D) OTHER INFORMATION: /note= "N = A, C, T or G"

(xi) SEQUENCE DESCRIPTION: SEQ ID NO:50:

| | | | | | |
|---|---|---|---|---|---|
| TAATAAAATG | AACGGATTAA | ATGTGTATAT | AAAATAGATT | ACATTAGGCA | AGGGTGTCAT | 60 |
| GGGATTAGTG | TGACAGTGAC | CTTGTTGCTA | AGAGCAAAAG | CAAAACAATG | ACTTAAAAAC | 120 |
| AAGTACACTA | GGCACTGAGT | GGAGGAGAGA | GATGGAGGCA | GACGCTACAG | GAAAAAAGCT | 180 |
| GATTAAAAAG | GGGCCTTTGA | TTCCACAGGC | ACAAAAATCC | ACAGCCAGGA | ATTTGCTGCC | 240 |
| ACCTCTGAGT | CAGGCAGGGG | GTGGGGGTGC | ACAATTCCAT | TAGTAGAGAA | ATGCCCAGTG | 300 |
| GATTTAGTCT | GAGAGTCACA | TTGCTTATTT | GGACCAGTAT | AGACAGAAAC | AAACCCAGCT | 360 |
| CACTTGTTTC | CTGGGACAGT | TGAGTTAGGG | GATGGCTTTT | GCAGAGCATT | CACCGCTGAC | 420 |
| CCCTCACCGC | CGGGACCTCT | GTAGCCGCTC | TATCTGGCTA | GCAAGGAAGA | TTCGTTCAGA | 480 |
| CCTGACTGCT | CTTATGGAAG | CTTATGTAAG | TTGCCTGTTT | TCCTGTTGTG | TCTTTTCACC | 540 |
| TCACTTCTTC | TGATCCAGCC | CCTTACCATC | ATGCTTCAGG | CCGTTACCAG | CTATGCAAGA | 600 |
| CCTAACCATA | CAGTCATTTG | TATATTGGGC | ACCTATCATT | TGACATGGCC | CCTTCCCTTG | 660 |
| AGGAAACTCA | TGAGACCTTA | TTTTCTTTCT | GTAGGCTATC | TAGGAGACAT | GTTCCTTGAA | 720 |
| TAAGAAAATA | CAGGCTTCTA | GATAGAATTG | GTTATATATC | TTGGAGGCTG | TTCTTAATAT | 780 |
| GATTACCTTA | TATGATTACC | TTAATATGAT | TACCTACGAG | TCCTAGTTCT | ACCAGAATAC | 840 |
| ATTAACCATA | TTTGGGATCT | TCGTGTACAT | TGTTGTGATT | TTTTGAGCTG | GTAAATGAAA | 900 |
| AGCAGAGTGA | GGTTTATAGG | ACTGAGAGAA | CAGTATAAAC | CCAACGAGTT | CTCCTATAT | 960 |
| GGTATAAGCA | TCTGTGTATG | AATTACAATC | AAAAGTGTTN | CCCTGTGTCT | AAATAGAAAG | 1020 |
| GTAACCTACA | CTGCCAAAAA | AAAAAAGAAA | AAAGCCATAG | AAGNATCACT | GGGGACTTGA | 1080 |
| GGAAGTGTCA | GATTCAGATA | GGTTTTCTGA | TAGAAGAATA | TTCCCAACAG | TCTTTACCTA | 1140 |
| AGGCCTGTCA | TGGAAACACT | CCAGGCTCCT | GTAGAGAGTT | CTGATTTAGG | TTCTTTATGA | 1200 |
| ACTAATTTAT | CTTCATATAG | CCCTACTAGT | CAGAAATCAC | ACTCTTCAAA | ATACCAATTT | 1260 |
| TTAAAAATAA | TTTCCATTGA | ATTCTCCAAT | AAAGGATTGT | CCTTACCATT | GAAAGTGGGC | 1320 |
| AATGGAGCAG | AGAAAAATTG | GAAAAATTCT | ATGATGGCTA | TATTCTAGGG | CTTCCCAGGT | 1380 |
| GTAGGGCTTC | CCAGTGTCTT | CAGGGGTATT | TAAAATGTGT | AGACTCCAGT | ATCATTATAC | 1440 |
| TATTCCAGTT | TCCAGGAGGT | GTTTCAAATA | GGAAGGAAAG | ATTATTCTAG | GCCAGTCAGT | 1500 |
| GGTTTTCAAG | TGAAAGCTCT | AGATCCCTCC | CGAGAAAAAT | GAAGCGTAGT | CAAAGCGGTA | 1560 |
| CATATAATTT | CAGGGAAGAT | GGGGGTCTTC | CTAGGTCAGT | CATGGACCCC | AAGTGAAGTA | 1620 |
| AGAATTCCTG | TTCTAGACTT | CCTATTTTCT | TTGCAATTTG | GATCCTTGAC | CAGGGAAGCG | 1680 |
| AATAAGATTG | TATATGAGAT | TTAGAGGTTC | AGTGAGAATG | GTGGCATGAA | TACAGAAGAT | 1740 |
| GTGGTGTTTT | TCTGTATCCT | TGGCCAGGTG | AAGCATCAAG | GTCTGAATGA | GAACATCAAC | 1800 |
| CTGGACTCTG | TGGATGGTGT | GCCAATGGCA | AGCACTGATC | GATGGAGTGA | GCTGACGGAG | 1860 |
| GCAGAGCGAC | TCCAAGAGAA | CCTCCGAGCT | TACCGTACCT | TCCATGTTAT | GTTGGCCAGG | 1920 |
| CTGTTAGAAG | ACCAGCGGGA | ACATTTTACT | CCAGCTGAAG | ATGACTTCCA | TCAAGCAATA | 1980 |
| CACACCATTG | TCCTCCAAGT | CGCTGCCTTT | GCTTACCAGC | TGGAAGAATT | AATGGTGCTC | 2040 |

-continued

| | | | | |
|---|---|---|---|---|
|CTGGAGCACA|AGGTCCCCCC|CAGTGAGGCT|GATGGTACGC|CCCTCAGCGT TGGAGGTGGT|2100|
|GGTCTCTTTG|AGAAGAAGCT|GTGGGGCCTG|AAGGTGCTGC|AAGAGCTTTC ACAGTGGACA|2160|
|GTGAGGTCCA|TCCGTGACCT|TCGAGTCATC|TCCTCTCATC|AGGCTGGGGT CCCAGCACAC|2220|
|GGGAGCCATC|ATGTCGCTAA|GGACAAGAAA|ATGTAGCAGT|TACCTCCCTT CTTTCTTAGT|2280|
|TGCCTTCTAT|TCTAATGGAA|TAGACAGTTC|TCTGAGGCCT|CACTTCCCAT TCTTATTTTT|2340|
|GAAAAAAGA|CTGCAAGCAT|TTTTGTAACT|AGGGTTGGAG|ACATGGACAA ATGGGCATGC|2400|
|AGGTTTAGTG|TGAGAGTGTG|TGTGCGTTGG|GGCCATGAGA|GAGCGAGGGC AGGGACGCCC|2460|
|CCACAGTGCA|CTAACCTCTC|CCTACCCACT|AAATACCCTT|TACAGACATT AACAGCCGC|2520|
|ACAGGATAAA|TATATTTTTA|ACTCTAGTTC|TGGATGACTG|GTCTGAGAAG ACTTAAATAG|2580|
|TGAATTAAAA|ATCACAGAGT|CTAGCCAGTT|CAAACCCTTG|GACAATAAAA ATAGTAACTA|2640|
|AACATTTATT|GAGTATCTAC|TATATTGAAG|CACTATGCCA| |2680|

(2) INFORMATION FOR SEQ ID NO:51:

(i) SEQUENCE CHARACTERISTICS:
      (A) LENGTH: 4267 base pairs
      (B) TYPE: nucleic acid
      (C) STRANDEDNESS: single
      (D) TOPOLOGY: linear (xi) SEQUENCE DESCRIPTION: SEQ ID NO:51:

| | | | | |
|---|---|---|---|---|
|CTCGAGAGGG|AGTGAGGGTT|AAAACTCTGT|GGTGCAACGG|AAACGAATCC AACTGGGAAA|60|
|CCATGAGGCT|GTGGGTTGGA|TCCCCGGCCT|CGCTCAATGG|GTTAAGGATC CAGCACGGCG|120|
|CTGCCGTGAG|CTGTGGTGTA|GGTCGCAGAC|GAAGCTTGGA|TCCCACTTGG CTGTGGCTGT|180|
|GGCTGTGGCT|GTGGTGTAGG|CCCGCAGCTG|TAACTGTAAT|TCGACCCCTA GCCTGGGAAC|240|
|CTCCACAAGC|CACGGGTGTG|GCCCTAAAAA|GCAAAAAAAC|GAAAGCAAAA AGAACACTCT|300|
|CAAAGCCTAA|ACTTTGAGCA|AAAAGAACAC|TCTCAAAGCC|TAAACTTTGA GCAGATGCCT|360|
|TACACCGCCC|CCACGCCTCT|CATCCCCTTT|CTGTCTGGGC|CTCCAGCTCC CTTCCCCCTT|420|
|AACCCAGAAA|TCCCAGACCT|CAGACCCAAG|GATTTCGAAT|CCCCAGGCCT TGGCCCAATT|480|
|CTATCATCCC|AGCACAGGAC|AAGAAAAAAG|CAGGGCCGGG|CCTTCTGGTC CTGCTCCTCT|540|
|CCCTGCCAGC|CCACCCCACC|AGTGGCATGG|AAAAAGCTCC|GGAATTACTG GGTGAAAAAA|600|
|ACCTCTTCCA|TGGGGCTGG|AATTAGGGGG|GGGGTGATGG|TTGCCAACCC CACCCCTCCC|660|
|CTCCCTCCCT|TCCCCCACCC|TGCTGTGTGA|AAGGGGAGGC|CAGCCCACTT CGTGACCCGA|720|
|CGGGGGCTGG|CCCAGCTGGC|CCCAGTTCTG|GAGGAGTGGG|CGGGGCGGGG GGAGCCCTAT|780|
|AATTGGCCGA|ATCTGGGCTC|CCTGAATCAT|ACTCAGCCCC|GGAGGAGGAA GGAGGAAGGA|840|
|GGAGGAGGAA|GCAACCGGTG|AGGAGCAGAC|CTGGGGCAC|AGAGATGGGC TCGGGGCTTT|900|
|CGGTGGGGGG|GGTGGGCTGT|CGGGGAGGA|GGAAATGACC|TGGCCCCCCG GGGCCACCAC|960|
|CGAGGCAGGA|GTTGGGGATG|AGGCTAGAGC|CCAGGGACTG|GACCTAGAAG GAGGGTGGGC|1020|
|AGCAGGAGGA|GGTTATCCGC|CTTGGCTGGA|AGGGGAGGTC|AGGGAAGCAG CGGGACCTGT|1080|
|AGGAAGAACC|AGACGAGCCA|GAGCCGACGA|ATTGTACTGG|CAGGTATGGC GCATCTACTC|1140|
|AAGTTTTGAG|CACACTAAGA|GCTCCATCGA|GGAGACCCAG|GGGTGGCGGC GACCAGGGT|1200|
|GACCTCGACC|GGGCTGGCGG|CAGGGTAGCT|AGAGCGTTGG|TGGAAGGACA TGTAAATGAG|1260|
|GATTAAATTA|GGGAATGAGT|GGAAAACAGG|GTTTAGATGT|GAAGTTGGAG CTTGGAATGT|1320|
|GAAGGTACCA|GGAAGAACGT|GAGCTTGGAG|CCCAGAAAGC|AAGGCTGGGG CTCACATGGG|1380|

```
ACTCCAGGGT GGAAGGGGTG GGGGGCGACG TGGGTGGAAT TTGAACCCTG GGAAAAAAGG    1440

AAGGCTTTTG GCCGCACCCG ACCTGGGGAT GGGGAGATAG GAGAAGACAA TGAGGGAATT    1500

ACACGGACAA TGGAAAGGAT CTGCTCGGGA AATATCTGCT TGGATTAGGC TGATGCAGAT    1560

AAGGGGGTGC AAGGCTTGGA AGGCTGTGAC TGGACAGGGC TGGGCTCTGG GTGAGAGGAG    1620

CGAGCCCCGC CGCTGTTGAG TGACAATTTC TCCCTCCTGC AGGTTGGCCA ATCGCAAGCC    1680

AGAAGATGAG GGTTCTGTGG GTTGCTTTGG TGGTAACCCT CCTCGCAGGT ATGGGGTGG    1740

GGCTTGCTCA GGTTCCCTGC CCCTCCCCCA TCCCCGGTGC CCCTCCTTCA TCCCTGGGTC    1800

TCTTCTGCTG GTCTCTCTTC CCCTTGAGGA GAGGCCTAGA TGTGAGGCCT CTCTGGCACT    1860

CCTTGCTTCT GAACAGCTCG TTTTACTCTC TGAGCCTCAG TTTCCCCATC TTTAAAATGG    1920

GAGTTATGTT GAGAGATTCC AGCTGTGGCT CAGCAGGTTA AGAACCCGAC TAGTATCCAT    1980

GAGGAAGAGG GTTCAATCCC CTGGCTTCGC TCAGCGGGTT AAGGATCCGG CGTTGCCATG    2040

AGCTGCGGCA TAAGTCGCAG ATGCAGCTCG AATCGGGTGT TGCTGTGGCT GTGGTGCAGG    2100

CTGGCAGCTA TCGCTTCCAT CGGACCCCTC GCCTGGGAAC TTCCACGTAT GCCACTGGTG    2160

CAGCCCTAAA AGACAAACAA ACAAAAACGA AGAAAGAGA AAAGAAAGGA AAGGGGCTT    2220

CTGTTTCTAA TGCGTTGTTG CCTGGCAGGG CGTGAGCATT AGATACGTGT CAGCTGTGAC    2280

TAGCGTGCAC GGAGCACACA ATCCATGCTT GTCCAGTAAT TAGACAGGCT GGGTGTCCTT    2340

CCACCCCCTC CCTGCCCACC AGTGCTCTAG AGAAGCCCAC CCACCAGGGC TGGGGGAGCA    2400

CCTGCTCTGT ACCAGGTACC GTGTGCTGGG AGGGGCAGA GGACCTGATG GCTGTGAACT    2460

GGCTCGGTGC AGGATGCCGG ACAGAGGACG AGCCGGGGCC GCCGCGGAG GTGCACGTGT    2520

GGTGGGAGGA GCCCAAGTGG CAGGGCAGCC AGCCCTGGGA GCAGGCCCTG GCCGCTTCT    2580

GGGATTACCT GCGCTGGGTG CAGTCCCTGT CTGACCAAGT GCAGGAGGAG CTGCTCAGCA    2640

CCAAGGTCAC CCAGGAACTG ACGTAAGTGC CCACCCGACT CCCGCCGCGC GCGCGCGCGC    2700

GCGCGCGCGC GCCTGACCCT CCTGGCGAAC CGTGTGTTCT GGACCCTCAG GCTCCACCCG    2760

TCCGGGTTTC CTTCTGTCCT TGTCGCCAAC TCTTGGGGGT CTGGGTCTCT GTTTCTTTTT    2820

TTTCCTTCCT CCTTTTTTGG GGGGAAAAAA CTTTTTCTTT TTTCTTTCAT TTGACTTCAT    2880

GTCTTGCTTT CTTTCCATCT TGAGCTCCTG CCTTCGCCTG TCTCTGGGTC AGTCTTGCCG    2940

TCCCTTGCTG TCTCTGAATC TCTGGCACGT CCTGGCCATC GCCAGCTCAG GAGCCCTCCT    3000

TCTCCCCCTC ACCGCCCCCG CCCTCTCTGC GCCCAGGGAG CTGATAGAGG AGAGCATGAA    3060

GGAGGTGAAG GCCTACCGCG AGGAGCTGGA GGCGCAGCTG GGCCCCGTGA CCCAGGAGAC    3120

GCAGGCGCGC CTGTCCAAGG AGCTGCAGGC GGCGCAGGCC CGCGTGGGCG CCGACATGGA    3180

GGACGTGCGC AACCGCTTGG TGCTCTACCG CAGCGAGGTG CACAACATGT TGGGCCAGAC    3240

CACCGAGGAG CTGCGGAGCC GCCTGGCTTC CCACCTGCGC AAGCTGCGCA AGCGGCTGCT    3300

CCGCGACACC GAGGACCTGC AGAAGCGCCT GGCCGTGTAC CAGGCGGGGC TGCGCGAGGG    3360

CGCCGAGCGC AGCGTGAGCG CCCTCCGCGA GCGCCTCGGG CCCCTGGTGG AGCAGGGCCG    3420

ATTGCGCGCC GCCACCCTGA GTACCAGGGC CGGCCAGCCG CTGCGCGAGC GCGCGGAAGC    3480

CTGGGGCCAG AAGCTGCGCG ACGGCTGGA GGAGATGGGC AGCCGGACCC GCGACCGCCT    3540

GGATGAGATG CGTGAGCAGC TGGAGGAGGT GCGCACCAAA GTGGAGGAGC AGGGCAGCCA    3600

GTTGCGCCTG CAGGCCGAGG GATTCCACGC CCTCCTCAAA GGCTGGTTCG AGCCTCTGGT    3660

GGAAGACATA CGGCGCCAGT GGGCCGGGCT GGTGGAGAGG ATGCAGTCGG CCGTGAGCAT    3720
```

-continued

| | | | | | |
|---|---|---|---|---|---|
| AAGCTCCTCC | ACCTCTGCGC | CCAGTGATAA | TCAGTGAGTG | CCCTCTCATC | CGGGCACCCC 3780 |
| CTTCGGGGCC | CCGTTCCTGC | CCAACTCCCC | CGCCTCCCCC | AGCCTTAGAT | GCCCTCTTGG 3840 |
| TGGGCCCCTG | CTTAATAAAG | ATTCATCAAG | CTTCACAGCA | GCTTCTGGGT | GTCCCCGGTG 3900 |
| TGATTTCTCA | GCTCCAGCCT | CAGTTTCCCT | TTCCTTCCCT | GCACTGACCA | CCCAGTTCTC 3960 |
| TGTCCTGCCC | TCTGCCTGTG | TGTGTCTATT | TGTCTCTTCT | CCCCCTTTTC | TTTTTTTTTG 4020 |
| GCCGAGCCCA | TGGCATGCGG | AAGTTCCCCC | GGCCAGGGAT | TGAACCCATG | CCACAGCCGC 4080 |
| CACAACGAAG | GATCCTTAAC | TACTAGGCCA | CCAGGGAACT | CCATCCTTTC | TAACTCTGTC 4140 |
| TTTGCTTTCC | CTTTTTTAGC | GTTTTAGGGC | TGCACCCTCA | GCATGTGGAA | GTCCCCAGGC 4200 |
| TAGGGGTCAA | ATTGGCGCTA | CAGCTGCCAG | CCTACACCAC | AGCCCCAGCA | ACGCAGGATT 4260 |
| CCTCGAG | | | | | 4267 |

What is claimed is:

1. A method of growing porcine primordial germ cells, comprising growing a cell culture comprising porcine primordial germ cells from an embryo of a pig on feeder cells for a time sufficient to obtain undifferentiated porcine primordial germ cells, said feeder cells at a density of between about $2.5 \times 10^5$ cells/cm$^2$ and about $10^6$ cells/cm$^2$, in a culture medium comprising an effective amount of basic fibroblast growth factor.

2. The method of claim 1, wherein said cell culture comprising porcine primordial germ cells is isolated from in embryo of said pig.

3. The method of claim 2, wherein said cell culture comprising porcine primordial germ cells is isolated by a process comprising the steps of:
   a) removing the genital ridge from said embryo;
   b) disrupting said genital ridge in an appropriate solution, thereby releasing porcine primordial germ cells; and
   c) collecting said porcine primordial germ cells, to provide said cell culture comprising porcine primordial germ cells.

4. The method of claim 1, wherein said porcine primordial germ cells comprise at least a first exogenous DNA segment.

5. The method of claim 1, wherein said feeder cells are STO cells.

6. The method of claim 1, wherein said culture medium comprises basic fibroblast growth factor at a concentration of between about 5 ng/ml and about 100 µg/ml.

7. The method of claim 1, wherein said culture medium further comprises an effective amount of uteroferrin.

8. The method of claim 7, wherein said culture medium comprises uteroferrin at a concentration of between about 1 ng/ml and about 100 µg/ml.

9. The method of claim 1, wherein said culture medium further comprises an effective amount of α2-macroglobulin.

10. The method of claim 9, wherein said culture medium comprises α2-macroglobulin at a concentration of between about 10 ng/ml and about 10 µg/ml.

11. The method of claim 1, wherein said culture medium further comprises an effective amount of leukemia inhibitory factor.

12. The method of claim 11, wherein said culture medium comprises leukemia inhibitory factor at a concentration of between about 5 ng/ml and about 100 µg/ml.

13. The method of claim 1, wherein said culture medium further comprises an effective amount of soluble stem cell factor.

14. The method of claim 13, wherein said culture medium comprises soluble stem cell factor at a concentration of between about 1 ng/ml and about 100 µg/ml.

15. The method of claim 1, wherein said culture medium further comprises an effective amount of amino acids non-essential with respect to said pig.

16. The method of claim 15, wherein said culture medium comprises amino acids non-essential to said pig at a concentration of between about 10 nM and about 250 nM.

17. The method of claim 1, wherein said culture medium further comprises an effective amount of L-glutamine.

18. The method of claim 17, wherein said culture medium comprises L-glutamine at a concentration of between about 0.1 mM and about 50 mM.

19. The method of claim 1, wherein said culture medium further comprises an effective amount of β-mercaptoethanol.

20. The method of claim 19, wherein said culture medium comprises β-mercaptoethanol at a concentration of between about 1 µM and about 1 mM.

21. The method of claim 1, wherein said culture medium comprises Dulbecco's modified Eagle's media or Ham's F10 media.

22. The method of claim 1, wherein said culture medium comprises Dulbecco's modified Eagle's media at about 50% volume/volume and Ham's F10 media at about 50% volume/volume.

23. The method of claim 1, wherein said culture medium comprises an effective amount of basic fibroblast growth factor and an effective amount of at least one of uteroferrin, α2-macroglobulin, leukemia inhibitory factor, soluble stem cell factor, amino acids non-essential with respect to said pig, L-glutamine or α-mercaptoethanol.

24. The method of claim 23, wherein said culture medium comprises an effective amount of basic fibroblast growth factor and a combined effective amount of at least two of uteroferrin, α2-macroglobulin, leukemia inhibitory factor, soluble stem cell factor, amino acids non-essential with respect to said pig, L-glutamine or β-mercaptoethanol.

25. The method of claim 24, wherein said culture medium comprises an effective amount of basic fibroblast growth factor and a combined effective amount of at least three of uteroferrin, α2-macroglobulin, leukemia inhibitory factor, soluble stem cell factor, amino acids non-essential with respect to said pig, L-glutamine or β-mercaptoethanol.

26. The method of claim 25, wherein said culture medium comprises an effective amount of basic fibroblast growth factor and a combined effective amount of uteroferrin, α2-macroglobulin and leukemia inhibitory factor.

27. The method of claim 26, wherein said culture medium comprises basic fibroblast growth factor at a concentration of between about 5 ng/ml and about 100 μg/ml, uteroferrin at a concentration of between about 1 ng/ml and about 100 μg/ml, α2-macroglobulin at a concentration of between about 10 ng/ml and about 10 μg/ml and leukemia inhibitory factor at a concentration of between about 5 ng/ml and about 100 μg/ml.

28. The method of claim 1, wherein said culture medium comprises:
   a) between about 5 ng/ml and about 100 μg/ml of basic fibroblast growth factor;
   b) between about 1 ng/ml and about 100 μg/ml of uteroferrin;
   c) between about 10 ng/ml and about 10 μg/ml of α2-macroglobulin;
   d) between about 5 ng/ml and about 100 μg/ml of leukemia inhibitory factor;
   e) between about 1 ng/ml and about 100 μg/ml of soluble stem cell factor;
   f) between about 10 nM and about 250 nM of amino acids nonessential with respect to said pig;
   g) between about 0.1 mM and about 50 mM of L-glutamine;
   h) between about 1 μM and about 1 mM of β-mercaptoethanol;
   i) about 50% volume/volume of Dulbecco's modified Eagle's media; and
   j) about 50% volume/volume of Ham's F10 media.

29. The method of claim 1, wherein the porcine primordial germ cells are maintained in an undifferentiated state for between about 2 passages and about 14 passages.

30. A method of growing porcine primordial germ cells, comprising growing a cell culture comprising porcine primordial germ cells from an embryo of a pig on STO feeder cells for a time sufficient to obtain undifferentiated porcine primordial germ cells, said STO feeder cells at a density of between about $2.5 \times 10^5$ cells/cm$^2$ and about $10^6$ cells/cm$^2$, in a culture medium comprising an effective amount of basic fibroblast growth factor.

31. A method of growing porcine primordial germ cells, comprising growing a cell culture comprising porcine primordial germ cells from an embryo of a pig on feeder cells for a time sufficient to obtain undifferentiated porcine primordial germ cells, said feeder cells at a density of between about $2.5 \times 10^5$ cells/cm$^2$ and about $10^6$ cells/cm$^2$, in a culture medium comprising an effective amount of basic fibroblast growth factor, said culture medium including no exogenously added soluble stem cell factor.

32. A method of growing porcine primordial germ cells, comprising growing a cell culture comprising porcine primordial germ cells from an embryo of a pig on feeder cells for a time sufficient to obtain undifferentiated porcine primordial germ cells, said feeder cells at a density of between about $2.5 \times 10^5$ cells/cm$^2$ and about $10^6$ cells/cm$^2$, in a culture medium comprising an effective amount of basic fibroblast growth factor, said culture medium including no exogenously added leukemia inhibitory factor.

33. A method of growing porcine primordial germ cells, comprising growing a cell culture comprising porcine primordial germ cells from an embryo of a pig on feeder cells for a time sufficient to obtain undifferentiated porcine primordial germ cells, said feeder cells at a density of between about $2.5 \times 10^5$ cells/cm$^2$ and about $10^6$ cells/cm$^2$, in a culture medium comprising an effective amount of basic fibroblast growth factor, said culture medium including no exogenously added soluble stem cell factor or leukemia inhibitory factor.

34. A method of growing porcine primordial germ cells, comprising growing a cell culture comprising porcine primordial germ cells from an embryo of a pig on feeder cells other than S1/S1$^4$ or S1-m220 for a time sufficient to obtain undifferentiated porcine primordial germ cells, said feeder cells at a density of between about $2.5 \times 10^5$ cells/cm$^2$ and about $10^6$ cells/cm$^2$, in a culture medium comprising an effective amount of basic fibroblast growth factor.

35. A method of growing porcine primordial germ cells, comprising growing a cell culture comprising porcine primordial germ cells from an embryo of a pig on feeder cells other than S1/S1$^4$ or S1-m220 for a time sufficient to obtain undifferentiated porcine primordial germ cells, said feeder cells at a density of between about $2.5 \times 10^5$ cells/cm$^2$ and about $10^6$ cells/cm$^2$, in a culture medium comprising an effective amount of basic fibroblast growth factor, said culture medium including no exogenously added soluble stem cell factor or leukemia inhibitory factor.

36. A method of preparing a porcine primordial germ cell-derived cell line, comprising:
   a) plating a cell culture comprising porcine primordial germ cells on feeder cells, said feeder cells at a density of between about $2.5 \times 10$ cells/cm$^2$ and about $10^6$ cells/cm$^2$, in a culture medium comprising an effective amount of basic fibroblast growth factor; and
   b) culturing the plated porcine primordial germ cells for a period of time effective to provide a porcine primordial germ cell-derived cell line.

37. A method of preparing porcine primordial germ cells that contain a selected DNA segment, comprising:
   a) introducing said selected DNA segment into a composition comprising porcine primordial germ cells to obtain candidate porcine primordial germ cells that contain said selected DNA segment; and
   b) plating said candidate porcine primordial germ cells that contain said selected DNA segment on feeder cells, said feeder cells at a density of between about $2.5 \times 10^5$ cells/cm$^2$ and about $10^6$ cells/cm$^2$, in a culture medium comprising an effective amount of basic fibroblast growth factor, to obtain said porcine primordial germ cells that contain said selected DNA segment.

38. The method of claim 37, further comprising culturing said porcine primordial germ cells that contain said selected DNA segment for between about 2 and about 14 passages.

39. The method of claim 37, wherein said selected DNA segment is introduced into said porcine primordial germ cells by electroporation, particle bombardment or viral transformation.

40. The method of claim 37, wherein said selected DNA segment comprises at least a first coding region encoding a selected protein.

41. The method of claim 40, wherein said first coding region encodes a selected marker protein.

42. The method of claim 41, wherein said first coding region encodes green fluorescent protein.

43. The method of claim 40, wherein said first coding region encodes a protein, wherein said protein is an interleukin, collagen, interferon, blood protein, hormone, growth factor, cytokine, enzyme, receptor, binding protein, immune system protein, antigen, muscle protein or oncogene receptor.

44. The method of claim 43, wherein said first coding region encodes a protein, wherein said protein is a SREHP, GP63, actinobacillus, pleuropneumoniae, pseudomonas aeruynosa, OprF, myelin basic protein, insulin, hCD59, DAF (CD55), factor IX, urokinase, α-antitrypsin, tissue plasminogen activator, protein C, activin, adenosine dearinase, angiotensinogen I, antithrombin III, alpha I antitrypsin, apolipoprotein A-I, apolipoprotein A-II, apolipoprotein C-I, apolipoprotein C-II, apolipoprotein C-III, apolipoprotein E, atrial natriuretic factor, chorionic gonadotropin, alpha chain, beta chain, pro (rennin) chymosin, factor B complement, complement C2, complement C3, complement C4, complement C9, corticotropin releasing factor, epidermal growth factor, c-erb B, epoxide dehydratase, erythropoietin, C1 esterase inhibitor, factor VIII, factor IX, Christmas factor, factor X, fibrinogen A alpha, gamma B beta, gastrin releasing peptide, prepro glucagon, growth hormone, RF growth hormone, somatocrinin, hemopexin, inhibin, prepro insulin, insulin-like growth factor I, insulin-like growth factor II, alpha interferon, multiple leukocyte, fibroblast beta interferon, gamma interferon, interleukin-1, T-cell interleukin-2, growth factor, interleukin-3, two forms kininogen, beta subunit leuteinizing hormone, leuteinizing hormone, releasing hormone, lymphotoxin, mast cell growth factor, beta subunit nerve growth factor, PGDF c-sis oncogene, chain A, pancreatic polypeptide, icosapeptide, parathyroid hormone, prepro plasminogen, plasminogen activator, prolactin, proopiomelanocortin, protein C, prothromnbin, relaxin, prepro renin, somatostatin, prepro tachykinin, substance P, substance K, urokinase or prepro vasoactive intestinal peptide protein.

45. The method of claim 40, wherein said selected DNA segment further comprises at least a second coding region encoding a selected protein.

46. The method of claim 45, wherein said first coding region encodes a selected protein and said second coding region encodes a selected marker protein.

47. The method of claim 37, wherein said DNA segment is operatively positioned under the control of a promoter.

48. The method of claim 47, wherein said promoter is a CMV, Oct-4 or pgk promoter.

49. The method of claim 41, wherein said selected DNA segment is operatively positioned in reverse orientation under the control of a promoter, wherein said promoter directs the expression of an antisense product.

50. The method of claim 37, wherein said DNA segment further comprises two selected DNA regions that flank said DNA segment, thereby directing the homologous recombination of said DNA segment into genomic DNA of said porcine primordial germ cells.

51. The method of claim 50, wherein said selected DNA regions comprise porcine genomic DNA.

52. The method of claim 51, wherein said selected DNA regions comprise genomic DNA from the Oct-4 gene.

53. The method of claim 50, wherein said DNA segment further comprises two selected DNA sequences that flank said DNA segment, thereby directing excision of said DNA segment under appropriate conditions.

54. The method of claim 53, wherein said selected DNA sequences are loxP sites.

55. A method of producing a transgenic pig, comprising:
a) introducing a selected DNA segment into a cell culture comprising porcine primordial germ cells to obtain candidate porcine primordial germ cells that contain said selected DNA segment;
b) plating said candidate porcine primordial germ cells that contain said selected DNA segment on feeder cells, said feeder cells at a density of between about $2.5 \times 10^5$ cells/cm$^2$ and about $10^6$ cells/cm$^2$, in a culture medium comprising an effective amount of basic fibroblast growth factor, to obtain undifferentiated porcine primordial germ cells that contain said selected DNA segment; and
c) generating a transgenic pig from said undifferentiated porcine primordial germ cells that contain said selected DNA segment, wherein said selected DNA segment is contained and expressed in somatic and germ cells of said transgenic pig.

56. The method of claim 55, wherein said cell culture comprising porcine primordial germ cells contains undifferentiated cultured cells from an undifferentiated porcine primordial germ cell-derived cell line.

57. The method of claim 55, wherein said transgenic pig is generated by a method comprising:
(a) injecting said undifferentiated porcine primordial germ cells that contain said selected DNA segment into a blastocyst from a pig;
(b) transferring said blastocyst into a synchronized recipient female pig to produce a pregnant pig; and
(c) allowing gestation in said pregnant pig to proceed for a period of time sufficient to allow the development of a viable transgenic pig.

58. The method of claim 55, wherein said transgenic pig is generated by a method comprising;
(a) isolating a nucleus from said undifferentiated porcine primordial germ cells that contain said selected DNA segment and injecting said nucleus into an enucleated oocyte from a pig;
(b) transferring said oocyte into a synchronized recipient female pig to produce a pregnant pig; and
(c) allowing gestation in said pregnant pig to proceed for a period of time sufficient to allow the development of a viable transgenic pig.

59. The method of claim 55, wherein said transgenic pig is generated by a method comprising:
(a) aggregating said undifferentiated porcine primordial germ cells that contain said selected DNA segment with an early stage embryo of a pig;
(b) transferring said embryo into a synchronized recipient female pig to produce a pregnant pig; and
(c) allowing gestation in said pregnant pig to proceed for a period of time sufficient to allow the development of a viable transgenic pig.

60. The method of claim 55, wherein said selected DNA segment comprises at least a first coding region that encodes a protein selected from the group consisting of an interleukin, collagen, interferon, blood protein, hormone, growth factor, cytokine, enzyme, receptor, binding protein, immune system protein, antigen, muscle protein and an oncogene receptor.

61. The method of claim 60, wherein said selected DNA segment comprises at least a first coding region that encodes a protein selected from the group consisting of SREHP, GP63, actinobacillus, pleuropneumoniae, pseudomonas aeruynosa, OprF, myelin basic protein, insulin, hCD59, DAF (CD55), factor IX, urokinase, α-antitrypsin, tissue plasminogen activator, protein C, activin, adenosine deaminase, angiotensinogen 1, antithrombin III, alpha I antitrypsin, apolipoprotein A-I, apolipoprotein A-II, apolipoprotein C-I, apolipoprotein C-II, apolipoprotein C-III, apolipoprotein E, atrial natriuretic factor, chorionic gonadotropin, alpha chain, beta chain, pro (rennin) chymosir, factor B complement, complement C2, complement C3, complement C4, complement C9, corticotropin releasing factor, epidermal growth factor, c-erb B, epoxide dehydratase, erythropoietin, C1 esterase inhibitor, factor VIII, factor IX, Christmas factor, factor X, fibrinogen A alpha, gamma B beta, gastrin releasing peptide, prepro glucagon, growth hormone, RF growth hormone, somatocrinin, hemopexin, inhibin, prepro insulin, insulin-like growth factor I, insulin-like growth factor II, alpha interferon, multiple leukocyte, fibroblast beta interferon, gamma interferon, interleukin-1, T-cell interleukin-2, growth factor, interleukin-3, two forms kininogen, beta subunit leuteinizing hormone, leuteinizing hormone, releasing hormone, lymphotoxin, mast cell growth factor, beta subunit nerve growth factor, PGDF c-sis oncogene, chain A. pancreatic polypeptide, icosapeptide, parathyroid hormone, prepro plasminogen, plasminogen activator, prolactini, proopiomelanocortin, protein C, prothrombin, relaxin, prepro renin, somatostatin, prepro tachykinin, substance P, substance K, urokinase and prepro vasoactive intestinal peptide protein.

62. A cell culture comprising:
  (a) porcine primordial germ cells;
  (b) feeder cells sufficient to achieve a density of between about $2.5 \times 10^5$ cells/cm$^2$ and about $10^6$ feeder cells/cm$^2$; and
  (c) basic fibroblast growth factor in an amount effective to promote the growth and continued proliferation of said porcine primordial germ cells.

63. The cell culture of claim 62, wherein said porcine primordial germ cells comprise at least a first exogenous DNA segment.

64. The cell culture of claim 62, wherein said feeder cells are STO cells.

65. The cell culture of claim 62, further comprising one or more of uteroferrin, α2-macroglobulin, leukemia inhibitory factor, soluble stem cell factor, amino acids non-essential with respect to said porcine primordial germ cells, L-glutamine, β-mercaptoethanol, Dulbecco's modified Eagle's media or Ham's F10 media in an amount effective to promote the growth and continued proliferation of said porcine primordial germ cells.

66. A kit comprising, in suitable container means:
  (a) porcine primordial germ cells;
  (b) feeder cells sufficient to achieve a density of between about $2.5 \times 10^5$ cells/cm$^2$ and about $10^6$ feeder cells/cm$^2$; and
  (c) basic fibroblast growth factor in an amount effective to promote the growth and continued proliferation of said porcine primordial germ cells.

67. A method of preparing a porcine blastocyst that contains a selected DNA segment, comprising:
  a) introducing said selected DNA segment into a cell culture comprising porcine primordial germ cells to obtain candidate porcine primordial germ cells that contain said selected DNA segment;
  b) plating said candidate porcine primordial germ cells that contain said selected DNA segment on feeder cells, said feeder cells at a density of between about $2.5 \times 10^5$ cells/cm$^2$ and about $10^6$ cells/cm$^2$, in a culture medium comprising an effective amount of basic fibroblast growth factor, to obtain undifferentiated porcine primordial germ cells that contain said selected DNA segment; and
  c) injecting said undifferentiated porcine primordial germ cells that contain said selected DNA segment into a porcine blastocyst, thereby preparing a porcine blastocyst that contains said selected DNA segment.

68. A method of preparing a porcine oocyte that contains a selected DNA segment, comprising:
  a) introducing said selected DNA segment into a cell culture comprising porcine primordial germ cells to obtain candidate porcine primordial germ cells that contain said selected DNA segment;
  b) plating said candidate porcine primordial germ cells that contain said selected DNA segment on feeder cells, said feeder cells at a density of between about $2.5 \times 10^5$ cells/cm$^2$ and about $10^6$ cells/cm$^2$, in a culture medium comprising an effective amount of basic fibroblast growth factor, to obtain undifferentiated porcine primordial germ cells that contain said selected DNA segment;
  c) isolating a nucleus from said undifferentiated porcine primordial germ cells that contain said selected DNA segment; and
  d) injecting said nucleus into an enucleated porcine oocyte, thereby preparing a porcine oocyte that contains said selected L)NA segment.

69. A method of preparing an early stage porcine embryo that contains a selected DNA segment, comprising:
  a) introducing a selected DNA segment into a cell culture comprising porcine primordial germ cells to obtain candidate porcine primordial germ cells that contain said selected DNA segment;
  b) plating said candidate porcine primordial germ cells that contain said selected DNA segment on feeder cells, said feeder cells at a density of between about $2.5 \times 10^5$ cells/cm$^2$ and about $10^6$ cell/cm$^2$, in a culture medium comprising an effective amount of basic fibroblast growth factor, to obtain undifferentiated porcine primordial germ cells that contain said selected DNA segment; and
  c) aggregating said undifferentiated porcine primordial germ cells that contain said selected DNA segment with an early stage porcine embryo, thereby preparing an early stage porcine embryo that contains said selected DNA segment.

* * * * *

UNITED STATES PATENT AND TRADEMARK OFFICE
CERTIFICATE OF CORRECTION

PATENT NO. : 6,271,436 B1
DATED : August 7, 2001
INVENTOR(S) : Piedrahita and Bazer It is certified that error appears in the above-identified patent and that said Letters Patent is hereby corrected as shown below:

Column 178, claim 23,
Line 51, delete "α" and insert -- β -- therefor.

Column 181, claim 44,
Line 4, delete "dearinase" and insert -- deaminase -- therefor.

Column 181, claim 49,
Line 40, delete "41" and insert -- 37 -- therefor.

Column 182, claim 61,
Line 61, delete "1" and insert -- I -- therefor.

Column 183, claim 61,
Line 15, delete "prolactini" and insert -- prolactin -- therefor.

Column 184, claim 68,
Line 34, delete "L)NA" and insert -- DNA -- therefore.

Signed and Sealed this

Eleventh Day of December, 2001

Attest:

*Nicholas P. Godici*

NICHOLAS P. GODICI
*Attesting Officer*   *Acting Director of the United States Patent and Trademark Office*